United States Patent
Zaveri et al.

(10) Patent No.: US 10,829,471 B2
(45) Date of Patent: Nov. 10, 2020

(54) PIPERIDINYL NOCICEPTIN RECEPTOR COMPOUNDS

(71) Applicant: Astraea Therapeutics, Inc., Mountain View, CA (US)

(72) Inventors: Nurulain Zaveri, Saratoga, CA (US); Dennis Yasuda, Campbell, CA (US)

(73) Assignee: Astraea Therapeutics, LLC

(*) Notice: Subject to any disclaimer, the term of this patent is extended or adjusted under 35 U.S.C. 154(b) by 0 days.

(21) Appl. No.: 16/433,506

(22) Filed: Jun. 6, 2019

(65) Prior Publication Data

US 2019/0300500 A1 Oct. 3, 2019

Related U.S. Application Data

(62) Division of application No. 16/029,185, filed on Jul. 6, 2018, now Pat. No. 10,358,432, which is a division of application No. 15/368,508, filed on Dec. 2, 2016, now Pat. No. 10,112,924.

(60) Provisional application No. 62/261,871, filed on Dec. 2, 2015.

(51) Int. Cl.
| | |
|---|---|
| *C07D 401/04* | (2006.01) |
| *C07D 471/10* | (2006.01) |
| *C07D 401/14* | (2006.01) |
| *C07D 405/14* | (2006.01) |
| *C07D 471/04* | (2006.01) |
| *A61P 25/20* | (2006.01) |
| *A61P 25/16* | (2006.01) |

(52) U.S. Cl.
CPC ......... *C07D 401/04* (2013.01); *C07D 401/14* (2013.01); *C07D 405/14* (2013.01); *C07D 471/04* (2013.01); *C07D 471/10* (2013.01)

(58) Field of Classification Search
CPC .. C07D 401/04; C07D 401/14; C07D 405/14; C07D 471/04; C07D 471/10
See application file for complete search history.

(56) References Cited

U.S. PATENT DOCUMENTS

| | | | |
|---|---|---|---|
| 28,819 A | 6/1860 | Thompson | |
| 3,536,809 A | 10/1970 | Applezweig | |
| 3,598,123 A | 8/1971 | Zaffaroni | |
| 3,710,795 A | 1/1973 | Higuchi et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,044,126 A | 8/1977 | Cook et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,522,811 A | 6/1985 | Eppstein et al. | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,591,767 A | 1/1997 | Mohr et al. | |
| 5,639,476 A | 6/1997 | Oshlack et al. | |
| 5,639,480 A | 6/1997 | Bodmer et al. | |
| 5,672,618 A | 9/1997 | Heath, Jr. et al. | |
| 5,674,533 A | 10/1997 | Santus et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,840,674 A | 11/1998 | Yatvin et al. | |
| 5,860,957 A | 1/1999 | Jacobsen et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,948,433 A | 9/1999 | Burton et al. | |
| 5,972,366 A | 10/1999 | Haynes et al. | |
| 5,972,891 A | 10/1999 | Kamei et al. | |
| 5,980,945 A | 11/1999 | Ruiz | |

(Continued)

FOREIGN PATENT DOCUMENTS

| | | |
|---|---|---|
| EP | 1254895 A1 | 11/2002 |
| EP | 1308439 A1 | 5/2003 |

(Continued)

OTHER PUBLICATIONS

Rowe, Raymond C., Paul Sheskey, and Marian Quinn. Handbook of pharmaceutical excipients. Libros Digitales-Pharmaceutical Press, 2009; excerpt Hydroxypropyl cellulose; p. 317-322).*

(Continued)

*Primary Examiner* — John M Mauro
(74) *Attorney, Agent, or Firm* — Young Basile Hanlon & MacFarlane, P.C.

(57) ABSTRACT

The present invention provides novel piperidinyl-containing nociceptin receptor ligand compounds and pharmaceutical compositions useful in the treatment of neurological diseases and conditions where such ligands mediate the negative effects of the condition. Such neurological diseases and conditions include acute and chronic pain, substance abuse/dependence, alcohol addiction, anxiety, depression, sleep disorders, gastrointestinal disorders, renal disorders, cardiovascular disorders and Parkinson's disease.

15 Claims, No Drawings

(56) References Cited

U.S. PATENT DOCUMENTS

| | | | |
|---|---|---|---|
| 5,983,134 A | 11/1999 | Ostrow | |
| 5,985,307 A | 11/1999 | Hanson et al. | |
| 5,985,317 A | 11/1999 | Venkateshwaran et al. | |
| 5,993,855 A | 11/1999 | Yoshimoto et al. | |
| 6,004,534 A | 12/1999 | Langer et al. | |
| 6,010,715 A | 1/2000 | Wick et al. | |
| 6,024,975 A | 2/2000 | D'Angelo et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,197,350 B1 | 3/2001 | Yamagata et al. | |
| 6,248,363 B1 | 6/2001 | Patel et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,264,970 B1 | 7/2001 | Hata et al. | |
| 6,267,981 B1 | 7/2001 | Okamoto et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 6,740,634 B1 | 5/2004 | Saikawa et al. | |
| 6,869,960 B2 | 3/2005 | Ito et al. | |
| 7,241,770 B2 | 7/2007 | Mentzel et al. | |
| 2003/0158219 A1 | 8/2003 | Ito et al. | |
| 2005/0228023 A1 | 10/2005 | Zaveri et al. | |
| 2009/0124614 A1 | 5/2009 | Battista et al. | |
| 2013/0225552 A1 | 8/2013 | Allen et al. | |
| 2015/0315201 A1 | 11/2015 | Tafesse | |

FOREIGN PATENT DOCUMENTS

| | | |
|---|---|---|
| EP | 2141163 A1 | 1/2010 |
| EP | 2878601 A1 | 6/2015 |
| WO | 2004056830 A1 | 7/2004 |
| WO | 2005/016913 A1 | 2/2005 |
| WO | 2005/025506 A2 | 3/2005 |
| WO | 2005060947 A2 | 7/2005 |
| WO | 2008/060621 A2 | 5/2008 |
| WO | 2011029915 A1 | 3/2011 |
| WO | 2011/101409 A1 | 8/2011 |
| WO | 2014/106238 A1 | 7/2014 |
| WO | 2014/157687 A1 | 10/2014 |
| WO | 20140174021 A1 | 10/2014 |
| WO | 20140184069 A1 | 11/2014 |
| WO | 2015044269 A1 | 4/2015 |
| WO | 2016062789 A1 | 4/2016 |
| WO | 2016062791 A1 | 4/2016 |
| WO | 2017/096323 A1 | 6/2017 |

OTHER PUBLICATIONS

Partial Supplementary European Search Report in corresponding European Application No. 16871683, dated Jul. 15, 2019, 21 pgs.
Adapa, I.D., et al. Neuropeptides 31(5): 403-408 (1997).
Buchwald et al., Implantable Infusion Pump Management of Insulin Resistant Diabetes Mellitus. Surgery 88:507 (1980).
Carstensen, Jens T., Drug Stability: Principles & Practice, 2d. Ed., Marcel Dekker, NY, NY, (1995), pp. 379-380.
Ciccocioppo, R., et al. Peptides. 21(7):1071-1080 (2000).
Dooley, C.T., et al. J. Pharmacol. Exp. Ther. 283(2): 735-741 (1977).
Gintzler, et al. Eur. J. Pharmacol. 325: 29-34 (1997).
Goodson, Medical Applications of Controlled Release, vol. 2, pp. 115-138 (1984).
Hu, et al. Pain. 148(1): 107-113 (2010).
Khroyan, et al. J. Pharmacol. Exp. Ther. 320(2): 934-943 (2007).
Khroyan, et al. Eur. J. Pharmacol. 610(1-3): 49-54 (2009).
Khroyan, et al. J. Pharmacol. Exp. Ther. 339(2) 687-693 (2011).
Lambert, et al. Br. J. Anaesthesia. 114(3): 364-366 (2015).
Langer, R. New Methods of Drug Delivery. Science 249:1527-1533 (1990).
Lin, et al. ACS Chem. Neurosci. 4(2): 214-224 (2013).
Linz, et al. J. Pharm. Exp. Ther. 349(3): 535-548 (2014).
Marti, et al. Mov. Disord. 25: 1723-32 (2010).
Marti, M., et al. 2012.
Mollereau, et al. FEBS Lett. 341: 33-8 (1994).
Mustazza, et al. J. Med. Chem. 51: 1058-1062 (2008).
Negus, et al. J. Pharmacol. Exp. Ther. 270(3): 1025-1034 (1994).
Negus, et al. J. Pharmacol. Exp. Ther. 286(1): 362-375 (1998).
NINDS, Interagency Pain Research Coordinating Committee. National Pain Strategy. NIH NINDS: 2015. http://iprcc.nih.gov/National_Pain_Strategy/NPS_Main.htm.
Podlesnik, et al. Psychopharmacology. 213(1): 53-60 (2011).
Pubchem CID 24776401 Date Created: May 8, 2008 p. 3, compound listed. Date Accessed: Jan. 30, 2017.
Relieving Pain in America: A Blueprint for Transforming Prevention, Care, Education and Research. Institute of Medicine of the National Academies (Jun. 2011).
Saudek, et al. N. Engl. J. Med. 321: 574 (1989).
Schrag, et al. Mov. Disorders. 22: 938-945 (2007).
Sefton, M. Implantable Pumps. CRC Cit. Ref. Biomed. Eng. 14:201 (1987).
Sukhtankar, et al. J. Pharmacol. Exp. Ther. 346: 11-22 (2013).
Sukhtankar, et al. Res. Dev. of Opioid-Related Ligands ACS. 1131: 393-416 (2013).
Sukhtankar, et al. Psychopharmacology. 231(7): 1377-1387 (2014).
Toll, et al. J. Pharmacol. Exp. Ther. 331:954-64 (2009).
Varty, et al. J. Pharmaco. Exp. Ther. 326: 672-82 (2008).
Wadenburg. CNS Drug Rev. 9(2):187-198 (2003).
Zaveri, et al. J. Med. Chem. 47: 2973-2976 (2004).
Zaveri, et al. AAPS J. 7: E345-52 (2005).
Zaveri, et al. Structure-activity relationships of Nociceptin Receptor (NOP) Ligands and the Design of BiFunctional NOP/mu opioid receptor-targeted Ligands. Research and Development of Opioid-Related Ligands. Chapter 8, pp. 145-160 (2013).
Guillory, K., Chapter 5, pp. 202-205 in Polymorphism in Pharmaceutical Solids, (Brittain, H. ed.), Marcel Dekker, Inc., New York, NY 1999.
Brittain, H., Chapter 6, pp. 205-208 in Polymorphism in Pharmaceutical Solids, (Brittain, H. ed.), Marcel Dekker, Inc. New York, (1999).
Helin-Tanninen, M., "Oral Solids." Practical Pharmaceutics. Springer, Cham, 2015. 51-75.
Zaveri, N.T., "The nociceptin/orphanin FQ receptor (NOP) as a target for drug abuse medications." Current topics in medicinal chemistry 11.9 (20 11): 1151-1156.

* cited by examiner

PIPERIDINYL NOCICEPTIN RECEPTOR COMPOUNDS

CLAIM OF PRIORITY UNDER 35 U.S.C. § 119(E) AND 35 U.S.C. § 121

This application claims priority under 35 U.S.C. § 119 (e) from U.S. Provisional Application Ser. No. 62/261,871, filed Dec. 2, 2015, Ser. No. 15/368,508, filed Dec. 2, 2016 and is a divisional of Ser. No. 16/029,185, filed Jul. 6, 2018 which are hereby incorporated by reference in their entirety.

STATEMENT AS TO FEDERALLY SPONSORED RESEARCH

This invention was made with government support under grant numbers R01DA014026, R01DA027811, R43NS070664, R43HL115984, HHSN275201300005C and HHSN275201500005C awarded by U.S. Department of Human Health and Services, National Institutes of Health. The government has certain rights in the invention.

FIELD

Provided herein are novel compounds and pharmaceutical compositions thereof which modulate the nociceptin receptor. Such compounds may be useful in the treatment of acute and chronic pain, substance abuse/dependence, alcohol addiction, anxiety, depression, sleep disorders, gastrointestinal disorders, renal disorders, cardiovascular disorders, and treatment and/or prevention of Parkinson's disease.

BACKGROUND

The NOP receptor, previously called the opioid receptor-like receptor (ORL1, XOR1 and LC132) belongs to the opioid receptor family and has nucleotide and amino acid homology to the mu, delta and kappa opioid receptors. However, the NOP receptor does not bind opiate ligands with high affinity, as would be expected for an opioid receptor. The endogenous 17-amino acid peptide ligand for NOP, nociceptin or orphanin FQ (N/OFQ), poor affinity for mu, delta, and kappa opioid receptors.

N/OFQ, when injected intracerebroventricularly (i.c.v. or ICV) into mice, leads to a decrease in hot plate escape jumping latency and a decrease in tail flick latency due to attenuation of stress-induced, opioid-mediated antinociception. Additional studies have demonstrated the presence of NOP and N/OFQ precursor protein and mRNA in pain-processing pathways.

A growing body of evidence suggests that the N/OFQ-NOP receptor system plays a significant role in the reward process and drug abuse. There is a moderate to high density of NOP receptors in areas implicated in drug reward, including the nucleus accumbens, ventral tegmental area, medial prefrontal cortex, lateral hypothalamus, amygdala and the bed nucleus of stria terminalis. ICV administration of N/OFQ suppresses basal and drug-stimulated dopamine release in the nucleus accumbens. N/OFQ has been shown to block the rewarding properties of several common drugs of abuse. In particular, N/OFQ can block acquisition of conditioned place preference (CPP) induced by morphine, cocaine, amphetamines and alcohol.

The inhibitory effect of N/OFQ on morphine CPP and the inhibition of morphine-induced dopamine release in mesolimbic areas suggest that N/OFQ may function as an "anti-opioid" peptide with respect to reward as well as pain (Ciccocioppo, R., et al., Peptides, 2000, 21(7): 1071-1080). These studies confirmed the involvement of NOP receptors in drug addiction and suggested the utility of a NOP agonist as a drug abuse medication Every year, about 100 million adult Americans experience some form of pain, a condition that costs the nation between $560 billion and $635 billion annually in lost productivity and treatment ("Relieving Pain in America: A Blueprint for Transforming Prevention, Care, Education and Research; Institute of Medicine of the National Academies, June 2011). Opioid analgesics are the mainstay of pain treatment and often the only treatment option that provides significant relief. However, opioid analgesics (which are mainly mu opioid receptor (MOP) agonists) are controlled substances that have abuse potential and are riddled with many lifestyle side effects such as constipation, nausea and tolerance, that impede their long-term safety and effectiveness and create other societal disorders (the abuse of prescription pain-killers). Analgesics that do not have opioid-related liabilities are therefore vital for addressing the large need for safe and effective pain treatments, as mandated in the recently released National Pain Strategy (NINDS, Interagency Pain Research Coordinating Committee. National Pain Strategy; NIH NINDS: 2015. http://iprcc.nih.gov/National_Pain_Strategy/NPS_Main.htm).

From the opioid receptor family of mu, delta (DOP), kappa (KOP) and nociceptin (NOP) opioid receptors, KOP and DOP agonists have also been investigated as analgesics but do not show strong analgesia compared to MOP agonists, and show poor dose-separation with compromising side-effects such as dysphoria (for KOP agonists) (Wadenberg CNS Drug Rev., 2003, 9(2): 187-198) and convulsions (for DOP agonists) (Negus et al., J. Pharmacol. Exp. Ther., 1994, 270(3): 1025-1034; Negus et al., J. Pharmacol. Exp. Ther., 1998, 286(1): 362-375). Kappa-type agonist-antagonists such as nalbuphine, butorphanol have been used clinically for decades, but are considered weaker analgesics than MOP-based analgesics.

On the other hand, NOP receptor-targeted ligands are clearly emerging as potential analgesics, from recent developments (Lin et al., ACS Chem. Neurosci., 2013, 4(2): 214-224; Linz et al., J. Pharm. Exp. Ther., 2014, 349(3): 535-548; Lambert et al., Br. J. Anaesthesia, 2015, 114(3): 364-366). The NOP receptor and its endogenous ligand N/OFQ are the fourth members of the opioid family. The NOP receptor is present in the same pain pathways as the other opioid receptors and has a generally inhibitory function on neuronal transmission. The role of the NOP receptor in pain and analgesia is revealing new data, that suggests that NOP agonists may have superior analgesic potential, similar to mu opioid agonists like morphine, but not possess other liabilities like dependence and respiratory depression (Podlesnik et al., Psychopharmacology, 2011, 213(1):53-60; Sukhtankar et al., Res. Dev. of Opioid-Related Ligands ACS, 2013, 1131:393-416).

Studies with systemic administration of nonpeptide NOP agonists reveal that NOP agonists have potent anti-nociceptive activity in several animal models of pain, particularly neuropathic and inflammatory pain (Khroyan et al., Eur. J. Pharmacol., 2009, 610(1-3):49-54; Khroyan et al., J. Pharmacol. Exp. Ther., 2011, 339(2):687-693; Sukhtankar et al., Psychopharmacology, 2014, 231(7):1377-1387). Notably, studies in non-human primates have been more encouraging and consistent, compared to studies in rodents and show that peptide NOP agonists such as N/OFQ and UFP-112 produce spinal antinociception in primates, when administered intrathecally (Hu et al., Pain, 2010, 148(1):107-113) and nonpeptide NOP agonist Ro64-6198 given s.c. produces antinociception against capsaicin-induced allodynia and thermal pain (Podlesnik, et al., Psychopharmacology, 2011, 213(1): 53-60). Antinociceptive potencies and efficacy of NOP agonists was comparable to that of morphine (Sukhtankar et al., Psychopharmacology, 2014, 231(7): 1377-1387), but importantly, there was an absence of itch, respiratory depression and reinforcing effects at efficacy doses. These findings in primates strongly support the clinical potential of NOP agonists as a novel approach for "analgesia without opioid liabilities" (Lin et al., ACS Chem. Neurosci., 2013, 4(2): 214-224).

Studies have shown that bifunctional NOP/mu opioid agonists may also provide a novel approach for developing non-addicting analgesics (Khroyan et al., J. Pharmacol. Exp. Ther., 2007, 320(2): 934-943; Khroyan et al., J. Pharmacol. Exp. Ther., 2011, 339(2):687-693). Others have further confirmed that nonpeptide bifunctional NOP/mu agonists show potent antinociceptive effects in rodent and primate models of pain (Linz et al., J. Pharm. Exp. Ther., 2014, 349(3): 535-548).

Parkinson's disease (PD) is clinically characterized by hypo/akinesia, rigidity, gait disturbance and resting tremor and other non-motor symptoms such as depression and cognitive decline. PD is a costly disease both for the individual and society. Annually, the PD patient spends significantly more than healthy individuals in direct costs annually (e.g. drugs and hospitalization) and indirect costs (e.g. absence from work, early retirement; informal home care). Therefore, in the economics of PD treatment, therapies that forestall motor disabilities or cognitive impairment would provide a significant reduction in indirect costs with minimal increases in overall medication costs. It has been long recognized that PD patients stably responding to dopaminergic therapy (the current first choice for therapy) gradually develop two progressive clinical phenomena, motor fluctuations and dyskinesias (involuntary movements), that are even more disabling, and for which there is "only one" FDA-approved therapy. The dopamine (DA) precursor levodopa (L,3,4-dihydroxyphenylalanine; L-DOPA) is the cornerstone of PD therapy, often given currently in combination with COMT and MAO inhibitors, to extend its bioavailability and therapeutic action.

However, chronic L-DOPA therapy is associated with the eventual appearance (within 10 years in ~80% of patients) of motor complications (motor fluctuations and dyskinesias) that limit its clinical effectiveness and greatly reduce the quality of life of patients. Thus, the development of drugs able to delay the development of dyskinesia and/or to attenuate its expression in already dyskinetic patients is the main unmet medical need in PD. Levodopa-induced dyskinesias (LID) represent an important cause of disability and social distress in PD patients, contributing to the risk of falls and the necessity for caregivers, especially in advanced PD cases that have other neurodegenerative pathologies (i.e., memory complaints, hallucinations and comorbidities) (Schrag et al., *Mov. Disorders*, 2007, 22:938-945. There are very limited treatment options for dyskinesia and the only marketed antidyskinetic drug, amantadine, a glutamate antagonist, has poor and short-lasting clinical efficacy.

The N/OFQ-NOP receptor system is widely expressed in brain cortical and subcortical areas, particularly in striatum, globus pallidus and substantia nigra (SN) neurons, areas that undergo neurodegenerative changes in PD. Endogenous N/OFQ has been shown to contribute to development of PD symptoms because N/OFQ levels are elevated in the SNr following dopamine (DA) cell loss or impairment of DA transmission. Such an increase is also observed in the CSF of PD patients (Marti, et al., 2010). NOP receptor antagonists reverse parkinsonian symptoms in neurodegenerative (6-OHDA hemi-lesioned rat, MPTP-treated mouse and macaque) and functional (reserpinized or haloperidol-treated animals) models of PD. Genetic deletion of the N/OFQ gene protects mice from the neurotoxic action of MPTP. Mechanistic studies revealed that the antiparkinsonian action of NOP antagonists is accomplished through normalization of the imbalance between excitatory (GLU) and inhibitory (GABA) inputs impinging on nigro-thalamic neurons, generated by striatal DA deafferentation. NOP antagonists also potentiate the symptomatic effect of levodopa. Therefore, NOP receptor antagonists may provide symptomatic and neuroprotective benefit in PD patients.

On the other hand, NOP receptor agonists have been shown to attenuate the expression of abnormal involuntary movements (AIMs, a rodent correlate of LID) in dyskinetic rats and nonhuman primates challenged with L-DOPA. Thus, NOP receptor ligands have promising efficacy in Parkinson's disease animal models.

Ito et al., International Publication No. WO 2005/016913 and Spear et al., International Publication No. WO 2014/106238 disclose compounds with activity at the NOP receptor with utility as treatments for pain and CNS disorders. Piperidinyl-containing compounds with activity at the NOP receptor have been disclosed in Zaveri et al., U.S. Patent Application No. 2005/0228023, Tafesse, U.S. Patent Application No. 2015/0315201 and Mustazza et al., *J. Med. Chem.* 2008, 51:1058-1062. Allen et al., U.S. Patent Application No. 2013/0225552 discloses heterobicyclic compounds that are PDE10 inhibitors. However, there is still a need for novel NOP receptor ligands.

SUMMARY

The present invention satisfies this and other needs providing novel piperdinyl nociceptin receptor compounds. The novel piperdinyl nociceptin receptor compounds may be useful in treating and preventing a variety of disease states.

In one aspect, a compound of structural formula (I) is provided:

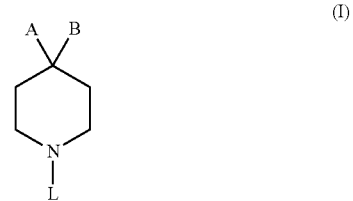

(I)

or salts, hydrates or solvates thereof where A is

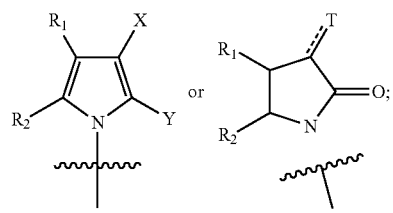

B is hydrogen; or alternatively, A and B are absent and the carbon atom to which they are attached is the carbon atom adjacent to the amide carbonyl atom in

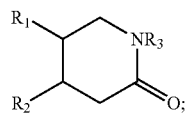

$R_1$ and $R_2$ together with the carbon atoms to which they are attached form aryl, substituted aryl, heteroaryl or substituted heteroaryl; X is hydrogen, —C=NOR$_4$, —C(O)NR$_5$R$_6$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; Y is hydrogen, —C=NOR$_7$, —C(O)NR$_8$R$_9$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; T is =NR$_{10}$; =CR$_{11}$R$_{12}$—, —NR$_{13}$R$_{14}$—, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; R$_3$ is hydrogen, alkyl, substituted alkyl, aryl substituted aryl, arylalkyl, substituted arylalkyl, heteroalkyl, substituted heteroalkyl, heteroaryl, substituted heteroaryl, heteroarylalkyl or substituted heteroarylalkyl; provided that R$_3$ is not hydrogen or methyl when R$_1$ and R$_2$ form a phenyl ring and L is

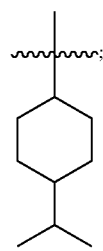 [SMILES: *C1CCC(C(C)C)CC1]

$R_4$ is hydrogen, alkyl or substituted alkyl; $R_5$ is hydrogen, alkyl or substituted alkyl; $R_6$ is hydrogen, alkyl, substituted alkyl or OR$_{15}$; $R_7$ is hydrogen, alkyl or substituted alkyl; $R_6$ and $R_9$ are independently hydrogen, alkyl or substituted alkyl; $R_{10}$ is hydrogen, alkyl, substituted alkyl, —OR$_{16}$ or —NR$_{17}$R$_{18}$; $R_{11}$ is hydrogen, alkyl, substituted alkyl, —C(O)R$_{19}$ or —CN; $R_{12}$ is hydrogen, —C(O)R$_{20}$, or —CN; $R_{13}$ is hydrogen or —C(O)R$_{21}$; $R_{14}$ is hydrogen or —C(O)R$_{22}$; provided that both $R_{13}$ and $R_{14}$ are not both hydrogen; $R_{15}$ is hydrogen, alkyl or substituted alkyl $R_{16}$ is hydrogen, alkyl or substituted alkyl; $R_{17}$ is hydrogen or —C(O)R$_{23}$; $R_{18}$ is hydrogen or —C(O)R$_{24}$; $R_{19}$ and $R_{20}$ are independently —NR$_{25}$R$_{26}$, —OR$_{27}$, alkyl, substituted alkyl, heteroalkyl or substituted heteroalkyl; $R_{21}$ and $R_{22}$ are independently —NR$_{28}$R$_{29}$, —OR$_{30}$, alkyl, substituted alkyl, heteroalkyl or substituted heteroalkyl; $R_{23}$ and $R_{24}$ are independently alkyl or substituted alkyl; $R_{25}$, $R_{26}$, $R_{27}$, $R_{28}$, $R_{29}$ and $R_{30}$ are independently, hydrogen, alkyl or substituted alkyl; and L is (C$_3$-C$_8$) cycloalkyl, (C$_3$-C$_8$) substituted cycloalkyl, (C$_3$-C$_8$) cycloheteroalkyl, (C$_3$-C$_8$) substituted cycloheteroalkyl,

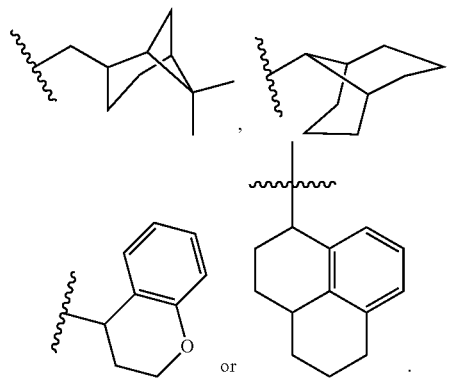

Also provided are derivatives, including salts, esters, enol ethers, enol esters, solvates, hydrates, metabolites and prodrugs of the compounds described herein. Further provided are compositions, which include the compounds provided herein and a vehicle.

Methods of treating, preventing, or ameliorating symptoms of medical disorders such as, for example, Parkinson's disease, cardiovascular disorders, gastrointestinal disorders, alcohol addiction, acute and chronic pain, anxiety, depression, pain, sleep disorders and substance abuse/dependence are also provided herein. In practicing the methods, therapeutically effective amounts of the compounds or pharmaceutical compositions thereof are administered to a subject.

Methods of modulating the nociceptin receptor t with the compounds and compositions described herein are also provided herein. In practicing the methods, therapeutically effective amounts of the compounds or pharmaceutical compositions are administered.

DETAILED DESCRIPTION

Definitions

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). The term 'cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantly.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_5$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$—, =N—N=, —N=N—, —N=N—NR$^{503}$R$^{404}$, —PR$^{505}$, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease or disorder is known as 'prophylaxis.' In some embodiments, the compounds provided herein provide superior prophylaxis because of lower long term side effects over long time periods.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —R$^a$, halo, —O$^-$, =O, —OR$^b$, —SR$^b$, —S$^-$, =S, —NR$^c$R$^c$, =NR$^b$, =N—OR$^b$, trihalomethyl, —CF$_3$, —CN, —OCN, —SCN, —NO, —NO$_2$, —N—OR$^b$, —N—NR$^c$R$^c$, —NR$^b$S(O)$_2$R$^b$, =N$_2$, —N$_3$, —S(O)$_2$R$^b$, —S(O)$_2$NR$^b$R$^b$, —S(O)$_2$O$^-$, —S(O)$_2$OR$^b$, —OS(O)$_2$R$^b$, —OS(O)$_2$O$^-$, —OS(O)$_2$OR$^b$, —OS(O)$_2$NR$^c$NR$^c$, —P(O)(O$^-$)$_2$, —P(O)(OR$^b$)

(O⁻), —P(O)(OR^b)(OR^b), —C(O)R^b, —C(O)NR^b—OR^b—C(S)R^b, —C(NR^b)R^b, —C(O)O⁻, —C(O)OR^b, —C(S)OR^b, —C(O)NR^cR^c, —C(NR^b)NR^cR^c, —OC(O)R^b, —OC(S)R^b, —OC(O)O⁻, —OC(O)OR^b, —OC(O)NR^cR^c, —OC(NCN)NR^cR^c—OC(S)OR^b, —NR^bC(O)R^b, —NR^bC(S)R^b, —NR^bC(O)O⁻, —NR^bC(O)OR^b, —NR^bC(NCN)OR^b, —NR^bS(O)₂NR^cR^c, —NR^bC(S)OR^b, —NR^bC(O)NR^cR^c, —NR^bC(S)NR^cR^c, —NR^bC(S)NR^bC(O)R^a, —NR^bS(O)₂OR^b, —NR^bS(O)₂R^b, —NR^bC(NCN)NR^cR^c, —NR^bC(NR^b)R^b and —NR^bC(NR^b)NR^cR^c, where R^a is independently alkyl, heteroalkyl, aryl, arylalkyl, heteroaryl and heteroarylalkyl; each R^b is independently hydrogen, R^a, substituted alkyl, substituted heteroalkyl, substituted aryl, substituted arylalkyl, substituted heteroaryl and substituted heteroarylalkyl; and each R^c is independently R^b or alternatively, the two R^cs are taken together with the nitrogen atom to which they are bonded form a 4-, 5-, 6- or 7-membered cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —NR^cR^c is meant to include —NH₂, —NH-alkyl, N-pyrrolidinyl and N-morpholinyl.

Similarly, substituent groups useful for substituting unsaturated carbon atoms in the specified group or radical include, but are not limited to, —R^a, halo, —O⁻, —OR^b, —SR^b, —S⁻, —NR^cR^c, trihalomethyl, —CF₃, —CN, —OCN, —SCN, —NO, —NO₂, —N₃, —S(O)₂R^b, —S(O)₂O⁻, —S(O)₂OR_b, —OS(O)₂R^b, —OS(O)₂O⁻, —OS(O)₂OR_b, —P(O)(O⁻)₂, —P(O)(OR_b)(O⁻), —P(O)(OR^b)(OR^b), —C(O)R^b, —C(S)R^b, —C(NR^b)R^b, —C(O)O⁻, —C(O)OR^b, —C(S)OR^b, —C(O)NR^cR^c, —C(NR^b)NR^cR^c, —OC(O)R^b, —OC(S)R^b, —OC(O)O⁻, —OC(O)OR^b, —OC(S)OR^b, —OC(O)NR^cR^c, —OS(O)₂NR^cNR^c, —NR^bC(O)R^b, —NR^bC(S)R^b, —NR^bC(O)O⁻, —NR^bC(O)OR^b, —NR^bS(O)₂OR^a, —NR^bS(O)₂R^a, —NR^bC(S)OR^b, —NR^bC(O)NR^cR^c, —NR^bC(NR^b)R^b and —NR^bC(NR^b)NR^cR^c, where R^a, R^b and R^c are as previously defined.

Substituent groups useful for substituting nitrogen atoms in heteroalkyl and cycloheteroalkyl groups include, but are not limited to, —R^a, —O⁻, —OR^b, —SR^b, —S⁻, —NR^cR^c, trihalomethyl, —CF₃, —CN, —NO, —NO₂, —S(O)₂R^b, —S(O)₂O⁻, —S(O)₂OR_b, —OS(O)₂R^b, —OS(O)₂O⁻, —OS(O)₂OR^b, —P(O)(O⁻)₂, —P(O)(OR^b)(O⁻), —P(O)(OR^b)(OR^b), —C(O)R^b, —C(S)R^b, —C(NR^b)R^b, —C(O)OR^b, —C(S)OR^b, —C(O)NR^cR^c, —C(NR^b)NR^cR^c, —OC(O)R^b, —OC(S)R^b, —OC(O)OR^b, —OC(S)OR^b, —NR^bC(O)R^b, —NR^bC(S)R^b, —NR^bC(O)OR^b, —NR^bC(S)OR^b, —NR^bC(O)NR^cR^c, —NR^bC(NR^b)R^b and —NR^bC(NR^b)NR^cR^c, where R^a, R^b and R^c are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

Compounds

The present invention provides novel piperdinyl nociceptin receptor ligands useful in the treatment of neurological diseases and conditions where such ligands mediate the negative effects of the condition. Such neurological diseases and conditions include, for example, acute and chronic pain, substance abuse/dependence, alcohol addiction, anxiety, depression, sleep disorders, gastrointestinal disorders, renal disorders, cardiovascular disorders, and Parkinson's disease.

In some embodiments, a compound of structural formula (I) is provided:

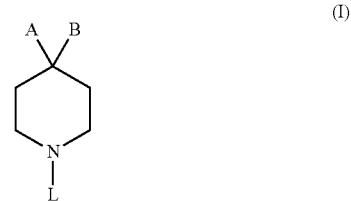

(I)

or salts, hydrates or solvates thereof where A is

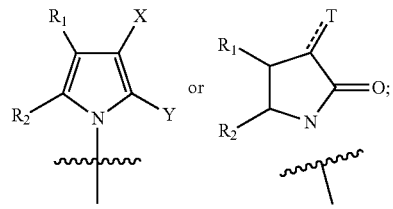

B is hydrogen; or alternatively, A and B are absent and the carbon atom to which they are attached is the carbon atom adjacent to the amide carbonyl atom in

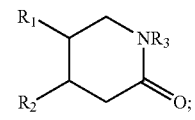

$R_1$ and $R_2$ together with the carbon atoms to which they are attached form aryl, substituted aryl, heteroaryl or substituted heteroaryl; X is hydrogen, —C=NOR$_4$, —C(O)NR$_5$R$_6$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; Y is hydrogen, —C=NOR$_7$, —C(O)NR$_8$R$_9$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; T is =NR$_{10}$; =CR$_{11}$R$_{12}$—, —NR$_{13}$R$_{14}$—, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; R$_3$ is hydrogen, alkyl, substituted alkyl, aryl substituted aryl, arylalkyl, substituted arylalkyl, heteroalkyl, substituted heteroalkyl, heteroaryl, substituted heteroaryl, heteroarylalkyl or substituted heteroarylalkyl; provided that R$_3$ is not hydrogen or methyl when R$_1$ and R$_2$ form a phenyl ring and L is

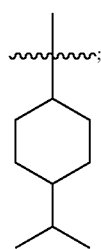 [SMILES: *C1CCC(C(C)C)CC1]

$R_4$ is hydrogen, alkyl or substituted alkyl; $R_5$ is hydrogen, alkyl or substituted alkyl; $R_6$ is hydrogen, alkyl, substituted alkyl or $OR_{15}$; $R_7$ is hydrogen, alkyl or substituted alkyl; $R_8$ and $R_9$ are independently hydrogen, alkyl or substituted alkyl; $R_{10}$ is hydrogen, alkyl, substituted alkyl, —$OR_{16}$ or —$NR_{17}R_{18}$; $R_{11}$ is hydrogen, alkyl, substituted alkyl, —$C(O)R_{19}$ or —CN; $R_{12}$ is hydrogen, —$C(O)R_{20}$, or —CN; $R_{13}$ is hydrogen or —$C(O)R_{21}$; $R_{14}$ is hydrogen or —$C(O)R_{22}$; provided that both $R_{13}$ and $R_{14}$ are not both hydrogen; $R_{15}$ is hydrogen, alkyl or substituted alkyl $R_{16}$ is hydrogen, alkyl or substituted alkyl; $R_{17}$ is hydrogen or —$C(O)R_{23}$; $R_{18}$ is hydrogen or —$C(O)R_{24}$; $R_{19}$ and $R_{20}$ are independently —$NR_{25}R_{26}$, —$OR_{27}$, alkyl, substituted alkyl, heteroalkyl or substituted heteroalkyl; $R_{21}$ and $R_{22}$ are independently —$NR_{28}R_{29}$, —$OR_{30}$, alkyl, substituted alkyl, heteroalkyl or substituted heteroalkyl; $R_{23}$ and $R_{24}$ are independently alkyl or substituted alkyl; $R_{25}$, $R_{26}$, $R_{27}$, $R_{28}$, $R_{29}$ and $R_{30}$ are independently, hydrogen, alkyl or substituted alkyl; and L is $(C_3-C_8)$ cycloalkyl, $(C_3-C_8)$ substituted cycloalkyl, $(C_3-C_8)$ cycloheteroalkyl, $(C_3-C_8)$ substituted cycloheteroalkyl,

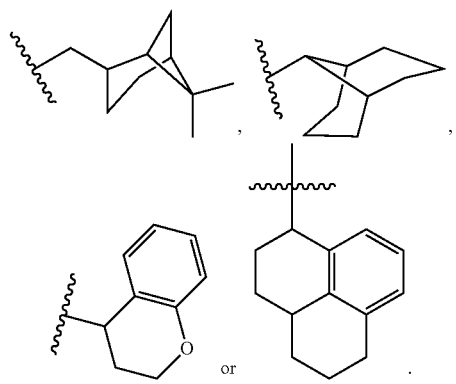

In some embodiments, $R_1$ and $R_2$ together with the carbon atoms to which they are attached form phenyl, substituted phenyl, pyridyl or substituted pyridyl.

In some embodiments, L is $(C_3-C_8)$ cycloalkyl, $(C_3-C_8)$ substituted cycloalkyl or $(C_3-C_8)$ cycloheteroalkyl. In other embodiments, L is

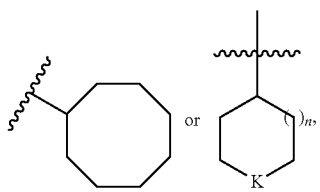

n is 0, 1 or 2, K is —$NR_{31}$— or —O— and $R_{31}$ is hydrogen, alkyl or substituted alkyl. In still other embodiments, L is a substituted cyclohexyl group. In still other embodiments, L is

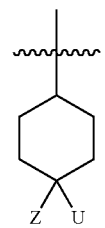

wherein Z is alkyl, substituted alkyl aryl, substituted aryl, arylalkyl, substituted arylalkyl, heteroalkyl, substituted heteroalkyl, heteroaryl, substituted heteroaryl, heteroarylalkyl or substituted heteroarylalkyl; and U is hydrogen, alkyl or absent. In still other embodiments, Z is alkyl, substituted alkyl, heteroalkyl or substituted heteroalkyl. In still other embodiments, Z is

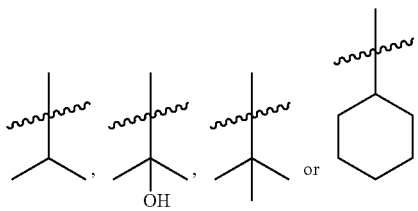

and U is hydrogen. In still other embodiments, Z is methyl and U is methyl. In still other embodiments, Z is

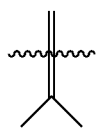 [SMILES: *=C(C)C]

and U is absent.

In some embodiments, A is

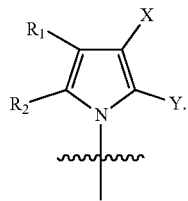

In other embodiments, $R_1$ and $R_2$ form phenyl, substituted phenyl, pyridyl or substituted pyridyl. In still other embodiments, a compound of structural formula (II) is provided:

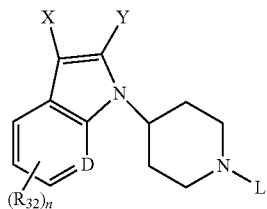

(II)

where D is —CH— or —N—, $R_{32}$ is alkyl, halo, —$OR_{33}$, —$NHR_{34}$, —$CF_3$ or —CN; n is an integer between 0 and 4; $R_{33}$ is hydrogen, alkyl, —(CO)$NR_{35}R_{36}$ or —$SO_2NR_{37}R_{38}$; and $R_{34}$, $R_{35}$, $R_{36}$, $R_{37}$ and $R_{38}$ are independently hydrogen or alkyl. In still other embodiments, X is hydrogen, —C=$NOR_4$, —C(O)$NR_5R_6$, alkyl, substituted alkyl, aryl, substituted aryl, heteroalkyl or substituted heteroalkyl; and Y is hydrogen, —C=$NOR_7$, —C(O)$NR_8R_9$, alkyl, substituted alkyl, aryl, substituted aryl, heteroalkyl or substituted heteroalkyl. In still other embodiments, X is hydrogen; and Y is —C=$NOR_7$, —C(O)$NR_8R_9$, alkyl, substituted alkyl, aryl, substituted aryl, heteroalkyl or substituted heteroalkyl. In still other embodiments, X is —C=$NOR_4$, —C(O)$NR_5R_6$, alkyl, substituted alkyl, aryl, substituted aryl, heteroalkyl or substituted heteroalkyl; and Y is hydrogen. In still other embodiments, X is —C=$NOR_4$, —C(O)$NR_5R_6$, alkyl, substituted alkyl, aryl, substituted aryl, heteroalkyl, substituted heteroalkyl; and Y is —C=$NOR_7$, —C(O)$NR_8R_9$, alkyl, substituted alkyl, aryl, substituted aryl, heteroalkyl or substituted heteroalkyl.

In some embodiments, A is

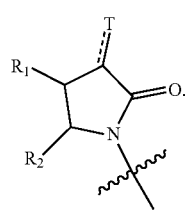

In other embodiments, $R_1$ and $R_2$ form phenyl, substituted phenyl, pyridyl or substituted pyridyl. In still other embodiments, a compound of structural formula (III) is provided:

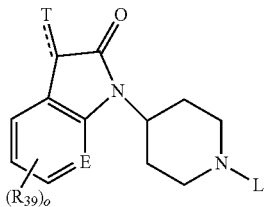

(III)

where E is —CH— or —N—, $R_{39}$ is alkyl, halo, —$OR_{40}$, —$NHR_{41}$, —$CF_3$ or —CN; o is an integer between 0 and 4; $R_{40}$ is hydrogen, alkyl, —(CO)$NR_{42}R_{43}$ or —$SO_2NR_{44}R_{45}$; and $R_{41}$, $R_{42}$, $R_{43}$, $R_{44}$ and $R_{45}$ are independently hydrogen or alkyl.

In some embodiments, A and B are absent and the carbon atom to which they are attached is the carbon atom adjacent to the amide carbonyl atom in

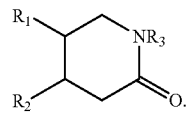

In other embodiments, $R_1$ and $R_2$ form phenyl, substituted phenyl, pyridyl or substituted pyridyl. In still other embodiments, a compound of structural Formula (IV) is provided:

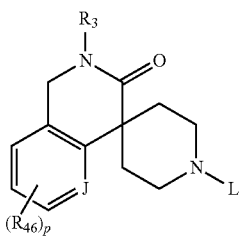

(IV)

wherein J is —CH— or —N—, $R_{46}$ is alkyl, halo, —$OR_{47}$, —$NHR_{48}$, —$CF_3$ or —CN; p is an integer between 0 and 4; $R_{47}$ is hydrogen, alkyl, —(CO)$NR_{49}R_{50}$, —$SO_2NR_{51}R_{52}$; and $R_{48}$, $R_{49}$, $R_{50}$, $R_{51}$ and $R_{52}$ are independently hydrogen or alkyl.

Table 1 illustrates compounds of structural formula (II). In some embodiments, the 1,4-substituents on the cyclohexyl ring are cis to each other.

TABLE 1

| No. | Structure* | IUPAC Name | NMR (300 or 400 MHz) or TLC |
|---|---|---|---|
| 1 | 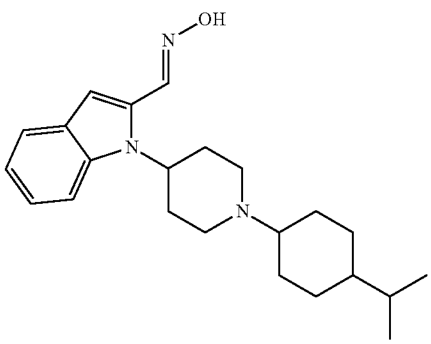 [SMILES: CC(C)C1CCC(N2CCC(n3c(/C=N/O)cc4ccccc43)CC2)CC1] | (E/Z)-1-(1-(cis-4-isopropylcyclohexyl)piperidin-4-yl)-1H-indole-2-carbaldehyde oxime | $^1$H NMR (CDCl$_3$) δ 10.7 (br, 1H), 8.70 (s, 1H), 7.59 (m, 2H), 7.18 (t, J = 5.7 Hz, 1H), 7.07 (t, J = 5.7 Hz, 1H), 6.83 (s, 1H), 4.89 (m, 1H), 3.24 (d, J = 8.4 Hz, 2H), 2.65 (dq, J = 9.6, 2.1 Hz, 2H), 2.45 (m, 1H), 2.31 (t, J = 8.7 Hz, 2H), 1.56-1.93 (m, 9H), 1.43 (m, 2H), 1.19 (m, 1H), 0.94 (d, J = 4.8 Hz, 6H) |
| 2 | 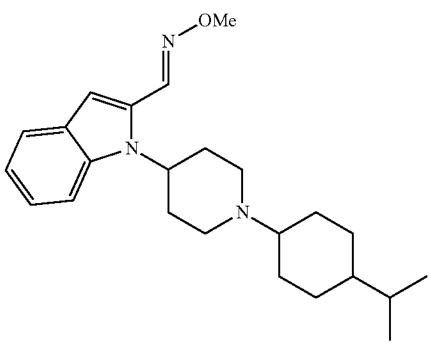 [SMILES: CO/N=C/c1cc2ccccc2n1C1CCN(C2CCC(C(C)C)CC2)CC1] | (E/Z)-1-(1-(cis-4-isopropylcyclohexyl)piperidin-4-yl)-1H-indole-2-carbaldehyde O-methyl oxime | $^1$H NMR (400 MHz, CDCl$_3$) δ 8.25 (s, 1H), 7.68 (d, J = 8.8 Hz, 1H), 7.60 (d, J = 8.0 Hz, 1H), 7.21 (t, J = 7.6 Hz, 1H), 7.09 (t, J = 7.6 Hz, 1H), 6.74 (s, 1H), 5.04 (m, 1H), 4.00 (s, 3H), 3.20 (d, J = 11.2 Hz, 2H), 2.57 (dq, J = 12.4, 4.0 Hz, 2H), 2.35 (m, 1H), 2.20 (t, J = 11.2 Hz, 2H), 1.91 (d, J = 10.8 Hz, 2H), 1.79-1.52 (m, 7H), 1.41 (m, 2H), 1.16 (m, 1H), 0.92 (d, J = 6.6 Hz, 6H) |
| 3 | 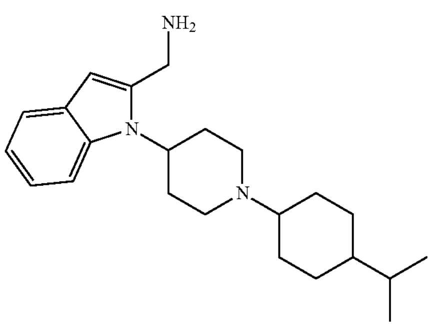 [SMILES: CC(C)C1CCC(N2CCC(n3c(CN)cc4ccccc43)CC2)CC1] | 1-(1-(cis-4-isopropylcyclohexyl)piperidin-4-yl)-1H-indole-2-yl)methanamine | $^1$H NMR (CDCl$_3$) δ 7.64 (d, J = 6.3 Hz, 1H), 7.56 (d, J = 5.4 Hz, 1H), 7.14 (dt, J = 5.4, 0.9 Hz, 1H), 7.06 (dt, J = 5.4, 0.9 Hz, 1H), 6.38 (s, 1H), 4.25 (m, 1H), 4.04 (s, 2H), 3.20 (d, J = 9.0 Hz, 2H), 2.61 (dq, J = 7.2, 1.8 Hz, 2H), 2.36 (m, 1H), 2.24, (t, J = 8.4 Hz, 2H), 1.87 (dd, J = 9.3, 1.5 Hz, 2H), 1.50-1.80 (m, 8H), 1.42 (m, 2H), 1.16 (m, 1H), 0.92 (d, J = 4.8 Hz, 6H) |
| 4 | 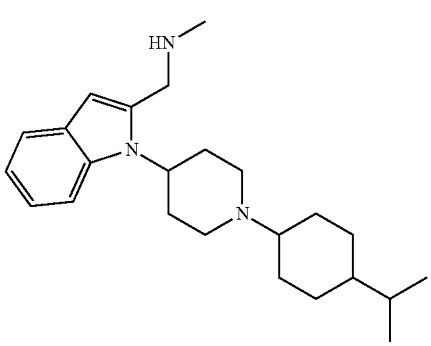 [SMILES: CNCc1cc2ccccc2n1C1CCN(C2CCC(C(C)C)CC2)CC1] | 1-(1-(1-(cis-4-isopropylcyclohexyl)piperidin-4-yl)-1H-indole-2-yl)-N-methylmethanamine | $^1$H NMR (CDCl$_3$) δ 7.66 (d, J = 8.1 Hz, 1H), 7.56 (d, J = 8.1 Hz, 1H), 7.13 (dt, J = 8.4, 1.4 Hz, 1H), 7.05 (m, 1H), 6.36 (s, 1H), 4.34 (m, 1H), 3.89 (s, 2H), 3.20 (d, J = 11.7 Hz, 2H), 2.62 (m, 2H), 2.49 (s, 3H), 2.36 (m, 1H), 2.22 (t, J = 11.7 Hz, 2H), 1.85 (d, J = 11.7 Hz, 2H), 1.80-1.35 (m, 10H), 1.16 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 5 | 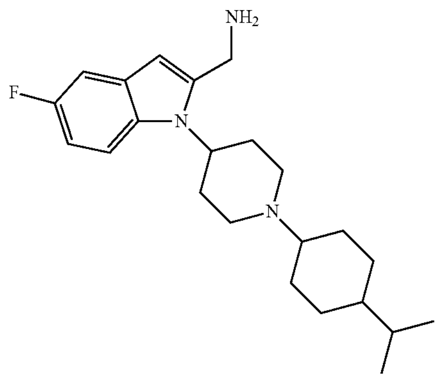 | (5-fluoro)-1-(1-(cis-4-isopropylcyclohexyl)piperidin-4-yl)-1H-indole-2-yl)methanamine | $^1$H NMR (400 MHz, CDCl$_3$) δ 7.54 (dd, J = 9.2, 4.0 Hz, 1H), 7.19 (dd, J = 9.2, 2.4 Hz, 1H), 6.88 (td, J = 9.2, 2.4 Hz, 1H), 6.33 (s, 1H), 4.23 (m, 1H), 4.02 (s, 2H), 3.19 (d, J = 11.6 Hz, 2H), 2.55 (dq, J = 12.4, 4.0 Hz, 2H), 2.35 (m, 1H), 2.22 (t, J = 11.6 Hz, 2H), 1.87 (dd, J = 12.4, 2.0 Hz, 2H), 1.77-1.63 (m, 7H), 1.54 (m, 2H), 1.41 (m, 2H), 1.16 (m, 1H), 0.92 (d, J = 6.6 Hz, 6H) |
| 6 | 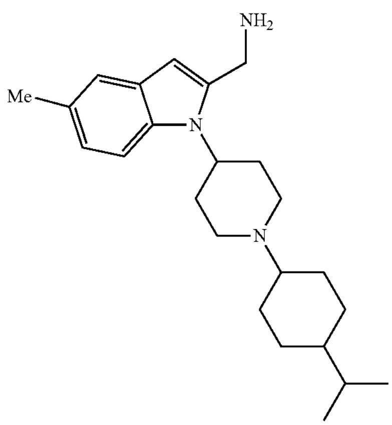 [SMILES: Cc1ccc2c(c1)cc(CN)n2C1CCN(C2CCC(C(C)C)CC2)CC1] | (1-(1-(cis-4-isopropylcyclohexyl)piperidin-4-yl)-5-methyl-1H-indole-2-yl)methanamine | $^1$H NMR (400 MHz, CDCl$_3$) δ 7.53 (d, J = 8.8 Hz, 1H), 7.35 (s, 1H), 6.96 (dd, J = 8.8, 1.6 Hz, 1H), 6.28 (s, 1H), 4.20 (m, 1H), 4.03 (br, 2H), 3.19 (d, J = 11.6 Hz, 2H), 2.58 (dq, J = 12.4, 4.0 Hz, 2H), 2.43 (s, 3H), 2.35 (m, 1H), 2.23 (t, J = 11.2 Hz, 2H), 1.86 (dd, J = 12.0, 2.0 Hz, 2H), 1.79-1.63 (m, 5H), 1.55 (m, 2H), 1.41 (m, 2H), 1.16 (m, 1H), 0.92 (d, J = 6.6 Hz, 6H) |
| 7 | 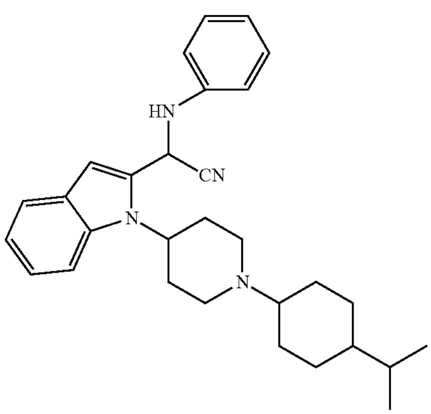 [SMILES: CC(C)C1CCC(N2CCC(n3c(C(C#N)Nc4ccccc4)cc4ccccc43)CC2)CC1] | 2-(1-(1-(cis-4-isopropylcyclohexyl)piperidin-4-yl)-1H-indole-2-yl)-2-(phenylamino)acetonitrile | $^1$H NMR (CDCl$_3$) δ 7.71 (d, J = 8.4 Hz, 1H), 7.65 (d, J = 7.8 Hz, 1H), 7.33 (t, J = 7.8 Hz, 2H), 7.24 (m, 1H), 7.14 (t, J = 7.2 Hz, 1H), 6.97 (t, J = 7.2 Hz, 1H), 6.89 (s, 1H), 6.85 (d, J = 7.8 Hz, 2H), 5.61 (d, J = 8.7 Hz, 2H), 4.07 (m, 1H), 3.94 (d, J = 8.7 Hz, 1H), 3.15 (m, 2H), 2.61 (m, 2H), 2.29 (m, 1H), 2.13 (m, 1H), 1.98 (m, 1H), 1.87 (d, J = 14.0 Hz, 2H), 1.76-1.30 (m, 8H), 1.13 (m, 1H), 0.90 (d, J = 6.6 Hz, 6H) |
| 8 | 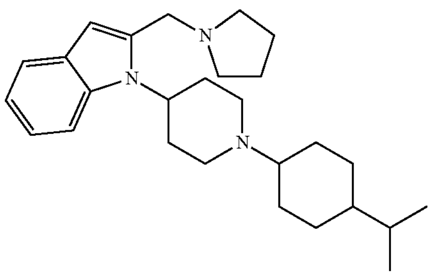 [SMILES: CC(C)C1CCC(N2CCC(n3c(CN4CCCC4)cc4ccccc43)CC2)CC1] | 1-(1-(cis-4-isopropylcyclohexyl)piperidin-4-yl)-2-(pyrrolidin-1-ylmethyl)-1-H-indole | $^1$H NMR (CDCl$_3$) δ 7.66 (d, J = 8.1 Hz, 1H), 7.54 (d, J = 6.9 Hz, 1H), 7.12 (dt, J = 8.1, 1.2 Hz, 1H), 7.04 (dt, J = 7.5, 1.2 Hz, 1H), 6.32 (s, 1H), 4.48 (m, 1H), 3.74 (s, 2H), 3.19 (d, J = 11.7 Hz, 2H), 2.57 (m, 6H), 2.35 (m, 1H), 2.18 (t, J = 12.4 Hz, 2H), 1.86-1.49 (m, 13H), 1.47-1.34 (m, 2H), 1.16 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 9 | 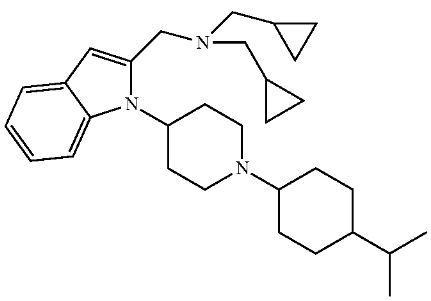 [SMILES: CC(C)C1CCC(N2CCC(n3c(CN(CC4CC4)CC4CC4)cc4ccccc43)CC2)CC1] | 1-cyclopropyl-N-(cyclopropylmethyl)-N-((1-(1-(cis-4-isopropylcyclohexyl)piperidin-4-yl)-1H-indole-2-yl)methyl)methanamine | $^1$H NMR (400 MHz, CDCl$_3$) δ 7.69 (d, J = 8.4 Hz, 1H), 7.55 (d, J = 8.0 Hz, 1H), 7.12 (t, J = 8.0 Hz, 1H), 7.04 (t, J = 8.0 Hz, 1H), 6.31 (s, 1H), 4.80 (m, 1H), 3.80 (s, 2H), 3.19 (d, J = 11.6 Hz, 2H), 2.62 (dq, J = 12.4, 4.0 Hz, 2H), 2.39 (d, J = 6.4 Hz, 4H), 2.34 (m, 1H), 2.21 (dt, J = 11.6, 1.6 Hz, 2H), 1.86 (d, J = 12.0 Hz, 2H), 1.78-1.53 (m, 7H), 1.41 (m, 2H), 1.16 (m, 1H), 0.92 (m, 8H), 0.50 (m, 4H), 0.10 (q, J = 5.6 Hz, 4H) |
| 10 | 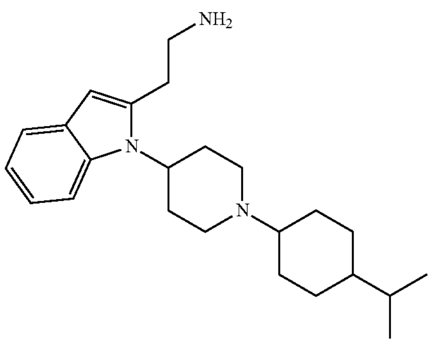 [SMILES: CC(C)C1CCC(N2CCC(n3c(CCN)cc4ccccc43)CC2)CC1] | 2-(1-(1-(cis-4-isopropylcyclohexyl)piperidin-4-yl)-1H-indole-2-yl)ethan-1-amine | $^1$H NMR (CDCl$_3$) δ NMR (300J = 8.1 Hz, 1H), 7.52 (d, J = 8.1 Hz, 1H), 7.09 (m, 2H), 6.28 (s, 1H), 5.4 (br, 2H), 4.10 (m, 1H), 3.29 (d, J = 11.7 Hz, 2H), 3.04 (m, 2H), 2.93 (m, 2H), 2.35 (m, 1H), 2.21 (t, J = 7.2 Hz, 2H), 1.50-1.88 (m, 11H), 1.4 (m, 2H), 1.15 (m, 1H), 0.92 (d, J = 6.6 Hz, 6H) |
| 11 | 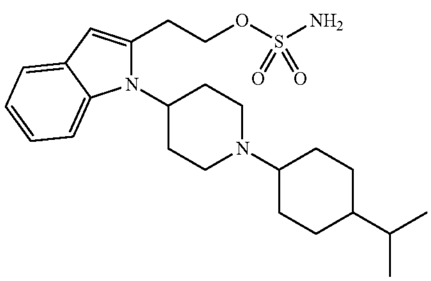 [SMILES: CC(C)C1CCC(N2CCC(n3c(CCOS(N)(=O)=O)cc4ccccc43)CC2)CC1] | 2-(1-(1-(cis-4-isopropylcyclohexyl)piperidin-4-yl)-1H-indole-2-yl)ethyl sulfamate | $^1$H NMR (CDCl$_3$) δ 7.64 (d, J = 6.3 Hz, 1H), 7.54 (d, J = 5.7 Hz, 1H), 7.15 (t, J = 5.7 Hz, 1H), 7.07 (t, J = 5.7 Hz, 1H), 6.34 (s, 1H), 4.50 (t, J = 5.1 Hz, 2H), 4.13 (m, 1H), 3.28 (t, J = 5.1 Hz, 2H), 3.22 (d, J = 8.4 Hz, 2H), 2.64 (m, 2H), 2.40 (m, 1H), 2.27 (t, J = 8.4 Hz, 2H), 1.84 (d, J = 8.4 Hz, 2H), 1.76 (m, 2H), 1.55-1.70 (m, 3H), 1.41 (m, 2H), 1.26 (m, 2H), 1.17 (m, 1H), 0.92 (d, J = 5.1 Hz, 6H) |
| 12 | 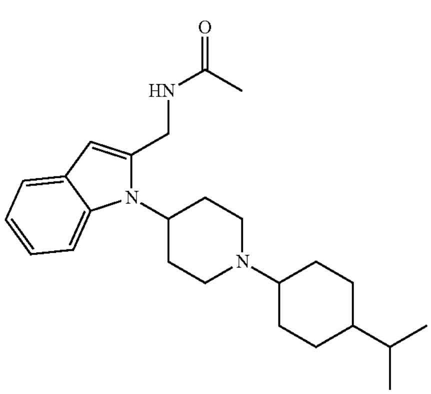 [SMILES: CC(=O)NCc1cc2ccccc2n1C1CCN(C2CCC(C(C)C)CC2)CC1] | N-((1-(1-(cis-4-isopropylcyclohexyl)piperidin-4-yl)-1H-indole-2-yl)methyl)acetamide | $^1$H NMR (CDCl$_3$) δ 7.54 (d, J = 7.5 Hz, 1H), 7.18 (t, J = 7.5 Hz, 1H), 7.07 (t, J = 7.5 Hz, 1H), 6.42 (s, 1H), 4.64 (d, J = 5.7 Hz, 2H), 3.17 (m, 2H), 2.61 (m, 2H), 2.09 (m, 4H), 1.78 (d, J = 12.3 Hz, 2H), 1.76-1.50 (m, 10H), 1.42 (m, 2H), 1.19 (m, 1H) 0.94 (d, J = 6.6 Hz, 6H) |

TABLE 1-continued

| No. | Structure* | IUPAC Name | NMR (300 or 400 MHz) or TLC |
|---|---|---|---|
| 13 | 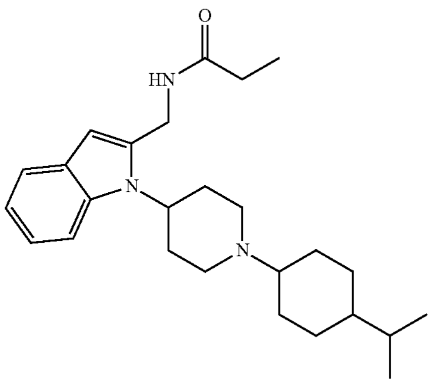 [SMILES: CCC(=O)NCc1cc2ccccc2n1C1CCN(C2CCC(C(C)C)CC2)CC1] | N-((1-(1-(cis-4-isopropylcyclohexyl)piperidin-4-yl)-1H-indole-2-yl)methyl)propionamide | $^1$H NMR (400 MHz, CDCl$_3$) δ 7.68 (d, J = 8.0 Hz, 1H), 7.56 (d, J = 8.0 Hz, 1H), 7.16 (t, J = 8.0 Hz, 1H), 7.08 (t, J = 8.0 Hz, 1H), 6.40 (s, 1H), 5.56 (br, 1H), 4.66 (d, J = 5.6 Hz, 2H), 4.17 (m, 1H), 3.17 (d, J = 11.6 Hz, 2H), 2.62 (dq, J = 12.4, 4.0 Hz, 2H), 2.36 (m, 1H), 2.23 (m, 4H), 1.79-1.51 (m, 9H), 1.41 (m, 2H), 1.19 (m, 4H), 0.92 (d, J = 6.6 Hz, 6H) |
| 14 | 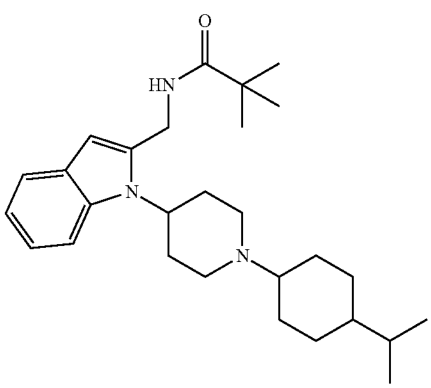 [SMILES: CC(C)C1CCC(N2CCC(n3c(CNC(=O)C(C)(C)C)cc4ccccc43)CC2)CC1] | N-((1-(1-(cis-4-isopropylcyclohexyl)piperidin-4-yl)-1H-indole-2-yl)methyl)pivalamide | $^1$H NMR (CDCl$_3$) δ 7.69 (d, J = 8.4 Hz, 1H), 7.57 (d, J = 7.5 Hz, 1H), 7.17 (m, 1H), 7.09 (m, 1H), 6.41 (s, 1H), 5.72 (br, 1H), 4.64 (d, J = 5.4 Hz, 2H), 4.13 (m, 1H), 3.16 (d, J = 11.6 Hz, 2H), 2.61 (dq, J = 12.4, 3.6 Hz, 2H), 2.34 (m, 1H), 2.19 (dt, J = 11.6, 1.8 Hz, 2H), 1.82-1.49 (m, 9H), 1.41 (m, 2H), 1.22 (s, 9H), 1.15 (m, 1H) 0.92 (d, J = 6.6 Hz, 6H) |
| 15 | 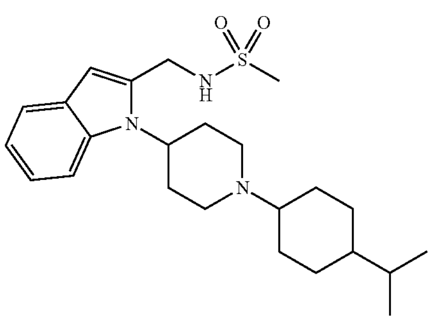 [SMILES: CC(C)C1CCC(N2CCC(n3c(CNS(C)(=O)=O)cc4ccccc43)CC2)CC1] | N-((1-(1-(cis-4-isopropylcyclohexyl)piperidin-4-yl)-1H-indole-2-yl)methyl)methanesulfonamide | $^1$H NMR (400 MHz, CDCl$_3$) δ 7.69 (d, J = 8.4 Hz, 1H), 7.58 (dt, J = 8.0 Hz, 1H), 7.19 (t, J = 8.4 Hz, 1H), 7.09 (t, J = 8.0 Hz, 1H), 6.47 (s, 1H), 4.51 (m, 3H), 4.26 (m, 1H), 3.20 (d, J = 11.6 Hz, 2H), 2.96 (s, 3H), 2.61 (dq, J = 12.4, 4.0 Hz, 2H), 2.36 (m, 1H), 2.25 (t, J = 12.0 Hz, 2H), 1.87 (dd, J = 8.0, 2.0 Hz, 2H), 1.77-1.53 (m, 7H), 1.41 (m, 2H), 1.19-1.12 (m, 1H), 0.92 (d, J = 6.6 Hz, 6H) |
| 16 | 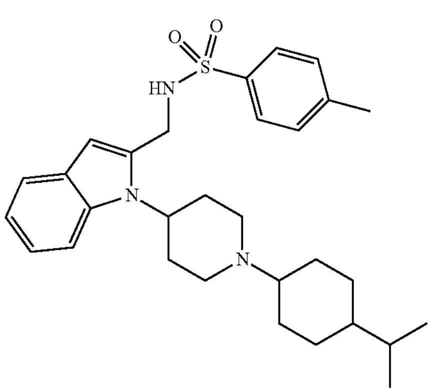 [SMILES: Cc1ccc(S(=O)(=O)NCc2cc3ccccc3n2C2CCN(C3CCC(C(C)C)CC3)CC2)cc1] | N-((1-(1-(cis-4-isopropylcyclohexyl)piperidin-4-yl)-1H-indole-2-yl)methyl)-4-methylbenzenesulfonamide | $^1$H NMR (400 MHz, CDCl$_3$) δ 7.82 (d, J = 8.4 Hz, 2H), 7.68 (d, J = 8.0 Hz, 1H), 7.52 (d, J = 7.4 Hz, 1H), 7.37 (d, J = 8.4 Hz, 1H), 7.17 (t, J = 7.4 Hz, 1H), 7.06 (t, J = 8.0 Hz, 1H), 6.28 (s, 1H), 4.41 (t, J = 6.4 Hz, 1H), 4.25 (m, 3H), 3.15 (d, J = 11.6 Hz, 2H), 2.58 (dq, J = 12.4, 4.0 Hz, 2H), 2.47 (s, 3H), 2.35 (m, 1H), 2.20 (t, J = 11.6 Hz, 2H), 1.84 (dd, J = 12.0, 2.0 Hz, 2H), 1.79-1.62 (m, 5H), 1.55 (m, 2H), 1.41 (m, 2H), 1.16 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 17 | 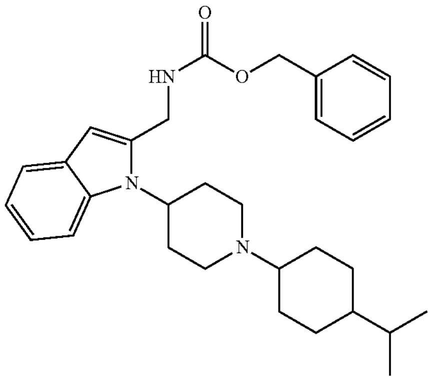 [SMILES: CC(C)C1CCC(N2CCC(n3c(CNC(=O)OCc4ccccc4)cc4ccccc43)CC2)CC1] | benzyl ((1-(1-(cis-4-isopropylcyclohexyl)piperidin-4-yl)-1H-indole-2-yl)methyl)carbamate | ¹H NMR (CDCl₃) δ 7.65 (d, J = 8.1 Hz, 1H), 7.55 (d, J = 7.6 Hz, 1H), 7.40-7.31 (m, 5H), 7.15 (t, J = 7.6 Hz, 1H), 7.06 (t, J = 7.6 Hz, 1H), 6.39 (s, 1H), 5.17 (s, 2H), 4.90 (br, 1H), 4.59 (d, J = 5.7 Hz, 2H), 4.15 (m, 1H), 3.10 (d, J = 10.0 Hz, 2H), 2.56 (dq, J = 12.1, 3.7 Hz, 2H), 2.30 (m, 1H), 2.11 (t, J = 11.9 Hz, 2H), 1.82-1.33 (m, 12H), 1.15 (m, 1H), 0.93 (d, J = 6.6 Hz, 6H) |
| 18 | 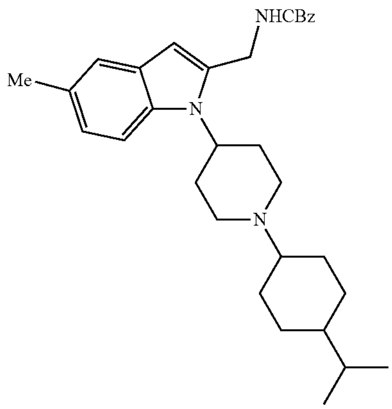 | benzyl ((1-(1-(cis-4-isopropylcyclohexyl)piperidin-4-yl)-5-methyl-1H-indole-2-yl)methyl)carbamate | ¹H NMR (400 MHz, CDCl₃) δ 7.54 (d, J = 8.4 Hz, 1H), 7.35 (m, 5H), 6.98 (dd, J = 8.4, 1.2 Hz, 1H), 6.30 (s, 1H), 5.16 (s, 2H), 4.89 (m, 1H), 4.57 (d, J = 5.6 Hz, 2H), 4.12 (m, 1H), 3.08 (d, J = 10.8 Hz, 2H), 2.54 (dq, J = 12.4, 4.0 Hz, 2H), 2.42 (s, 3H), 2.31 (m, 1H), 2.11 (t, J = 11.2 Hz, 2H), 1.78-1.49 (m, 9H), 1.40 (m, 2H), 1.17 (m, 1H), 0.92 (d, J = 6.6 Hz, 6H) |
| 19 | 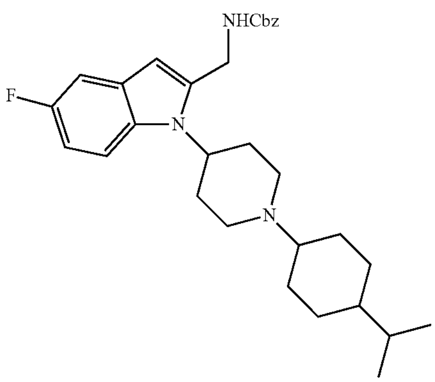 [SMILES: CC(C)C1CCC(N2CCC(n3c(CNC(=O)OCc4ccccc4)cc4cc(F)ccc43)CC2)CC1] | benzyl ((5-fluoro-1-(1-(cis-4-isopropylcyclohexyl)piperidin-4-yl)-1H-indole-2-yl)methyl)carbamate | ¹H NMR (400 MHz, CDCl₃) δ 7.55 (dd, J = 9.2, 4.0 Hz, 1H), 7.36 (m, 5H), 7.18 (dd, J = 9.2, 2.8 Hz, 1H), 6.90 (dt, J = 9.2, 2.8 Hz, 1H), 6.34 (s, 1H), 5.17 (s, 2H), 4.92 (m, 1H), 4.58 (d, J = 5.6 Hz, 2H), 4.14 (m, 1H), 3.09 (d, J = 11.2 Hz, 2H), 2.50 (dq, J = 12.4, 4.0 Hz, 2H), 2.30 (m, 1H), 2.10 (t, J = 11.2 Hz, 2H), 1.79-1.60 (m, 7H), 1.52 (m, 2H), 1.41 (m, 2H), 1.16 (m, 1H), 0.92 (d, J = 6.6 Hz, 6H) |
| 20 | 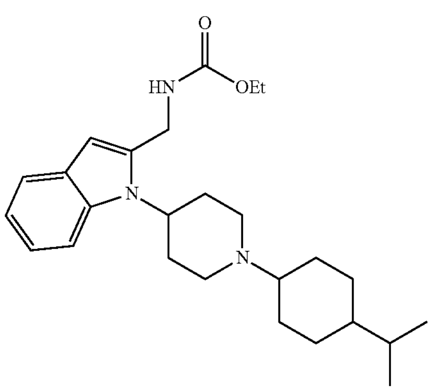 [SMILES: CCOC(=O)NCc1cc2ccccc2n1C1CCN(C2CCC(C(C)C)CC2)CC1] | ethyl ((1-(1-(cis-4-isopropylcyclohexyl)piperidin-4-yl)-1H-indole-2-yl)methyl)carbamate | ¹H NMR (CDCl₃) δ 7.66 (d, J = 8.1 Hz, 1H), 7.56 (d, J = 7.6 Hz, 1H), 7.16 (t, J = 7.6 Hz, 1H), 7.07 (t, J = 7.6 Hz, 1H), 6.40 (s, 1H), 4.79 (br, 1H), 4.57 (d, J = 5.6 Hz, 2H), 4.18 (m, 3H), 3.18 (d, J = 12.0 Hz, 2H), 2.60 (dq, J = 12.8, 4.1 Hz, 2H), 2.34 (m, 2H), 2.21 (t, J = 12.0 Hz, 2H), 1.88-1.34 (m, 10H), 1.27 (t, J = 7.1 Hz, 3H), 1.18 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 21 | 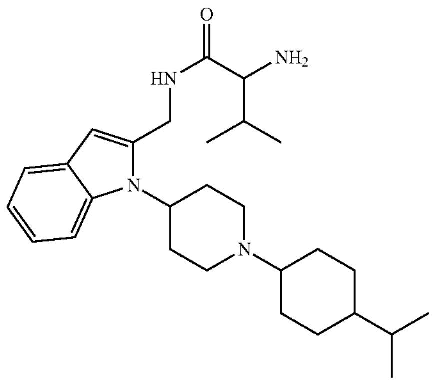 [SMILES: CC(C)C1CCC(N2CCC(n3c(CNC(=O)C(N)C(C)C)cc4ccccc43)CC2)CC1] | 2-amino-N-((1-(1-(cis-4-isopropylcyclohexyl)piperidin-4-yl)-1H-indol-2-yl)methyl)-3-methylbutanamide | $^1$H NMR (CDCl$_3$) δ 7.68 (d, J = 7.6 Hz, 1H), 7.57 (d, J = 7.6 Hz, 2H), 7.16 (t, J = 7.6 Hz, 1H), 7.08 (t, J = 7.6 Hz, 1H), 6.42 (s, 1H), 4.71 (dd, J = 15.1, 6.1 Hz, 1H), 4.57 (dd, J = 15.1, 6.1 Hz, 1H), 3.27 (d, J = 3.7 Hz, 2H), 3.17 (d, J = 11.0 Hz, 2H), 2.60 (m, 2H), 2.40 (m, 2H), 2.19 (m, 2H), 1.88-1.38 (m, 14H), 1.16 (m, 1H), 1.02 (d, J = 7.0 Hz, 3H), 0.92 (d, J = 6.6 Hz, 6H), 0.85 (d, J = 7.0 Hz, 3H) |
| 22 | 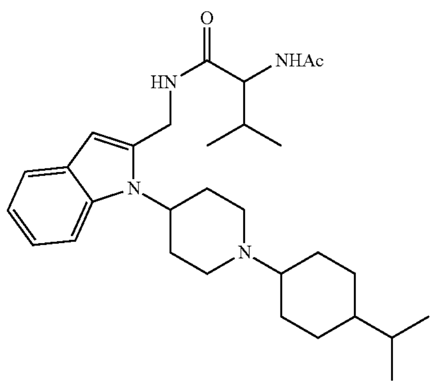 [SMILES: CC(=O)NC(C(=O)NCc1cc2ccccc2n1C1CCN(C2CCC(C(C)C)CC2)CC1)C(C)C] | 2-acetamido-N-((1-(1-(cis-4-isopropylcyclohexyl)piperidin-4-yl)-1H-indol-2-yl)methyl)-3-methylbutanamide | $^1$H NMR (CDCl$_3$) δ 7.65 (d, J = 8.1 Hz, 1H), 7.55 (d, J = 7.8 Hz, 1H), 7.16 (t, J = 7.8 Hz, 1H), 7.07 (t, J = 7.4 Hz, 1H), 6.39 (m, 1H), 6.06 (d, J = 9.0 Hz, 1H), 4.68 (dd, J = 15.2, 5.5 Hz, 1H), 4.56 (dd, J = 15.2, 5.4 Hz, 1H), 4.26 (m, 1H), 4.08 (m, 1H), 3.15 (m, 2H), 2.56 (m, 2H), 2.32 (m, 1H), 2.17 (m, 2H), 1.94 (s, 3H), 1.86-1.32 (m, 12H), 1.15 (m, 1H), 1.01-0.88 (m, 12H) |
| 23 | 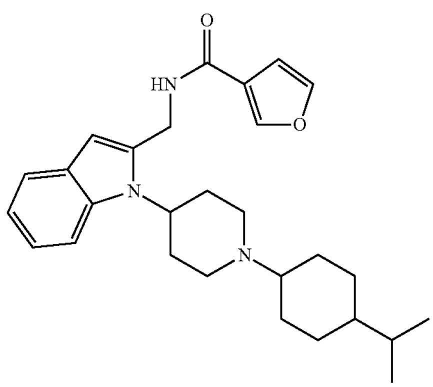 [SMILES: CC(C)C1CCC(N2CCC(n3c(CNC(=O)c4ccoc4)cc4ccccc43)CC2)CC1] | N-((1-(1-(cis-4-isopropylcyclohexyl)piperidin-4-yl)-1H-indol-2-yl)methyl)furan-3-carboxamide | $^1$H NMR (CDCl$_3$) δ 7.94 (s, 1H), 7.69 (d, J = 8.4 Hz, 1H), 7.58 (d, J = 7.8 Hz, 1H), 7.44 (t, J = 1.8 Hz, 1H), 7.18 (dt, J = 7.2, 1.4 Hz, 1H), 7.09 (t, J = 7.2 Hz, 1H), 6.56 (d, J = 1.8 Hz, 1H), 6.46 (s, 1H), 5.84 (br, 1H), 4.81 (d, J = 5.7 Hz, 2H), 4.22 (m, 1H), 3.13 (d, J = 11.7 Hz, 1H), 2.58 (dt, J = 11.2, 3.3 Hz, 2H), 2.31 (m, 1H), 2.18 (t, J = 11.4 Hz, 12H), 1.83-1.31 (m, 6H), 1.14 (m, 1H), 0.91 (d, J = 6.6 Hz, 6H) |
| 24 | 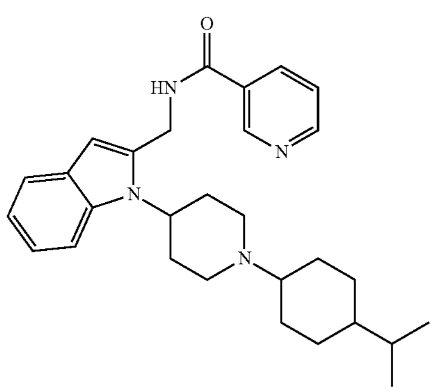 [SMILES: CC(C)C1CCC(N2CCC(n3c(CNC(=O)c4cccnc4)cc4ccccc43)CC2)CC1] | N-((1-(1-(cis-4-isopropylcyclohexyl)piperidin-4-yl)-1H-indol-2-yl)methyl)nicotinamide | $^1$H NMR (CDCl$_3$) δ 8.97 (d, J = 1.5 Hz, 1H), 8.75 (dd, J = 4.8, 1.5 Hz, 1H), 8.10 (dt, J = 7.8, 2.1 Hz, 1H), 7.68 (d, J = 8.4 Hz, 1H), 7.58 (d, J = 7.5 Hz, 1H), 7.40 (m, 1H), 7.18 (dt, J = 7.2, 1.2 Hz, 1H), 7.09 (m, 1H), 6.49 (s, 1H), 6.27 (br, 1H), 4.89 (d, J = 5.7 Hz, 2H), 4.24 (m, 1H), 3.14 (d, J = 11.1 Hz, 2H), 2.61 (m, 2H), 2.31 (m, 1H), 2.18 (t, J = 12.0 Hz, 2H), 1.83-1.35 (m, 11H), 1.13 (m, 1H), 0.91 (d, J = 6.6 Hz, 6H) |

TABLE 1-continued

| No. | Structure* | IUPAC Name | NMR (300 or 400 MHz) or TLC |
|---|---|---|---|
| 25 | 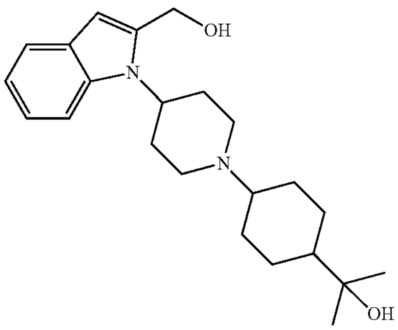 [SMILES: CC(C)(O)C1CCC(N2CCC(n3c(CO)cc4ccccc43)CC2)CC1] | 2-(cis-4-(4-(2-(hydroxymethyl)-1H-indole-1-yl)piperidin-1-yl)cyclohexyl)propanol-2-ol | $^1$H NMR (CDCl$_2$) δ 7.61 (m, 1H), 7.19 (m, 1H), 7.08 (t, J = 7.8 Hz, 1H), 6.45 (s, 1H), 4.81 (d, J = 3.3 Hz, 2H), 4.40 (m, 1H), 3.31 (d, J = 11.1 Hz, 2H), 2.62 (m, 2H), 2.30 (br, 1H), 2.19-1.85 (m, 7H), 1.58 (m, 6H), 1.43 (m, 2H), 1.25 (s, 6H) |
| 26 | 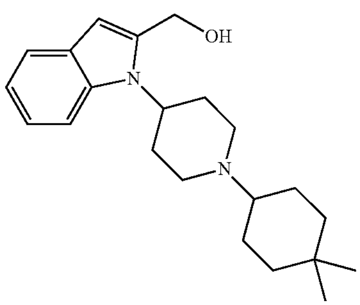 [SMILES: CC1(C)CCC(N2CCC(n3c(CO)cc4ccccc43)CC2)CC1] | (1-(1-(4,4-dimethylcyclohexyl)piperidin-4-yl)-1H-indole-2-yl)methanol | $^1$H NMR (400 MHz, CDCl$_3$) δ 7.72 (d, J = 8.4 Hz, 1H), 7.58 (d, J = 7.8 Hz, 1H), 7.17 (m, 1H), 7.08 (t, J = 7.4 Hz, 1H), 6.43 (s, 1H), 4.81 (s, 2H), 4.37 (m, 1H), 3.11 (d, J = 11.6 Hz, 2H), 2.65 (dq, J = 12.4, 4.0 Hz, 2H), 2.44 (dt, J = 11.6, 1.6 Hz, 2H), 2.32 (tt, J = 12.0, 4.0 Hz, 1H), 1.99 (br, 1H), 1.91 (dd, J = 12.0, 2.0 Hz, 2H), 1.69 (m, 2H), 1.48 (m, 4H), 1.23 (dt, J = 13.6, 3.6 Hz, 2H), 0.93 (s, 6H) |
| 27 | 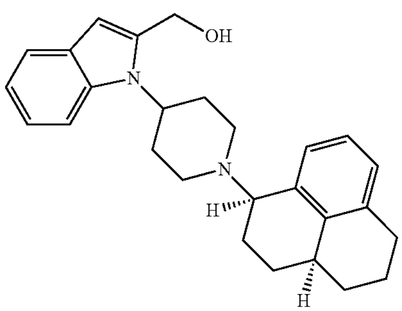 [SMILES: OCc1cc2ccccc2n1C1CCN([C@@H]2CC[C@@H]3CCCc4cccc2c43)CC1] | (1-(1-(trans-2,3,3a,4,5,6-hexahydro-1H-phenalen-1-yl)piperidin-4-yl)-1H-indol-2-yl)methanol | $^1$H NMR (CDCl$_3$) δ NMR (300J = 8.1 Hz, 1H), 7.60 (t, J = 8.1 Hz, 2H), 7.20 (q, J = 7.2 Hz, 2H), 7.08 (t, J = 8.1 Hz, 1H), 7.00 (d, J = 7.2 Hz, 1H), 6.43 (s, 1H), 4.81 (s, 2H), 4.38 (m, 1H), 3.86 (m, 1H), 3.03 (m, 1H), 2.75-2.88 (m, 5H), 2.48 (m, 2H), 2.34 (m, 1H), 1.74-2.10 (m, 9H), 1.35 (m, 2H) |
| 28 | 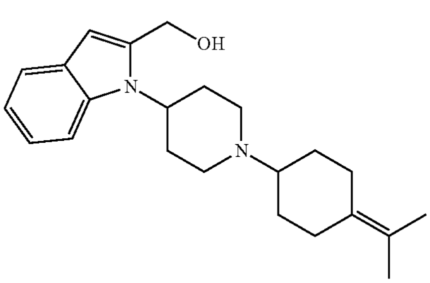 [SMILES: CC(C)=C1CCC(N2CCC(n3c(CO)cc4ccccc43)CC2)CC1] | (1-1-(4-propan-2-ylidene)cyclohexyl)piperidin-4-yl)-1H-indol-2-yl)methanol | $^1$H NMR (CDCl$_3$) δ 7.72 (d, J = 8.4 Hz, 1H), 7.58 (d, J = 7.8 Hz, 1H), 7.17 (t, J = 7.5 Hz, 1H), 7.07 (t, J = 7.5 Hz, 1H), 6.44 (s, 1H), 4.81 (s, 2H), 4.35 (m, 1H), 3.09 (d, J = 11.6 Hz, 2H), 2.65 (m, 5H), 2.81-2.54 (m, 1H), 2.46 (t, J = 11.6 Hz, 2H), 1.92 (t, J = 12.0 Hz, 4H), 1.69 (m, 8H), 1.32 (dq, J = 12.0, 4.0 Hz, 2H) |

TABLE 1-continued

| No. | Structure* | IUPAC Name | NMR (300 or 400 MHz) or TLC |
|---|---|---|---|
| 29 | 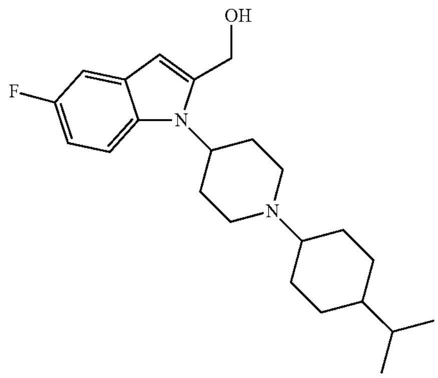 [SMILES: CC(C)C1CCC(N2CCC(n3c(CO)cc4cc(F)ccc43)CC2)CC1] | (5-fluoro-1-(1-(cis-4-isopropylcyclohexyl)piperidin-4-yl)-1H-indol-2-yl)methanol | $^1$H NMR (CDCl$_3$) δ 7.41 (dd, J = 6.0, 2.1 Hz, 1H), 6.95 (dt, J = 6.0, 2.1 Hz, 1H), 6.51 (dd, J = 6.9, 3.6 Hz, 1H), 3.91 (d, J = 6.0 Hz, 1H), 3.28 (m, 1H), 2.92 (m, 2H), 2.24 (m, 3H), 2.04 (m, 2H), 1.47-1.73 (m, 8H), 1.38 (m, 2H), 1.13 (m, 1H), 0.88 (d, J = 5.1 Hz, 6H) |
| 30 | 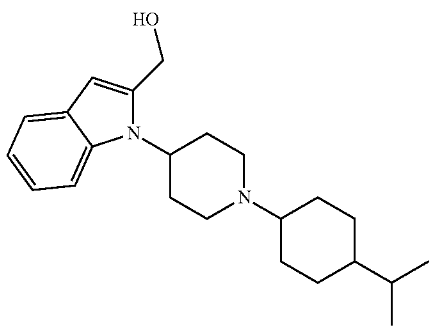 [SMILES: CC(C)C1CCC(N2CCC(n3c(CO)cc4ccccc43)CC2)CC1] | (1-(1-(cis-4-isopropylcyclohexyl)piperidin-4-yl)-1H-indol-2-yl)methanol | $^1$H NMR (400 MHz, CDCl$_3$) δ 7.69 (d, J = 8.0 Hz, 1H), 7.58 (d, J = 8.0 Hz, 1H), 7.18 (t, J = 7.6 Hz, 1H), 7.08 (t, J = 7.6 Hz, 1H), 6.44 (s, 1H), 4.81 (d, J = 4.8 Hz, 2H), 4.37 (m, 1H), 3.19 (d, J = 11.6 Hz, 2H), 2.61 (dq, J = 12.4, 3.2 Hz, 2H), 2.37 (m, 1H), 2.26 (t, J = 11.6 Hz, 2H), 1.89 (d, J = 12.0 Hz, 2H), 1.70 (m, 5H), 1.55 (m, 2H), 1.40 (m, 2H), 1.16 (m, 1H), 0.92 (d, J = 6.8 Hz, 6H) |
| 31 | 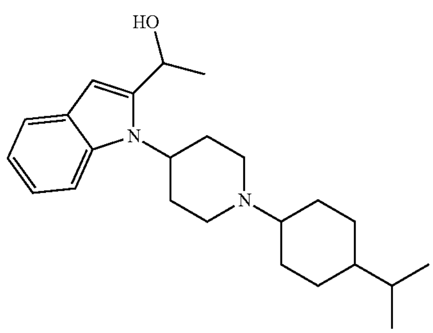 [SMILES: CC(O)c1cc2ccccc2n1C1CCN(C2CCC(C(C)C)CC2)CC1] | 1-(1-(1-(cis-4-isopropylcyclohexyl)piperidin-4-yl)-1H-indol-2-yl)ethan-1-ol | $^1$H NMR (CDCl$_3$) δ 7.70 (d, J = 8.4 Hz, 1H), 7.58 (d, J = 7.8 Hz, 1H), 7.16 (t, J = 7.8 Hz, 1H), 7.06 (t, J = 7.8 Hz, 1H), 6.46 (s, 1H), 5.07 (br, 1H), 4.46 (m, 1H), 3.19 (d, J = 11.6 Hz, 2H), 2.65 (m, 2H), 2.35 (m, 1H), 2.25 (m, 2H), 1.95-1.50 (m, 13H), 1.41 (m, 2H), 1.16 (m, 1H), 0.92 (d, J = 6.6 Hz, 6H) |
| 32 | 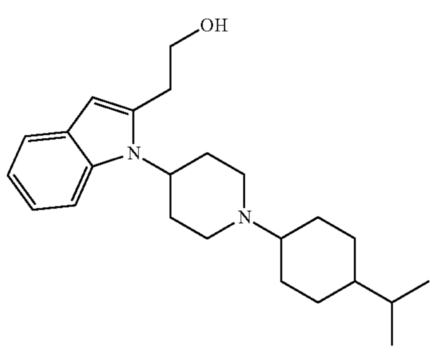 [SMILES: CC(C)C1CCC(N2CCC(n3c(CCO)cc4ccccc43)CC2)CC1] | 2-(1-(1-(cis-4-isopropylcyclohexyl)piperidin-4-yl)-1H-indol-2-yl)ethan-1-ol | $^1$H NMR (CDCl$_3$) δ 7.65 (d, J = 9.0 Hz, 1H), 7.55 (d, J = 9.0 Hz, 1H), 7.13 (t, J = 5.4 Hz, 1H), 7.07 (t, J = 5.4 Hz, 1H), 6.33 (s, 1H), 4.14 (m, 1H), 3.94 (t, J = 4.8 Hz, 2H), 3.20 (d, J = 8.7 Hz, 2H), 3.09 (t, J = 4.8 Hz, 2H), 2.64 (q, J = 7.5 Hz, 2H), 2.36 (m, 1H), 2.22 (t, J = 8.7 Hz, 2H), 1.51-1.87 (m, 9H), 1.42 (m, 2H), 1.27 (m, 1H), 0.92 (d, J = 4.8 Hz, 6H) |

TABLE 1-continued

| No. | Structure* | IUPAC Name | NMR (300 or 400 MHz) or TLC |
|---|---|---|---|
| 33 | 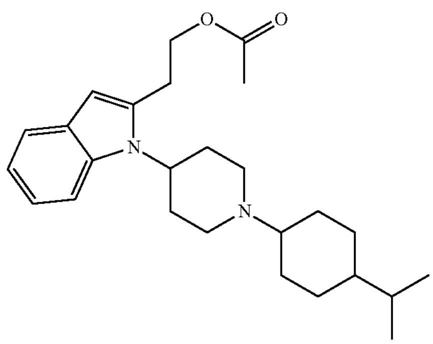 [SMILES: CC(=O)OCCc1cc2ccccc2n1C1CCN(C2CCC(C(C)C)CC2)CC1] | 2-(1-(1-(cis-4-isopropylcyclohexyl)piperidin-4-yl)-1H-indol-2-yl)ethyl acetate | ¹H NMR (CDCl₃) δ 7.64 (d, J = 8.1 Hz, 1H), 7.53 (d, J = 8.1 Hz, 1H), 7.02-7.15 (m, 2H), 6.29 (s, 1H), 4.38 (t, J = 7.2 Hz, 2H), 4.16 (m, 1H), 3.21 (d, J = 11.7 Hz, 2H), 3.12 (t, J = 7.2 Hz, 2H), 2.65 (dq, J = 12.6, 3.3 Hz, 2H), 2.38 (m, 1H), 2.26 (dt, J = 11.7, 1.8 Hz, 2H), 2.08 (m, 5H), 1.55-1.88 (m, 7H), 1.40 (m, 2H), 1.17 (m, 1H), 0.91 (d, J = 6.3 Hz, 6H) |
| 34 | 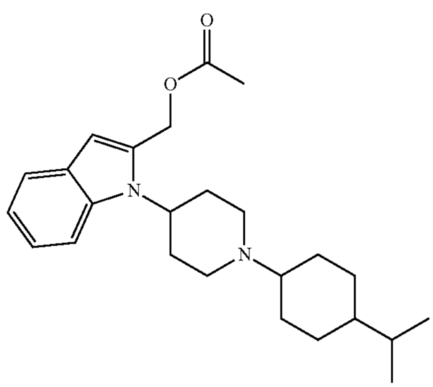 [SMILES: CC(=O)OCc1cc2ccccc2n1C1CCN(C2CCC(C(C)C)CC2)CC1] | 1-(1-(cis-4-isopropylcyclohexyl)piperidin-4-yl)-1H-indol-2-yl)methyl acetate | ¹H NMR (CDCl₃) δ 7.67 (d, J = 8.1 Hz, 1H), 7.59 (d, J = 8.1 Hz, 1H), 7.19 (dt, J = 7.2, 0.9 Hz, 1H), 7.08 (dt, J = 7.2, 0.9 Hz, 1H), 6.54 (s, 1H), 4.13 (m, 1H), 3.20 (d, J = 11.7 Hz, 2H), 2.62 (dq, J = 12.6, 3.3 Hz, 2H), 2.38 (m, 1H), 2.20 (dt, J = 11.7, 1.5 Hz, 2H), 2.08 (s, 3H), 1.50-1.90 (m, 12H), 1.40 (m, 2H), 1.16 (m, 1H), 0.91 (d, J = 6.6 Hz, 6H) |
| 35 | 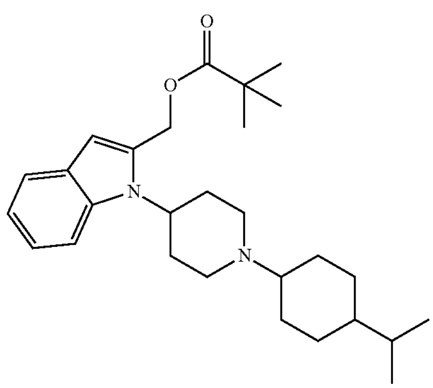 [SMILES: CC(C)C1CCC(N2CCC(n3c(COC(=O)C(C)(C)C)cc4ccccc43)CC2)CC1] | 1-(1-(cis-4-isopropylcyclohexyl)piperidin-4-yl)-1H-indol-2-yl)methyl pivalate | ¹H NMR (400 MHz, CDCl₃) δ 7.73 (d, J = 8.4 Hz, 1H), 7.60 (d, J = 8.0 Hz, 1H), 7.20 (t, J = 7.2 Hz, 1H), 7.09 (t, J = 7.2 Hz, 1H), 6.56 (s, 1H), 5.25 (s, 2H), 4.17 (m, 1H), 3.31 (d, J = 12.0 Hz, 2H), 2.78 (q, J = 12.0 Hz, 2H), 2.55 (q, J = 6.4 Hz, 1H), 2.32 (t, J = 11.6 Hz, 2H), 1.90 (d, J = 12.4 Hz, 2H), 1.80 (m, 2H), 1.64 (m, 5H), 1.43 (m, 2H), 1.22 (s, 9H), 1.20 (m, 1H), 0.92 (d, J = 6.4 Hz, 6H) |
| 36 | 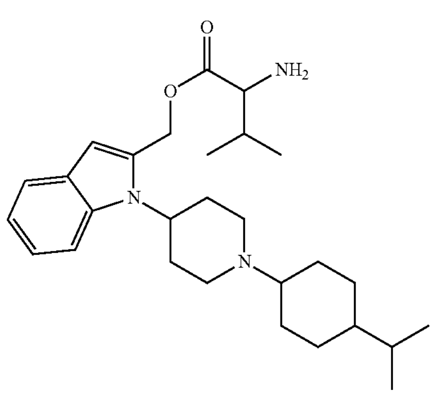 [SMILES: CC(C)C1CCC(N2CCC(n3c(COC(=O)C(N)C(C)C)cc4ccccc43)CC2)CC1] | 1-(1-(cis-4-isorpopylcyclohexyl)piperidin-4-yl)-1H-indol-2-yl)methyl valinate | ¹H NMR (CDCl₃) δ 7.67 (d, J = 8.7 Hz, 1H), 7.60 (d, J = 8.1 Hz, 1H), 7.20 (t, J = 8.1 Hz, 1H), 7.09 (t, J = 7.8 Hz, 1H), 6.57 (s, 1H), 5.32 (d, J = 3.5 Hz, 2H), 4.15 (m, 1H), 3.31 (d, J = 5.0 Hz, 1H), 3.21 (d, J = 9.8 Hz, 2H), 2.62 (m, 1H), 2.33 (m, 1H), 2.18 (t, J = 11.4 Hz, 2H), 2.02 (m, 1H), 1.87 (m, 1H), 1.80-1.35 (m, 13H), 1.17 (m, 1H), 1.00-0.87 (m, 12H) |

TABLE 1-continued

| No. | Structure* | IUPAC Name | NMR (300 or 400 MHz) or TLC |
|---|---|---|---|
| 37 | 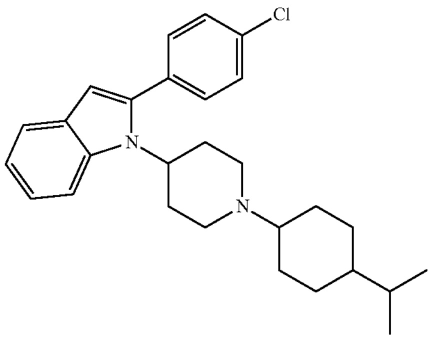 [SMILES: CC(C)C1CCC(N2CCC(n3c(-c4ccc(Cl)cc4)cc4ccccc43)CC2)CC1] | 2-(4-chlorophenyl)-1-(1-(cis-4-isopropylcyclohexyl)piperidin-4-yl)-1H-indole | $^1$H NMR (400 MHz, CDCl$_3$) δ 7.77 (d, J = 8.4 Hz, 1H), 7.63 (d, J = 8.0 Hz, 1H), 7.46 (d, J = 8.4 Hz, 1H), 7.38 (d, J = 8.4 Hz, 1H), 7.21 (t, J = 8.0 Hz, 1H), 7.13 (t, J = 8.0 Hz, 1H), 6.48 (s, 1H), 4.13 (m, 1H), 3.13 (d, J = 11.6 Hz, 2H), 2.69 (dq, J = 12.4, 4.0 Hz, 2H), 2.30 (sept, J = 3.4 Hz, 1H), 2.05 (dt, J = 11.6, 1.6 Hz, 2H), 1.82 (dd, J = 12.0, 1.6 Hz, 2H), 1.75-1.60 (m, 5H), 1.50 (m, 2H), 1.39 (m, 2H), 1.21-1.11 (m, 1H), 0.92 (d, J = 6.6 Hz, 6H) |
| 38 | 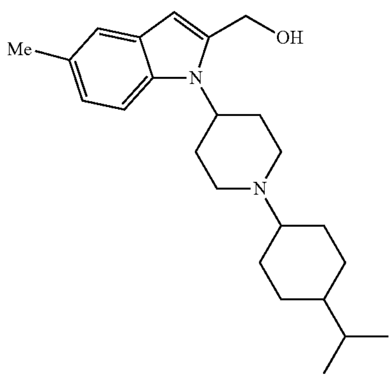 [SMILES: Cc1ccc2c(c1)cc(CO)n2C1CCN(C2CCC(C(C)C)CC2)CC1] | 1-(1-(cis-4-isopropylcyclohexyl)piperidin-4-yl)-5-methyl-1H-indol-2-yl)methanol | $^1$H NMR (400 MHz, CDCl$_3$) δ 7.57 (d, J = 8.8 Hz, 1H), 7.37 (s, 1H), 7.00 (dd, J = 8.0, 1.6 Hz, 1H), 6.35 (s, 1H), 4.79 (s, 2H), 4.33 (m, 1H), 3.18 (d, J = 11.6 Hz, 2H), 2.60 (dq, J = 12.4, 4.0 Hz, 2H), 2.43 (s, 3H), 2.35 (m, 1H), 2.26 (t, J = 12.4 Hz, 2H), 1.88 (dd, J = 12.4, 2.0 Hz, 2H), 1.78-1.53 (m, 8H), 1.41 (m, 2H), 1.17 (m, 1H), 0.92 (d, J = 6.6 Hz, 6H) |
| 39 | 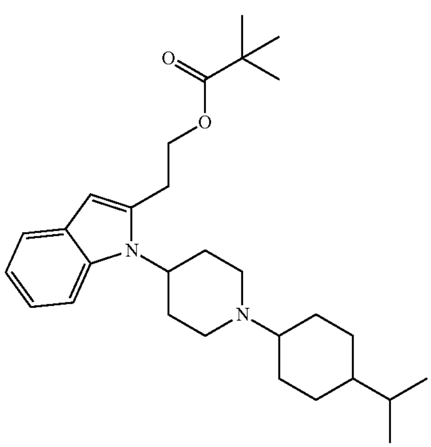 [SMILES: CC(C)C1CCC(N2CCC(n3c(CCOC(=O)C(C)(C)C)cc4ccccc43)CC2)CC1] | 2-(1-(1-(cis-4-isopropylcyclohexyl)piperidin-4-yl)-1H-indol-2-yl)ethyl pivalate | $^1$H NMR (CDCl$_3$) δ 7.64 (d, J = 8.1 Hz, 1H), 7.54 (d, J = 8.1 Hz, 1H), 7.08 (m, 2H), 6.30 (s, 1H), 4.37 (t, J = 7.2 Hz, 2H), 4.14 (m, 1H), 3.21 (d, J = 11.6 Hz, 2H), 3.11 (t, J = 7.2 Hz, 2H), 2.63 (dq, J = 12.0, 3.6 Hz, 2H), 2.36 (m, 1H), 2.25 (t, J = 11.6 Hz, 2H), 1.88-1.52 (m, 9H), 1.42 (m, 2H), 1.22 (s, 9H), 1.16 (m, 1H), 0.92 (d, J = 6.6 Hz, 6H) |
| 40 | 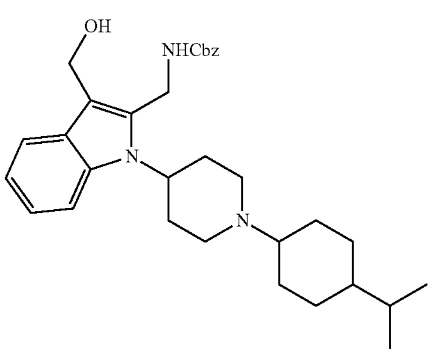 [SMILES: CC(C)C1CCC(N2CCC(n3c(CNC(=O)OCc4ccccc4)c(CO)c4ccccc43)CC2)CC1] | benzyl ((3-(hydroxymethyl)-1-(1-(cis-4-isopropylcyclohexyl)piperidin-4-yl)-1H-indol-2-yl)methyl)carbamate | R$_f$ = 0.25 (30:70:3 drops EtOAc:Hexanes:NH$_4$OH (aq.), UV, I$_2$) |

TABLE 1-continued

| No. | Structure* | IUPAC Name | NMR (300 or 400 MHz) or TLC |
|---|---|---|---|
| 41 | 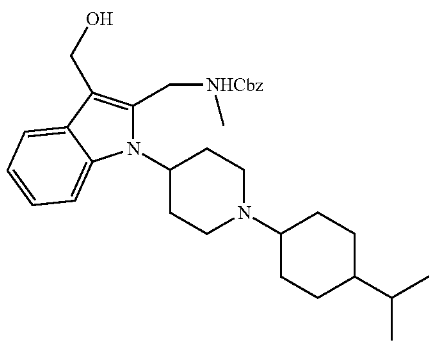 | benzyl ((3-(hydroxymethyl)-1-(1-(cis-4-isopropylcyclohexyl)piperidin-4-yl)-1H-indol-2-yl)methyl)(methyl)carbamate | ¹H NMR (400 MHz, CDCl₃) δ 7.71 (t, J = 7.2 Hz, 2H), 7.43-7.30 (m, 5H), 7.20 (t, J = 7.4 Hz, 1H), 7.14 (t, J = 7.4 Hz, 1H), 5.23 (s, 2H), 4.91 (s, 2H), 4.82 (s, 2H), 4.26 (br, 1H), 3.04 (d, J = 10.0 Hz, 2H), 2.78 (s, 3H), 2.57 (qd, J = 12.4, 4.0 Hz, 2H), 2.27 (m, 1H), 2.05 (m, 2H), 1.78-1.44 (m, 9H), 1.39 (m, 2H), 1.15 (m, 1H), 0.92 (d, J = 6.6 Hz, 6H) |
| 42 | 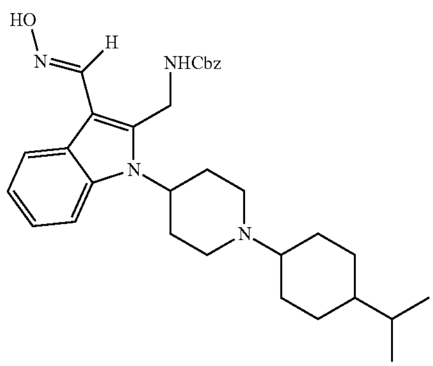 [SMILES: CC(C)C1CCC(N2CCC(n3c(CNC(=O)OCc4ccccc4)c(/C=N/O)c4ccccc43)CC2)CC1] | benzyl ((3-((E/Z)-(hydroxyamino)methyl-1-(1-(cis-4-isopropylcyclohexyl)piperidin-4-yl)-1H-indol-2-yl)methyl)carbamate | ¹H NMR (CDCl₃) δ 8.53 (s, 1H), 7.89 (d, J = 8.9 Hz, 1H), 7.76 (d, J = 7.1 Hz, 1H), 7.31 (m, 5H), 7.15 (m, 2H), 5.35 (br, 1H), 5.10 (s, 2H), 4.69 (d, J = 6.3 Hz, 2H), 4.48 (br, 1H), 3.12 (d, J = 11.4 Hz, 2H), 2.65 (q, J = 12.0 Hz, 2H), 2.36 (m, 1H), 2.24 (m, 2H), 1.83-1.47 (m, 10H), 1.40 (m, 2H), 1.16 (m, 1H), 0.92 (d, J = 6.6 Hz, 6H) |
| 43 | 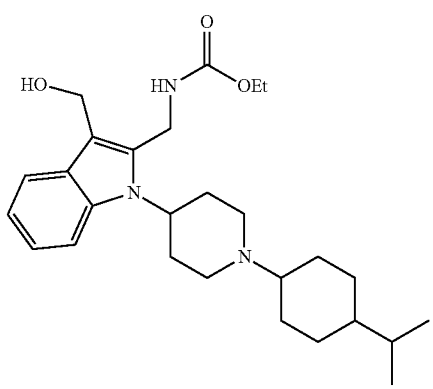 [SMILES: CCOC(=O)NCc1c(CO)c2ccccc2n1C1CCN(C2CCC(C(C)C)CC2)CC1] | ethyl ((3-(hydroxymethyl)-1-(1-(cis-4-isopropylcyclohexyl)piperidin-4-yl)-1H-indol-2-yl)methyl)carbamate | ¹H NMR (400 MHz, CDCl₃) δ 7.69 (t, J = 6.8 Hz, 1H), 7.20 (dt, J = 6.8, 1.2 Hz, 1H), 7.13 (dt, J = 6.8, 1.2 Hz, 1H), 5.04 (br, 1H), 4.90 (s, 2H), 4.62 (d, J = 5.6 Hz, 2H), 4.28-4.08 (m, 3H), 3.20 (d, J = 12.0 Hz, 2H), 2.63 (dq, J = 12.0, 4.0 Hz, 2H), 2.36 (m, 1H), 2.23 (t, J = 8.7 Hz, 1H), 1.87-1.51 (m, 11H), 1.42 (m, 2H), 1.25 (m, 4H), 0.92 (d, J = 6.6 Hz, 6H) |
| 44 | 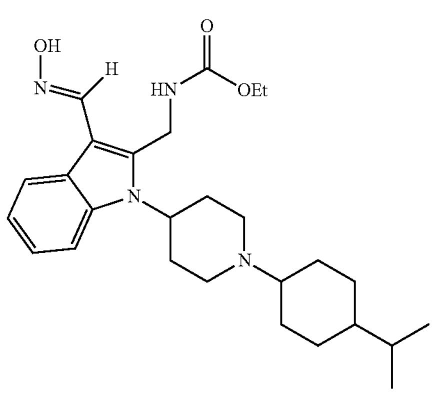 [SMILES: CCOC(=O)NCc1c(/C=N/O)c2ccccc2n1C1CCN(C2CCC(C(C)C)CC2)CC1] | ethyl ((3-((E/Z)-(hydroxyimino)methyl)-1-(1-(cis-4-isopropylcyclohexyl)piperidin-4-yl)-1H-indol-2-yl)methyl)carbamate | ¹H NMR (400 MHz, CDCl₃) δ 8.78 (br, 1H), 8.56 (s, 1H), 7.89 (d, J = 6.8 Hz, 1H), 7.81 (d, J = 7.2 Hz, 1H), 7.14 (m, 2H), 5.30 (br, 1H), 4.66 (d, J = 6.0 Hz, 2H), 4.53 (m, 1H), 4.16 (m, 2H), 3.22 (d, J = 11.2 Hz, 2H), 2.73 (dq, J = 12.4, 4.0 Hz, 2H), 2.40 (m, 3H), 1.73 (m, 11H), 1.41 (m, 2H), 1.21 (m, 3H), 0.91 (d, J = 6.6 Hz, 6H) |

TABLE 1-continued

| No. | Structure* | IUPAC Name | NMR (300 or 400 MHz) or TLC |
|---|---|---|---|
| 45 | 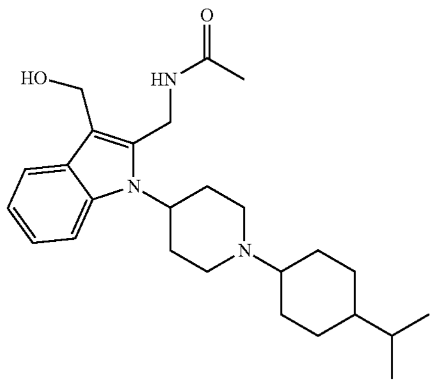 [SMILES: CC(=O)NCc1c(CO)c2ccccc2n1C1CCN(C2CCC(C(C)C)CC2)CC1] | N-((3-(hydroxymethyl)-1-(1-(cis-4-isopropylcyclohexyl)piperidin-4-yl)-1H-indol-2-yl)methyl)acetamide | $^1$H NMR (400 MHz, CDCl$_3$) δ 7.68 (t, J = 8.8 Hz, 2H), 7.19 (t, J = 7.2 Hz, 1H), 7.12 (t, J = 7.2 Hz, 1H), 6.05 (br, 1H), 5.40 (br, 1H), 4.90 (s, 2H), 4.70 (d, J = 5.6 Hz, 2H), 4.27 (m, 1H), 3.17 (d, J = 11.6 Hz, 2H), 2.62 (dq, J = 12.4, 3.6 Hz, 2H), 2.36 (m, 1H), 2.25 (t, J = 11.0 Hz, 2H), 2.01 (s, 2H), 1.96 (s, 3H), 1.80-1.50 (m, 7H), 1.40 (m, 2H), 1.16 (m, 1H), 0.92 (d, J = 6.6 Hz, 6H) |
| 46 | 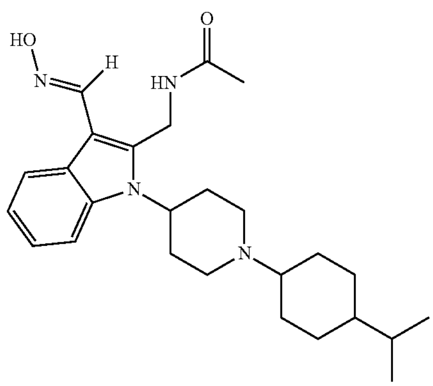 [SMILES: CC(=O)NCc1c(/C=N/O)c2ccccc2n1C1CCN(C2CCC(C(C)C)CC2)CC1] | N-((3-((E/Z)-(hydroxyimino)methyl)-1-(1-(cis-4-isopropylcyclohexyl)piperidin-4-yl)-1H-indol-2-yl)methyl)acetamide | $^1$H NMR (400 MHz, CDCl$_3$) δ 8.56 (s, 1H), 7.87 (m, 1H), 7.79 (m, 1H), 7.12 (dt, J = 7.0, 3.4 Hz, 2H), 6.11 (d, J = 5.6 Hz, 2H), 4.75 (d, J = 5.6 Hz, 2H), 4.57 (m, 1H), 3.20 (d, J = 11.2 Hz, 2H), 2.71 (dq, J = 12.4, 4.0 Hz, 2H), 2.38 (m, 3H), 1.88-1.73 (m, 6H), 1.65 (m, 6H), 1.40 (m, 2H), 1.17 (m, 1H), 0.91 (d, J = 6.6 Hz, 6H) |
| 47 | 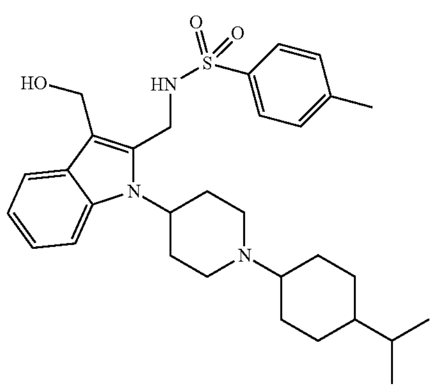 [SMILES: Cc1ccc(S(=O)(=O)NCc2c(CO)c3ccccc3n2C2CCN(C3CCC(C(C)C)CC3)CC2)cc1] | N-((3-(hydroxymethyl)-1-(1-(cis-4-isopropylcyclohexyl)piperidin-4-yl)-1H-indol-2-yl)methyl)-4-methylbenzenesulfonamide | $^1$H NMR (CDCl$_3$) δ 7.78 (d, J = 8.4 Hz, 2H), 7.69 (d, J = 8.1 Hz, 1H), 7.62 (d, J = 8.1 Hz, 1H), 7.32 (d, J = 8.4 Hz, 2H), 7.20 (t, J = 8.1 Hz, 1H), 7.11 (t, J = 7.2 Hz, 1H), 4.90 (br, 1H), 4.71 (s, 2H), 4.31 (m, 3H), 3.15 (d, J = 12.4 Hz, 2H), 2.57 (dq, J = 12.4, 4.0 Hz, 2H), 2.46 (s, 3H), 2.34 (m, 1H), 2.21 (t, J = 12.6 Hz, 2H), 1.85-1.50 (m, 10H), 1.40 (m, 2H), 1.16 (m, 1H), 0.92 (d, J = 6.6 Hz, 6H) |
| 48 | 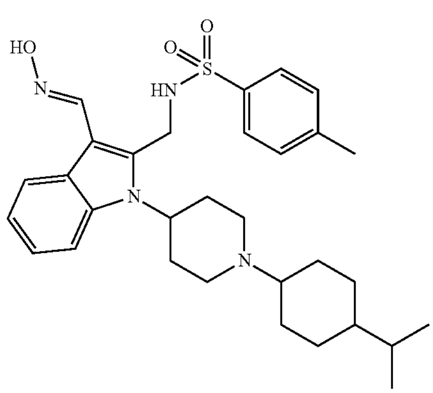 [SMILES: Cc1ccc(S(=O)(=O)NCc2c(/C=N/O)c3ccccc3n2C2CCN(C3CCC(C(C)C)CC3)CC2)cc1] | N-((3-((E/Z)-(hydroxyimino)methyl)-1-(1-(cis-4-isopropylcyclohexyl)piperidin-4-yl)-1H-indol-2-yl)methyl)-4-methylbenzenesulfonamide | $^1$H NMR (CDCl$_3$) δ 8.29 (s, 1H), 7.78 (m, 5H), 7.29 (m, 1H), 7.15 (m, 2H), 5.12 (br, 1H), 4.39 (m, 3H), 3.17 (d, J = 12.4 Hz, 2H), 2.62 (dq, J = 12.4, 4.0 Hz, 2H), 2.42 (m, 4H), 2.28 (t, J = 11.6 Hz, 2H), 1.95-1.55 (m, 10H), 1.43 (m, 2H), 1.16 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 49 | 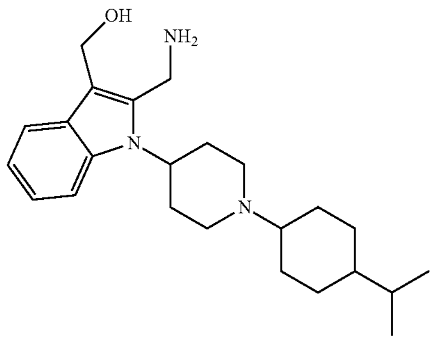 [SMILES: CC(C)C1CCC(N2CCC(n3c(CN)c(CO)c4ccccc43)CC2)CC1] | (2-(aminomethyl)-1-(1-(cis-4-isopropylcyclohexyl)piperidin-4-yl)-1H-indol-3-yl)methanol | $^1$H NMR (CDCl$_3$) δ 7.66 (t, J = 8.7 Hz, 2H), 7.22-7.08 (m, 2H), 4.88 (s, 2H), 4.34 (m, 1H), 4.14 (s, 2H), 3.21 (d, J = 11.7 Hz, 2H), 2.61 (q, J = 11.4 Hz, 2H), 2.38 (m, 1H), 2.25 (t, J = 10.9 Hz, 2H), 1.88 (d, J = 14.5 Hz, 3H), 1.82-1.40 (m, 11H), 1.17 (m, 1H), 0.92 (d, J = 6.6 Hz, 6H) |
| 50 | 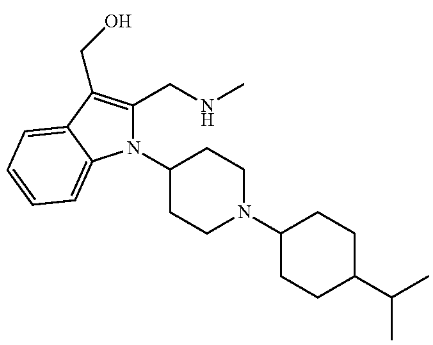 [SMILES: CNCc1c(CO)c2ccccc2n1C1CCN(C2CCC(C(C)C)CC2)CC1] | 1-(1-(cis-4-isopropylcyclohexyl)piperidin-4-yl)-2-((methylamino)methyl)-1H-indol-2-yl)methanol | $^1$H NMR (400 MHz, CDCl$_3$) δ 7.65 (m, 1H), 7.15 (m, 1H), 4.87 (s, 2H), 4.34 (m, 1H), 4.00 (s, 2H), 3.20 (d, J = 11.6 Hz, 2H), 2.58 (d,q J = 12.4, 4.0 Hz, 2H), 2.49 (s, 3H), 2.36 (m, 1H), 2.23 (dt, J = 12.0, 2.0 Hz, 2H), 1.85 (dd, J = 12.0, 2.0 Hz, 2H), 1.78-1.51 (m, 9H), 1.41 (m, 2H), 1.17 (m, 1H), 0.92 (d, J = 6.6 Hz, 6H) |
| 51 | 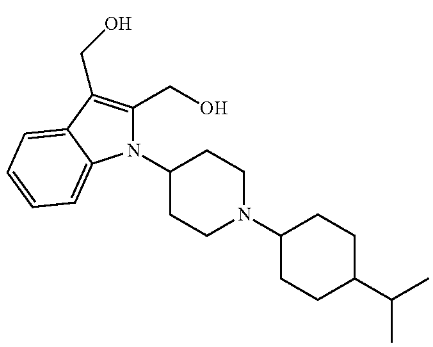 [SMILES: CC(C)C1CCC(N2CCC(n3c(CO)c(CO)c4ccccc43)CC2)CC1] | 1-(1-(cis-4-isopropylcyclohexyl)piperidin-4-yl)-1H-indole-2,3-yl)dimethanol | $^1$H NMR (400 MHz, CDCl$_3$) δ 7.67 (d, J = 8.4 Hz, 2H), 7.20 (t, J = 8.4 Hz, 1H), 7.13 (t, J = 8.0 Hz, 1H), 4.86 (s, 2H), 4.83 (s, 2H), 4.38 (m, 1H), 3.17 (d, J = 11.6 Hz, 2H), 2.59 (q, J = 12.0 Hz, 2H), 2.37 (m, 1H), 2.25 (t, J = 11.0 Hz, 2H), 1.52-1.89 (m, 9H), 1.43 (m, 2H), 1.18 (m, 1H), 0.92 (d, J = 6.4 Hz, 6H) |
| 52 | 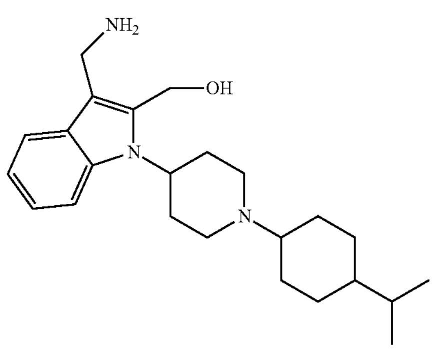 [SMILES: CC(C)C1CCC(N2CCC(n3c(CO)c(CN)c4ccccc43)CC2)CC1] | 3-(aminomethyl)-1-(1-(cis-4-isopropylcyclohexyl)piperidin-4-yl)-1H-indole-2-yl)methanol | $^1$H NMR (400 MHz, CDCl$_3$) δ 7.64 (d, J = 8.0 Hz, 1H), 7.58 (d, J = 8.0 Hz, 1H), 7.17 (t, J = 7.2 Hz, 1H), 7.10 (t, J = 7.2 Hz, 1H), 4.88 (s, 2H), 4.30 (m, 1H), 4.12 (s, 2H), 3.19 (d, J = 11.6 Hz, 2H), 2.80 (br, 3H), 2.58 (dq, J = 12.4, 4.0 Hz, 2H), 2.35 (sept, J = 3.6 Hz, 1H), 2.24 (dt, J = 12.0, 2.0 Hz, 2H), 1.88 (dd, J = 12.0, 2.0 Hz, 2H), 1.79-1.50 (m, 7H), 1.41 (m, 2H), 1.15 (m, 1H), 0.92 (d, J = 6.6 Hz, 6H) |

TABLE 1-continued

| No. | Structure* | IUPAC Name | NMR (300 or 400 MHz) or TLC |
|---|---|---|---|
| 53 | 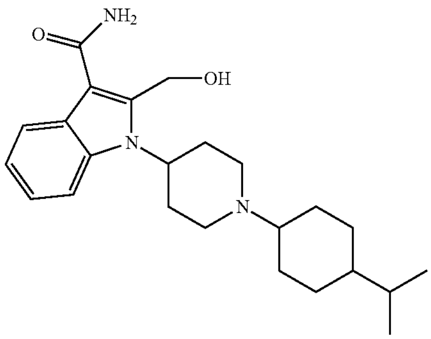 [SMILES: CC(C)C1CCC(N2CCC(n3c(CO)c(C(N)=O)c4ccccc43)CC2)CC1] | 2-(hydroxymethyl)-1-(1-(cis-4-isopropylcyclohexyl)piperidin-4-yl)-1H-indole-3-carboxamide | $^1$H NMR (CDCl$_3$) δ 7.75 (m, 2H), 7.26 (m, 2H), 5.90 (br, 2H), 5.00 (s, 1H), 4.65 (br, 1H), 4.44 (m, 1H), 3.22 (d, J = 11.6 Hz, 2H), 2.60 (dq, J = 12.0, 4.0 Hz, 2H), 2.36 (m, 1H), 2.25 (t, J = 11.6 Hz, 2H), 1.91 (dd, J = 12.0. 2.4 Hz, 2H), 1.64 (m, 8H), 1.41 (m, 2H), 1.16 (m, 1H), 0.92 (d, J = 6.6 Hz, 6H) |
| 54 | 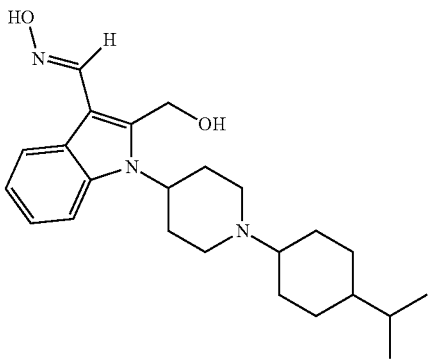 [SMILES: CC(C)C1CCC(N2CCC(n3c(CO)c(/C=N/O)c4ccccc43)CC2)CC1] | (E/Z)-2-(hydroxymethyl)-1-(1-(cis-4-isopropylcyclohexyl)piperidin-4-yl)-1H-indole-3-carbaldehyde oxime | $^1$H NMR (400 MHz, DMSO-d$_6$) δ 10.6 (br, 1H), 8.39 (s, 1H), 8.07 (d, J = 8.0, 1H), 7.59 (d, J = 8.0 Hz, 1H), 7.18 (dt, J = 7.2, 1.4 Hz, 1H), 7.09 (t, J = 7.2 Hz, 1H), 4.74 (s, 2H), 4.45 (m, 1H), 3.14 (d, J = 11.4 Hz, 2H), 2.47-2.29 (m, 3H), 2.18 (t, J = 8.0 Hz, 2H), 1.82 (dd, J = 12.4, 4.0 Hz, 2H), 1.75-1.33 (m, 10H), 1.12 (m, 1H), 0.89 (d, J = 6.6 Hz, 6H) |
| 55 | 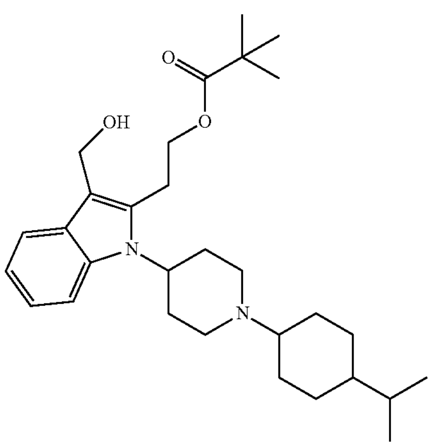 [SMILES: CC(C)C1CCC(N2CCC(n3c(CCOC(=O)C(C)(C)C)c(CO)c4ccccc43)CC2)CC1] | 2-(3-(hydroxymethyl)-1-(1-(cis-4-isopropylcyclohexyl)piperidin-4-yl)-1H-indol-2-yl)ethyl pivalate | R$_f$ = 0.40 (60:40:3 drops EtOAc:Hexanes:NH$_4$OH (aq.), UV, I$_2$) |
| 56 | 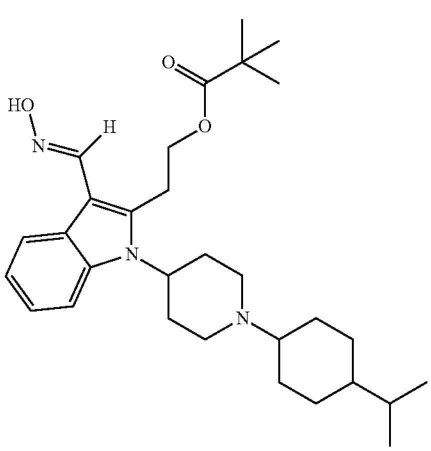 [SMILES: CC(C)C1CCC(N2CCC(n3c(CCOC(=O)C(C)(C)C)c(/C=N/O)c4ccccc43)CC2)CC1] | 2-(3-((E/Z)-(hydroxyimino)methyl-1-(1-(cis-4-isopropylcyclohexyl)piperidin-4-yl)-1H-indol-2-yl)ethyl pivalate | $^1$H NMR (CDCl$_3$) δ 8.48 (s, 1H), 8.08 (d, J = 8.4 Hz, 1H), 7.71 (d, J = 7.1 Hz, 1H), 7.17 (m, 2H), 4.24 (m, 3H), 3.25 (m, 4H), 2.71 (m, 2H), 2.47-2.23 (m, 3H), 1.93-1.52 (m, 10H), 1.42 (m, 2H), 1.20 (m, J = 5.2 Hz, 10H), 0.92 (d, J = 6.6 Hz, 6H) |

TABLE 1-continued

| No. | Structure* | IUPAC Name | NMR (300 or 400 MHz) or TLC |
|---|---|---|---|
| 57 | 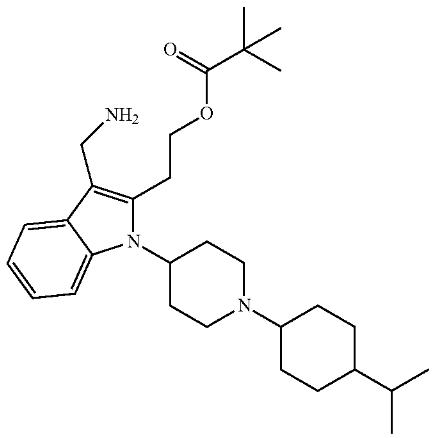 [SMILES: CC(C)C1CCC(N2CCC(n3c(CCOC(=O)C(C)(C)C)c(CN)c4ccccc43)CC2)CC1] | 2-(3-(aminomethyl)-1-(1-(cis-4-isopropylcyclohexyl)piperidin-4-yl)-1H-indol-2-yl)ethyl pivalate | ¹H NMR (CDCl₃) δ 7.66 (m, 2H), 7.12 (m, 2H), 4.13 (m, 5H), 3.20 (m, 4H), 2.70 (m, 2H), 2.35 (m, 3H), 1.89-1.50 (m, 11H), 1.42 (m, 2H), 1.22 (s, 9H), 1.16 (m, 1H), 0.92 (d, J = 6.6 Hz, 6H) |
| 58 | 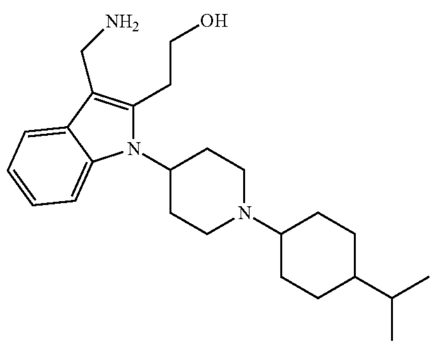 [SMILES: CC(C)C1CCC(N2CCC(n3c(CCO)c(CN)c4ccccc43)CC2)CC1] | 2-(3-(aminomethyl)-1-(1-(cis-4-isopropylcyclohexyl)piperidin-4-yl)-1H-indol-2-yl)ethan-1-ol | ¹H NMR (DMSO-d₆) δ 7.67 (d, J = 7.8 Hz, 1H), 7.59 (d, J = 8.1 Hz, 1H), 7.10 (m, 2H), 4.30 (m, 1H), 4.17 (s, 2H), 3.82 (s, 2H), 3.62 (t, J = 6.0 Hz, 2H), 3.12 (m, 4H), 2.48-2.23 (m, 6H), 1.79-1.32 (m, 11H), 1.14 (m, 1H), 0.89 (d, J = 6.6 Hz, 6H) |
| 59 | 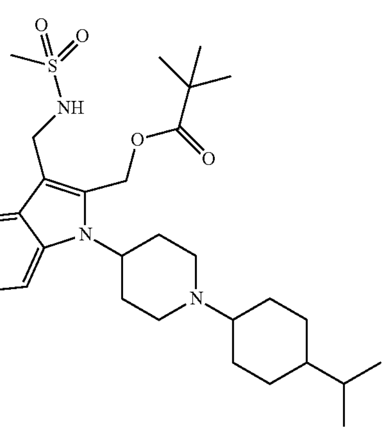 | 2-(1-(1-(cis-4-isopropylcyclohexyl)piperidin-4-yl)-3-methylsulfonamidomethyl)-1H-indol-2-yl)ethyl pivalate | ¹H NMR (DMSO-d₆) δ 7.75 (d, J = 7.8 Hz, 1H), 7.69 (d, J = 7.8 Hz, 1H), 7.24 (m, 2H), 7.09 (t, J = 7.2 Hz, 1H), 5.33 (s, 2H), 4.34 (m, 3H), 4.10 (s, 2H), 2.77 (s, 4H), 2.62 (m, 4H), 1.87 (m, 2H), 1.88-1.58 (m, 8H), 1.40 (m, 2H), 1.15 (m, 10H), 0.89 (d, J = 6.6 Hz, 6H) |

TABLE 1-continued

| No. | Structure* | IUPAC Name | NMR (300 or 400 MHz) or TLC |
|---|---|---|---|
| 60 | 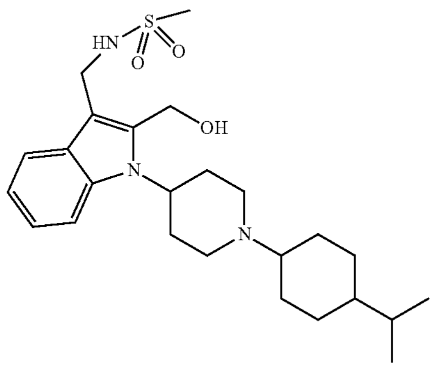 [SMILES: CC(C)C1CCC(N2CCC(n3c(CO)c(CNS(C)(=O)=O)c4ccccc43)CC2)CC1] | 2-(1-(1-(cis-4-isopropylcyclohexyl)piperidin-4-yl)-3-methylsulfonamidomethyl)-1H-indol-2-yl)ethan-1-ol | $^1$H NMR (CDCl) δ 7.64 (m, 1H), 7.21 (t, J = 7.2 Hz, 1H), 7.13 (t, J = 7.2 Hz, 1H), 4.81 (s, 2H), 4.52 (s, 2H), 4.36 (m, 1H), 3.11 (m, 2H), 2.60 (s, 6H), 2.29 (m, 2H), 1.83-1.40 (m, 13H), 1.18 (m, 1H), 0.92 (d, J = 6.6 Hz, 6H) |
| 61 | 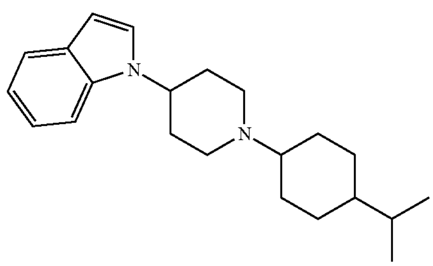 [SMILES: CC(C)C1CCC(N2CCC(n3ccc4ccccc43)CC2)CC1] | 1-(1-(cis-4-isopropylcyclohexyl)piperidin-4-yl)-1H-indole | $^1$H NMR (CDCl$_3$) δ 7.64 (d, J = 6.0 Hz, 1H), 7.39 (d, J = 6.0 Hz, 1H), 7.26 (m, 1H), 7.20 (t, J = 6.0 Hz, 1H), 7.11 (t, J = 6.0 Hz, 1H), 6.52 (d, J = 2.4 Hz, 1H), 4.23 (m, 1H), 3.20 (d, J = 9.0 Hz, 2H), 2.30 (m, 3H), 2.08 (m, 4H), 1.51-1.78 (m, 7H), 1.40 (m, 2H), 1.17 (m, 1H), 0.9 (d, J= 4.8 Hz, 6H) |
| 62 | 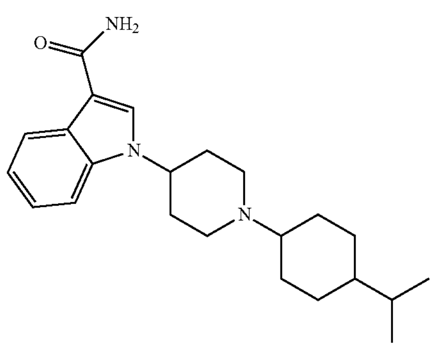 [SMILES: CC(C)C1CCC(N2CCC(n3cc(C(N)=O)c4ccccc43)CC2)CC1] | 1-(1-(cis-4-isopropylcyclohexyl)piperidin-4-yl)-1H-indole-3-carboxamide | $^1$H NMR (CDCl$_3$) δ □8.00 (m, 1H), 7.90 (m, 1H), 7.49 (m, 1H), 7.29 (m, 1H), 5.78 (br, 2H), 4.23 (m, 1H), 3.26 (d, J = 8.7 Hz, 2H), 2.37 (m, 2H), 2.28 (t, J = 8.7 Hz, 2H), 2.10 (m, 4H), 1.75-1.52 (m, 6H), 1.40 (m, 2H), 1.16 (m, 1H), 0.90 (d, J = 5.1 Hz, 6H) |
| 63 | 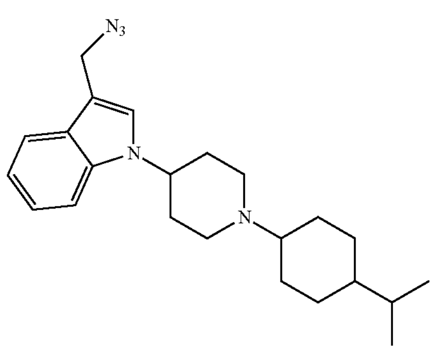 [SMILES: CC(C)C1CCC(N2CCC(n3cc(CN=[N+]=[N-])c4ccccc43)CC2)CC1] | 3-azidomethyl-1-(1-(cis-4-isopropylcyclohexyl)piperidin-4-yl)-1H-indole | $^1$H NMR (CDCl$_3$) δ 7.68 (d, J = 7.8 Hz, 1H), 7.40 (d, J = 8.1 Hz, 1H), 7.27 (m, 2H), 7.17 (t, J = 6.9 Hz, 1H), 4.54 (s, 2H), 4.19 (m, 1H), 3.21 (d, J = 11.1 Hz, 2H), 2.30 (m, 3H), 2.08 (m, 4H), 1.78-1.51 (m, 7H), 1.40 (m, 2H), 1.15 (m, 1H), 0.91 (d, J = 6.6 Hz, 6H) |

TABLE 1-continued

| No. | Structure* | IUPAC Name | NMR (300 or 400 MHz) or TLC |
|---|---|---|---|
| 64 | 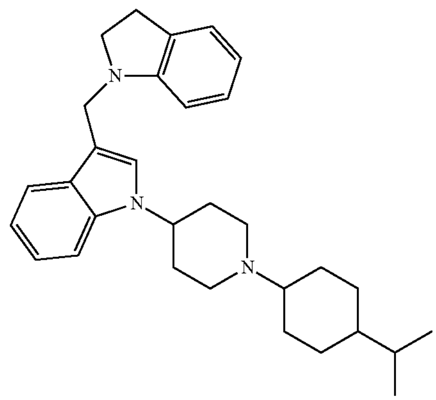 [SMILES: CC(C)C1CCC(N2CCC(n3cc(CN4CCc5ccccc54)c4ccccc43)CC2)CC1] | 3-(indolin-1-ylmethyl)-1-(1-(cis-4-isopropylcyclohexyl)piperidin-4-yl)-1H-indole | $^1$H NMR (CDCl$_3$) δ ☐7.70 (d, J = 6.0 Hz, 1H), 7.38 (d, J = 6.3 Hz, 1H), 7.22 (t, J = 5.4 Hz, 2H), 7.11 (t, J = 6.0 Hz, 3H), 6.88 (m, 2H), 4.42 (s, 2H), 4.17 (m, 1H), 3.28 (t, J = 6.3 Hz, 2H), 3.18 (d, J = 9.0 Hz, 2H), 2.91 (t, J = 6.3 Hz, 2H), 2.37-2.24 (m, 3H), 2.40 (m, 4H), 1.77-1.51 (m, 7H), 1.40 (m, 2H), 1.15 (m, 1H), 0.90 (d, J = 5.1 Hz, 6H) |
| 65 | 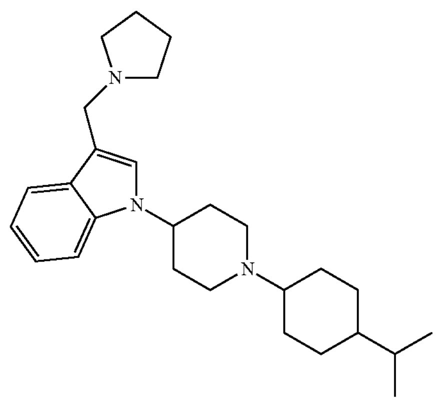 [SMILES: CC(C)C1CCC(N2CCC(n3cc(CN4CCCC4)c4ccccc43)CC2)CC1] | 1-(1-(cis-4-isopropylcyclohexyl)piperidin-4-yl)-3-(pyrrolin-1-ylmethyl)-1H-indole | $^1$H NMR (CDCl$_3$) δ 7.70 (d, J = 7.8 Hz, 1H), 7.36 (d, J = 8.1 Hz, 1H), 7.21 (m, 2H), 7.11 (t, J = 7.5 Hz, 1H), 4.17 (m, 1H), 3.84 (s, 2H), 3.19 (d, J = 12.0 Hz, 2H), 2.59 (s, 4H), 2.27 (m, 3H), 2.04 (m, 5H), 1.82-1.48 (m, 12H), 1.40 (m, 2H), 1.15 m, 1H), 0.91 (d, J = 6.6 Hz, 6H) |
| 66 | 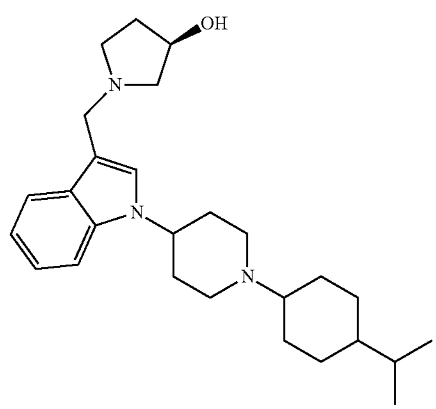 [SMILES: CC(C)C1CCC(N2CCC(n3cc(CN4CC[C@@H](O)C4)c4ccccc43)CC2)CC1] | (R)-1-((1-(1-(cis-4-isopropylcyclohexyl)piperidin-4-yl)-1H-indol-3-yl)methyl)pyrrolin-3-ol | $^1$H NMR (400 MHz, CDCl$_3$) δ 7.69 (d, J = 8.0 Hz, 1H), 7.37 (d, J = 8.0 Hz, 1H), 7.20 (m, 1H), 7.11 (t, J = 7.2 Hz, 1H), 4.32 (m, 1H), 4.17 (m, 1H), 3.86 (s, 2H), 3.19 (d, J = 12.0 Hz, 2H), 2.93 (m, 1H), 2.74 (dd, J = 10.4, 1.0 Hz, 1H), 2.61 (dd, J = 10.4, 5.2 Hz, 1H), 2.45-1.94 (m, 11H), 1.78-1.51 (m, 7H), 1.41 (m, 2H), 1.15 (m, 1H), 0.91 (d, J = 6.6 Hz, 6H) |

TABLE 1-continued

| No. | Structure* | IUPAC Name | NMR (300 or 400 MHz) or TLC |
|---|---|---|---|
| 67 | 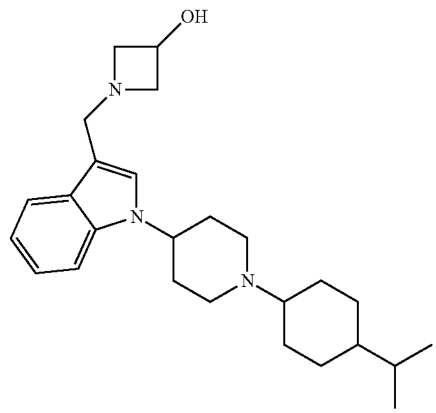 [SMILES: CC(C)C1CCC(N2CCC(n3cc(CN4CC(O)C4)c4ccccc43)CC2)CC1] | 1-((1-(1-(cis-4-isopropylcyclohexyl)piperidin-4-yl)-1H-indol-3-yl)methyl)azetidin-3-ol | $^1$H NMR (400 MHz, CDCl$_3$) δ 7.65 (d, J= 7.6 Hz, 1H), 7.58 (br, 1H), 7.36 (d, J = 8.4 Hz, 1H), 7.21 (m, 2H), 7.12 (m, 1H), 4.44 (p, J = 6.0 Hz, 1H), 4.17 (m, 1H), 3.84 (s, 2H), 3.69 (m, 3H), 3.19 (d, J = 12.4 Hz, 2H), 3.03 (m, 2H), 2.29 (m, 3H), 2.12-1.89 (m, 3H), 1.76-1.47 (m, 7H), 1.40 (m, 2H), 1.14 (m, 1H), 0.90 (d, J = 6.6 Hz, 6H) |
| 68 | 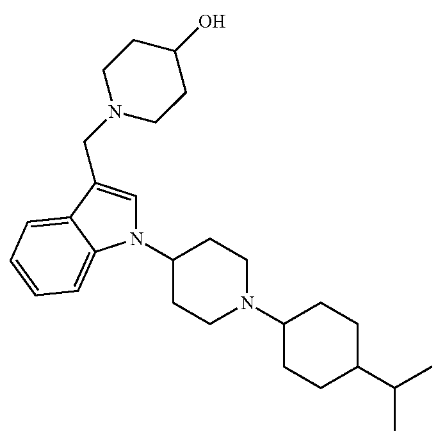 [SMILES: CC(C)C1CCC(N2CCC(n3cc(CN4CCC(O)CC4)c4ccccc43)CC2)CC1] | 1-((1-(1-(cis-4-isopropylcyclohexyl)piperidin-4-yl)-1H-indol-3-yl)methyl)piperidin-4-ol | $^1$H NMR (CDCl$_3$) δ 7.71 (d, J = 7.8 Hz, 1H), 7.37 (d, J = 8.1 Hz, 1H), 7.21 (m, 1H), 7.11 (t, J = 7.2 Hz, 1H), 4.16 (m, 1H), 3.78 (m, 3H), 3.19 (d, J = 11.6 Hz, 3H), 2.87 (m, 2H), 2.38-2.20 (m, 4H), 2.15-1.91 (m, 5H), 1.78-1.48 (m, 11H), 1.41 (m, 2H), 1.15 (m, 1H), 0.91 (d, J = 6.6 Hz, 6H) |
| 69 | 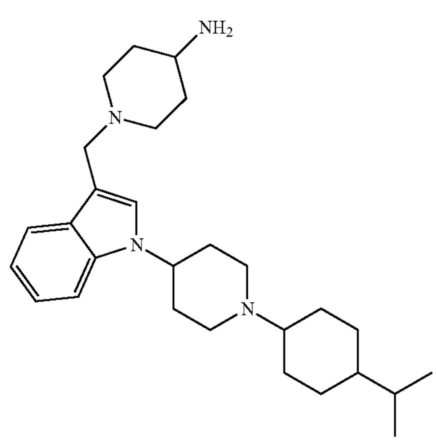 [SMILES: CC(C)C1CCC(N2CCC(n3cc(CN4CCC(N)CC4)c4ccccc43)CC2)CC1] | 1-((1-(1-(cis-4-isopropylcyclohexyl)piperidin-4-yl)-1H-indol-3-yl)methyl)piperidin-4-amine | H$^1$ NMR (CDCl$_3$): δ 7.70 (dd, J = 2.4, 4.2 Hz, 2 H), 7.53 (dd, J = 2.4, 4.2 Hz, 2 H), 7.4 (br s, 1H), 4.24-4.21 (m, 3H), 3.48 (q, J = 5.1, 10.5 Hz, 4H), 2.08 (s, 14H), 1.69-1.68 (m, 2H), 1.45-1.40 (m, 3H), 1.35-1.29 (m, 4H), 1.20 (t, J = 5.1 Hz, 3H), 0.94-0.88 (m, 6H). |

TABLE 1-continued

| No. | Structure* | IUPAC Name | NMR (300 or 400 MHz) or TLC |
|---|---|---|---|
| 70 | 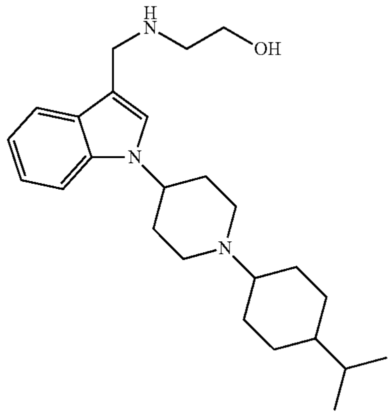 [SMILES: CC(C)C1CCC(N2CCC(n3cc(CNCCO)c4ccccc43)CC2)CC1] | 2-((1-(1-(cis-4-isopropylcyclohexyl)piperidin-4-yl)-1H-indol-3-yl)methyl)amino)ethan-1-ol | H¹ NMR (CDCl₃): δ 7.56 (d, J = 5.7 Hz, 1H), 7.36 (d, J = 6.3 Hz, 1H), 7.18 (t, J = 5.1 Hz, 2H), 7.06 (d, J = 5.7 Hz, 1H), 4.22-4.21 (m, 1H), 3.66 (br s, 1H), 3.22 (s, 1H), 2.79 (s, 1 H), 2.32 (br s, 3H), 2.10 (s, 4H), 1.72-1.61 (m, 7H), 1.43-1.32 (m, 2H), 1.26 (s, 2H), 1.15 (s, 1H), 0.89 (d, J = 4.8 Hz, 6H). |
| 71 | 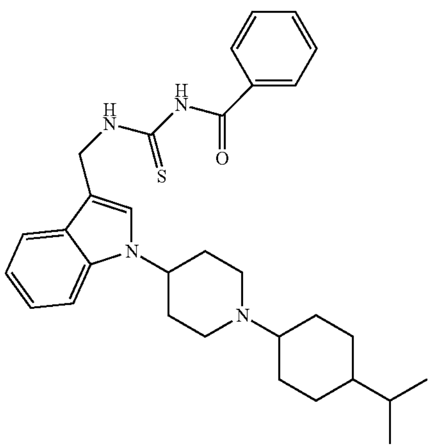 [SMILES: CC(C)C1CCC(N2CCC(n3cc(CNC(=S)NC(=O)c4ccccc4)c4ccccc43)CC2)CC1] | N-(((1-(1-(cis-4-isopropylcyclohexyl)piperidin-4-yl)-1H-indol-3-yl)methyl)carbamothioyl)benzamide | H¹ NMR (CDCl₃): δ 10.81 (s, 1H), 9.05 (s, 1H), 8.12 (d, J = 5.7 Hz, 1H), 7.78 (dd, J = 5.7, 13.8 Hz, 1H), 7.69 (d, J = 5.7 Hz, 1H), 7.58 (t, J = 5.4 Hz, 1H), 7.55-7.39 (m, 4H), 7.3 (s, 1H), 7.22-7.14 (m, 1H), 5.01 (d, J = 3.9 Hz, 1H), 4.37-4.34 (m, 1H), 3.55 (d, J = 9 Hz, 2H), 3.0 (br s, 1H), 2.72 (t, J = 8.1, 2H), 2.53 (q, J = 8.4, 9.6 Hz, 2H), 2.18 (d, J = 9.3 Hz, 2H), 1.86 (dd, J = 9.9, 19.5 Hz, 4H), 1.68-1.63 (m, 3H), 1.43 (t, J = 9.6 Hz, 2H), 1.26-1.22 (m, 1H), 0.89 (d, J = 4.8 Hz, 6 H). |
| 72 | 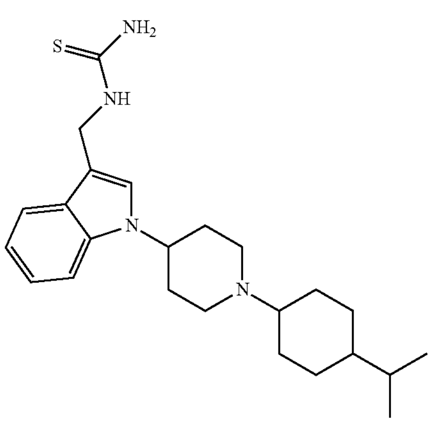 [SMILES: CC(C)C1CCC(N2CCC(n3cc(CNC(N)=S)c4ccccc43)CC2)CC1] | 1-((1-(1-(cis-4-isopropylcyclohexyl)piperidin-4-yl)-1H-indol-3-yl)methyl)thiourea | H¹ NMR (CDCl₃): δ 7.61 (br s, 1H), 7.37 (d, J = 6 Hz, 1H), 7.24 (S, 2H), 7.11 (t, J = 5.1 Hz, 1H), 6.58 (br s, 1H), 5.82 (s, 2H), 4.88 (br s, 1H), 4.45 (br s, 1H), 4.18 (s, 1H), 3.14 (d, J = 6.9 Hz, 2H), 2.33 (s, 1H), 2.22 (t, J = 9.3 Hz, 2H), 2.02-1.97 (m, 4H), 1.71-1.61 (m, 5H), 1.56-1.54 (m, 2H), 1.42-1.39 (m, 2H), 1.14 (br s, 1H), 0.89 (d, J = 4.8 Hz, 6H). |

TABLE 1-continued

| No. | Structure* | IUPAC Name | NMR (300 or 400 MHz) or TLC |
|---|---|---|---|
| 73 | 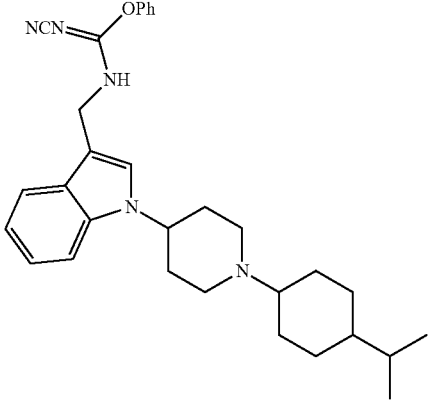 | phenyl (E)-N'-cyano-N-((1-(1-(cis-4-isopropylcyclohexyl)piperidin-4-yl)-1H-indol-3-yl)methyl)carbamimidate | $H^1$ NMR (CDCl$_3$): δ 7.66 (d, J = 5.7 Hz, 1H), 7.42 (d, J = 5.7 Hz, 3H), 7.29 (d, J = 6.9 Hz, 2H), 7.27 (s, 2H), 7.13 (dd, J = 5.4, 14.4 Hz, 3H), 6.39 (br s, 1H), 4.81 (s, 2H), 4.65 (d, J = 9 Hz, 2H), 4.24 (br s, 1H), 3.20 (d, J = 8.1 Hz, 2H), 2.28 (dd, J = 10.2, 19.8 Hz, 3H), 2.04 (t, J = 11.4 Hz, 4H), 1.72-1.59 (m, 7H), 1.37 (q, J = 7.2, 9.6 Hz, 2H), 1.16 (br s, 1H), 0.90 (d, J = 4.8 Hz, 6H). |
| 74 | 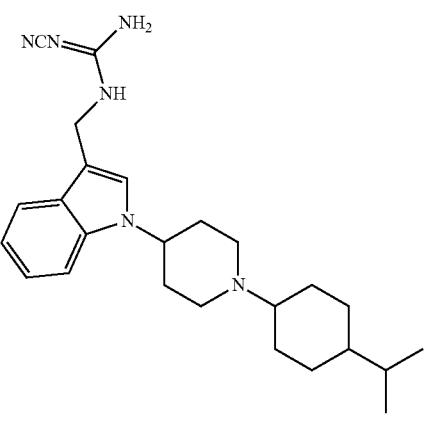 | (Z)-2-cyano-1-((1-(1-cis-4-isopropylcyclohexyl)piperidin-4-yl)-1H-indol-3-yl)methyl)guanidine | $H^1$ NMR (CDCl$_3$): δ 7.58 (d, J = 5.4 Hz, 1H), 7.34 (d, J = 6 Hz, 1H), 7.21 (d, J = 5.1 Hz, 3H), 7.09 (t, J = 4.8, 1H), 5.84 (br s, 2H), 4.53 (s, 2H), 4.29 (br s, 1H), 3.63 (s, 2H), 3.32 (d, J = 7.5 Hz, 2H), 2.78 (br s, 1H), 2.63 (br s, 2H), 2.27-2.22 (m, 2H), 1.90 (br s, 4H), 1.70-1.62 (m, 3H), 1.44 (br s, 2H), 1.22 (d, J = 11.7 Hz, 3H), 0.91 (d, J = 4.8 Hz, 6H). |
| 75 | 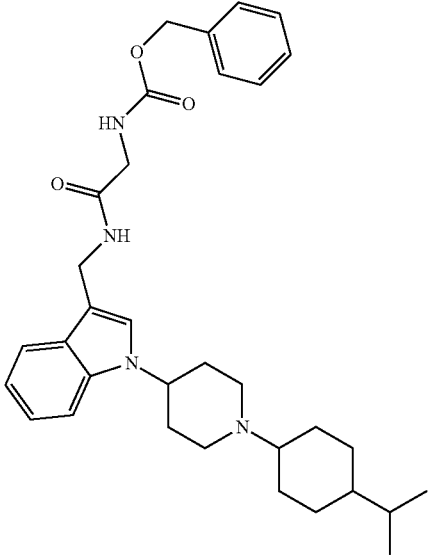 [SMILES: CC(C)C1CCC(N2CCC(n3cc(CNC(=O)CNC(=O)OCc4ccccc4)c4ccccc43)CC2)CC1] | benzyl (2-cyano-(((1-(1-cis-4-isopropylcyclohexyl)piperidin-4-yl)-1H-indol-3-yl)methyl)amino)-2-oxoethyl)carbamate | $H^1$ NMR (CDCl$_3$): δ 7.59 (d, J = 5.7 Hz, 1H), 7.36 (d, J = 6.3 Hz, 1H), 7.32 (s, 5H), 7.25-7.22 (m, 2H), 7.11 (t, J = 5.7 Hz, 1H), 6.11 (s, 1H), 5.45 (s, 1H), 5.08 (s, 2H), 4.20-4.18 (m, 1H), 3.85 (d, J = 4.2 Hz, 2H), 3.22 (d, J = 8.7 Hz, 2H), 2.44 (s, 1H), 2.31 (d, J = 7.8 Hz, 2H), 2.09 (t, J = 7.8 Hz, 4H), 1.73 (br s, 2H), 1.68-1.63 (m, 3H), 1.43-1.38 (m, 2H), 1.17-1.16 (m, 1H), 0.89 (d, J = 4.8 Hz, 6H) |

TABLE 1-continued

| No. | Structure* | IUPAC Name | NMR (300 or 400 MHz) or TLC |
|---|---|---|---|
| 76 | 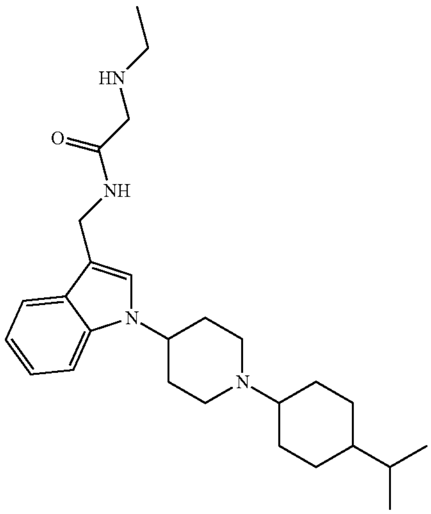 [SMILES: CCNCC(=O)NCc1cn(C2CCN(C3CCC(C(C)C)CC3)CC2)c2ccccc12] | 2-(ethylamino)-N-((1-(1-cis-4-isopropylcyclohexyl)piperidin-4-yl)-1H-indol-3-yl)methyl)acetamido | H¹ NMR (CDCl$_3$): δ 7.59 (t, J = 7.8 Hz, 1H), 7.35 (d, J = 8.1 Hz, 1H), 7.20 (t, J = 4.8 Hz, 2H), 7.09 (t, J = 7.5 Hz, 1H), 5.31 (s, 1H), 4.60 (d, J = 5.4 Hz, 2H), 4.32 (br s, 1H), 3.42-3.36 (m, 4H), 2.71-2.44 (m, 9H), 2.11 (d, J = 11.7 Hz, 2H), 1.88-1.64 (m, 5H), 1.408 (q, J = 10.2, 13.2 Hz, 2H), 1.28-1.20 (m, 1H), 1.07 (t, 6.9 Hz, 3H), 0.92 (d, J = 6.3 Hz, 6 H). |
| 77 | 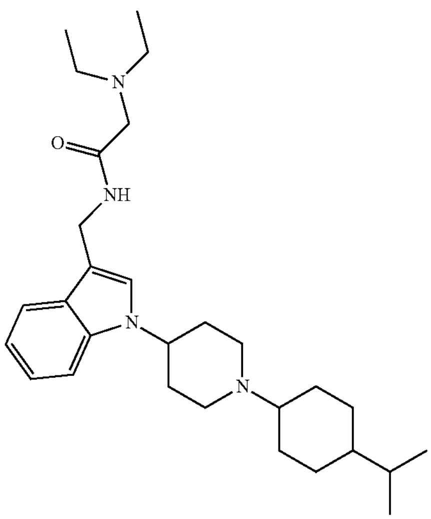 [SMILES: CCN(CC)CC(=O)NCc1cn(C2CCN(C3CCC(C(C)C)CC3)CC2)c2ccccc12] | 2-(diethylamino)-N-((1-(1-cis-4-isopropylcyclohexyl)piperidin-4-yl)-1H-indol-3-yl)methyl)acetamido | H¹ NMR (CDCl$_3$): δ 7.65 (d, J = 7.5 Hz, 1H), 7.34 (d, J = 8.4 Hz, 1H), 7.25-7.21 (m, 2H), 7.10 (t, J = 7.5 Hz, 1H), 5.18 (d, J = 15 Hz, 1H), 4.23 (br s, 1H), 4.10 (d, J = 15 Hz, 1H), 3.81 (q, J = 5.1, 10.8 Hz, 1H), 3.63 (d, J = 14.4 Hz, 1H), 3.28 (br s, 2H), 2.98 (d, 13.5 Hz, 1H), 2.72-2.64 (m, 1H), 2.39 (br s, 2H), 2.27 (m, 2.20 (m, 2H), 2.13 (br s, 3H), 1.77-1.68 (m, 6H), 1.46-1.42 (m, 2H), 1.33-1.28 (m, 3H), 1.20-1.1.19 (m, 1H), 1.02 (t, J = 7.2 Hz, 6H), 0.91 (d, J = 6.6 Hz, 6H). |
| 78 | 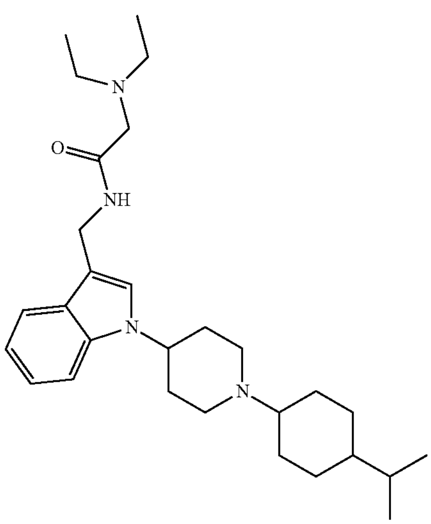 [SMILES: CCN(CC)CC(=O)NCc1cn(C2CCN(C3CCC(C(C)C)CC3)CC2)c2ccccc12] | N-((1-(1-cis-4-isopropylcyclohexyl)piperidin-4-yl)-1H-indol-3-yl)methyl)-5-((oxo-2-phenyl-1λ³-ethylidene)amino)pentanamide | H¹ NMR (CDCl$_3$): δ 7.61 (d, J = 6.0 Hz, 1H), 7.36-7.30 (m, 5H), 7.21 (t, J = 11.4 Hz, 1H), 7.19 (s, 1H), 7.11 (t, J = 11.1 Hz, 1H), 5.7 (br s, 1H), 5.12-5.00 (m, 2H), 4.87 (br s, 1H), 4.58 (d, J = 3.6 Hz, 2H), 4.22-4.21 (m, 1H), 3.30 (d, J = 8.4 Hz, 2H), 3.13 (p, J = 4.8, 12, 17.1 Hz, 2H), 2.61-2.60 (m, 1H), 2.42 (t, J = 8.7 Hz, 2H), 2.28 (t, J = 5.4 Hz, 2H), 2.22 (d, J = 9 Hz, 1H), 2.14 (t, J = 5.4 Hz, 2H), 2.06 (d, 2H), 1.83-1.799 (m, 2H), 1.64 (d, J = 3.9 Hz, 5H), 1.61-1.33 (m, 5H), 1.16 (1H), 0.89 (d, J = 5.1 Hz, 6H). |

TABLE 1-continued

| No. | Structure* | IUPAC Name | NMR (300 or 400 MHz) or TLC |
|---|---|---|---|
| 79 | 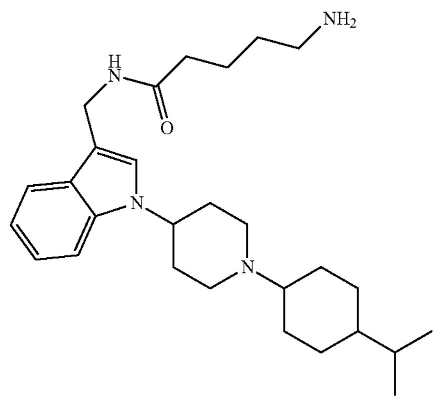 [SMILES: CC(C)C1CCC(N2CCC(n3cc(CNC(=O)CCCCN)c4ccccc43)CC2)CC1] | 5-amino-N-((1-(1-cis-4-isopropylcyclohexyl)piperidin-4-yl)-1H-indol-3-yl)methyl)pentanamide | H$^1$ NMR (CDCl$_3$): δ 7.61 (d, J = 7.5 Hz, 1H), 7.36 (d, J = 8.1 Hz, 1H), 7.20 (t, J = 5.1 Hz, 2H), 7.10 (t, J = 7.5 Hz, 1H), 5.93 (s, 1H), 4.59 (d, J = 5.1 Hz, 2H), 4.22-4.20 (m, 1H), 3.57 (t, J = 5.4 Hz, 4H), 3.22 (d, J = 11.4 Hz, 2H), 2.56-2.5 (m, 3H), 2.43-2.32 (m, 2H), 2.17 (t, J = 7.5 Hz, 2H), 2.12 (s, 2H), 1.78-1.51 (m, 11H), 1.45-1.31 (m, 4H), 1.29-1.16-(m, 1H), 0.90 (d, J = 6.6 Hz, 6H). |
| 80 | 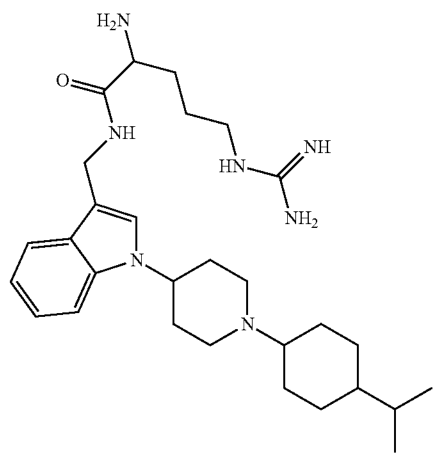 [SMILES: CC(C)C1CCC(N2CCC(n3cc(CNC(=O)C(N)CCCNC(=N)N)c4ccccc43)CC2)CC1] | 2-amino-5-guanidino-N-((1-(1-cis-4-isopropylcyclohexyl)piperidin-4-yl)-1H-indol-3-yl)methyl)pentanamide | H$^1$ NMR (DMSO-d$_6$): δ 8.32 (s, 2H), 7.72 (br s, 1H), 7.50 (d, J = 6 Hz, 1H), 7.44 (d, J = 6.3 Hz, 1H), 7.41 (s, 1H), 7.08 (t, J = 6 Hz, 1 H), 6.95 (t, J = 5.7 Hz, 1H), 4.39 (dd, J = 3.6, 10.8 Hz, 1H), 4.31-4.24 (m, 2H), 3.83 (br s, 1H), 3.066 (brs, 3H), 2.90 (m, 1H), 2.66 (s, 2H), 2.28 (d, J = 13.5, 2H), 2.16 (t, J = 8.4 Hz, 3H), 1.91-1.85 (m, 4H), 1.70 (br, s, 2H), 1.54 (br s, 4H), 1.41-1.35 (m, 4H), 1.14-1.09 (m, 1H), 0.85 (d, J = 4.8 Hz, 6H). |
| 81 | 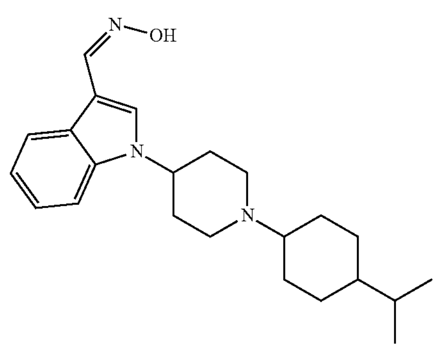 [SMILES: CC(C)C1CCC(N2CCC(n3cc(/C=N\O)c4ccccc43)CC2)CC1] | (E/Z)-1-(1-cis-4-isopropylcyclohexyl)piperidin-4-yl)-1H-indol-3-carbaldehyde oxime | $^1$H NMR (CDCl$_3$, Major Isomer) δ 10.8 (br, 1H), 8.47 (s, 1H), 7.78 (m, 2H), 7.41 (d, J = 6.0, 1H), 7.28 (m, 1H), 7.23 (m, 1H), 4.31 (m, 1H), 3.30 (d, J = 8.7 Hz, 2H), 2.55 (m, 1H), 2.46 (t, J = 7.8 Hz, 2H), 2.23 (m, 3H), 1.86 (m, 2H), 1.60-1.80 (m, 6H), 1.43 (m, 2H), 1.19 (m, 1H), 0.91 (d, J = 5.1, 6H); 1H NMR (300 MHz, CDCl3, Minor Isomer) δ 8.30 (s, 1H), 8.07 (d, J = 6.0 Hz, 1H), 7.48 (s, 1H), 7.40 (d, J = 6.0 Hz, 1H), 7.28 (t, J = 5.4 Hz, 1H), 7.20 (t, J = 5.4 Hz, 1H), 4.23 (m, 1H), 3.22 (d, J = 5.7 Hz, 2H), 2.35 (m, 3H), 2.13 (m, 4H), 1.55-1.80 (m, 7H), 1.43 (m, 2H), 1.17 (m, 1H), 0.91 (d, J = 5.1 Hz, 6H) |
| 82 | 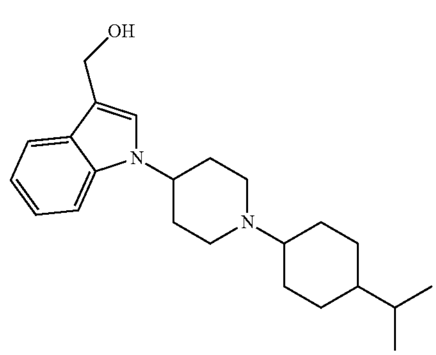 [SMILES: CC(C)C1CCC(N2CCC(n3cc(CO)c4ccccc43)CC2)CC1] | (1-(1-cis-4-isopropylcyclohexyl)piperidin-4-yl)-1H-indol-3-yl)methanol | H$^1$ NMR (CDCl$_3$): δ 7.73 (d, J = 5.7 Hz, 1H), 7.37 (d, J = 6 Hz, 1H), 7.26 (s, 1H), 7.22 (d, J = 6 Hz, 1H), 7.13 (t, J = 5.4 Hz, 1H), 4.87 (s, 2H), 4.20 (m, 1H), 3.15 (d, 8.7 J = Hz, 2H), 2.33 (br s, 1H), 2.23 (t, J = 8.4, Hz, 2H), 1.98 (dd, J = 9, 18.3 Hz, 4H), 1.73-1.69 (m, 4H), 1.61 (t, J = 4.8 Hz, 2H), 1.58-1.56 (m, δ1H), 1.42-1.39 (m, 2H), 1.26 (br s, 1H), 1.02 (br s, 1H), 0.86 (dd, J = 4.8, 6.9 Hz, 6H). |

TABLE 1-continued

| No. | Structure* | IUPAC Name | NMR (300 or 400 MHz) or TLC |
|---|---|---|---|
| 83 | 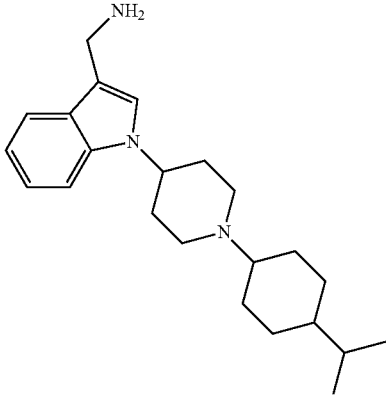 [SMILES: CC(C)C1CCC(N2CCC(n3cc(CN)c4ccccc43)CC2)CC1] | (1-(1-cis-4-isopropylcyclohexyl)piperidin-4-yl)-1H-indol-3-yl)methanamine | H$^1$ NMR (DMSO-d$_6$): δ 7.58 (d, J = 6.0 Hz, 1H), 7.44 (d, J = 6.3 Hz, 1H), 7.37 (s, 1H), 7.10 (t, J = 5.7 Hz, 1H), 6.98 (t, J = 5.7 Hz, 1H), 4.26-4.25 (m, 1H), 3.86 (s, 1H), 3.16 (s, 2H), 3.077 (d, J = 8.7 Hz, 3H), 2.27 (br s, 1H), 2.18 (t, J = 8.4 Hz, 2H), 1.91-1.86 (m, 4H), 1.71 (br s, 2H), 1.55-1.50 (m, 3H), 1.38 (dd, J = 9.3, 18.3 Hz, 4H), 1.097 (s, 1H), 0.858 (d, J = 5.1 Hz, 6H). |
| 84 | 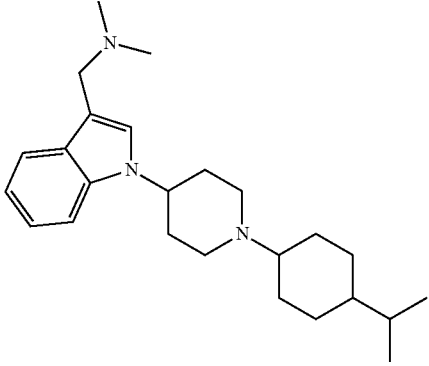 [SMILES: CC(C)C1CCC(N2CCC(n3cc(CN(C)C)c4ccccc43)CC2)CC1] | 1-(1-(1-cis-4-isopropylcyclohexyl)piperidin-4-yl)-1H-indol-3-yl)-N,N-dimethylmethanamine | H$^1$ NMR (CDCl$_3$): δ 7.73 (d, J = 6 Hz, 1H), 7.62 (d, J = 6 Hz, 1H), 7.37 (d, J = 6 Hz, 1H), 7.22 (d, J = 5.1 Hz, 1H), 7.17-7.14 (m, 1H), 5.61-5.43 (m, 6H), 4.87 (s, 1H), 4.65 (d, J = 3.9 Hz, 1H), 4.59 (d, J = 3.6 Hz, 1H), 4.19 (t, J = 5.4 Hz, 1H), 3.21 (d, J = 7.5 Hz, 2H), 2.38-2.30 (m, 3H), 2.18-1.98 (m, 6H), 1.71-1.60 (m, 5H), 1.43-1.37 (m, 2H), 1.14 (t, J = 3.3 Hz, 1H), 0.89 (d, J = 5.1 Hz, 6H). |
| 85 | 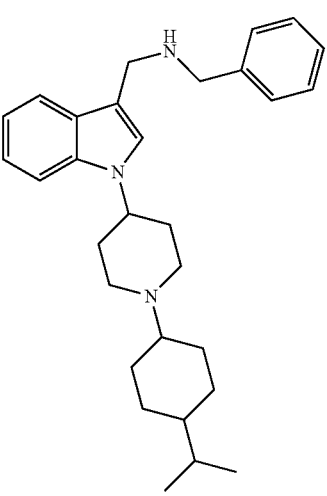 [SMILES: CC(C)C1CCC(N2CCC(n3cc(CNCc4ccccc4)c4ccccc43)CC2)CC1] | N-benzyl-1-(1-(1-cis-4-isopropylcyclohexyl)piperidin-4-yl)-1H-indol-3-yl)methanamine | H$^1$ NMR (CDCl$_3$): δ 7.64-7.61 (m, 1H), 7.37-7.31 (m, 4H), 7.23-7.18 (m, 3H), 7.12-7.07 (m, 2H), 4.18-4.17 (m, 1H), 4.07 (s, 1H), 4.00 (s, 1H), 3.88 (s, 1H), 3.17 (d, J = 8.4 Hz, 2H), 2.32-2.18 (m, 4H), 2.06-2.07 (m, 5H), 1.69-1.63 (m, 4H), 1.55-1.54 (m, 3H), 1.39 (br s, 2H), 1.71-1.15 (br s, 1H), 0.89 (d, J = 4.8 Hz, 6H). |

TABLE 1-continued

| No. | Structure* | IUPAC Name | NMR (300 or 400 MHz) or TLC |
|---|---|---|---|
| 86 | 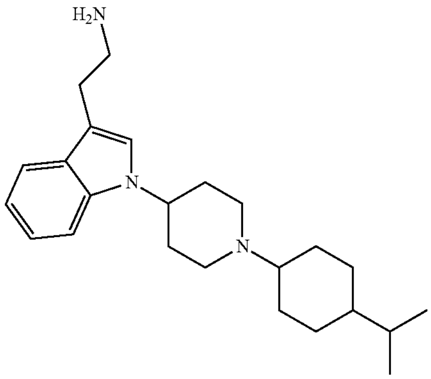 [SMILES: CC(C)C1CCC(N2CCC(n3cc(CCN)c4ccccc43)CC2)CC1] | 2-(1-(1-cis-4-isopropylcyclohexyl)piperidin-4-yl)-1H-indol-3-yl)ethan-1-amine | $^1$H NMR (CDCl$_3$) d 7.61 (d, J = 5.7 Hz, 1H), 7.37 (d, J = 6.0 Hz, 1H), 7.21 (t, J = 5.7 Hz, 1H), 7.10 (m, 2H), 4.18 (m, 1H), 3.19 (d, J = 8.7 Hz, 2H), 3.02 (t, J = 5.1 Hz, 2H), 2.91 (t, J = 5.1 Hz, 2H), 2.33 (m, 1H), 2.26 (t, J = 8.7 Hz, 2H), 2.12-2.00 (m, 4H), 1.78-1.36 (m, 11H), 1.15 (m, 1H), 0.90 (d, J = 4.8 Hz, 6H) |
| 87 | 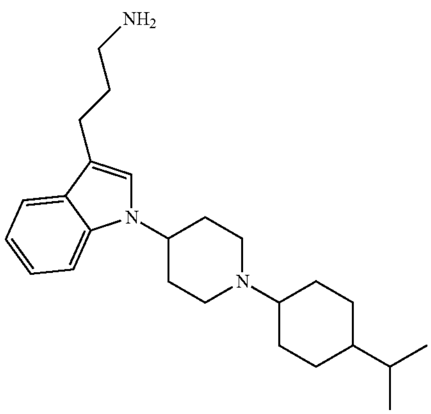 [SMILES: CC(C)C1CCC(N2CCC(n3cc(CCCN)c4ccccc43)CC2)CC1] | 3-(1-(1-cis-4-isopropylcyclohexyl)piperidin-4-yl)-1H-indol-3-yl)propan-1-amine | $^1$H NMR (CDCl$_3$) δ, 7.60 (d, J = 6.0 Hz, 1H), 7.35 (d, J = 6.0 Hz, 1H), 7.19 (t, J = 5.4 Hz, 1H), 7.09 (t, J = 5.4 Hz, 1H), 7.04 (s, 1H), 4.17 (m, 1H), 3.18 (d, J = 9.0 Hz, 2H), 2.79 (m, 4H), 2.33 (m, 1H), 2.25 (dt, J = 9.0, 1.8 Hz, 2H), 2.10-1.97 (m, 6H), 1.90 (p, J = 5.4 Hz, 2H), 1.78-1.52 (m, 7H), 1.41 (m, 2H), 1.14 (m, 1H), 0.90 (d, J = 4.8 Hz, 6H) |
| 88 | 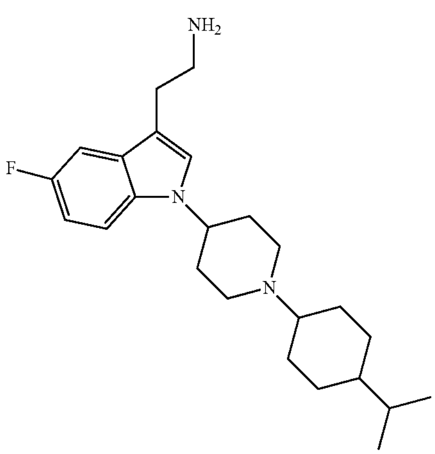 [SMILES: CC(C)C1CCC(N2CCC(n3cc(CCN)c4cc(F)ccc43)CC2)CC1] | 2-(5-fluoro-1-(1-cis-4-isopropylcyclohexyl)piperidin-4-yl)-1H-indol-3-yl)ethan-1-amine | $^1$H NMR (CDCl$_3$) δ, 7.25 (m, 2H), 7.13 (s, 1H), 6.94 (dt, J = 6.9, 1.8 Hz, 1H), 4.13 (m, 1H), 3.19 (d, J = 8.7 Hz, 2H), 3.00 (t, J = 5.1 Hz, 2H), 2.86 (t, J = 5.1 Hz, 2H), 2.33 (m, 1H), 2.23 (t, J = 8.7 Hz, 2H), 2.10-1.96 (m, 4H), 1.75-1.50 (m, 7H), 1.41 (m, 4H), 1.16 (m, 1H), 0.91 (d, J = 6.1 Hz, 6H) |

TABLE 1-continued

| No. | Structure* | IUPAC Name | NMR (300 or 400 MHz) or TLC |
|---|---|---|---|
| 89 | 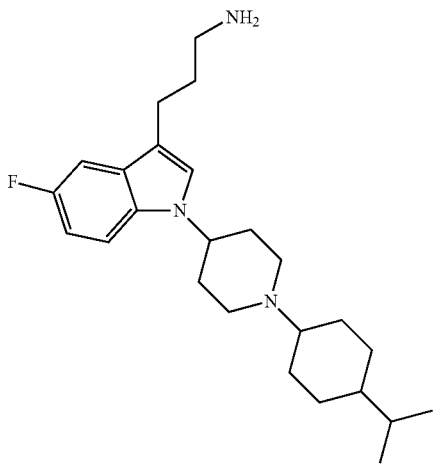 [SMILES: CC(C)C1CCC(N2CCC(n3cc(CCCN)c4cc(F)ccc43)CC2)CC1] | 3-(5-fluoro-1-(1-cis-4-isopropylcyclohexyl)piperidin-4-yl)-1H-indol-3-yl)propan-1-amine | $^1$H NMR (CDCl$_3$) δ, 7.23 (m, 2H), 7.07 (s, 1H), 6.93 (dt, J = 6.9, 1.8 Hz, 1H), 4.12 (m, 1H), 3.18 (d, J = 8.7 Hz, 2H), 2.77 (m ,4H), 2.32 (m, 1H), 2.40 (t, J = 8.7 Hz, 2H), 2.10-1.96 (m, 4H), 1.83 (p, J = 5.7 Hz, 2H), 1.75-1.36 (m, 11H), 1.16 (m, 1H), 0.90 (d, J = 5.1 Hz, 6H) |
| 90 | 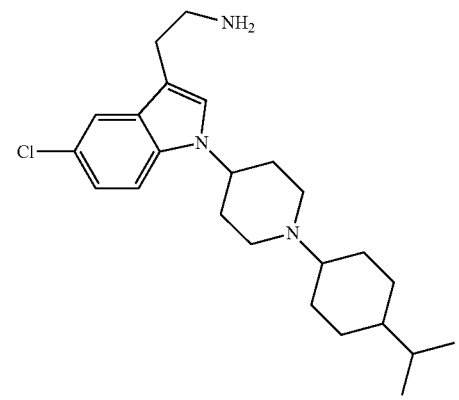 [SMILES: CC(C)C1CCC(N2CCC(n3cc(CCN)c4cc(Cl)ccc43)CC2)CC1] | 2-(5-chloro-1-(1-cis-4-isopropylcyclohexyl)piperidin-4-yl)-1H-indol-3-yl)ethan-1-amine | $^1$H NMR (CDCl$_3$) δ, 7.56 (d, J = 1.5 Hz, 1H), 7.27 (d, J = 6.3 Hz, 1H), 7.14 (dd, J = 6.6, 1.5 Hz, 1H), 7.06 (s, 1H), 4.12 (m, 1H), 3.18 (d, J = 8.7 Hz, 2H), 2.74 (m, 3H), 2.32 (m, 1H), 2.24 (t, J = 8.7 Hz, 2H), 2.04 (m, 5H), 1.83 (q, J = 5.4 Hz, 1H), 1.75-1.48 (m, 7H), 1.42 (m, 2H), 1.15 (m, 1H), 0.90 (d, J = 5.1 Hz, 6H) |
| 91 | 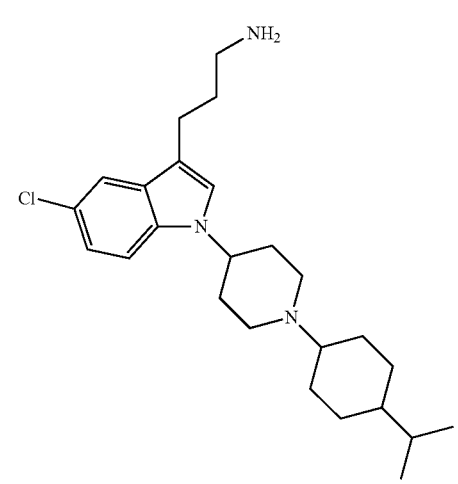 [SMILES: CC(C)C1CCC(N2CCC(n3cc(CCCN)c4cc(Cl)ccc43)CC2)CC1] | 3-(5-chloro-1-(1-cis-4-isopropylcyclohexyl)piperidin-4-yl)-1H-indol-3-yl)propan-1-amine | $^1$H NMR (CDCl$_3$) δ, 7.54 (m, 1H), 7.24 (d, J = 6.6 Hz, 1H), 7.13 (dd, J = 6.6, 1.5 Hz, 1H), 7.06 (s, 1H), 4.12 (m, 1H), 3.18 (d, J = 8.7 Hz, 2H), 2.76 (m, 3H), 2.33 (m, 1H), 2.24 (t, J = 8.7 Hz, 2H), 2.05 (m, 5H), 1.84 (m, 1H), 1.75-1.50 (m, 10H), 1.41 (m, 2H), 1.15 (m, 1H), 0.90 (d, J = 5.1 Hz, 6H) |

TABLE 1-continued

| No. | Structure* | IUPAC Name | NMR (300 or 400 MHz) or TLC |
|---|---|---|---|
| 92 | 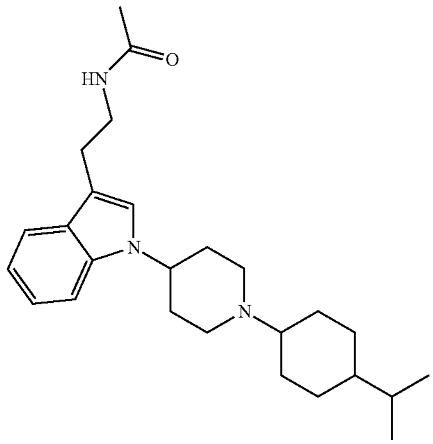 [SMILES: CC(=O)NCCc1cn(C2CCN(C3CCC(C(C)C)CC3)CC2)c2ccccc12] | N-(2-(1-(1-cis-4-isopropylcyclohexyl)piperidin-4-yl)-1H-indol-3-yl)acetamide | ¹H NMR (CDCl₃) δ, d 7.60 (d, J = 5.7 Hz, 1H), 7.38 (d, J = 6.3 Hz, 1H), 7.23 (t, J = 5.4 Hz, 1H), 7.12 (m, 2H), 5.32 (br, 1H), 4.19 (m, 1H), 3.58 (q, J = 4.8 Hz, 2H), 3.20 (d, J = 8.7 Hz, 2H), 2.97 (t, J = 4.8 Hz, 2H), 2.30 (m, 3H), 2.05 (m, 4H), 1.93 (s, 3H), 1.75-1.50 (m, 8H), 1.41 (m, 2H), 1.15 (m, 1H), 0.90 (d, J = 5.1 Hz, 6H) |
| 93 | 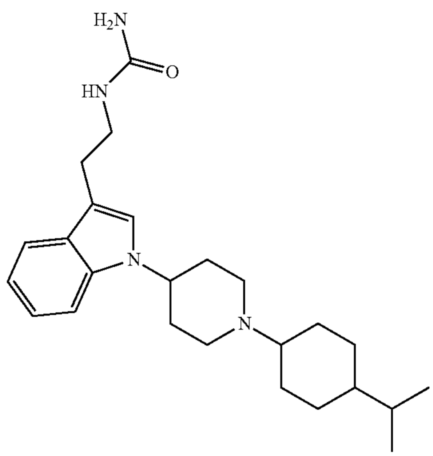 [SMILES: CC(C)C1CCC(N2CCC(n3cc(CCNC(N)=O)c4ccccc43)CC2)CC1] | 2-(1-(1-cis-4-isopropylcyclohexyl)piperidin-4-yl)-1H-indol-3-yl)ethyl)urea | ¹H NMR (CDCl₃) δ, 7.60 (d, J = 6.3 Hz, 1H), 7.37 (d, J = 6.3 Hz, 1H), 7.22 (t, J = 5.4 Hz, 1H), 7.11 (m, 2H), 4.55 (m, 1H), 4.18 (m, 3H), 3.50 (q, J = 4.8 Hz, 2H), 3.18 (d, J = 9.0 Hz, 2H), 2.97 (t, J = 4.8 Hz, 2H), 2.33 (m, 1H), 2.25 (m, 2H), 2.05 (m, 4H), 1.75-1.50 (m, 7H), 1.40 (m, 2H), 1.15 (m, 1H), 0.90 (d, J = 5.1 Hz, 6H) |
| 94 | 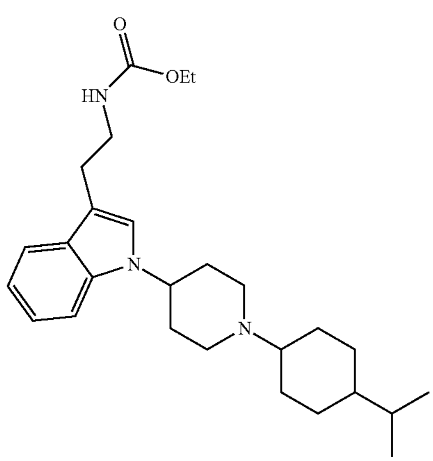 [SMILES: CCOC(=O)NCCc1cn(C2CCN(C3CCC(C(C)C)CC3)CC2)c2ccccc12] | ethyl (2-(1-(1-cis-4-isopropylcyclohexyl)piperidin-4-yl)-1H-indol-3-yl)ethyl)carbamate | ¹H NMR (CDCl₃) δ 7.60 (d, J = 7.8 Hz, 1H), 7.37 (d, J = 8.1 Hz, 1H), 7.22 (m, 1H), 7.11 (m, 2H), 4.70 (br, 1H), 4.13 (m, 3H), 3.49 (m, 2H), 3.20 (m, 2H), 2.97 (t, J = 6.9 Hz, 2H), 2.29 (m, 2H), 2.05 (m, 4H), 1.75-1.50 (m, 8H), 1.40 (m, 2H), 1.24 (t, J = 7.2 Hz, 3H), 1.16 (m, 1H), 0.91 (d, J = 6.6 Hz, 6H) |

TABLE 1-continued

| No. | Structure* | IUPAC Name | NMR (300 or 400 MHz) or TLC |
|---|---|---|---|
| 95 | 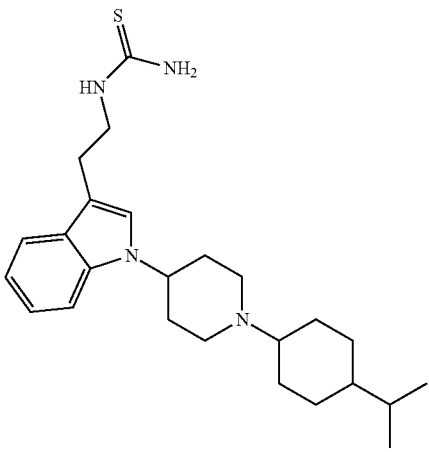 [SMILES: CC(C)C1CCC(N2CCC(n3cc(CCNC(N)=S)c4ccccc43)CC2)CC1] | 1-(2-(1-(1-cis-4-isopropylcyclohexyl)piperidin-4-yl)-1H-indol-3-yl)ethyl)thiourea | $^1$H NMR (CDCl$_3$) δ, 7.58 (br, 1H), 7.38 (d, J = 6.3 Hz, 1H), 7.23 (t, J = 5.4 Hz, 1H), 7.12 (m, 2H), 6.23 (br, 1H), 5.68 (br, 2H), 4.20 (m, 1H), 3.22 (d, J = 8.4 Hz, 2H), 3.06 (t, J = 5.1 Hz, 2H), 2.45-2.07 (m, 8H), 1.80-1.52 (m, 7H), 1.43 (m, 2H), 1.16 (m, 1H), 0.90 (d, J = 5.1 Hz, 6H) |
| 96 | 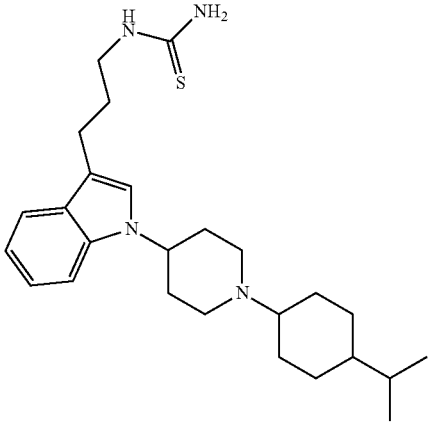 [SMILES: CC(C)C1CCC(N2CCC(n3cc(CCCNC(N)=S)c4ccccc43)CC2)CC1] | 1-(3-(1-(1-cis-4-isopropylcyclohexyl)piperidin-4-yl)-1H-indol-3-yl)propyl)thiourea | $^1$H NMR (CDCl$_3$) δ, 7.56 (d, J = 6.0 Hz, 1H), 7.36 (d, J = 6.0 Hz, 1H), 7.21 (t, J = 5.7 Hz, 1H), 7.10 (m, 2H), 6.26 (br, 1H), 5.66 (br, 2H), 4.17 (m, 1H), 3.19 (m, 3H), 2.85 (t, J = 5.1 Hz, 2H), 2.30 (m, 3H), 2.10-1.94 (m, 6H), 1.77-1.55 (m, 6H), 1.42 (m, 2H), 1.27 (m, 2H), 1.15 (m, 1H), 0.90 (d, J = 4.8 Hz, 6H) |
| 97 | 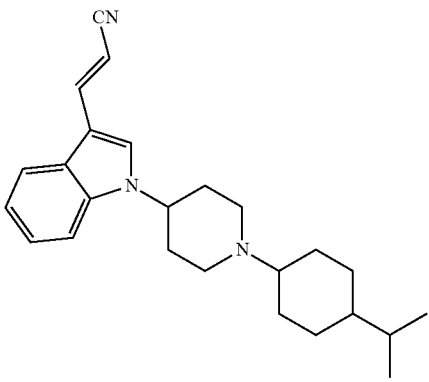 [SMILES: CC(C)C1CCC(N2CCC(n3cc(/C=C/C#N)c4ccccc43)CC2)CC1] | (E)-3-(1-(1-cis-4-isopropylcyclohexyl)piperidin-4-yl)-1H-indol-3-yl)acrylonitrile | $^1$H NMR (CDCl$_3$) δ, 7.77 (d, J = 6.3 Hz, 1H), 7.56-7.42 (m, 2H), 7.44 (d, J = 6.3 Hz, 1H), 7.34-7.25 (m, 2H), 5.74 (d, J = 12.3 Hz, 1H), 4.21 (m, 1H), 3.21 (d, J = 8.7 Hz, 2H), 2.34 (m, 1H), 2.26 (t, J = 8.4 Hz, 2H), 2.12 (m, 2H), 2.02 (m, 2H), 1.75-1.50 (m, 7H), 1.42 (m, 2H), 1.16 (m, 1H), 0.91 (d, J = 4.8 Hz, 6H) |

TABLE 1-continued

| No. | Structure* | IUPAC Name | NMR (300 or 400 MHz) or TLC |
|---|---|---|---|
| 98 | 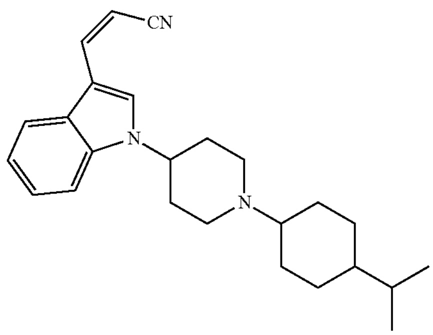 [SMILES: CC(C)C1CCC(N2CCC(n3cc(/C=C\C#N)c4ccccc43)CC2)CC1] | (Z)-3-(1-(1-cis-4-isopropylcyclohexyl)piperidin-4-yl)-1H-indol-3-l)acrylonitrile | $^1$H NMR (CDCl$_3$) δ, 8.39 (s, 1H), 7.71 (d, J = 5.7 Hz, 1H), 7.44 (m, 2H), 7.27 (m, 2H), 5.15 (d, J = 8.4 Hz, 1H), 4.26 (m, 1H), 3.22 (d, J = 7.8 Hz, 2H), 2.35 2.22 (m, 3H), 2.14 (m, 4H), 1.75-1.50 (m, 7H), 1.41 (m, 2H), 1.14 (m, 1H), 0.90 (d, J = 5.1 Hz, 6H) |
| 99 | 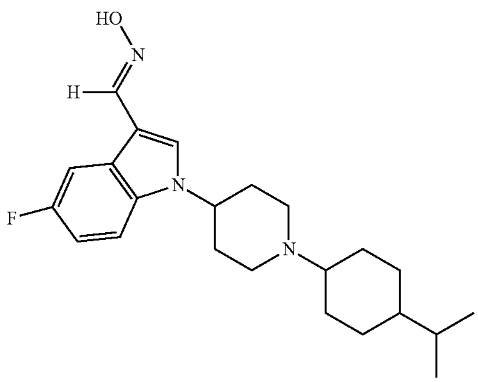 [SMILES: CC(C)C1CCC(N2CCC(n3cc(/C=N/O)c4cc(F)ccc43)CC2)CC1] | 5-fluoro-1-(1-(cis-4-isopropylcyclohexyl)piperidin-4-yl)-1H-indole-3-carbaldehyde oxime | |
| 100 | 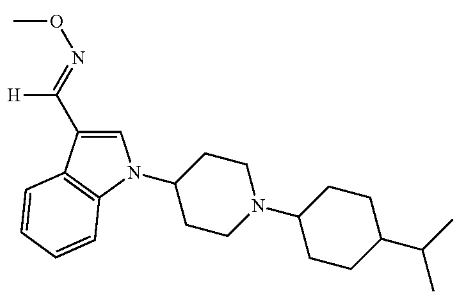 [SMILES: CO/N=C/c1cn(C2CCN(C3CCC(C(C)C)CC3)CC2)c2ccccc12] | 1-(1-(cis-4-isopropylcyclohexyl)piperidin-4-yl)-1H-indole-3-carbaldehyde O-methyl oxime | |
| 101 | 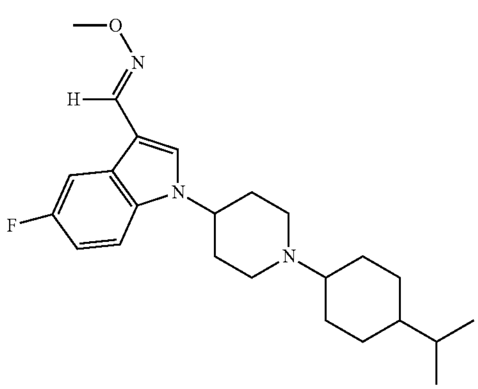 [SMILES: CO/N=C/c1cn(C2CCN(C3CCC(C(C)C)CC3)CC2)c2ccc(F)cc12] | 5-fluoro-1-(1-(cis-4-isopropylcyclohexyl)piperidin-4-yl)-1H-indole-3-carbaldehyde O-methyl oxime | |

TABLE 1-continued

| No. | Structure* | IUPAC Name | NMR (300 or 400 MHz) or TLC |
|---|---|---|---|
| 102 | 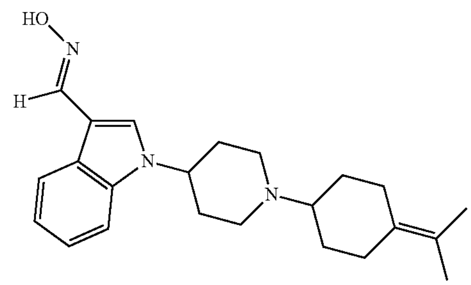 [SMILES: CC(C)=C1CCC(N2CCC(n3cc(/C=N/O)c4ccccc43)CC2)CC1] | 1-(1-(4-(propan-2-ylidene)cylcohexyl)piperidin-4-yl)-1H-indole-3-carbaldehyde oxime | |
| 103 | 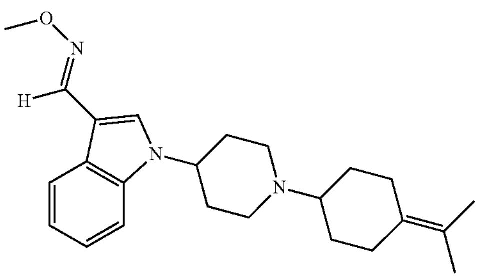 [SMILES: CO/N=C/c1cn(C2CCN(C3CCC(=C(C)C)CC3)CC2)c2ccccc12] | 1-(1-(4-(propan-2-ylidene)cyclohexyl)piperidin-4-yl)-1H-indole-3-carbaldehyde O-methyl oxime | |
| 104 | 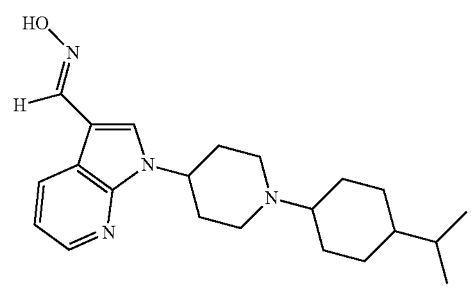 [SMILES: CC(C)C1CCC(N2CCC(n3cc(/C=N/O)c4cccnc43)CC2)CC1] | 1-(1-(cis-4-isopropylcyclohexyl)piperidin-4-yl)-1H-pyrrolo[2,3-b]pyridine-3-carbaldehyde oxime | |
| 105 | 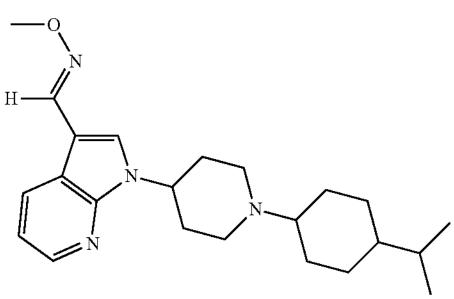 [SMILES: CO/N=C/c1cn(C2CCN(C3CCC(C(C)C)CC3)CC2)c2ncccc12] | 1-(1-(cis-4-isopropylcyclohexyl)piperidin-4-yl)-1H-pyrrolo[2,3-b]pyridine-3-carbaldehyde O-methyl oxime | |
| 106 | 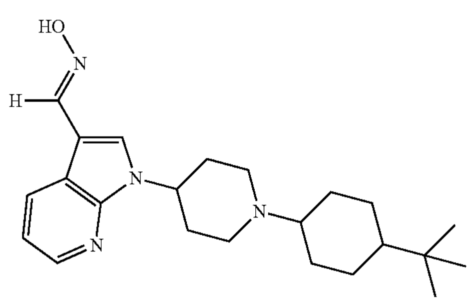 [SMILES: CC(C)(C)C1CCC(N2CCC(n3cc(/C=N/O)c4cccnc43)CC2)CC1] | 1-(1-(cis-4-(tert-butyl)cyclohexyl)piperidin-4-yl)-1H-indole-3-carbaldehyde oxime | |

TABLE 1-continued

| No. | Structure* | IUPAC Name | NMR (300 or 400 MHz) or TLC |
|---|---|---|---|
| 107 | 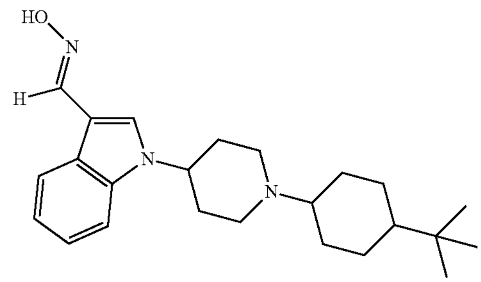 [SMILES: CC(C)(C)C1CCC(N2CCC(n3cc(/C=N/O)c4ccccc43)CC2)CC1] | 1-(1-(cis-4-(tert-butyl)cyclohexyl)piperidin-4-yl)-5-fluoro-1H-indole-3-carbaldehyde oxime | |
| 108 | 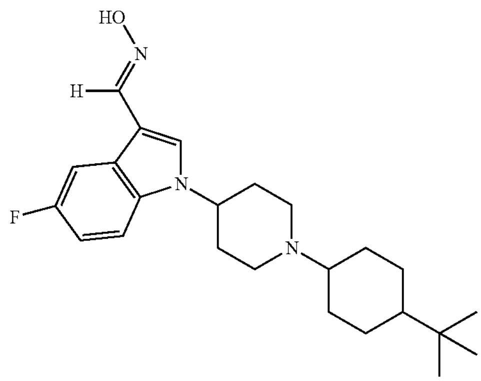 [SMILES: CC(C)(C)C1CCC(N2CCC(n3cc(/C=N/O)c4cc(F)ccc43)CC2)CC1] | 1-(1-(cis-4-(tert-butyl)cyclohexyl)piperidin-4-yl)-1H-pyrrolo[2,3-b]pyridine-3-carbaldehyde oxime | |
| 109 | 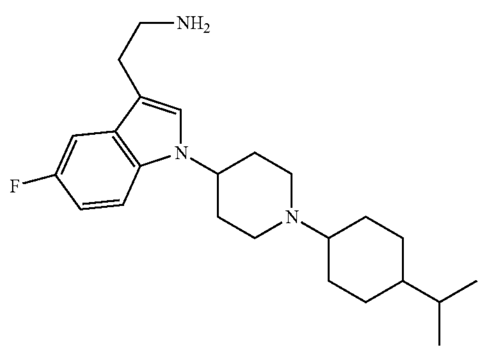 [SMILES: CC(C)C1CCC(N2CCC(n3cc(CCN)c4cc(F)ccc43)CC2)CC1] | 2-(5-fluoro-1-(1-(cis-4-isopropylcyclohexyl)piperidin-4-yl)-1H-indol-3-yl)ethan-1-amine | |
| 110 | 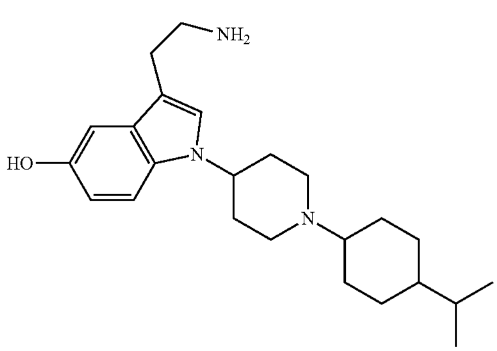 [SMILES: CC(C)C1CCC(N2CCC(n3cc(CCN)c4cc(O)ccc43)CC2)CC1] | 3-(2-aminoethyl)-1-(1-(cis-4-isopropylcyclohexyl)piperidin-4-yl)-1H-indol-5-ol | |

TABLE 1-continued

| No. | Structure* | IUPAC Name | NMR (300 or 400 MHz) or TLC |
|---|---|---|---|
| 111 | 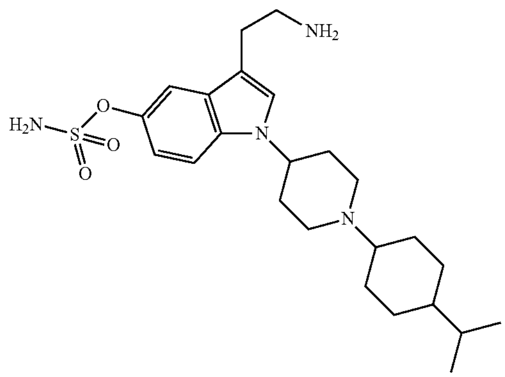 [SMILES: CC(C)C1CCC(N2CCC(n3cc(CCN)c4cc(OS(N)(=O)=O)ccc43)CC2)CC1] | 3-(2-aminoethyl)-1-(1-(cis-4-isopropylcyclohexyl)piperidin-4-yl)-1H-indol-5-yl sulfamate | |
| 112 | 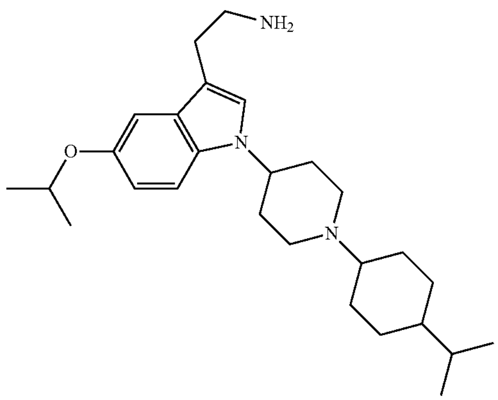 [SMILES: CC(C)Oc1ccc2c(c1)c(CCN)cn2C1CCN(C2CCC(C(C)C)CC2)CC1] | 2-(5-isopropoxy-1-(1-(cis-4-isopropylcyclohexyl)piperidin-4-yl)-1H-indol-3-yl)ethan-1-amine | |
| 113 | 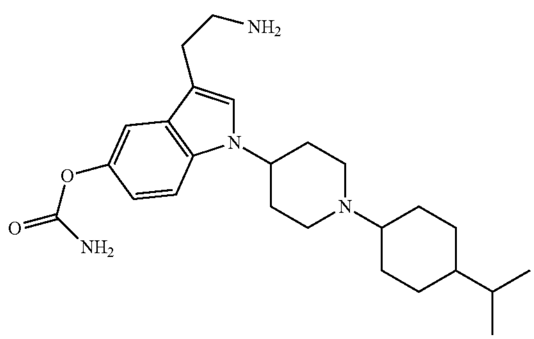 [SMILES: CC(C)C1CCC(N2CCC(n3cc(CCN)c4cc(OC(N)=O)ccc43)CC2)CC1] | 3-(2-aminoethyl)-1-(1-(cis-4-isopropylcyclohexyl)piperidin-4-yl)-1H-indol-5-yl carbamate | |
| 114 | 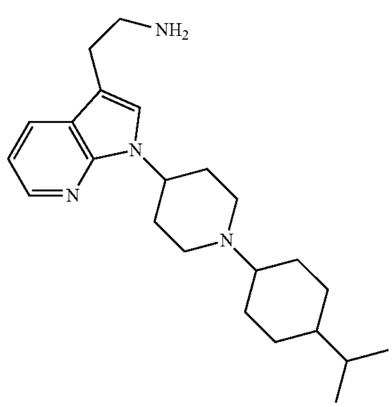 [SMILES: CC(C)C1CCC(N2CCC(n3cc(CCN)c4cccnc43)CC2)CC1] | 2-(1-(1-(cis-4-isopropylcyclohexyl)piperidin-4-yl)-1H-pyrrolo[2,3-b]pyridin-3-yl)ethan-1-amine | |

TABLE 1-continued

| No. | Structure* | IUPAC Name | NMR (300 or 400 MHz) or TLC |
|---|---|---|---|
| 115 | 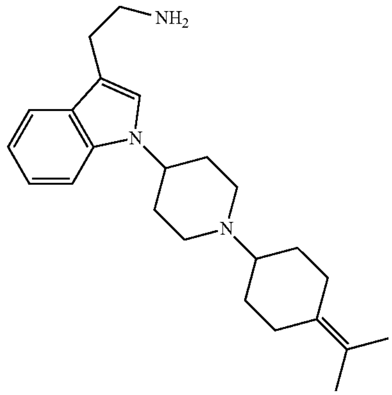 [SMILES: CC(C)=C1CCC(N2CCC(n3cc(CCN)c4ccccc43)CC2)CC1] | 2-(1-(1-(4-(propan-2-ylidene)cyclohexyl)piperidin-4-yl)-1H-indol-3-yl)ethan-1-amine | |
| 116 | 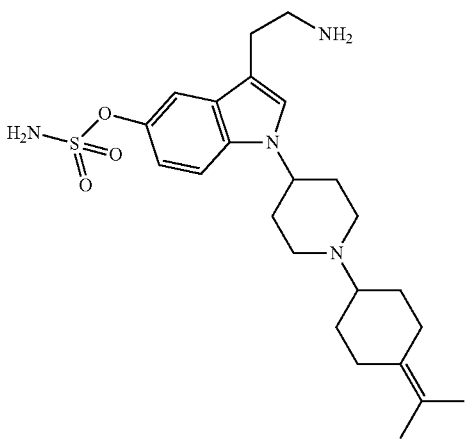 [SMILES: CC(C)=C1CCC(N2CCC(n3cc(CCN)c4cc(OS(N)(=O)=O)ccc43)CC2)CC1] | 3-(2-aminoethyl)-1-(1-(4-(propan-2-ylidene)cyclohexyl)piperidin-4-yl)-1H-indol-5-yl sulfamate | |
| 117 | 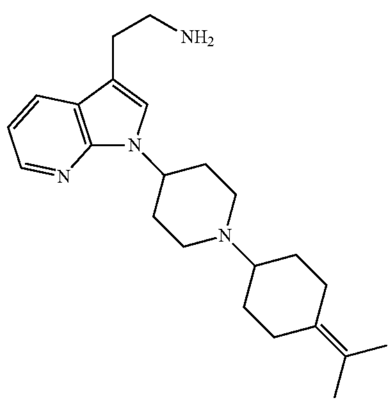 [SMILES: CC(C)=C1CCC(N2CCC(n3cc(CCN)c4cccnc43)CC2)CC1] | 2-(1-(1-(4-(propan-2-ylidene)cyclohexyl)piperidin-4-yl)-1H-pyrrolo[2,3-b]pyridin-3-yl)ethan-1-amine | |
| 118 | 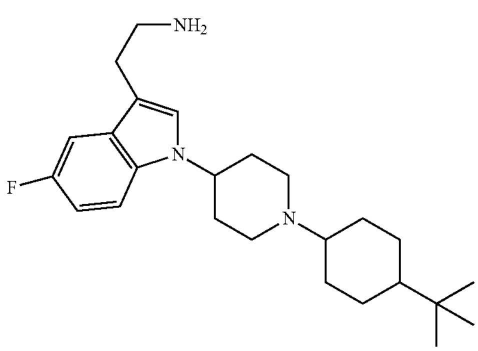 [SMILES: CC(C)(C)C1CCC(N2CCC(n3cc(CCN)c4cc(F)ccc43)CC2)CC1] | 2-(1-(1-(cis-4-(tert-butyl)cyclohexyl)piperidin-4-yl)-5-fluoro-1H-indol-3-yl)ethan-1-amine | |

TABLE 1-continued

| No. | Structure* | IUPAC Name | NMR (300 or 400 MHz) or TLC |
|---|---|---|---|
| 119 | 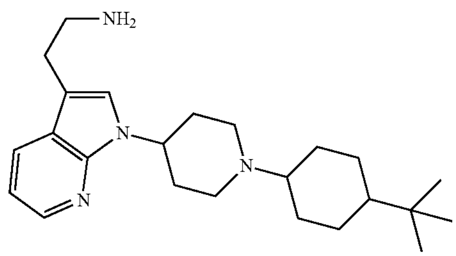 [SMILES: CC(C)(C)C1CCC(N2CCC(n3cc(CCN)c4cccnc43)CC2)CC1] | 2-(1-(1-(cis-4-(tert-butyl)cyclohexyl)piperidin-4-yl)-1H-pyrrolo[2,3-b]pyridin-3-yl)ethan-1-amine | |
| 120 | 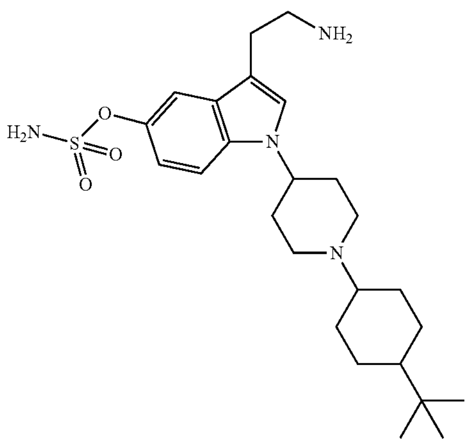 [SMILES: CC(C)(C)C1CCC(N2CCC(n3cc(CCN)c4cc(OS(N)(=O)=O)ccc43)CC2)CC1] | 3-(2-aminoethyl)-1-(1-(cis-4-(tert-butyl)cyclohexyl)piperidin-4-yl)-1H-indol-5-yl sulfamate | |
| 121 | 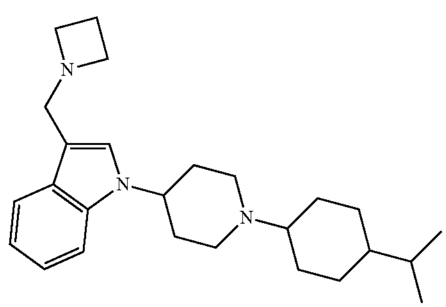 [SMILES: CC(C)C1CCC(N2CCC(n3cc(CN4CCC4)c4ccccc43)CC2)CC1] | 3-(azetidin-1-ylmethyl)-1-(1-(cis-4-isopropylcyclohexyl)piperidin-4-yl)-1H-indole | |
| 122 | 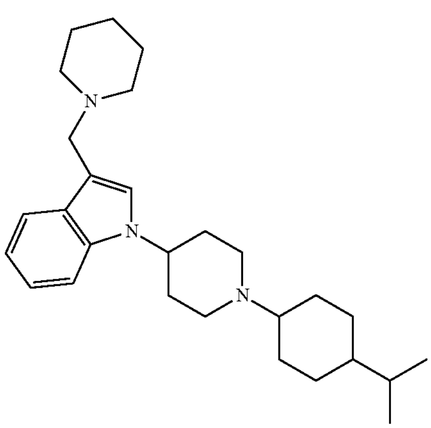 [SMILES: CC(C)C1CCC(N2CCC(n3cc(CN4CCCCC4)c4ccccc43)CC2)CC1] | 1-(1-(cis-4-isopropylcyclohexyl)piperidin-4-yl)-3-(piperidin-1-ylmethyl)-1H-indole | |

TABLE 1-continued

| No. | Structure* | IUPAC Name | NMR (300 or 400 MHz) or TLC |
|---|---|---|---|
| 123 | 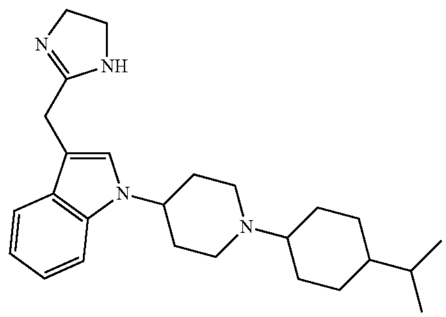 [SMILES: CC(C)C1CCC(N2CCC(n3cc(CC4=NCCN4)c4ccccc43)CC2)CC1] | 3-((4,5-dihydro-1H-imidazol-2-yl)methyl)-1-(1-(cis-4-isopropylcyclohexyl)piperidin-4-yl)-1H-indole | |
| 124 | 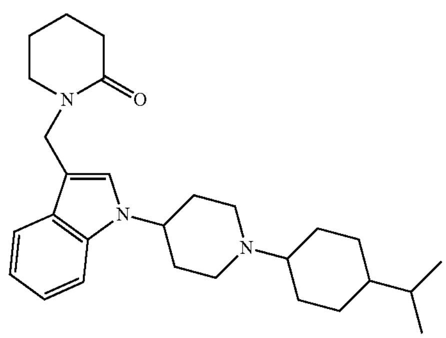 [SMILES: CC(C)C1CCC(N2CCC(n3cc(CN4CCCCC4=O)c4ccccc43)CC2)CC1] | 1-((1-(1-(cis-4-isopropylcyclohexyl)piperidin-4-yl)-1H-indol-3-yl)methyl)piperidin-2-one | |
| 125 | 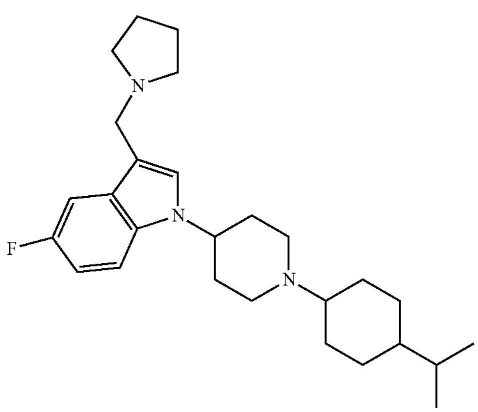 [SMILES: CC(C)C1CCC(N2CCC(n3cc(CN4CCCC4)c4cc(F)ccc43)CC2)CC1] | 5-fluoro-1-(1-(cis-4-isopropylcyclohexyl)piperidin-4-yl)-3-(pyrrolidin-1-ylmethyl)-1H-indole | |
| 126 | 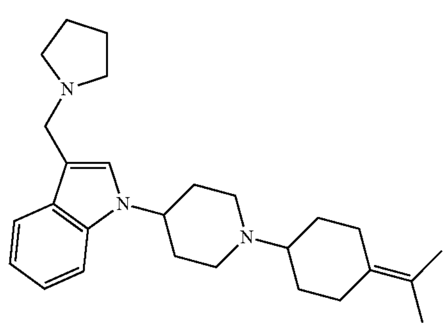 [SMILES: CC(C)=C1CCC(N2CCC(n3cc(CN4CCCC4)c4ccccc43)CC2)CC1] | 1-(1-(4-(propan-2-ylidene)cyclohexyl)piperidin-4-yl)-3-(pyrrolidin-1-ylmethyl)-1H-indole | |

TABLE 1-continued

| No. | Structure* | IUPAC Name | NMR (300 or 400 MHz) or TLC |
|---|---|---|---|
| 127 | 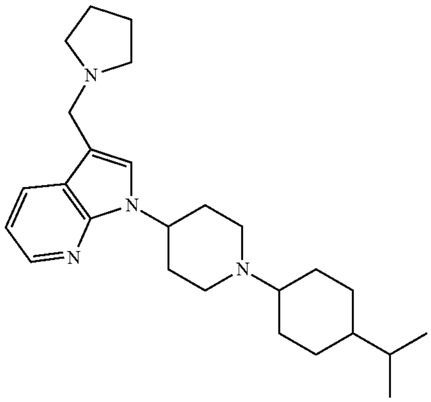 [SMILES: CC(C)C1CCC(N2CCC(n3cc(CN4CCCC4)c4cccnc43)CC2)CC1] | 1-(1-(cis-4-isopropylcyclohexyl)piperidin-4-yl)-3-(pyrrolidin-1-ylmethyl)-1H-pyrrolo[2,3-b]pyridine | |
| 128 | 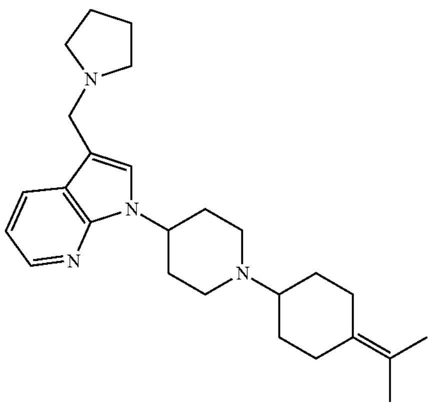 [SMILES: CC(C)=C1CCC(N2CCC(n3cc(CN4CCCC4)c4cccnc43)CC2)CC1] | 1-(1-(4-(propan-2-ylidene)cyclohexyl)piperidin-4-yl)-3-(pyrrolidin-1-ylmethyl)-1H-pyrrolo[2,3-b]pyridine | |
| 129 | 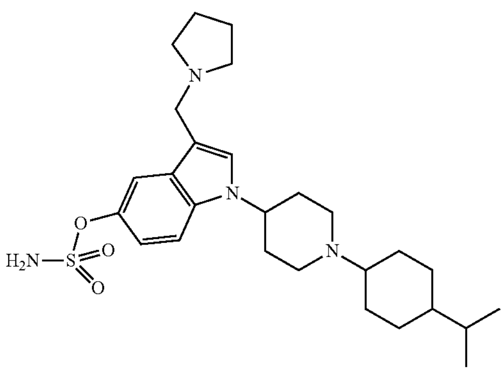 [SMILES: CC(C)C1CCC(N2CCC(n3cc(CN4CCCC4)c4cc(OS(N)(=O)=O)ccc43)CC2)CC1] | 1-(1-(cis-4-isopropylcyclohexyl)piperidin-4-yl)-3-(pyrrolidin-1-ylmethyl)-1H-indol-5-yl sulfamate | |
| 130 | 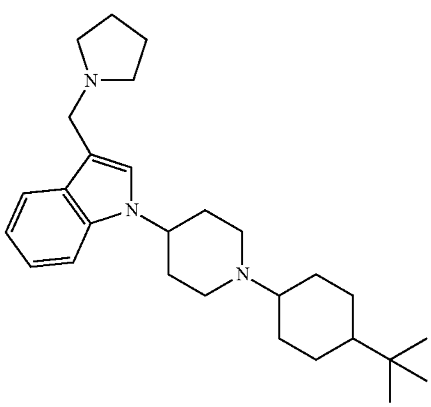 [SMILES: CC(C)(C)C1CCC(N2CCC(n3cc(CN4CCCC4)c4ccccc43)CC2)CC1] | 1-(1-(cis-4-(tert-butyl)cyclohexyl)piperidin-4-yl)-3-(pyrrolidin-1-ylmethyl)-1H-indole | |

TABLE 1-continued

| No. | Structure* | IUPAC Name | NMR (300 or 400 MHz) or TLC |
|---|---|---|---|
| 131 | 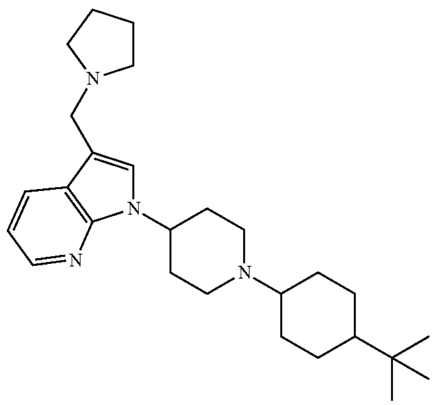 [SMILES: CC(C)(C)C1CCC(N2CCC(n3cc(CN4CCCC4)c4cccnc43)CC2)CC1] | 1-(1-(cis-4-(tert-butyl)cyclohexyl)piperidin-4-yl)-3-(pyrrolidin-1-ylmethyl)-1H-pyrrolo[2,3-b]pyridine | |
| 132 | 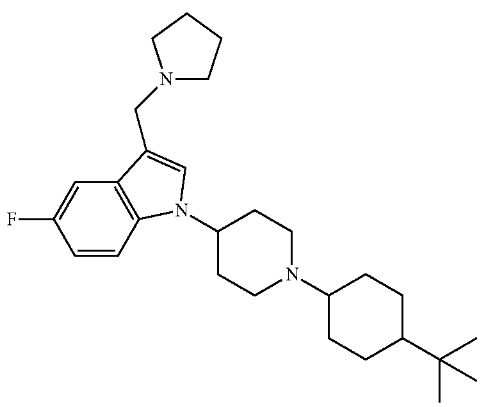 [SMILES: CC(C)(C)C1CCC(N2CCC(n3cc(CN4CCCC4)c4cc(F)ccc43)CC2)CC1] | 1-(1-(cis-4-(tert-butyl)cyclohexyl)piperidin-4-yl)-5-fluoro-3-(pyrrolidin-1-ylmethyl)-1H-indole | |
| 133 | 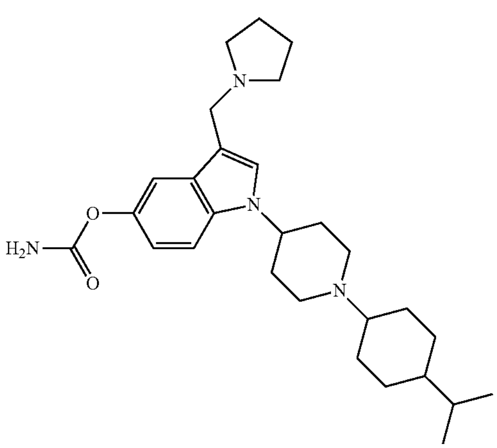 [SMILES: CC(C)C1CCC(N2CCC(n3cc(CN4CCCC4)c4cc(OC(N)=O)ccc43)CC2)CC1] | 1-(1-(cis-4-isopropylcyclohexyl)piperidin-4-yl)-3-(pyrrolidin-1-ylmethyl)-1H-indol-5-yl carbamate | |

TABLE 1-continued

| No. | Structure* | IUPAC Name | NMR (300 or 400 MHz) or TLC |
|---|---|---|---|
| 134 | 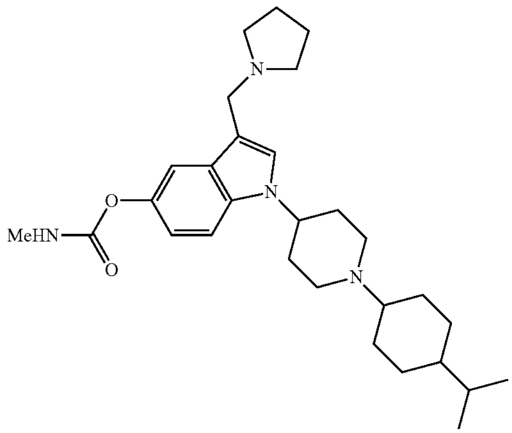 [SMILES: CNC(=O)Oc1ccc2c(c1)c(CN1CCCC1)cn2C1CCN(C2CCC(C(C)C)CC2)CC1] | 1-(1-(cis-4-isopropylcyclohexyl)piperidin-4-yl)-3-(pyrrolidin-1-ylmethyl)-1H-indol-5-yl methylcarbamate | |
| 135 | 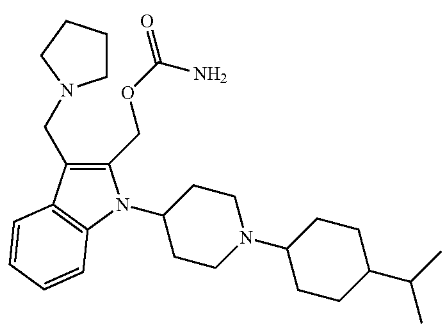 [SMILES: CC(C)C1CCC(N2CCC(n3c(COC(N)=O)c(CN4CCCC4)c4ccccc43)CC2)CC1] | (1-(1-(cis-4-isopropylcyclohexyl)piperidin-4-yl)-3-(pyrrolidin-1-ylmethyl)-1H-indol-2-yl)methyl carbamate | |
| 136 | 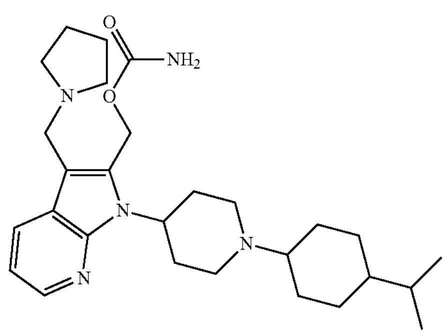 [SMILES: CC(C)C1CCC(N2CCC(n3c(COC(N)=O)c(CN4CCCC4)c4cccnc43)CC2)CC1] | (1-(1-(cis-4-isopropylcyclohexyl)piperidin-4-yl)-3-(pyrrolidin-1-ylmethyl)-1H-pyrrolo[2,3-b]pyridin-2-yl)methyl carbamate | |
| 137 | 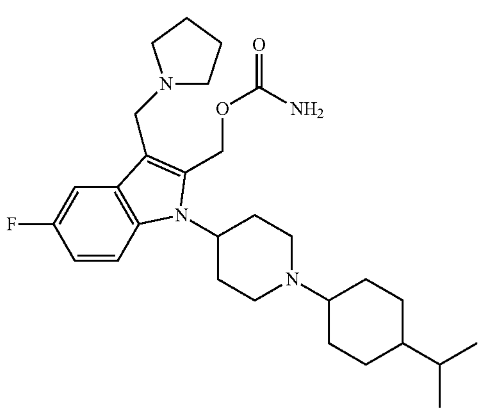 [SMILES: CC(C)C1CCC(N2CCC(n3c(COC(N)=O)c(CN4CCCC4)c4cc(F)ccc43)CC2)CC1] | (5-fluoro-1-(1-(cis-4-isopropylcyclohexyl)piperidin-4-yl)-3-(pyrrolidin-1-ylmethyl)-1H-indol-2-yl)methyl carbamate | |

| No. | Structure* | IUPAC Name | NMR (300 or 400 MHz) or TLC |
|---|---|---|---|
| 138 | 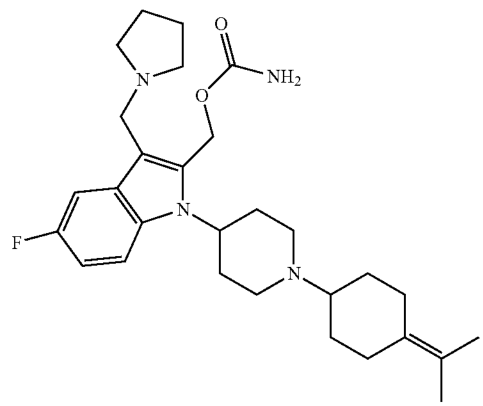 [SMILES: CC(C)=C1CCC(N2CCC(n3c(COC(N)=O)c(CN4CCCC4)c4cc(F)ccc43)CC2)CC1] | (5-fluoro-1-(1-(4-(propan-2-ylidene)cyclohexyl)piperidin-4-yl)-3-(pyrrolidin-1-ylmethyl)-1H-indol-2-yl)methyl carbamate | |
| 139 | 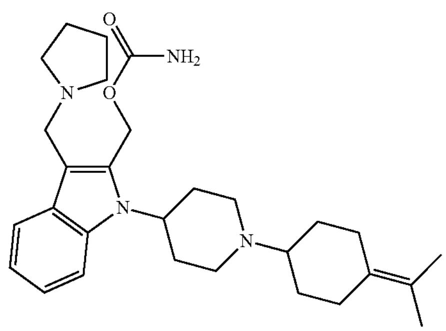 [SMILES: CC(C)=C1CCC(N2CCC(n3c(COC(N)=O)c(CN4CCCC4)c4ccccc43)CC2)CC1] | (1-(1-(4-(propan-2-ylidene)cyclohexyl)piperidin-4-yl)-3-(pyrrolidin-1-ylmethyl)-1H-indol-2-yl)methyl carbamate | |
| 140 | 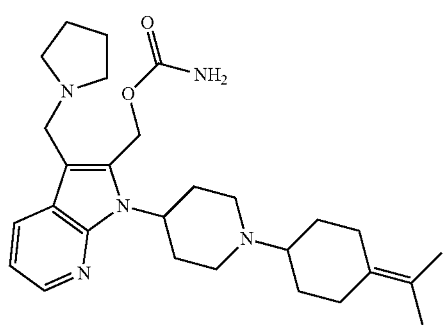 [SMILES: CC(C)=C1CCC(N2CCC(n3c(COC(N)=O)c(CN4CCCC4)c4cccnc43)CC2)CC1] | (1-(1-(4-(propan-2-ylidene)cyclohexyl)piperidin-4-yl)-3-(pyrrolidin-1-ylmethyl)-1H-pyrrolo[2,3-b]pyridin-2-yl)methyl carbamate | |
| 141 | 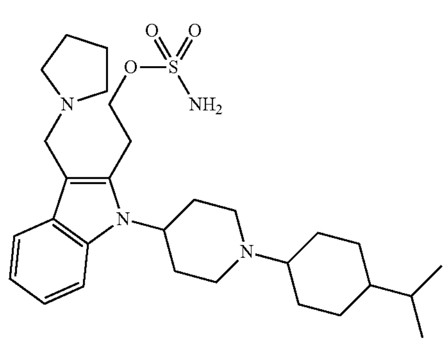 [SMILES: CC(C)C1CCC(N2CCC(n3c(CCOS(N)(=O)=O)c(CN4CCCC4)c4ccccc43)CC2)CC1] | 2-(1-(1-(cis-4-isopropylcyclohexyl)piperidin-4-yl)-3-(pyrrolidin-1-ylmethyl)-1H-indol-2-yl)ethy sulfamate | |

TABLE 1-continued

| No. | Structure* | IUPAC Name | NMR (300 or 400 MHz) or TLC |
|---|---|---|---|
| 142 | 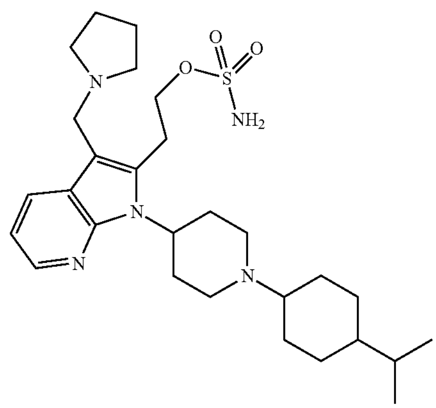 [SMILES: CC(C)C1CCC(N2CCC(n3c(CCOS(N)(=O)=O)c(CN4CCCC4)c4cccnc43)CC2)CC1] | 2-(1-(1-(cis-4-isopropylcyclohexyl)piperidin-4-yl)-3-(pyrrolidin-1-ylmethyl)-1H-pyrrolo[2,3-b]pyridin-2-yl)ethyl sulfamate | |
| 143 | 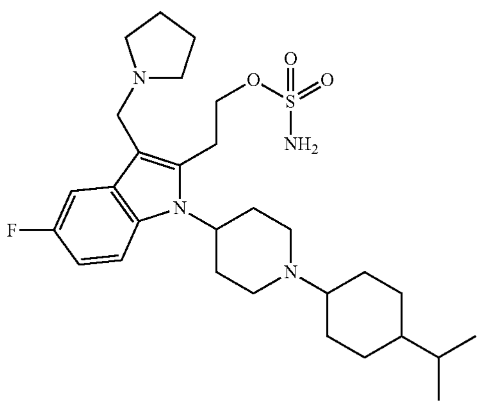 [SMILES: CC(C)C1CCC(N2CCC(n3c(CCOS(N)(=O)=O)c(CN4CCCC4)c4cc(F)ccc43)CC2)CC1] | 2-(5-fluoro-1-(1-(cis-4-isopropylcyclohexyl)piperidin-4-yl)-3-(pyrrolidin-1-ylmethyl)-1H-indol-2-yl)ethyl sulfamate | |
| 144 | 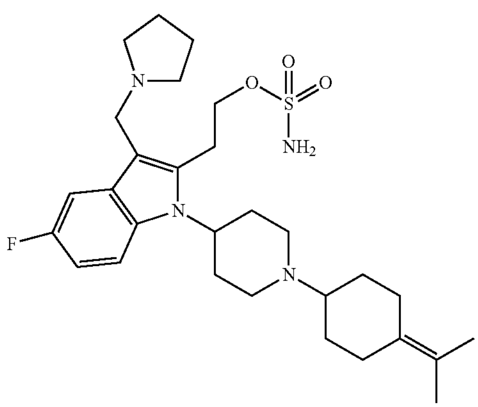 [SMILES: CC(C)=C1CCC(N2CCC(n3c(CCOS(N)(=O)=O)c(CN4CCCC4)c4cc(F)ccc43)CC2)CC1] | 2-(5-fluoro-1-(1-(4-(propan-2-ylidene)cyclohexyl)piperidin-4-yl)-3-(pyrrolidin-1-ylmethyl)-1H-indol-2-yl)ethyl sulfamate | |
| 145 | 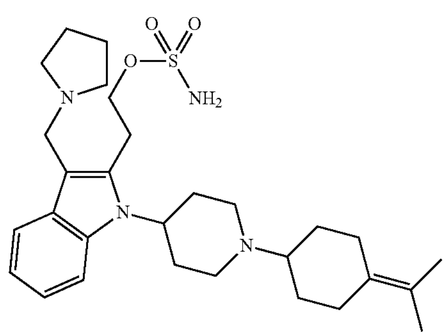 [SMILES: CC(C)=C1CCC(N2CCC(n3c(CCOS(N)(=O)=O)c(CN4CCCC4)c4ccccc43)CC2)CC1] | 2-(1-(1-(4-(propan-2-ylidene)cyclohexyl)piperidin-4-yl)-3-(pyrrolidin-1-ylmethyl)-1H-indol-2-yl)ethyl sulfamate | |

TABLE 1-continued

| No. | Structure* | IUPAC Name | NMR (300 or 400 MHz) or TLC |
|---|---|---|---|
| 146 | 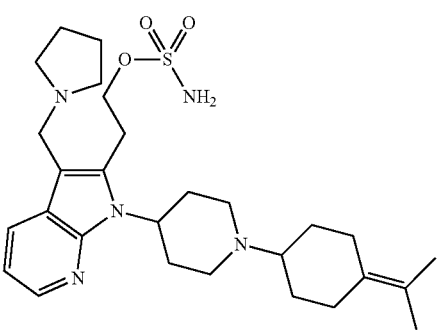 [SMILES: CC(C)=C1CCC(N2CCC(n3c(CCOS(N)(=O)=O)c(CN4CCCC4)c4cccnc43)CC2)CC1] | 2-(1-(1-(4-(propan-2-ylidene)cyclohexyl)piperidin-4-yl)-3-(pyrrolidin-1-ylmethyl)-1H-pyrrolo[2,3-b]pyridin-2-yl)ethyl sulfamate | |
| 147 | 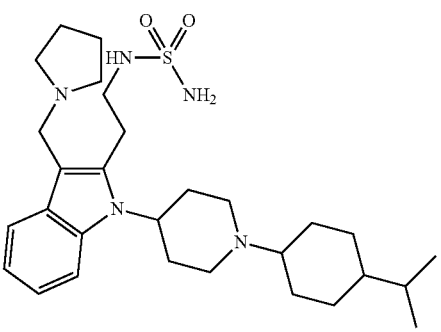 [SMILES: CC(C)C1CCC(N2CCC(n3c(CCNS(N)(=O)=O)c(CN4CCCC4)c4ccccc43)CC2)CC1] | N-(2-(1-(1-(cis-4-isopropylcyclohexyl)piperidin-4-yl)-3-(pyrrolidin-1-ylmethyl)-1H-indol-2-yl)ethyl)aminosulfonamide | |
| 148 | 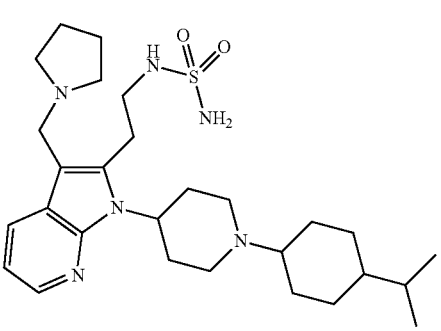 [SMILES: CC(C)C1CCC(N2CCC(n3c(CCNS(N)(=O)=O)c(CN4CCCC4)c4cccnc43)CC2)CC1] | N-(2-(1-(2-(cis-4-isopropylcyclohexyl)piperidin-4-yl)-3-(pyrrolidin-1-ylmethyl)-1H-pyrrolo[2,3-b]pyridin-2-yl)ethyl)aminosulfonamide | |
| 149 | 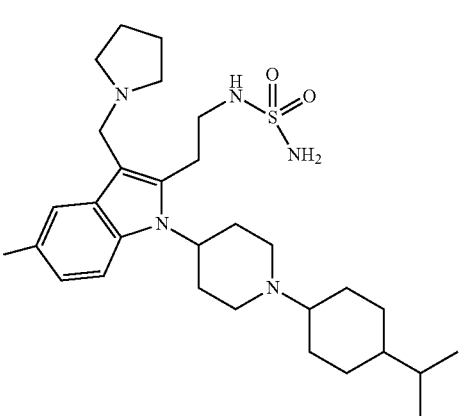 | N-(2-(5-fluoro-1-(1-(cis-4-isopropylcyclohexyl)piperidin-4-yl)-3-(pyrrolidin-1-ylmethyl)-1H-indol-2-yl)ethyl)aminosulfonamide | |

TABLE 1-continued

| No. | Structure* | IUPAC Name | NMR (300 or 400 MHz) or TLC |
|---|---|---|---|
| 150 | 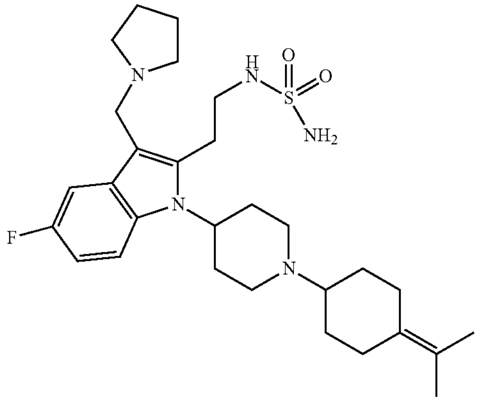 [SMILES: CC(C)=C1CCC(N2CCC(n3c(CCNS(N)(=O)=O)c(CN4CCCC4)c4cc(F)ccc43)CC2)CC1] | N-(2-(5-fluoro-1-(1-(4-(propan-2-ylidene)cyclohexyl)piperidin-4-yl)-3-(pyrrolidin-1-ylmethyl)-1H-indol-2-yl)ethyl)aminosulfonamide | |
| 151 | 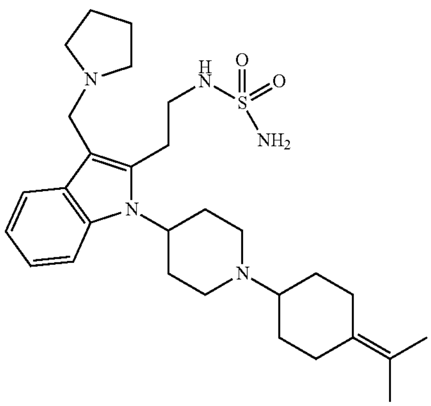 [SMILES: CC(C)=C1CCC(N2CCC(n3c(CCNS(N)(=O)=O)c(CN4CCCC4)c4ccccc43)CC2)CC1] | N-(2-(1-(1-(4-(propan-2-ylidene)cyclohexyl)piperidin-4-yl)-3-(pyrrolidin-1-ylmethyl)-1H-indol-2-yl)ethyl)aminosulfonamide | |
| 152 | 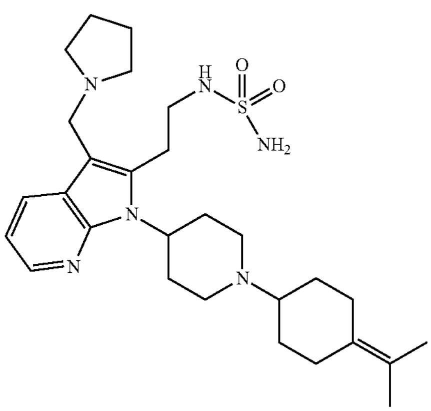 [SMILES: CC(C)=C1CCC(N2CCC(n3c(CCNS(N)(=O)=O)c(CN4CCCC4)c4cccnc43)CC2)CC1] | N-(2-(1-(1-(4-(propan-2-ylidene)cyclohexyl)piperidin-4-yl)-3-(pyrrolidin-1-ylmethyl)-1H-pyrrolo[2,3-b]pyridin-2-yl)ethyl)aminosulfonamide | |
| 153 | 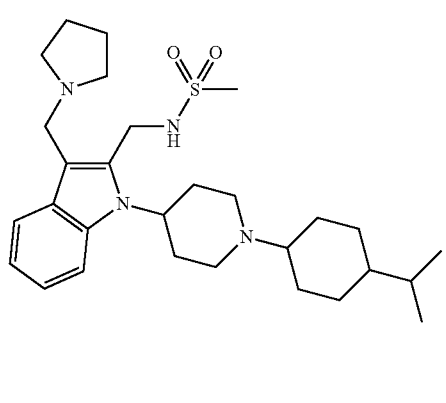 [SMILES: CC(C)C1CCC(N2CCC(n3c(CNS(C)(=O)=O)c(CN4CCCC4)c4ccccc43)CC2)CC1] | N-((1-(1-(cis-4-isopropylcyclohexyl)piperidin-4-yl)-3-(pyrrolidin-1-ylmethyl)-1H-indol-2-yl)methyl)methanesulfonamide | |

TABLE 1-continued

| No. | Structure* | IUPAC Name | NMR (300 or 400 MHz) or TLC |
|---|---|---|---|
| 154 | 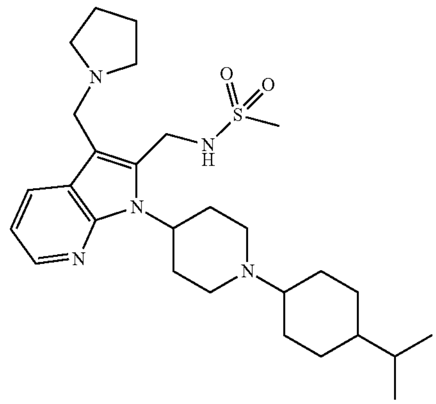 [SMILES: CC(C)C1CCC(N2CCC(n3c(CNS(C)(=O)=O)c(CN4CCCC4)c4cccnc43)CC2)CC1] | N-((1-(1-(cis-4-isopropylcyclohexyl)piperidin-4-yl)-3-(pyrrolidin-1-ylmethyl)-1H-pyrrolo[2,3-b]pyridin-2-yl)methyl)methanesulfonamide | |
| 155 | 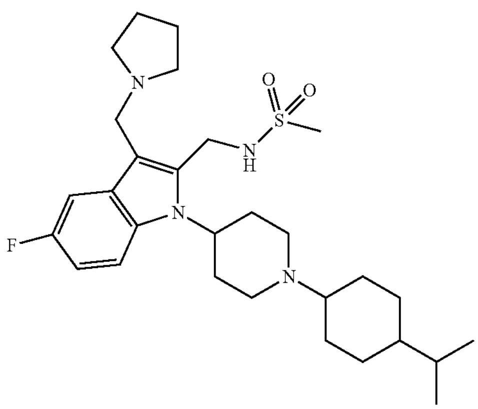 [SMILES: CC(C)C1CCC(N2CCC(n3c(CNS(C)(=O)=O)c(CN4CCCC4)c4cc(F)ccc43)CC2)CC1] | N-((5-fluoro-1-(1-(cis-4-isopropylcyclohexyl)piperidin-4-yl)-3-(pyrrolidin-1-ylmethyl)-1H-indol-2-yl)methyl)methanesulfonamide | |
| 156 | 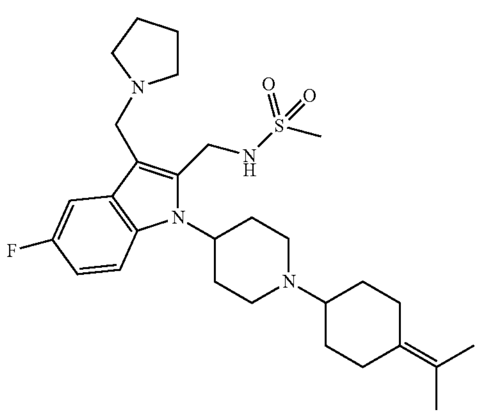 [SMILES: CC(C)=C1CCC(N2CCC(n3c(CNS(C)(=O)=O)c(CN4CCCC4)c4cc(F)ccc43)CC2)CC1] | N-((5-fluoro-1-(1-(4-(propan-2-ylidene)cyclohexyl)piperidin-4-yl)-3-(pyrrolidin-1-ylmethyl)-1H-indol-2-yl)methyl)methanesulfonamide | |

TABLE 1-continued

| No. | Structure* | IUPAC Name | NMR (300 or 400 MHz) or TLC |
|---|---|---|---|
| 157 | 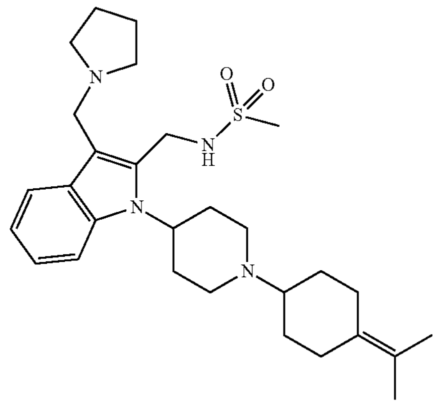 [SMILES: CC(C)=C1CCC(N2CCC(n3c(CNS(C)(=O)=O)c(CN4CCCC4)c4ccccc43)CC2)CC1] | N-((1-(1-(4-(propan-2-ylidene)cyclohexyl)piperidin-4-yl)-3-(pyrrolidin-1-ylmethyl)-1H-indol-2-yl)methyl)methane-sulfonamide | |
| 158 | 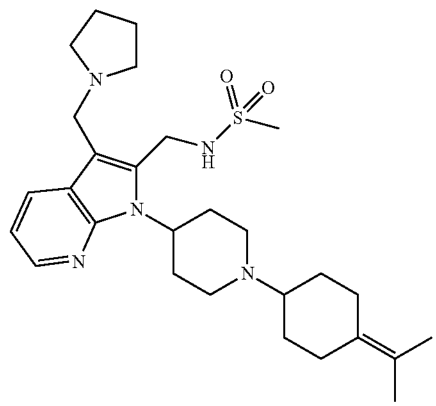 [SMILES: CC(C)=C1CCC(N2CCC(n3c(CNS(C)(=O)=O)c(CN4CCCC4)c4cccnc43)CC2)CC1] | N-((1-(1-(4-(propan-2-ylidene)cyclohexyl)piperidin-4-yl)-3-(pyrrolidin-1-ylmethyl)-1H-pyrrolo[2,3-b]pyridin-2-yl)methyl)methane-sulfonamide | |
| 159 | 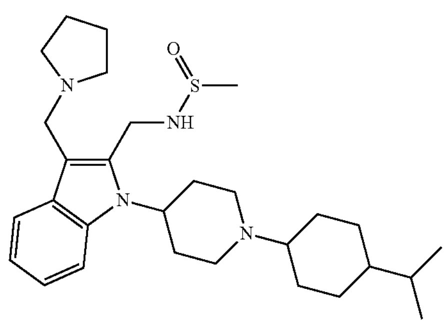 [SMILES: CC(C)C1CCC(N2CCC(n3c(CNS(C)=O)c(CN4CCCC4)c4ccccc43)CC2)CC1] | N-((1-(1-(cis-4-isopropylcyclohexyl)piperidin-4-yl)-3-(pyrrolidin-1-ylmethyl)-1H-indol-2-yl)methyl)acetamide | |
| 160 | 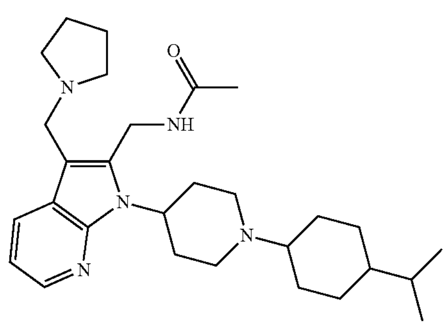 [SMILES: CC(=O)NCc1c(CN2CCCC2)c2cccnc2n1C1CCN(C2CCC(C(C)C)CC2)CC1] | N-((1-(1-(cis-4-isopropylcyclohexyl)piperidin-4-yl)-3-(pyrrolidin-1-ylmethyl)-1H-pyrrolo[2,3-b]pyridin-2-yl)methyl)acetamide | |

TABLE 1-continued

| No. | Structure* | IUPAC Name | NMR (300 or 400 MHz) or TLC |
|---|---|---|---|
| 161 | 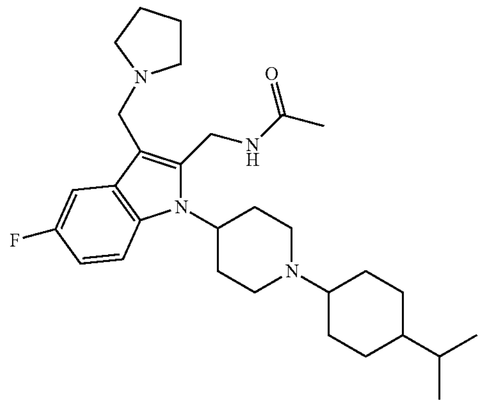 [SMILES: CC(=O)NCc1c(CN2CCCC2)c2cc(F)ccc2n1C1CCN(C2CCC(C(C)C)CC2)CC1] | N-((5-fluoro-1-(1-(cis-4-isopropylcyclohexyl)piperidin-4-yl)-3-(pyrrolidin-1-ylmethyl)-1H-indol-2-yl)methyl)acetamide | |
| 162 | 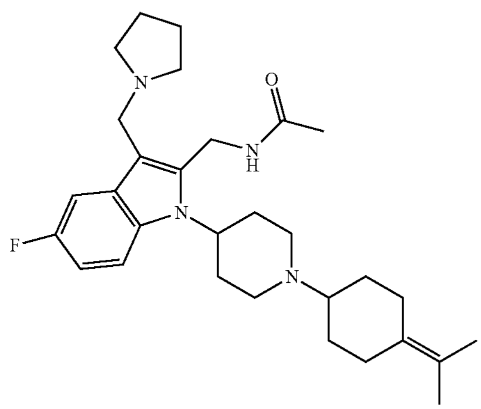 [SMILES: CC(=O)NCc1c(CN2CCCC2)c2cc(F)ccc2n1C1CCN(C2CCC(=C(C)C)CC2)CC1] | N-((5-fluoro-1-(1-(4-(propan-2-ylidene)cyclohexyl)piperidin-4-yl)-3-(pyrrolidin-1-ylmethyl)-1H-indol-2-yl)methyl)acetamide | |
| 163 | 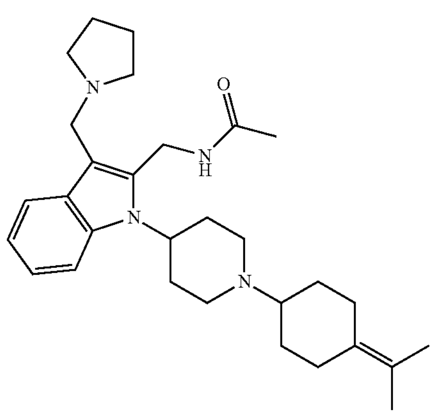 [SMILES: CC(=O)NCc1c(CN2CCCC2)c2ccccc2n1C1CCN(C2CCC(=C(C)C)CC2)CC1] | N-((1-(1-(4-(propan-2-ylidene)cyclohexyl)piperidin-4-yl)-3-(pyrrolidin-1-ylmethyl)-1H-indol-2-yl)methyl)acetamide | |

TABLE 1-continued

| No. | Structure* | IUPAC Name | NMR (300 or 400 MHz) or TLC |
|---|---|---|---|
| 164 | 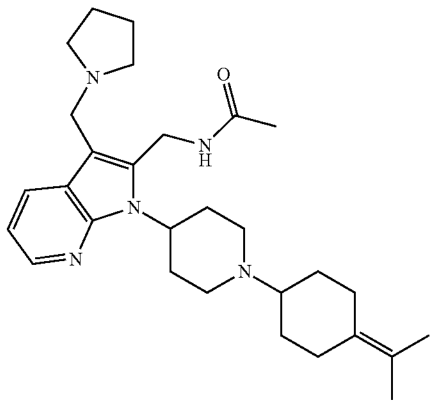 [SMILES: CC(=O)NCc1c(CN2CCCC2)c2cccnc2n1C1CCN(C2CCC(=C(C)C)CC2)CC1] | N-((1-(1-(4-(propan-2-ylidene)cyclohexyl)piperidin-4-yl)-3-(pyrrolidin-1-ylmethyl)-1H-pyrrolo[2,3-b]pyridin-2-yl)methyl)acetamide | |
| 165 | 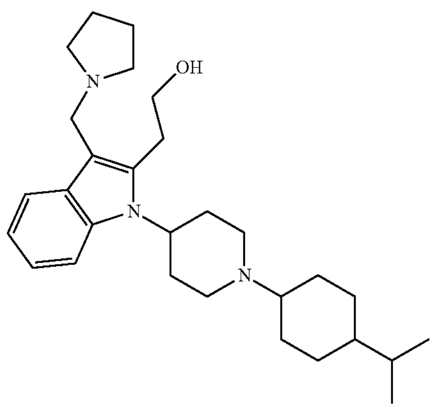 [SMILES: CC(C)C1CCC(N2CCC(n3c(CCO)c(CN4CCCC4)c4ccccc43)CC2)CC1] | 2-(1-(1-(cis-4-isopropylcyclohexyl)piperidin-4-yl)-3-(pyrrolidin-1-ylmethyl)-1H-indol-2-yl)ethan-1-ol | |
| 166 | 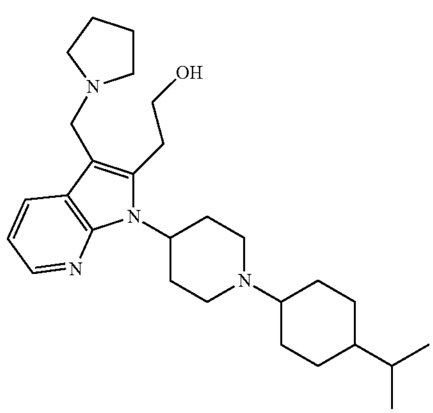 [SMILES: CC(C)C1CCC(N2CCC(n3c(CCO)c(CN4CCCC4)c4cccnc43)CC2)CC1] | 2-(1-(1-(cis-4-isopropylcyclohexyl)piperidin-4-yl)-3-(pyrrolidin-1-ylmethyl)-1H-pyrrolo[2,3-b]pyridin-2-yl)ethan-1-ol | |

TABLE 1-continued

| No. | Structure* | IUPAC Name | NMR (300 or 400 MHz) or TLC |
|---|---|---|---|
| 167 | 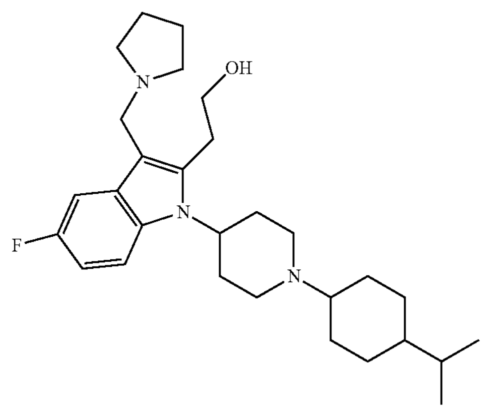 [SMILES: CC(C)C1CCC(N2CCC(n3c(CCO)c(CN4CCCC4)c4cc(F)ccc43)CC2)CC1] | 2-(5-fluoro-1-(1-(cis-4-isopropylcyclohexyl)piperidin-4-yl)-3-(pyrrolidin-1-ylmethyl)-1H-indol-2-yl)ethan-1-ol | |
| 168 | 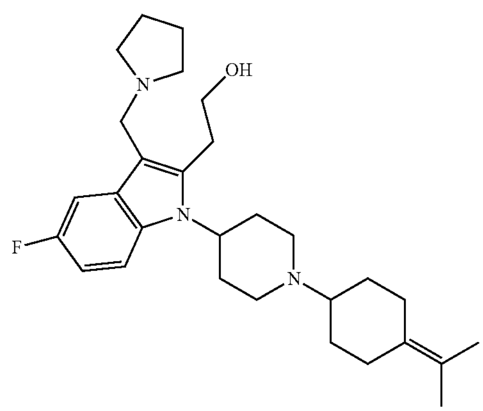 [SMILES: CC(C)=C1CCC(N2CCC(n3c(CCO)c(CN4CCCC4)c4cc(F)ccc43)CC2)CC1] | 2-(5-fluoro-1-(1-(4-(propan-2-ylidene)cyclohexyl)piperidin-4-yl)-3-(pyrrolidin-1-ylmethyl)-1H-indol-2-yl)ethan-1-ol | |
| 169 | 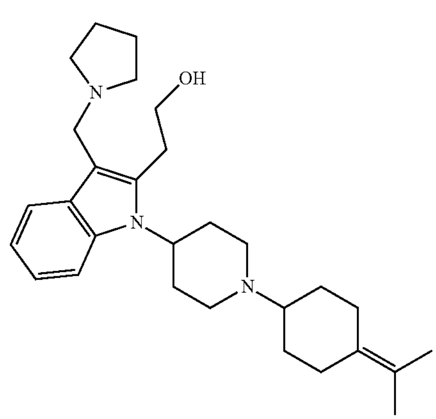 [SMILES: CC(C)=C1CCC(N2CCC(n3c(CCO)c(CN4CCCC4)c4ccccc43)CC2)CC1] | 2-(1-(1-(4-(propan-2-ylidene)cyclohexyl)piperidin-4-yl)-3-(pyrrolidin-1-ylmethyl)-1H-indol-2-yl)ethan-1-ol | |

TABLE 1-continued

| No. | Structure* | IUPAC Name | NMR (300 or 400 MHz) or TLC |
|---|---|---|---|
| 170 | 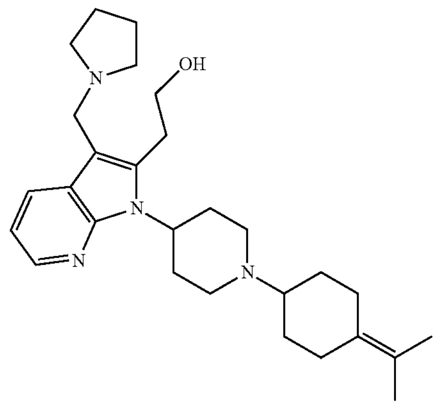 [SMILES: CC(C)=C1CCC(N2CCC(n3c(CCO)c(CN4CCCC4)c4cccnc43)CC2)CC1] | 2-(1-(1-(4-(propan-2-ylidene)cyclohexyl)piperidin-4-yl)-3-(pyrrolidin-1-ylmethyl)-1H-pyrrolo[2,3-b]pyridin-2-yl)ethan-1-ol | |
| 171 | 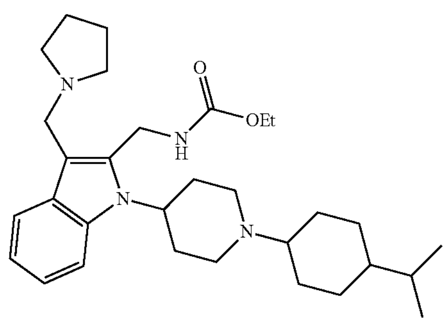 [SMILES: CCOC(=O)NCc1c(CN2CCCC2)c2ccccc2n1C1CCN(C2CCC(C(C)C)CC2)CC1] | ethyl ((1-(1-(cis-4-isopropylcyclohexyl)piperidin-4-yl)-3-(pyrrolidin-1-ylmethyl)-1H-indol-2-yl)methyl)carbamate | |
| 172 | 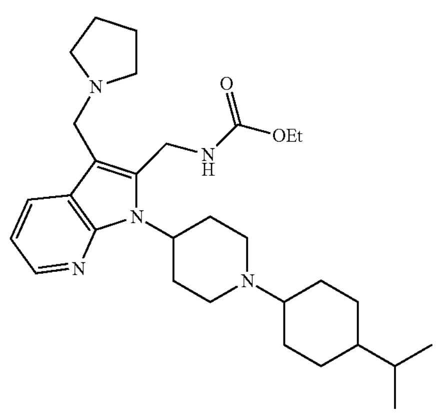 [SMILES: CCOC(=O)NCc1c(CN2CCCC2)c2cccnc2n1C1CCN(C2CCC(C(C)C)CC2)CC1] | ethyl ((1-(1-((1s,4s)-4-isopropylcyclohexyl)piperidin-4-yl)-3-(pyrrolidin-1-ylmethyl)-1H-pyrrolo[2,3-b]pyridin-2-yl)methyl)carbamate | |
| 173 | 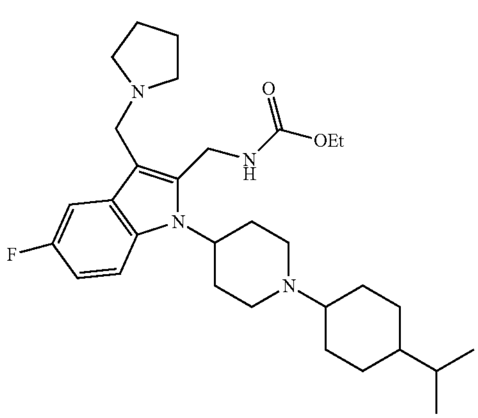 [SMILES: CCOC(=O)NCc1c(CN2CCCC2)c2cc(F)ccc2n1C1CCN(C2CCC(C(C)C)CC2)CC1] | ethyl ((5-fluoro-1-(1-(cis-4-isopropylcyclohexyl)piperidin-4-yl)-3-(pyrrolidin-1-ylmethyl)-1H-indol-2-yl)methyl)carbamate | |

TABLE 1-continued

| No. | Structure* | IUPAC Name | NMR (300 or 400 MHz) or TLC |
|---|---|---|---|
| 174 | 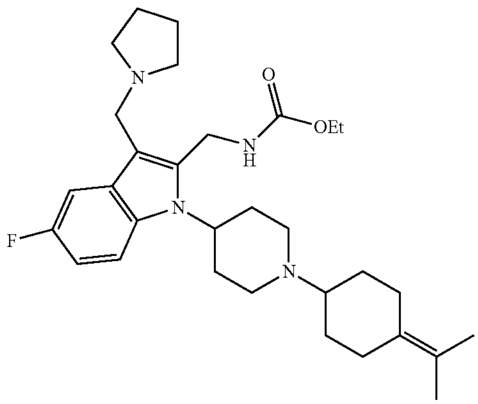 [SMILES: CCOC(=O)NCc1c(CN2CCCC2)c2cc(F)ccc2n1C1CCN(C2CCC(=C(C)C)CC2)CC1] | ethyl ((5-fluoro-1-(1-(4-(propan-2-ylidene)cyclohexyl)piperidin-4-yl)-3-(pyrrolidin-1-ylmethyl)-1H-indol-2-yl)methyl)carbamate | |
| 175 | 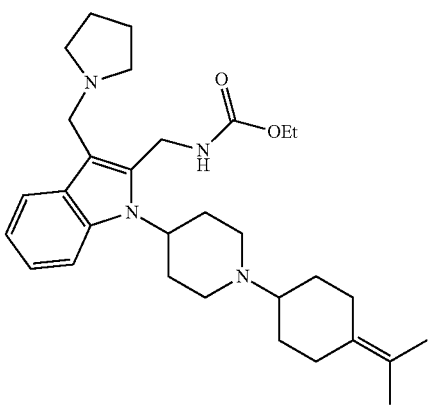 [SMILES: CCOC(=O)NCc1c(CN2CCCC2)c2ccccc2n1C1CCN(C2CCC(=C(C)C)CC2)CC1] | ethyl ((1-(1-(4-(propan-2-ylidene)cyclohexyl)piperidin-4-yl)-3-(pyrrolidin-1-ylmethyl)-1H-indol-2-yl)methyl)carbamate | |
| 176 | 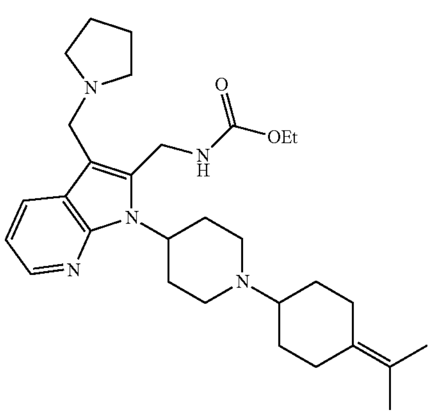 [SMILES: CCOC(=O)NCc1c(CN2CCCC2)c2cccnc2n1C1CCN(C2CCC(=C(C)C)CC2)CC1] | ethyl ((1-(1-(4-(propan-2-ylidene)cyclohexyl)piperidin-4-yl)-3-(pyrrolidin-1-ylmethyl)-1H-pyrrolo[2,3-b]pyridin-2-yl)methyl)carbamate | |

TABLE 1-continued

| No. | Structure* | IUPAC Name | NMR (300 or 400 MHz) or TLC |
|---|---|---|---|
| 177 | 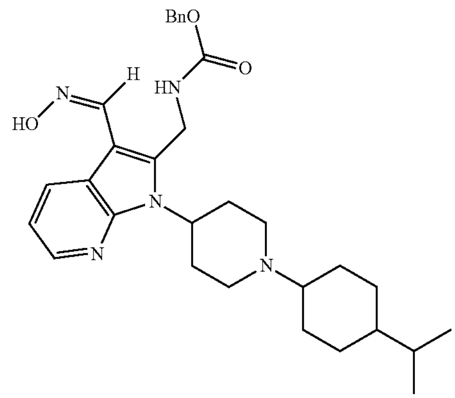 [SMILES: CC(C)C1CCC(N2CCC(n3c(CNC(=O)OCc4ccccc4)c(/C=N\O)c4cccnc43)CC2)CC1] | benzyl ((3-((hydroxyimino)methyl)-1-(1-(cis-4-isopropylcyclohexyl)piperidin-4-yl)-1H-pyrrolo[2,3-b]pyridin-2-yl)methyl)carbamate | |
| 178 | 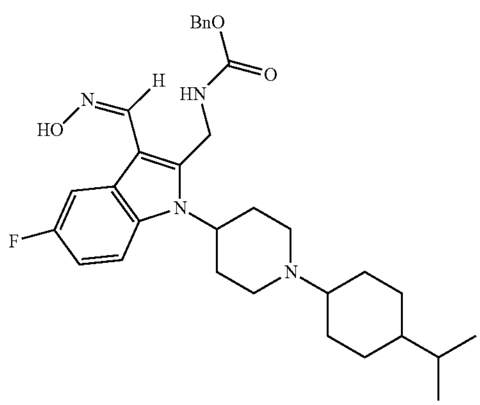 [SMILES: CC(C)C1CCC(N2CCC(n3c(CNC(=O)OCc4ccccc4)c(/C=N\O)c4cc(F)ccc43)CC2)CC1] | benzyl ((5-fluoro-3-((hydroxyimino)methyl)-1-(1-(cis-4-isopropylcyclohexyl)piperidin-4-yl)-1H-indol-2-yl)methyl)carbamate | |
| 179 | 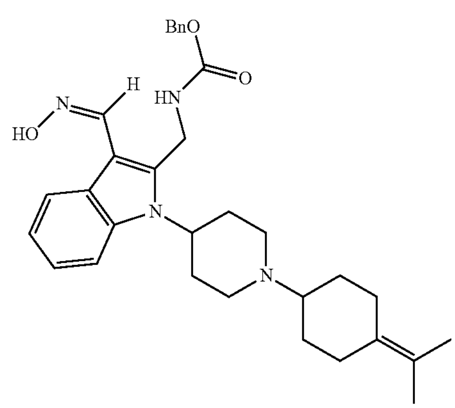 [SMILES: CC(C)=C1CCC(N2CCC(n3c(CNC(=O)OCc4ccccc4)c(/C=N\O)c4ccccc43)CC2)CC1] | benzyl ((3-((hydroxyimino)methyl)-1-(1-(4-(propan-2-ylidene)cyclohexyl)piperidin-4-yl)-1H-indol-2-yl)methyl)carbamate | |

| No. | Structure* | IUPAC Name | NMR (300 or 400 MHz) or TLC |
|---|---|---|---|
| 180 | 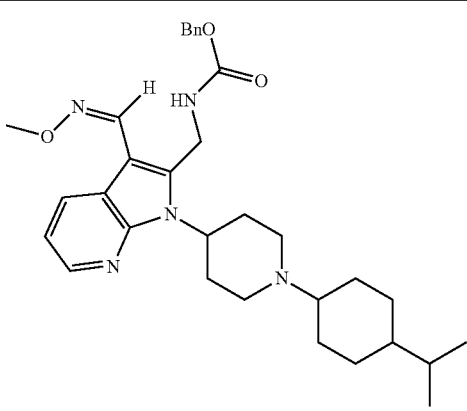 | benzyl ((1-(1-(cis-4-isopropylcyclohexyl)piperidin-4-yl)-3-((methoxyimino)methyl)-1H-indol-2-yl)methyl)carbamate | |
| 181 | 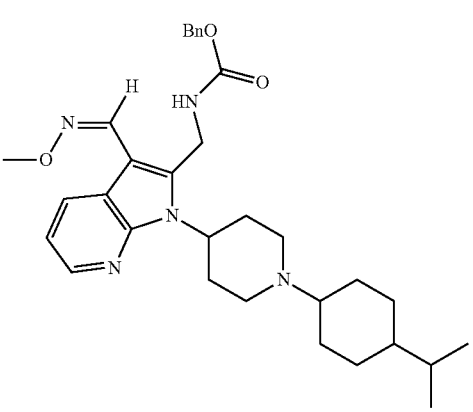 [SMILES: CO/N=C\c1c(CNC(=O)OCc2ccccc2)n(C2CCN(C3CCC(C(C)C)CC3)CC2)c2ncccc12] | benzyl ((1-(1-(cis-4-isopropylcyclohexyl)piperidin-4-yl)-3-((methoxyimino)methyl)-1H-pyrrolo[2,3-b]pyridin-2-yl)methyl)carbamate | |
| 182 | 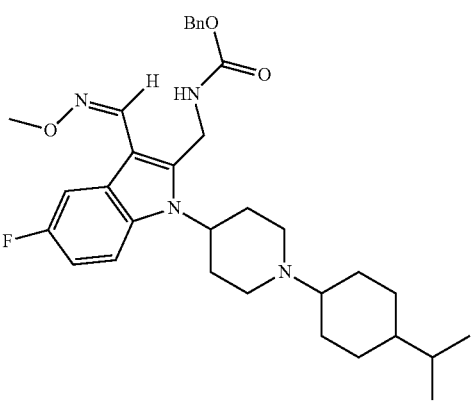 [SMILES: CO/N=C\c1c(CNC(=O)OCc2ccccc2)n(C2CCN(C3CCC(C(C)C)CC3)CC2)c2ccc(F)cc12] | benzyl ((5-fluoro-1-(1-(cis-4-isopropylcyclohexyl)piperidin-4-yl)-3-((methoxyimino)methyl)-1H-indol-2-yl)methyl)carbamate | |

| No. | Structure* | IUPAC Name | NMR (300 or 400 MHz) or TLC |
|---|---|---|---|
| 183 | 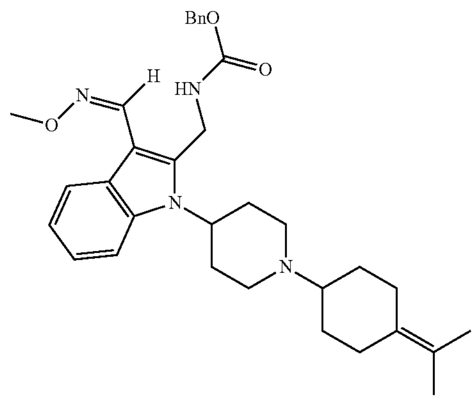 [SMILES: CO/N=C\c1c(CNC(=O)OCc2ccccc2)n(C2CCN(C3CCC(=C(C)C)CC3)CC2)c2ccccc12] | benzyl ((3-((methoxyimino)methyl)-1-(1-(4-(propan-2-ylidene)cylcohexyl)piperidin-4-yl)-1H-indol-2-yl)methyl)carbamate | |
| 184 | 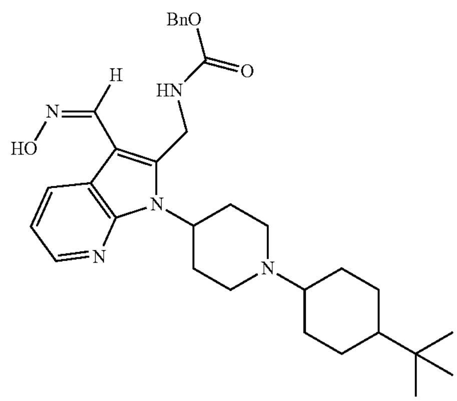 [SMILES: CC(C)(C)C1CCC(N2CCC(n3c(CNC(=O)OCc4ccccc4)c(/C=N\O)c4cccnc43)CC2)CC1] | benzyl ((1-(1-(cis-4-(tert-butyl)cyclohexyl)piperidin-4-yl)-3-((hydroxyimino)methyl)-1H-pyrrolo[2,3-b]pyridin-2-yl)methyl)carbamate | |
| 185 | 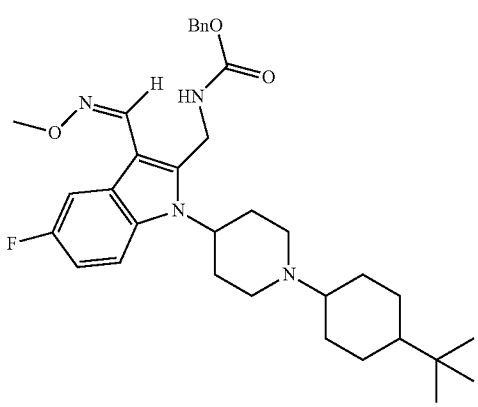 [SMILES: CO/N=C\c1c(CNC(=O)OCc2ccccc2)n(C2CCN(C3CCC(C(C)(C)C)CC3)CC2)c2ccc(F)cc12] | benzyl ((1-(1-(cis-4-(tert-butyl)cyclohexyl)piperidin-4-yl)-5-fluoro-3-((methoxyimino)methyl)-1H-indol-2-yl)methyl)carbamate | |
| 186 | 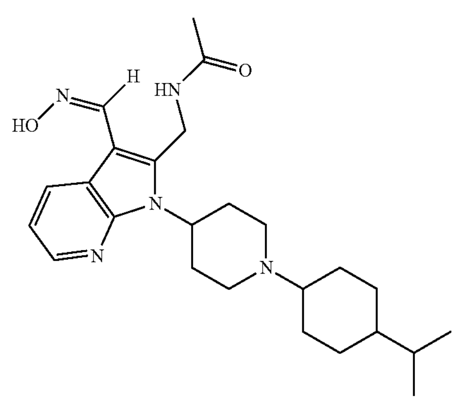 [SMILES: CC(=O)NCc1c(/C=N\O)c2cccnc2n1C1CCN(C2CCC(C(C)C)CC2)CC1] | benzyl ((3-((hydroxyimino)methyl)-1-(1-(cis-4-isopropylcyclohexyl)piperidin-4-yl)-1H-pyrrolo[2,3-b]pyridin-2-yl)methyl)carbamate | |

TABLE 1-continued

| No. | Structure* | IUPAC Name | NMR (300 or 400 MHz) or TLC |
|---|---|---|---|
| 187 | 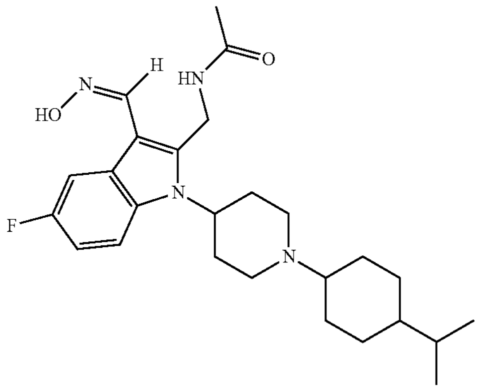 [SMILES: CC(=O)NCc1c(/C=N\O)c2cc(F)ccc2n1C1CCN(C2CCC(C(C)C)CC2)CC1] | benzyl ((5-fluoro-3-((hydroxyimino)methyl)-1-(1-(cis-4-isopropylcyclohexyl)piperidin-4-yl)-1H-indol-2-yl)methyl)carbamate | |
| 188 | 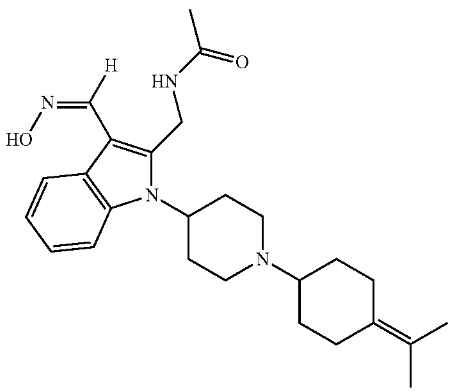 [SMILES: CC(=O)NCc1c(/C=N\O)c2ccccc2n1C1CCN(C2CCC(=C(C)C)CC2)CC1] | N-((3-((hydroxyimino)methyl)-1-(1-(4-(propan-2-ylidene)cyclohexyl)piperidin-4-yl)-1H-indol-2-yl)methyl)acetamide | |
| 189 | 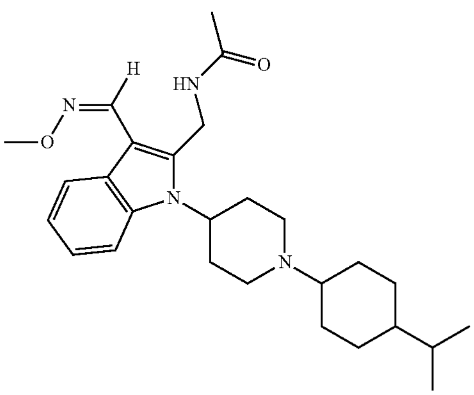 [SMILES: CO/N=C\c1c(CNC(C)=O)n(C2CCN(C3CCC(C(C)C)CC3)CC2)c2ccccc12] | benzyl ((1-(1-(cis-4-ispropylcyclohexyl)piperidin-4-yl)-3-((methoxyimino)methyl)-1H-indol-2-yl)methyl)carbamate | |
| 190 | 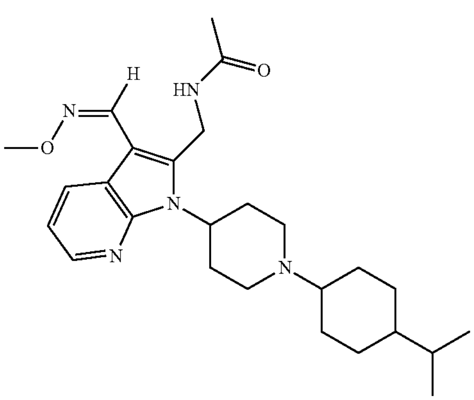 [SMILES: CO/N=C\c1c(CNC(C)=O)n(C2CCN(C3CCC(C(C)C)CC3)CC2)c2ncccc12] | benzyl ((1-(1-(cis-4-isopropylcyclohexyl)piperidin-4-yl)-3-((methoxyimino)methyl)-1H-pyrrolo[2,3-b]pyridin-2-yl)methyl)carbamate | |

TABLE 1-continued

| No. | Structure* | IUPAC Name | NMR (300 or 400 MHz) or TLC |
|---|---|---|---|
| 191 | 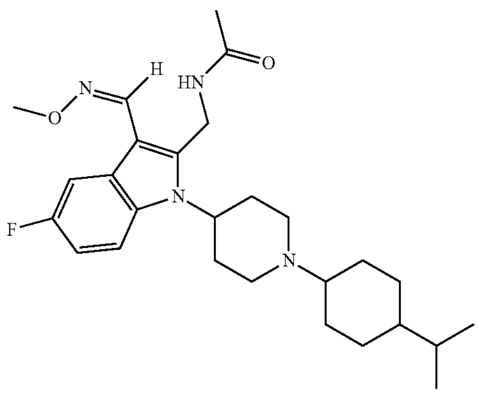 [SMILES: CO/N=C\c1c(CNC(C)=O)n(C2CCN(C3CCC(C(C)C)CC3)CC2)c2ccc(F)cc12] | benzyl ((5-fluoro-1-(1-(cis-4-isopropylcyclohexyl)piperidin-4-yl)-3-((methoxyimino)methyl)-1H-indol-2-yl)methyl)carbamate | |
| 192 | 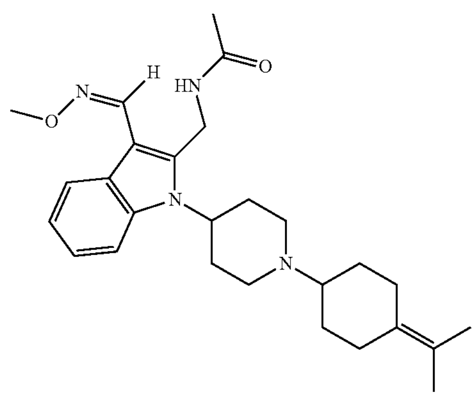 [SMILES: CO/N=C\c1c(CNC(C)=O)n(C2CCN(C3CCC(=C(C)C)CC3)CC2)c2ccccc12] | N-((3-((methoxyimino)methyl)-1-(1-(4-(propan-2-ylidene)cyclohexyl)piperidin-4-yl)-1H-indol-2-yl)methyl)acetamide | |
| 193 | 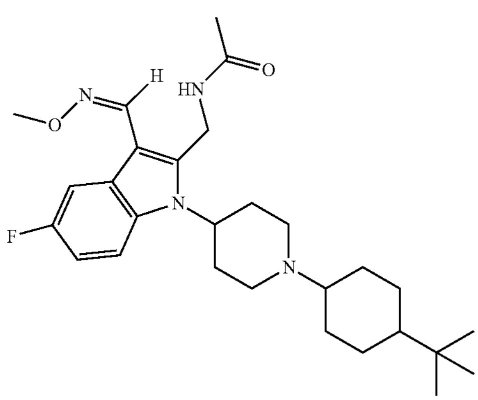 [SMILES: CO/N=C\c1c(CNC(C)=O)n(C2CCN(C3CCC(C(C)(C)C)CC3)CC2)c2ccc(F)cc12] | N-((1-(1-(cis-4-(tert-butyl)cyclohexyl)piperidin-4-yl)-5-fluoro-3-((methoxyimino)methyl)-1H-indol-2-yl)methyl)acetamide | |
| 194 | 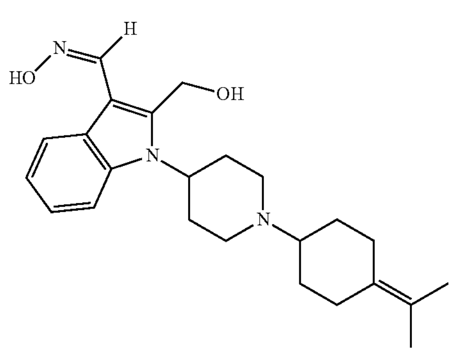 [SMILES: CC(C)=C1CCC(N2CCC(n3c(CO)c(/C=N\O)c4ccccc43)CC2)CC1] | 2-(hydroxymethyl)-1-(1-(4-(propan-2-ylidene)cyclohexyl)piperidin-4-yl)-1H-indole-3-carbaldehyde oxime | |

TABLE 1-continued

| No. | Structure* | IUPAC Name | NMR (300 or 400 MHz) or TLC |
|---|---|---|---|
| 195 | 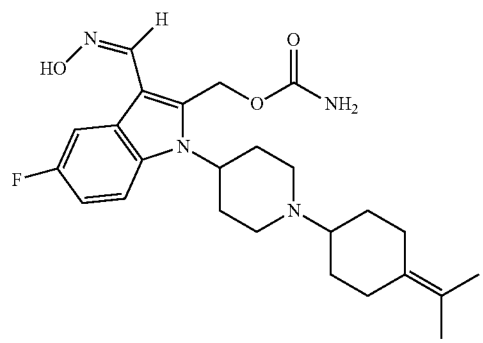 [SMILES: CC(C)=C1CCC(N2CCC(n3c(COC(N)=O)c(/C=N\O)c4cc(F)ccc43)CC2)CC1] | (5-fluoro-3-((hydroxyimino)methyl)-1-(1-(4-(propan-2-ylidene)cyclohexyl)piperidin-4-yl)-1H-indol-2-yl)methyl carbamate | |
| 196 | 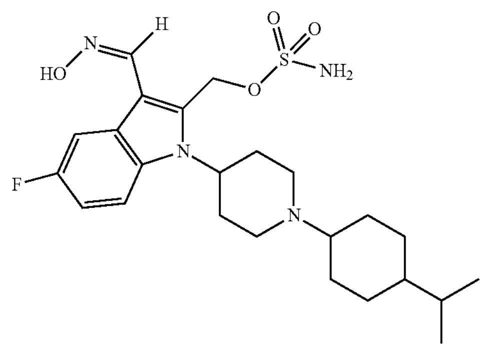 [SMILES: CC(C)C1CCC(N2CCC(n3c(COS(N)(=O)=O)c(/C=N\O)c4cc(F)ccc43)CC2)CC1] | (5-fluoro-3-((hydroxyimino)methyl)-1-(1-(cis-4-isopropylcyclohexyl)piperidin-4-yl)-1H-indol-2-yl)methyl sulfamate | |
| 197 | 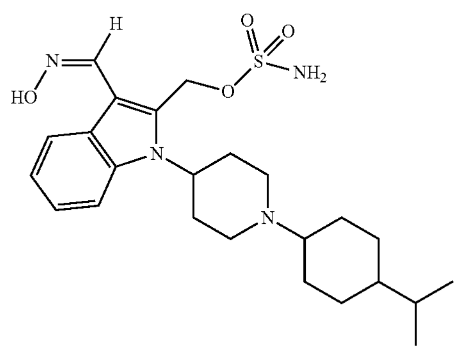 [SMILES: CC(C)C1CCC(N2CCC(n3c(COS(N)(=O)=O)c(/C=N\O)c4ccccc43)CC2)CC1] | (3-((hydroxyimino)methyl)-1-(1-(cis-4-isopropylcyclohexyl)piperidin-4-yl)-1H-indol-2-yl)methyl sulfamate | |
| 198 | 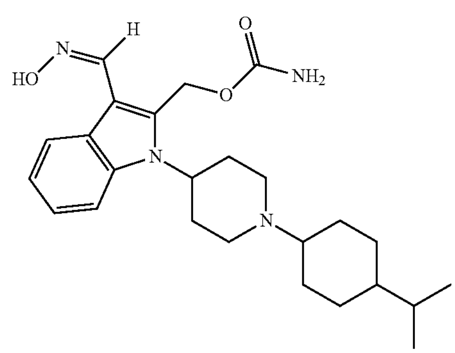 [SMILES: CC(C)C1CCC(N2CCC(n3c(COC(N)=O)c(/C=N\O)c4ccccc43)CC2)CC1] | (3-((hydroxyimino)methyl)-1-(1-(cis-4-isopropylcyclohexyl)piperidin-4-yl)-1H-indol-2-yl)methyl carbamate | |

TABLE 1-continued

| No. | Structure* | IUPAC Name | NMR (300 or 400 MHz) or TLC |
|---|---|---|---|
| 199 | 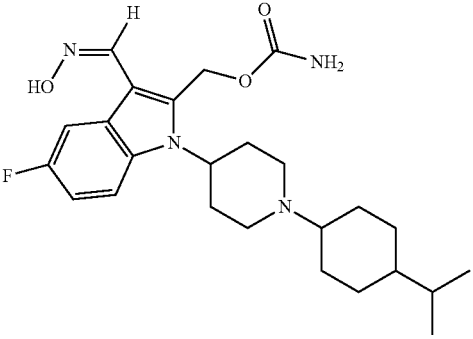 [SMILES: CC(C)C1CCC(N2CCC(n3c(COC(N)=O)c(/C=N\O)c4cc(F)ccc43)CC2)CC1] | (5-fluoro-3-((hydroxyimino)methyl)-1-(1-(cis-4-isopropylcyclohexyl)piepridin-4-yl)-1H-indol-2-yl)methyl carbamate | |
| 200 | 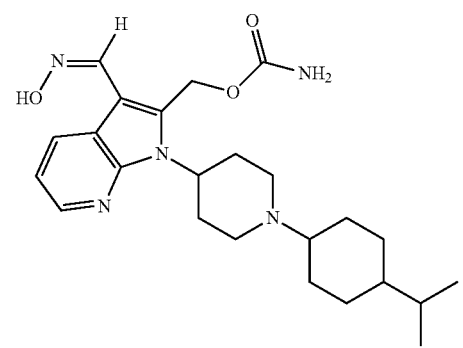 [SMILES: CC(C)C1CCC(N2CCC(n3c(COC(N)=O)c(/C=N\O)c4cccnc43)CC2)CC1] | (3-((hydroxyimino)methyl)-1-(1-(cis-4-isopropylcyclohexyl)piperidin-4-yl)-1H-pyrrolo[2,3-b]pyridin-2-yl)methyl carbamate | |
| 201 | 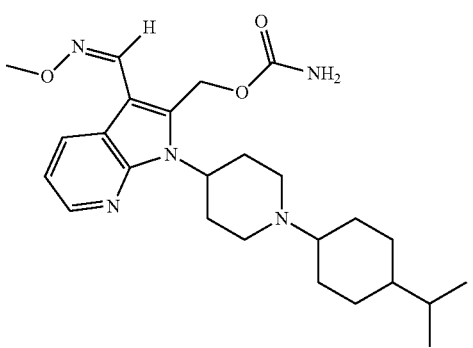 [SMILES: CO/N=C\c1c(COC(N)=O)n(C2CCN(C3CCC(C(C)C)CC3)CC2)c2ncccc12] | (1-(1-(cis-4-isopropylcyclohexyl)piperidin-4-yl)-3-((methoxyimino)methyl)-1H-pyrrolo[2,3-b]pyridin-2-yl)methyl carbamate | |
| 202 | 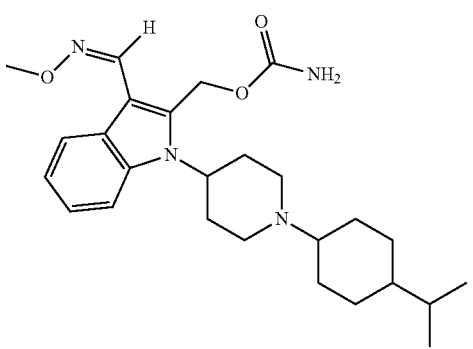 [SMILES: CO/N=C\c1c(COC(N)=O)n(C2CCN(C3CCC(C(C)C)CC3)CC2)c2ccccc12] | (1-(1-(cis-4-isopropylcyclohexyl)piperidin-4-yl)-3-((methoxyimino)methyl)-1H-indol-2-yl)methyl carbamate | |

TABLE 1-continued

| No. | Structure* | IUPAC Name | NMR (300 or 400 MHz) or TLC |
|---|---|---|---|
| 203 | 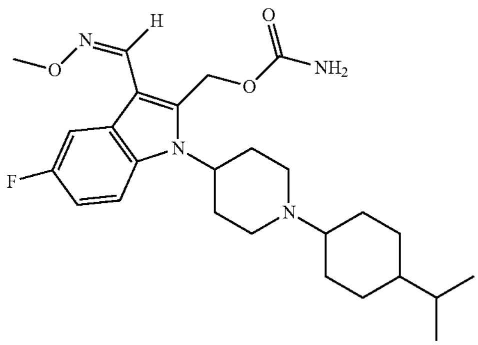 [SMILES: CO/N=C\c1c(COC(N)=O)n(C2CCN(C3CCC(C(C)C)CC3)CC2)c2ccc(F)cc12] | (5-fluoro-1-(1-(cis-4-isopropylcyclohexyl)piperidin-4-yl)-3-((methoxyimino)methyl)-1H-indol-2-yl)methyl carbamate | |
| 204 | 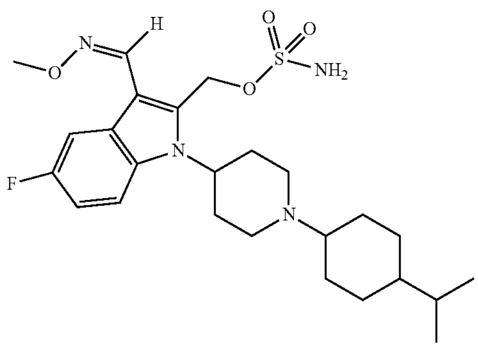 [SMILES: CO/N=C\c1c(COS(N)(=O)=O)n(C2CCN(C3CCC(C(C)C)CC3)CC2)c2ccc(F)cc12] | (5-fluoro-1-(1-(cis-4-isopropylcyclohexyl)piperidin-4-yl)-3-((methoxyimino)methyl)-1H-indol-2-yl)methyl sulfamate | |
| 205 | 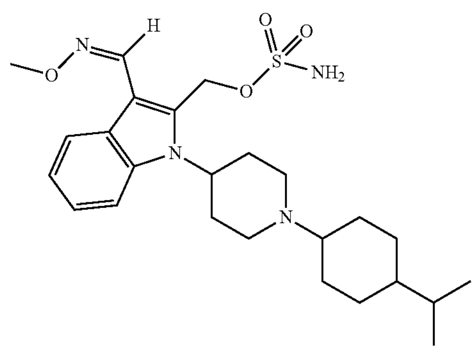 [SMILES: CO/N=C\c1c(COS(N)(=O)=O)n(C2CCN(C3CCC(C(C)C)CC3)CC2)c2ccccc12] | (1-(1-(cis-4-isopropylcyclohexyl)piperidin-4-yl)-3-((methoxyimino)methyl)-1H-indol-2-yl)methyl sulfamate | |
| 206 | 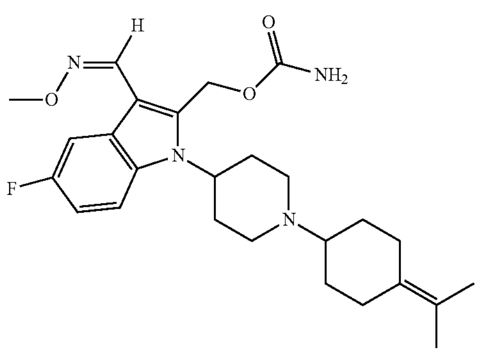 [SMILES: CO/N=C\c1c(COC(N)=O)n(C2CCN(C3CCC(=C(C)C)CC3)CC2)c2ccc(F)cc12] | (5-fluoro-3-((methoxyimino)methyl)-1-(1-(4-(propan-2-ylidene)cyclohexyl)piperidin-4-yl)-1H-indol-2-yl)methyl carbamate | |

TABLE 1-continued

| No. | Structure* | IUPAC Name | NMR (300 or 400 MHz) or TLC |
|---|---|---|---|
| 207 | 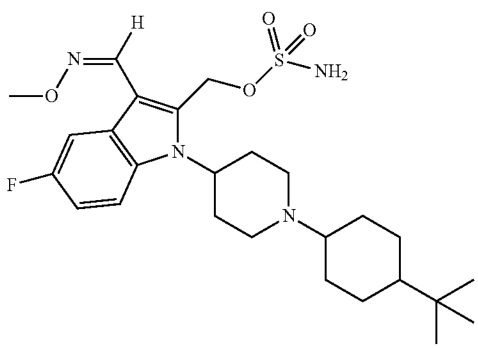 [SMILES: CO/N=C\c1c(COS(N)(=O)=O)n(C2CCN(C3CCC(C(C)(C)C)CC3)CC2)c2ccc(F)cc12] | (1-(1-(cis-4-(tert-butyl)cyclohexyl)piperidin-4-yl)-5-fluoro-3-((methoxyimino)methyl)-1H-indol-2-yl)methyl sulfamate | |
| 208 | 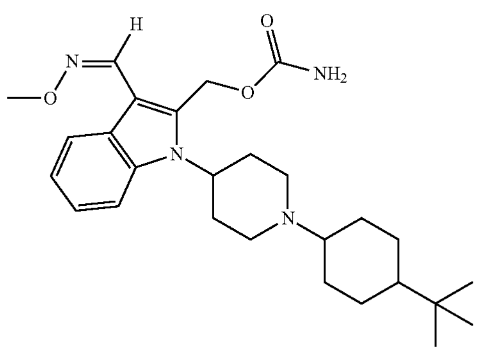 [SMILES: CO/N=C\c1c(COC(N)=O)n(C2CCN(C3CCC(C(C)(C)C)CC3)CC2)c2ccccc12] | (1-(1-(cis-4-(tert-butyl)cyclohexyl)piperidin-4-yl)-3-((methoxyimino)methyl)-1H-indol-2-yl)methyl carbamate | |
| 209 | 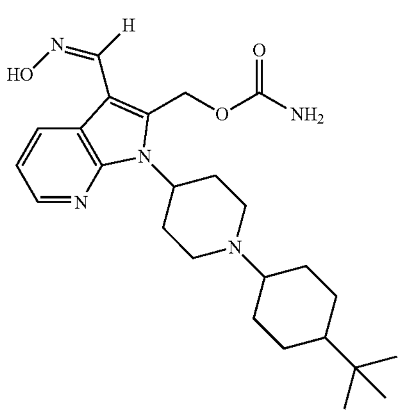 [SMILES: CC(C)(C)C1CCC(N2CCC(n3c(COC(N)=O)c(/C=N\O)c4cccnc43)CC2)CC1] | (1-(1-(cis-4-(tert-butyl)cyclohexyl)piperidin-4-yl)-3-((hydroxyimino)methyl)-1H-pyrrolo[2,3-b]pyridin-2-yl)methyl carbamate | |
| 210 | 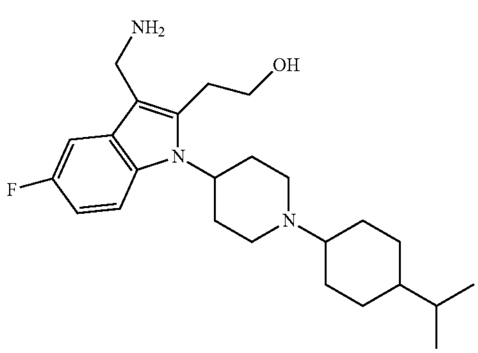 [SMILES: CC(C)C1CCC(N2CCC(n3c(CCO)c(CN)c4cc(F)ccc43)CC2)CC1] | 2-(3-(aminomethyl)-5-fluoro-1-(1-(cis-4-isopropylcyclohexyl piperidin-4-yl)-1H-indol-2-yl)ethan-1-ol | |

TABLE 1-continued

| No. | Structure* | IUPAC Name | NMR (300 or 400 MHz) or TLC |
|---|---|---|---|
| 211 | 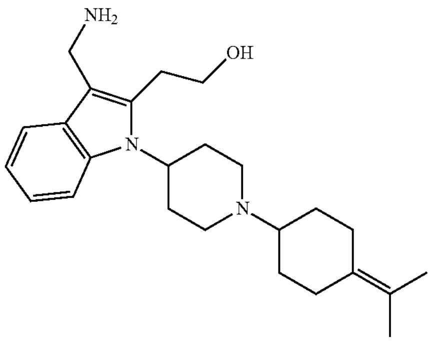 [SMILES: CC(C)=C1CCC(N2CCC(n3c(CCO)c(CN)c4ccccc43)CC2)CC1] | 2-(3-(aminomethyl)-1-(1-(4-(propan-2-ylidene)cyclohexyl)piperidin-4-yl)-1H-indol-2-yl)ethan-1-ol | |
| 212 | 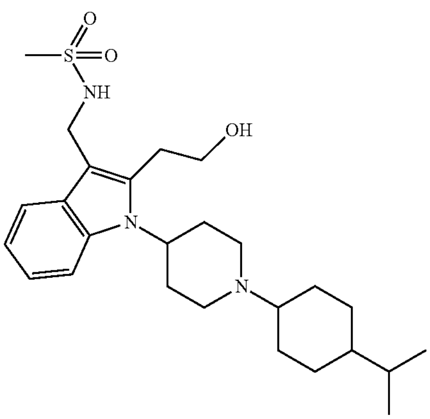 [SMILES: CC(C)C1CCC(N2CCC(n3c(CCO)c(CNS(C)(=O)=O)c4ccccc43)CC2)CC1] | N-((2-(2-hydroxyethyl)-1-(1-(cis-4-isopropylcyclohexyl)piperidin-4-yl)-1H-indol-3-yl)methyl)methanesulfonamide | |
| 213 | 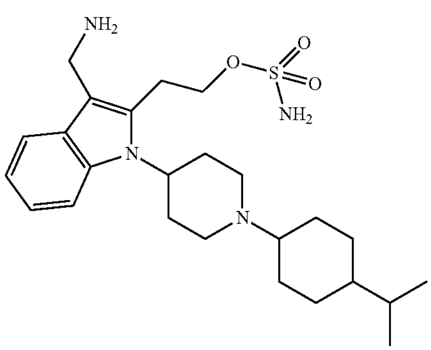 [SMILES: CC(C)C1CCC(N2CCC(n3c(CCOS(N)(=O)=O)c(CN)c4ccccc43)CC2)CC1] | 2-(3-(aminomethyl)-1-(1-(cis-4-isopropylcyclohexyl)piperidin-4-yl)-1H-indol-2-yl)ethyl sulfamate | |
| 214 | 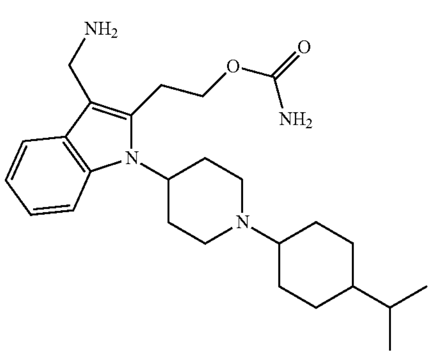 [SMILES: CC(C)C1CCC(N2CCC(n3c(CCOC(N)=O)c(CN)c4ccccc43)CC2)CC1] | 2-(3-(aminomethyl)-1-(1-(cis-4-isopropylcyclohexyl)piperidin-4-yl)-1H-indol-2-yl)ethyl carbamate | |

TABLE 1-continued

| No. | Structure* | IUPAC Name | NMR (300 or 400 MHz) or TLC |
|---|---|---|---|
| 215 | 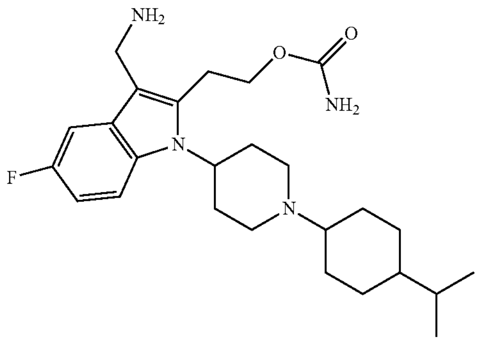 [SMILES: CC(C)C1CCC(N2CCC(n3c(CCOC(N)=O)c(CN)c4cc(F)ccc43)CC2)CC1] | 2-(3-(aminomethyl)-5-fluoro-1-(1-(cis-4-isopropylcyclohexyl)piperidin-4-yl)-1H-indol-2-yl)ethyl carbamate | |
| 216 | 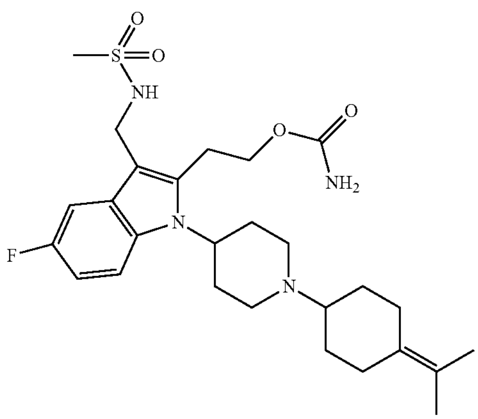 [SMILES: CC(C)=C1CCC(N2CCC(n3c(CCOC(N)=O)c(CNS(C)(=O)=O)c4cc(F)ccc43)CC2)CC1] | 2-(5-fluoro-3-(methylsulfonamido-methyl)-1-(1-(4-(propan-2-ylidene)cyclohexyl)piperidin-4-yl)-1H-indol-2-yl)ethyl carbamate | |
| 217 | 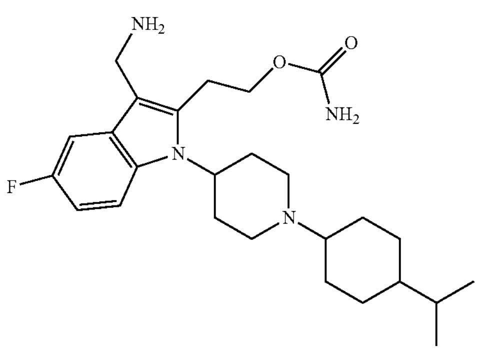 [SMILES: CC(C)C1CCC(N2CCC(n3c(CCOC(N)=O)c(CN)c4cc(F)ccc43)CC2)CC1] | 2-(3-(aminomethyl)-1-(1-(cis-4-isopropylcyclohexyl)piperidin-4-yl)-1H-pyrrolo[2,3-b]pyridin-2-yl)ethyl carbamate | |
| 218 | 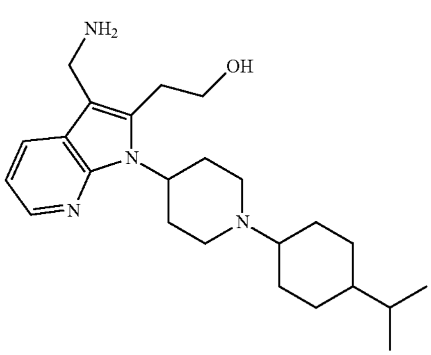 [SMILES: CC(C)C1CCC(N2CCC(n3c(CCO)c(CN)c4cccnc43)CC2)CC1] | 2-(3-(aminomethyl)-5-fluoro-1-(1-(cis-4-isopropylcyclohexyl)piperidin-4-yl)-1H-pyrrolo[2,3-b]pyridin-2-yl)ethan-1-ol | |

TABLE 1-continued

| No. | Structure* | IUPAC Name | NMR (300 or 400 MHz) or TLC |
|---|---|---|---|
| 219 | 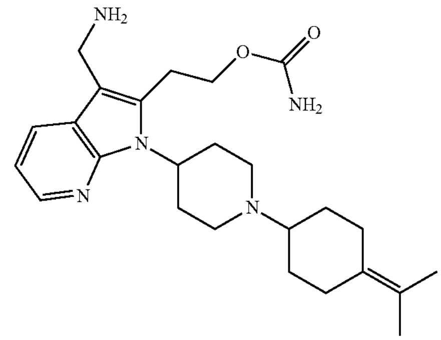 [SMILES: CC(C)=C1CCC(N2CCC(n3c(CCOC(N)=O)c(CN)c4cccnc43)CC2)CC1] | 2-(3-(aminomethyl)-1-(1-(4-(propan-2-ylidene)cyclohexyl)piperidin-4-yl)-1H-pyrrolo[2,3-b]pyridin-2-yl)ethyl carbamate | |
| 220 | 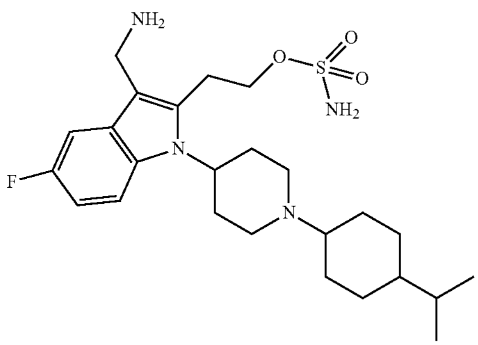 [SMILES: CC(C)C1CCC(N2CCC(n3c(CCOS(N)(=O)=O)c(CN)c4cc(F)ccc43)CC2)CC1] | 2-(3-(aminomethyl)-5-fluoro-1-(1-(cis-4-isopropylcyclohexyl)piperidin-4-yl)-1H-indol-2-yl)ethyl sulfamate | |
| 221 | 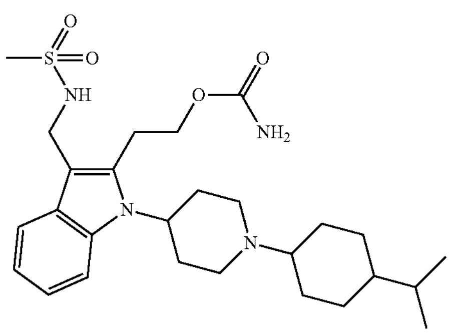 [SMILES: CC(C)C1CCC(N2CCC(n3c(CCOC(N)=O)c(CNS(C)(=O)=O)c4ccccc43)CC2)CC1] | 2-(1-(1-(cis-4-isopropylcyclohexyl)piepridin-4-yl)-3-(methylsulfonamido-methyl)-1H-pyrrolo[2,3-b]pyridin-2-yl)ethyl carbamate | |
| 222 | 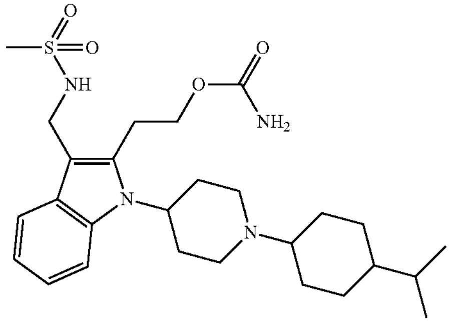 [SMILES: CC(C)C1CCC(N2CCC(n3c(CCOC(N)=O)c(CNS(C)(=O)=O)c4ccccc43)CC2)CC1] | 2-(1-(1-(cis-4-isopropylcyclohexyl)piperidin-4-yl)-3-(methylsulfonamido-methyl)-1H-indol-2-yl)ethyl carbamate | |

TABLE 1-continued

| No. | Structure* | IUPAC Name | NMR (300 or 400 MHz) or TLC |
|---|---|---|---|
| 223 | 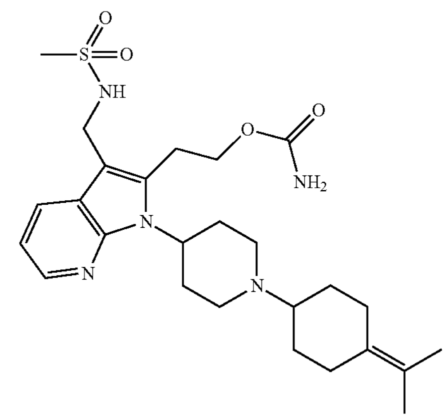 [SMILES: CC(C)=C1CCC(N2CCC(n3c(CCOC(N)=O)c(CNS(C)(=O)=O)c4cccnc43)CC2)CC1] | 2-(3-(methylsulfonamido-methyl)-1-(1-(4-(propan-2-ylidene)cyclohexyl)piperidin-4-yl)-1H-pyrrolo[2,3-b]pyridin-2-yl)ethyl carbamate | |
| 224 | 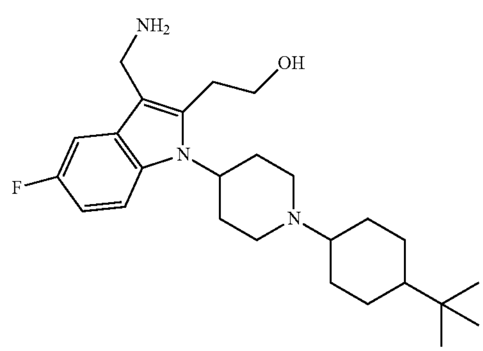 [SMILES: CC(C)(C)C1CCC(N2CCC(n3c(CCO)c(CN)c4cc(F)ccc43)CC2)CC1] | 2-(3-(aminomethyl)-1-(1-(cis-4-(tert-butyl)cyclohexyl)piperidin-4-yl)-5-fluoro-1H-indol-2-yl)ethan-1-ol | |
| 225 | 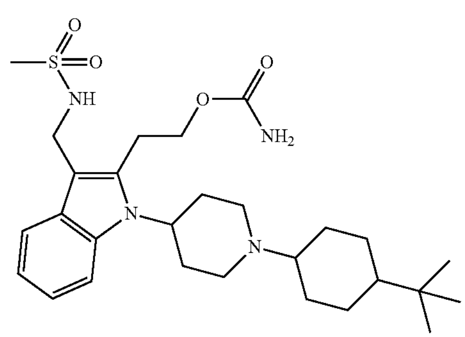 [SMILES: CC(C)(C)C1CCC(N2CCC(n3c(CCOC(N)=O)c(CNS(C)(=O)=O)c4ccccc43)CC2)CC1] | 2-(1-(1-(cis-4-(tert-butyl)cyclohexyl)piperidin-4-yl)-3-(methylsulfonamido-methyl)-1H-indol-2-yl)ethyl carbamate | |
| 226 | 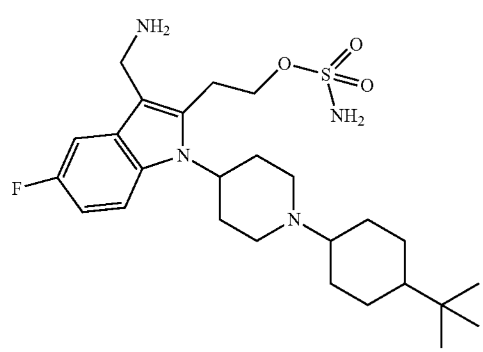 [SMILES: CC(C)(C)C1CCC(N2CCC(n3c(CCOS(N)(=O)=O)c(CN)c4cc(F)ccc43)CC2)CC1] | 2-(3-(aminomethyl)-1-(1-(cis-4-(tert-butyl)cyclohexyl)piperidin-4-yl)-5-fluoro-1H-indol-2-yl)ethyl sulfamate | |

TABLE 1-continued

| No. | Structure* | IUPAC Name | NMR (300 or 400 MHz) or TLC |
|---|---|---|---|
| 227 | 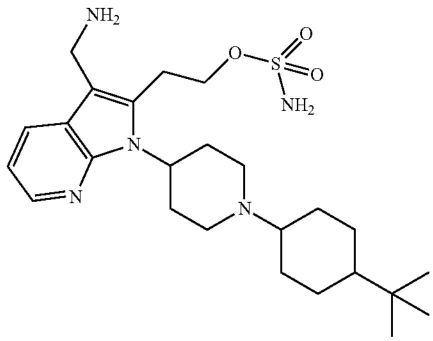 [SMILES: CC(C)(C)C1CCC(N2CCC(n3c(CCOS(N)(=O)=O)c(CN)c4cccnc43)CC2)CC1] | 2-(3-(aminomethyl)-1-(1-(cis-4-(tert-butyl)cyclohexyl)piperidin-4-yl)-1H-pyrrolo[2,3-b]pyridin-2-yl)ethyl sulfamate | |

Table 2 illustrates compounds of structural formula (III). In some embodiments, the 1,4-substituents on the cyclohexyl ring are cis to each other.

TABLE 2

| No. | Structure* | IUPAC Name | NMR (300 or 400 MHz) |
|---|---|---|---|
| 228 | 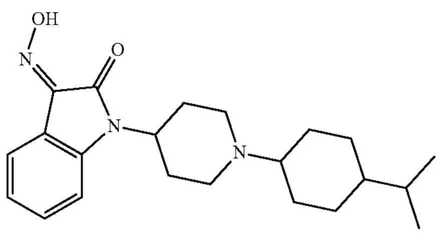 | (Z)-3-(hydroxyimino)-1-(1-((1s,4s)-4-isopropylcyclohexyl)piperidin-4-yl)indolin-2-one | $^1$H NMR (DMSO-$d_6$) δ 13.4 (1H, s), 8.00 (1H, d, J = 9 Hz), 7.40 (1H, t, J = 9 Hz), 7.18 (1H, d, J = 6 Hz), 7.05 (1H, t, J = 6 Hz), 4.00-4.02 (1H, m), 3.06 (2H, d, J = 9 Hz), 2.24-2.36 (3H, m), 2.08 (2H, t, J = 12 Hz), 1.52-1.69 (7H, m), 1.31-1.44 (4H, m), 1.06 (1H, s), 0.85 (6H, d, J = 6 Hz). |
| 229 | 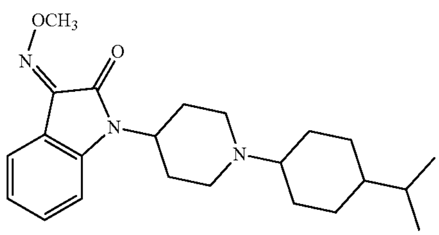 [SMILES: CC(C)C1CCC(N2CCC(N3C(=O)/C(=N\O)c4ccccc43)CC2)CC1] | (Z)-1-(1-((1s,4s)-4-isopropylcyclohexyl)piperidin-4-yl)-3-(methoxyimino)indolin-2-one | $^1$H NMR (CDCl$_3$) δ 8.39 (d, J = 5.4 Hz, 1H), 7.35 (t, J = 5.7 Hz, 1H), 7.17 (d, J = 5.7 Hz, 1H), 7.09 (t, J = 5.7 Hz, 1H), 4.39 (s, 3H), 4.30 (m, 1H), 3.17 (d, J = 6.0 Hz, 2H), 2.48-2.32 (m, 3H), 2.21 (m, 2H), 1.78-1.50 (m, 9H), 1.40 (m, 2H), 1.14 (m, 1H), 0.90 (d, 6H) |
| 230 | 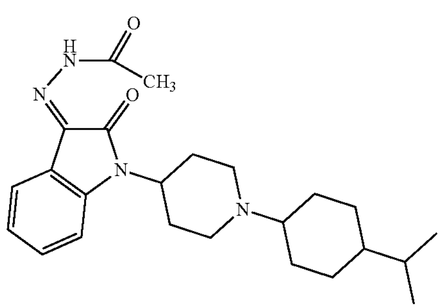 [SMILES: CC(=O)N/N=C1\C(=O)N(C2CCN(C3CCC(C(C)C)CC3)CC2)c2ccccc21] | N'-((Z)-1-(1-((1s,4s)-4-isopropylcyclohexyl)piperidin-4-yl)-2-oxoindolin-3-ylidene)acetohydrazide | $^1$H NMR (CDCl$_3$) δ 12.58 (br, 1H), 7.62 (d, J = 7.5 Hz, 1H), 7.35 (t, J = 7.5 Hz, 1H), 7.19 (d, J = 8.1 Hz, 1H), 7.10 (t, J = 7.5 Hz, 1H), 4.22 (m, 1H), 3.16 (d, J = 11.4 Hz, 2H), 2.42 (m, 5H), 2.20 (m, 3H), 1.80-1.46 (m, 9H), 1.39 (m, 2H), 1.25 (s, 1H), 1.15 (m, 1H), 0.91 (d, J = 6.6 Hz, 6H) |
| 231 | 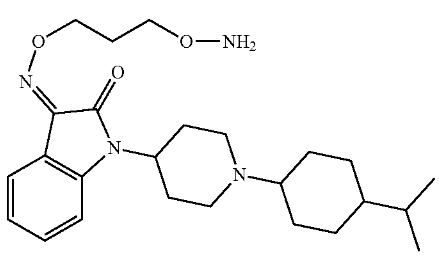 [SMILES: CC(C)C1CCC(N2CCC(N3C(=O)/C(=N\OCCCON)c4ccccc43)CC2)CC1] | (Z)-3-((3-(aminooxy)propoxy)imino)-1-(1-((1s,4s)-4-isopropylcyclohexyl)piperidin-4-yl)indolin-2-one | $^1$H NMR (DMSO-$d_6$) δ 7.91 (d, J = 7.5 Hz, 1H), 7.46 (t, J = 7.8 Hz, 1H), 7.22 (d, J = 8.1 Hz, 1H), 7.09 (t, J = 7.5 Hz, 1H), 5.98 (br, 2H), 4.46 (t, J = 6.3 Hz, 2H), 4.00 (m, 1H), 3.65 (t, J = 6.3 Hz, 2H), 3.07 (d, J = 11.1 Hz, 2H), 2.27 (m, 3H), 2.15-1.92 (m, 4H), 1.74-1.48 (m, 7H), 1.46-1.28 (m, 4H), 1.09 (m, 1H), 0.87 (d, J = 6.6 Hz, 6H) |

TABLE 2-continued

| No. | Structure* | IUPAC Name | NMR (300 or 400 MHz) |
|---|---|---|---|
| 232 | [structure] | (Z)-3-((2-hydroxyethoxy)imino)-1-(1-((1s,4s)-4-isopropylcyclohexyl)piperidin-4-yl)indolin-2-one | $^1$H NMR (DMSO-$d_6$) δ 7.96 (d, J = 7.5 Hz, 1H), 7.44 (t, J = 7.8 Hz, 1H), 7.20 (d, J = 8.1 Hz, 1H), 7.06 (t, J = 7.5 Hz, 1H), 4.85 (t, J = 5.4 Hz, 1H), 4.40 (t, J = 5.4 Hz, 2H), 4.00 (m, 1H), 3.73 (q, J = 5.4 Hz, 2H), 3.05 (d, J = 11.1 Hz, 2H), 2.28 (m, 3H), 2.08 (t, J = 11.4 Hz, 2H), 1.73-1.27 (m, 11H), 1.07 (m, 1H), 0.85 (d, J = 6.6 Hz, 6H) |
| 233 | [structure] | methyl 2-((Z)-1-(1-((1s,4s)-4-isopropylcyclohexyl)piperidin-4-yl)-2-oxoindolin-3-ylidene)acetate | $^1$H NMR (CD$_3$OD) δ 8.56 (d, J = 5.7 Hz, 1H), 7.50 (s, 1H), 7.22 (s, 1H), 7.10 (t, J = 5.7 Hz, 1H), 6.78 (s, 1H), 4.40 (m, 1H), 3.87 (s, 3H), 3.70 (m, 2H), 2.90 (m, 2H), 2.14-1.78 (m, 6H), 1.76 (m, 5H), 1.55 (m, 2H), 1.28 (m, 3H), 0.96 (d, J = 4.5 Hz, 6H) |
| 234 | [structure] | 2-((Z)-1-(1-((1s,4s)-4-isopropylcyclohexyl)piperidin-4-yl)-2-oxoindolin-3-ylidene)acetamido | $^1$H NMR (CDCl$_3$) δ 8.56 (d, J = 5.7 Hz, 1H), 7.32 (m, 1H), 7.10 (m, 1H), 7.04 (t, J = 6.0 Hz, 1H), 6.91 (s, 1H), 5.92 (br, 1H), 5.66 (br, 1H), 4.23 (m, 1H), (d, J = 8.1 Hz, 2H), 2.46-2.28 (m, 3H), 2.20 (t, J = 8.7 Hz, 2H), 1.74-1.48 (m, 10H), 1.39 (m, 2H), 1.14 (m, 1H), 0.90 (d, J = 5.1 Hz, 6H) |
| 235 | [structure] | 5-((Z)-1-(1-((1s,4s)-4-isopropylcyclohexyl)piperidin-4-yl)-2-oxoindolin-3-ylidene)-4-oxopentanamide | NMR (CDCl$_3$) δ 8.69 (d, J = 5.7 Hz, 1H), 7.30 (m, 1H), 7.09 (m, 1H), 7.03 (m, 1H), 6.98 (s, 1H), 5.78 (br, 1H), 5.59 (br, 1H), 4.23 (m, 1H), 3.72 (q, J = 4.2 Hz, 2H), 3.15 (m, 2H), 2.59 (t, J = 4.2 Hz, 2H), 2.45-2.14 (m, 5H), 1.65 (m, 10H), 1.40 (m, 2H), 1.14 (m, 1H), 0.90 (d, J = 4.8 Hz, 6H) |
| 236 | [structure] | 2-((Z)-1-(1-((1s,4s)-4-isopropylcyclohexyl)piperidin-4-yl)-2-oxoindolin-3-ylidene)acetonitrile | NMR CDCl$_3$) δ 8.09 (d, J = 5.7 Hz, 1H), 7.40 (t, J = 5.7 Hz, 1H), 7.14 (d, J = 6.0 Hz, 1H), 7.10 (t, J = 5.7 Hz, 1H), 6.31 (s, 1H), 4.20 (m, 1H), 3.15 (d, J = 5.4 Hz, 2H), 2.40 (m, 3H), 2.19 (t, J = 5.4 Hz, 2H), 1.78-1.49 (m, 7H), 1.52 (m, 2H), 1.40 (m, 2H), 1.15 (m, 1H), 0.90 (d, J = 5.1 Hz, 6H) |
| 237 | [structure] | N-(1-(1-((1s,4s)-4-isopropylcyclohexyl)piperidin-4-yl)-2-oxoindolin-3-yl)acetamido | $^1$H NMR (CD$_3$OD) δ 7.28 (m, 3H), 7.07 (t, J = 7.5 Hz, 1H), 4.99 (s, 1H), 4.40 (m, 1H), 3.70 (m, 2H), 3.22 (m, 4H), 3.01-2.71 (m, 2H), 2.13-1.86 (m, 9H), 1.74 (m, 3H), 1.55 (m, 2H), 1.26 (m, 1H), 0.96 (d, J = 6.6 Hz, 6H) |

TABLE 2-continued

| No. | Structure* | IUPAC Name | NMR (300 or 400 MHz) |
|---|---|---|---|
| 238 | 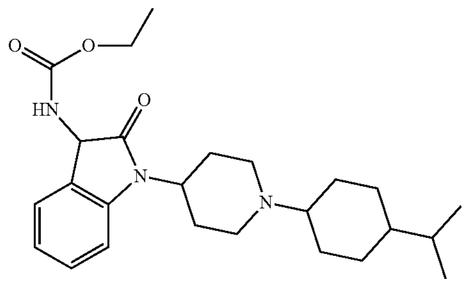 [SMILES: CCOC(=O)NC1C(=O)N(C2CCN(C3CCC(C(C)C)CC3)CC2)c2ccccc21] | ethyl (1-(1-((1s,4s)-4-isopropylcyclohexyl) piperidin-4-yl)-2-oxoindolin-3-yl)carbamate | ¹H NMR (CD₃OD) δ 7.33 (m, 2H), 7.19 (d, J = 8.1 Hz, 1H), 7.11 (q, J = 7.5 Hz, 1H), 4.33 (m, 1H), 4.11 (m, 2H), 3.71 (m, 1H), 3.24 (m, 4H), 3.05-2.70 (m, 2H), 2.16-1.86 (m, 5H), 1.75 (m, 4H), 1.56 (m, 2H), 1.26 (m, 6H), 0.96 (d, J = 6.6 Hz, 6H) |
| 239 | 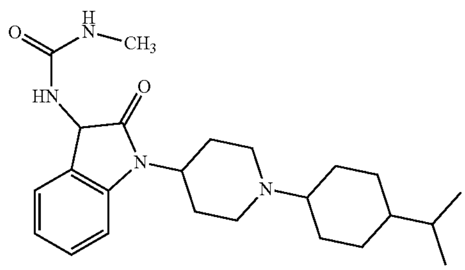 [SMILES: CNC(=O)NC1C(=O)N(C2CCN(C3CCC(C(C)C)CC3)CC2)c2ccccc21] | 1-(1-(1-((1s,4s)-4-isopropylcyclohexyl) piperidin-4-yl)-2-oxoindolin-3-yl)-3-methylurea | ¹H NMR (CDCl₃) δ 7.09 (d, J = 7.2 Hz, 1H), 7.01 (m, 1H), 6.77 (m, 2H), 4.65 (d, J = 4.8 Hz, 1H), 4.26(m 1H), 3.13 (m, 2H), 2.70 (m, 3H), 2.40-2.10 (m, 4H), 1.88-1.31 (m, 13 H), 1.14 (s, 1H), 0.90 (d, J = 6.6 Hz, 6H) |
| 240 | 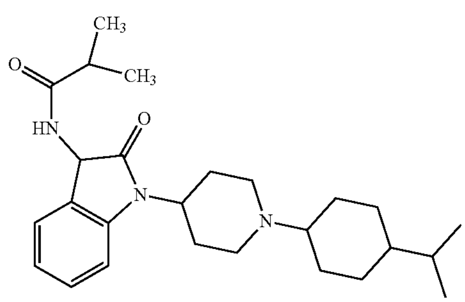 [SMILES: CC(C)C(=O)NC1C(=O)N(C2CCN(C3CCC(C(C)C)CC3)CC2)c2ccccc21] | N-(1-(1-((1s,4s)-4-isopropylcyclohexyl) piperidin-4-yl)-2-oxoindolin-3-yl)isobutyramide | ¹H NMR (CDCl₃) δ 7.35 (d, J = 7.5 Hz, 1H), 7.27 (m, 1H), 7.16 (d, J = 8.1 Hz, 1H), 7.03 (t, J = 7.5 Hz, 1H), 5.96 (d, J = 7.5 Hz, 1H), 5.36 (d, J = 7.5 Hz, 1H), 4.24 (m, 1H), 3.14 (d, J = 10.8 Hz, 2H), 2.52-2.27 (m, 3H), 2.18 (t, J = 11.7 Hz, 2H), 1.80-1.47 (m, 10H), 1.40 (m, 2H), 1.23 (m, 7H), 0.90 (d, 6H) |
| 241 | 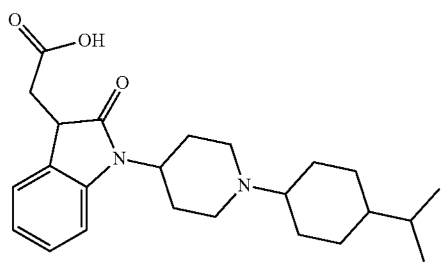 [SMILES: CC(C)C1CCC(N2CCC(N3C(=O)C(CC(=O)O)c4ccccc43)CC2)CC1] | 2-(1-(1-((1s,4s)-4-isopropylcyclohexyl) piperidin-4-yl)-2-oxoindolin-3-yl)acetic acid | ¹H NMR (CDCl₃) δ 12.8 (br, 1H), 7.42-7.18 (m 3H), 6.93 (t, J = 5.4 Hz, 1H), 4.52 (m, 1H), 3.62 (s, 1H), 3.50 (m, 1H), 3.30 (m, 1H), 3.10-2.75 (m, 7H), 2.05-1.40 (m, 11H), 1.22 (m, 1H), 0.91 (d, J = 3.9 Hz, 6H) |
| 242 | 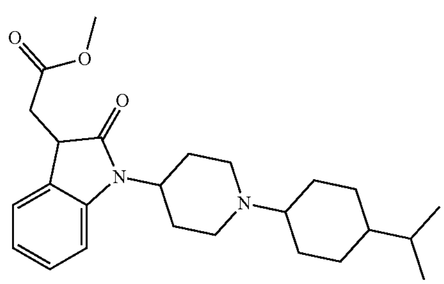 [SMILES: COC(=O)CC1C(=O)N(C2CCN(C3CCC(C(C)C)CC3)CC2)c2ccccc21] | methyl 2-(1-(1-((1s,4s)-4-isopropylcyclohexyl) piperidin-4-yl)-2-oxoindolin-3-yl)acetate | ¹H NMR (CD₃OD) δ 7.33-7.27 (m, 2H), 7.23 (d, J = 5.7 Hz, 1H), 7.06 (t, J = 5.7 Hz, 1H), 4.44 (m, 1H), 3.71 (t, J = 3.9 Hz, 3H), 3.55 (s, 3H), 3.27 (m, 4H), 3.13-2.80 (m, 3H), 2.13-1.91 (m, 6H), 1.77 (m, 3H), 1.56 (t, J = 9.6 Hz, 2H), 1.26 (m, 1H), 0.96 (d, 6H) |

TABLE 2-continued

| No. | Structure* | IUPAC Name | NMR (300 or 400 MHz) |
|---|---|---|---|
| 243 | 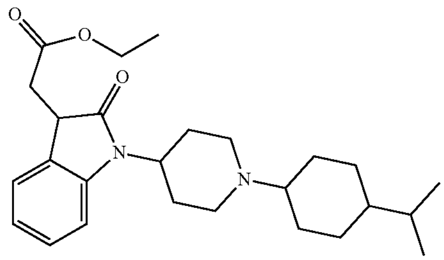 [SMILES: CCOC(=O)CC1C(=O)N(C2CCN(C3CCC(C(C)C)CC3)CC2)c2ccccc21] | ethyl 2-(1-(1-((1s,4s)-4-isopropylcyclohexyl)piperidin-4-yl)-2-oxoindolin-3-yl)acetate | ¹H NMR (CD₃OD) δ 7.30 (d, J = 5.7 Hz, 2H), 7.23 (d, J = 5.7 Hz, 1H), 7.06 (t, J = 5.7 Hz, 1H), 4.44 (m, 1H), 4.00 (m, 2H), 3.71 (m, 2H), 3.27 (m, 4H), 3.12-2.30 (m, 4H), 2.12-1.90 (m, 6H), 1.77 (m, 3H), 1.59 (m, 2H), 1.28 (m, 1H), 1.10 (t, J = 5.4 Hz, 3H), 0.96 (d, J = 4.8 Hz, 6H) |
| 244 | 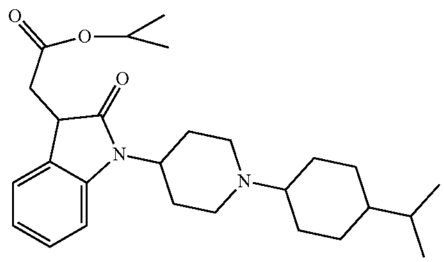 [SMILES: CC(C)OC(=O)CC1C(=O)N(C2CCN(C3CCC(C(C)C)CC3)CC2)c2ccccc21] | isopropyl 2-(1-(1-((1s,4s)-4-isopropylcyclohexyl)piperidin-4-yl)-2-oxoindolin-3-yl)acetate | ¹H NMR (CD₃OD) δ 7.37-7.20 (m, 3H), 7.05 (t, J = 4.8 Hz, 1H), 4.44 (m, 1H), 3.70 (m, 3H), 3.27 (m, 4H), 3.10-2.82 (m, 4H), 2.14-1.90 (m, 6H), 1.77 (m, 3H), 1.56 (m, 2H), 1.27 (m, 1H), 1.07 (t, J = 4.8 Hz, 6H), 0.95 (d, 6H) |
| 245 | 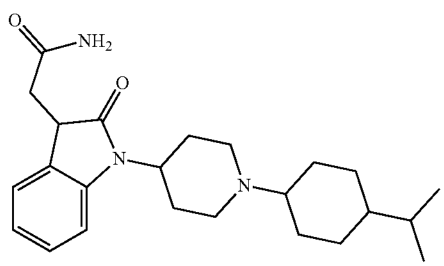 | 2-(1-(1-((1s,4s)-4-isopropylcyclohexyl)piperidin-4-yl)-2-oxoindolin-3-yl)acetamido | ¹H NMR (400 MHz, CDCl₃) δ 7.33 (d, J = 7.2 Hz, 1H), 7.24 (t, J = 7.6 Hz, 1H), 7.18 (d, J = 7.6 Hz, 1H), 7.05 (t, J = 7.6 Hz, 1H), 6.59 (br, 1H), 5.42 (br, 1H), 4.26 (m, 1H), 3.83 (t, J = 6.4 Hz, 1H), 3.15 (d, J = 11.2 Hz, 2H), 2.91 (dd, J = 15.6, 6.4 Hz, 1H), 2.65 (dd, J = 15.6, 6.4 Hz, 1H), 2.45-2.27 (m, 3H), 2.19 (t, J = 11.6 Hz, 2H), 1.75-1.61 (m, 8H), 1.52 (m, 2H), 1.39 (m, 1H), 1.14 (m, 1H), 0.90 (d, J = 6.6 Hz, 6H) |
| 246 | 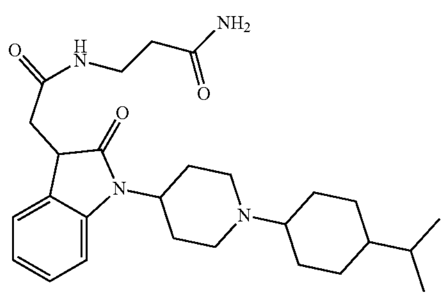 [SMILES: CC(C)C1CCC(N2CCC(N3C(=O)C(CC(=O)NCCC(N)=O)c4ccccc43)CC2)CC1] | 3-(2-(1-(1-((1s,4s)-4-isopropylcyclohexyl)piperidin-4-yl)-2-oxoindolin-3-yl)acetamido)propanamide | ¹H NMR (CD₃OD) δ 7.27 (m, 2H), 7.14 (d, J = 6.0 Hz, 1H), 7.05 (t, J = 5.7 Hz, 1H), 4.37 (m, 1H), 3.71(m, 2H), 3.39-3.20 (m, 5H), 2.96-2.72 (m, 5H), 2.31 (m, 2H), 2.13-1.88 (m, 6H), 1.76 (m, 3H), 1.56 (m, 2H), 1.25 (m, 1H), 0.96 (d, J = 5.1 Hz, 6H) |
| 247 | 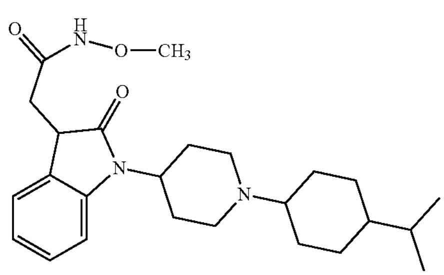 [SMILES: CONC(=O)CC1C(=O)N(C2CCN(C3CCC(C(C)C)CC3)CC2)c2ccccc21] | 2-(1-(1-((1s,4s)-4-isopropylcyclohexyl)piperidin-4-yl)-2-oxoindolin-3-yl)-N-methoxyacetamide | ¹H NMR (400 MHz, CDCl₃) δ 8.53 (1H, d, J = 8 Hz), 7.31 (1H, td, J = 8, 4 Hz), 7.10 (1H, d, J = 8 Hz), 7.02 (1H, t, J = 8 Hz), 6.83 (1H, s), 4.21-4.26 (1H, m), 3.13 (2H, d, J = 6 Hz), 2.29-2.45 (3H, m), 2.18 (2H, t, J = 12 Hz), 1.59-1.71 (7H, m), 1.56 (9H, s), 1.34-1.52 (4H, m), 1.13 (1H, s), 0.89 (6H, d, J = 8 Hz) |

TABLE 2-continued

| No. | Structure* | IUPAC Name | NMR (300 or 400 MHz) |
|---|---|---|---|
| 248 | 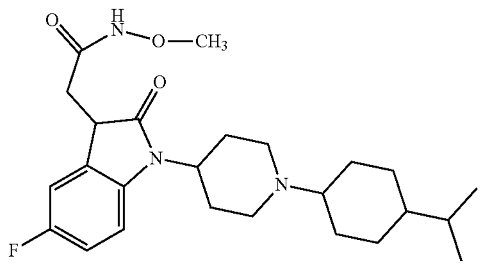 [SMILES: CONC(=O)CC1C(=O)N(C2CCN(C3CCC(C(C)C)CC3)CC2)c2ccc(F)cc21] | 2-(5-fluoro-1-(1-((1s,4s)-4-isopropylcyclohexyl)piperidin-4-yl)-2-oxoindolin-3-yl)-N-methoxyacetamide | $^1$H NMR (CD$_3$OD) δ 7.16 (dd, J = 8.4, 4.2 Hz, 1H), 7.07 (m, 1H), 4.42 (s, 3H), 3.69 (d, J = 11.4 Hz, 2H), 3.53 (s, 3H), 3.20 (m, 3H), 2.96-2.74 (m, 4H), 2.10-1.86 (m, 6H), 1.75 (m, 3H), 1.54 (m, 2H), 1.24 (m, 1H), 0.95 (d, J = 6.6 Hz, 6H) |
| 249 | 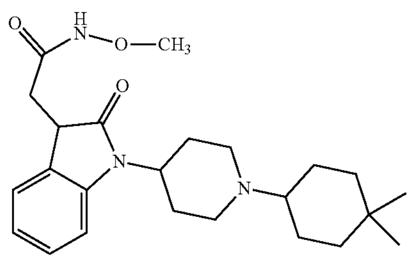 [SMILES: CONC(=O)CC1C(=O)N(C2CCN(C3CCC(C)(C)CC3)CC2)c2ccccc21] | 2-(1-(1-(4,4-dimethylcyclohexyl)piperidin-4-yl)-2-oxoindolin-3-yl)-N-methoxyacetamide | $^1$H NMR (CDCl$_3$) δ 7.30 (d, J = 7.5 Hz, 1H), 7.22 (m, 2H), 7.04 (m, 1H), 5.40 (br, 1H), 4.26 (m, 1H), 3.77 (s, 3H), 3.07 (d, J = 8.1 Hz, 2H), 2.68 (m, 1H), 2.45-2.25 (m, 5H), 1.68 (m, 6H), 1.45 (m, 4H), 1.23 (m, 2H), 0.90 (s, 6H) |
| 250 | 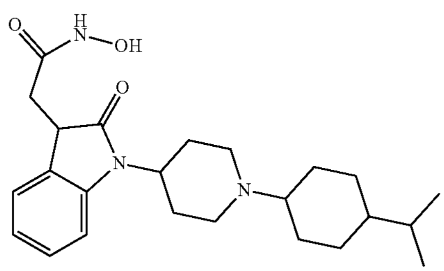 [SMILES: CC(C)C1CCC(N2CCC(N3C(=O)C(CC(=O)NO)c4ccccc43)CC2)CC1] | N-hydroxy-2-(1-(1-((1s,4s)-4-isopropylcyclohexyl)piperidin-4-yl)-2-oxoindolin-3-yl)acetamido | $^1$H NMR (CDCl$_3$) δ 7.31 (d, J = 7.5 Hz, 2H), 7.17 (m, 1H), 7.04 (t, J = 7.5 Hz, 1H), 4.18 (m, 1H), 3.80 (t, J = 6.6 Hz, 1H), 3.15 (d, J = 10.5 Hz, 2H), 2.80-2.20 (m, 7H), 1.67 (m, 9H), 1.39 (m, 2H), 1.15 (m, 1H), 0.90 (d, 6H) |
| 251 | 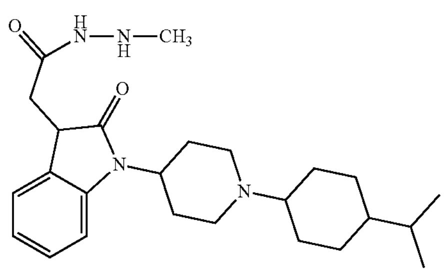 [SMILES: CNNC(=O)CC1C(=O)N(C2CCN(C3CCC(C(C)C)CC3)CC2)c2ccccc21] | 2-(1-(1-((1s,4s)-4-isopropylcyclohexyl)piperidin-4-yl)-2-oxoindolin-3-yl)-N'-methylacetohydrazide | $^1$H NMR (400 MHz, CDCl$_3$) δ 7.92 (br, 1H), 7.28 (m, 2H), 7.18 (d, J = 7.6 Hz, 1H), 7.04 (t, J = 7.6 Hz, 1H), 4.59 (br, 1H), 4.26 (m, 1H), 3.83 (t, J = 6.4 Hz, 1H), 3.14 (d, J = 10.8 Hz, 2H), 2.82 (dd, J = 15.6, 6.8 Hz, 1H), 2.60 (m, 4H), 2.45-2.15 (m, 3H), 2.19 (t, J = 11.6 Hz, 2H), 1.78-1.59 (m, 7H), 1.52 (m, 2H), 1.38 (m, 2H), 1.14 (m, 1H), 0.90 (d, 6H) |
| 252 | 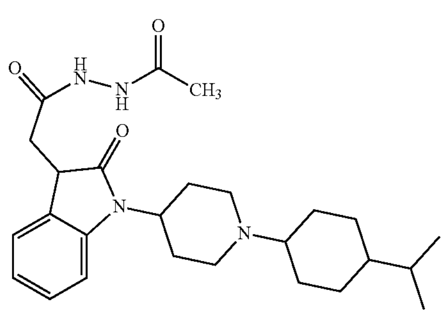 [SMILES: CC(=O)NNC(=O)CC1C(=O)N(C2CCN(C3CCC(C(C)C)CC3)CC2)c2ccccc21] | N'-acetyl-2-(1-(1-((1s,4s)-4-isopropylcyclohexyl)piperidin-4-yl)-2-oxoindolin-3-yl)acetohydrazide | $^1$H NMR (400 MHz, CDCl$_3$) δ 9.71 (br, 1H), 8.83 (br, 1H), 7.26 (d, J = 7.6 Hz, 1H), 7.23 (d, J = 7.6 Hz, 1H), 7.16 (d, J = 8.0 Hz, 1H), 7.02 (t, J = 7.6 Hz, 1H), 4.26 (m, 1H), 3.83 (t, J = 6.4 Hz, 1H), 3.12 (d, J = 10.4 Hz, 2H), 2.92 (dd, J = 16.0, 6.4 Hz, 1H), 2.73 (dd, J = 16.0, 6.4 Hz, 1H), 2.45-2.27 (m, 3H), 2.17 (t, J = 11.2 Hz, 2H), 2.03 (s, 3H), 1.77-1.46 (m, 9H), 1.38 (m, 1H), 1.13 (m, 2H), 0.90 (d, J = 6.6 Hz, 6H) |

TABLE 2-continued

| No. | Structure* | IUPAC Name | NMR (300 or 400 MHz) |
|---|---|---|---|
| 253 | 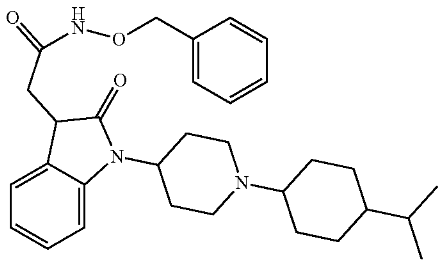 [SMILES: CC(C)C1CCC(N2CCC(N3C(=O)C(CC(=O)NOCc4ccccc4)c4ccccc43)CC2)CC1] | N-(benzyloxy)-2-(1-(1-((1s,4s)-4-isopropylcyclohexyl)piperidin-4-yl)-2-oxoindolin-3-yl)acetamido | $^1$H NMR (CDCl$_3$) δ 9.20 (br, 1H), 7.38 (m, 5H), 7.28 (m, 3H), 7.03 (m, 1H), 4.94 (m, 3H), 4.33 (m, 1H), 3.79 (m, 1H), 3.10 (d, J = 11.1 Hz, 2H), 2.78-2.45 (m, 4H), 2.33 (t, J = 11.7 Hz, 2H), 1.84-1.48 (m, 9H), 1.36 (m, 2H), 1.15 (m, 1H), 0.90 (d, J = 6.6 Hz, 6H) |
| 254 | 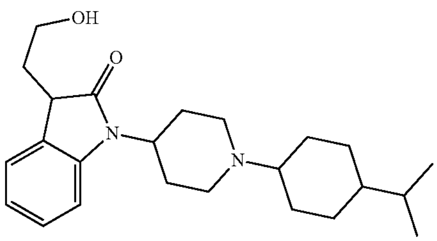 [SMILES: CC(C)C1CCC(N2CCC(N3C(=O)C(CCO)c4ccccc43)CC2)CC1] | 3-(2-hydroxyethyl)-1-(1-((1s,4s)-4-isopropylcyclohexyl)piperidin-4-yl)indolin-2-one | $^1$H NMR (DSMO-d$_6$) δ 10.15 (br, 1H), 7.69 (m, 1H), 7.52 (d, J = 5.4 Hz, 1H), 7.32 (d, J = 5.4 Hz, 1H), 7.25 (t, J = 5.4 Hz, 1H), 7.03 (t, J = 5.4 Hz, 1H), 4.51 (m, 1H), 3.60-3.12 (m, 8H), 2.82 (d, J = 6.3 Hz, 2H), 2.03 (m, 1H), 1.91-1.58 (m, 8H), 1.48-1.14 (m, 5H), 0.88 (d, J = 4.8 Hz, 6H) |
| 255 | 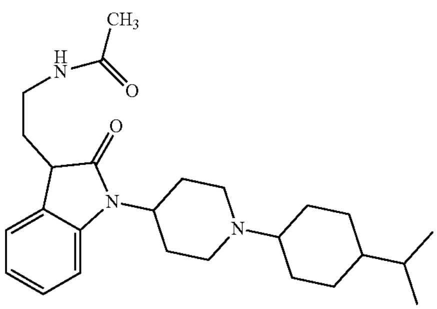 [SMILES: CC(=O)NCCC1C(=O)N(C2CCN(C3CCC(C(C)C)CC3)CC2)c2ccccc21] | N-(2-(1-(1-((1s,4s)-4-isopropylcyclohexyl)piperidin-4-yl)-2-oxoindolin-3-yl)ethyl)acetamido | $^1$H NMR (DSMO-d$_6$) δ 7.88 (s, 1H), 7.36 (d, J = 5.7 Hz, 1H), 7.27 (t, J = 5.7 Hz, 1H), 7.04 (t, J = 5.7 Hz, 1H), 3.50-3.00 (m, 12H), 1.98 (m, 2H), 1.79-1.58 (m, 12H), 1.38 (m, 2H), 1.14 (m, 1H), 0.90 (d, J = 4.8 Hz, 6H) |
| 256 | 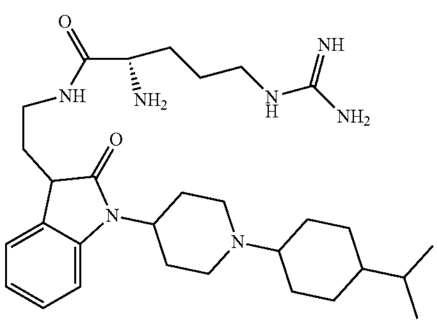 [SMILES: CC(C)C1CCC(N2CCC(N3C(=O)C(CCNC(=O)[C@@H](N)CCCNC(=N)N)c4ccccc43)CC2)CC1] | (2S)-2-amino-5-guanidino-N-(2-(1-(1-((1s,4R)-4-isopropylcyclohexyl)piperidin-4-yl)-2-oxoindolin-3-yl)ethyl)pentanamide | $^1$H NMR (CD$_3$OD) δ 7.40 (t, J = 5.7 Hz, 1H), 7.32 (t, J = 5.7 Hz, 1H), 7.20 (d, J = 5.7 Hz, 1H), 7.11 (t, J = 5.7 Hz, 1H), 4.44 (m, 1H), 3.83 (m, 2H), 3.71 (d, J = 8.7 Hz, 2H), 3.56 (m, 1H), 3.40-3.20 (m, 10H), 2.86 (m, 2H), 2.17-1.50 (m, 19H), 1.26 (m, 2H), 0.96 (d, 6H) |
| 257 | 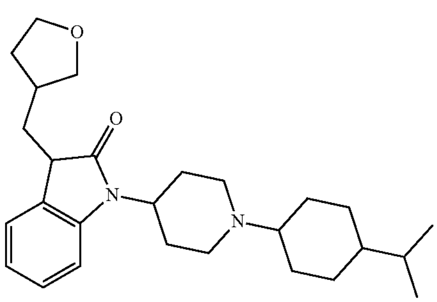 [SMILES: CC(C)C1CCC(N2CCC(N3C(=O)C(CC4CCOC4)c4ccccc43)CC2)CC1] | 1-(1-((1s,4s)-4-isopropylcyclohexyl)piperidin-4-yl)-3-((tetrahydrofuran-3-yl)methyl)indolin-2-one | $^1$H NMR (400 MHz, CDCl$_3$) δ 7.36 (d, J = 7.5 Hz, 1H), 7.29 (d, J = 7.5 Hz, 1H), 7.25-7.15 (m, 2H), 7.01 (m, 2H), 4.29 (m, 1H), 4.10 (m, 1H), 3.91 (m, 1H), 3.83 (m, 1H), 3.75 (m, 1H), 3.63 (m, 1H), 3.50 (t, J = 5.6 Hz, 1H), 3.13 (m, 2H), 2.24-2.05 (m, 6H), 1.97-1.47 (m, 12H), 1.41 (m, 2H), 1.15 (m, 1H), 0.90 (d, J = 6.6 Hz, 6H) |

TABLE 2-continued

| No. | Structure* | IUPAC Name | NMR (300 or 400 MHz) |
|---|---|---|---|
| 258 | 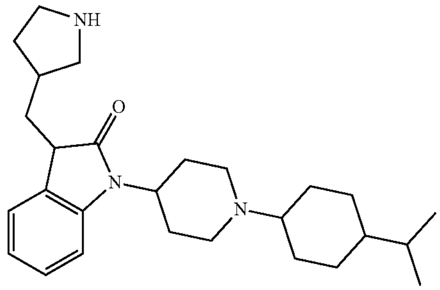 [SMILES: CC(C)C1CCC(N2CCC(N3C(=O)C(CC4CCNC4)c4ccccc43)CC2)CC1] | 1-(1-((1s,4s)-4-isopropylcyclohexyl)piperidin-4-yl)-3-(pyrrolidin-3-ylmethyl)indolin-2-one | $^1$H NMR (400 MHz, CDCl$_3$) δ 7.26 (m, 1H), 7.18 (m, 2H), 7.03 (t, J = 7.5 Hz, 1H), 5.36 (br, 1H), 4.28 (m, 1H), 3.69 (br, 2H), 3.42 (q, J = 5.6 Hz, 1H), 3.16-2.90 (m, 4H), 2.50-2.30 (m, 4H), 2.21 (t, J = 11.2 Hz, 2H), 2.03 (m, 2H), 1.78-1.33 (m, 11H), 1.22 (d, J = 5.6 Hz, 2H), 1.14 (m, 1H), 0.90 (d, J = 6.6 Hz, 6H) |
| 259 | 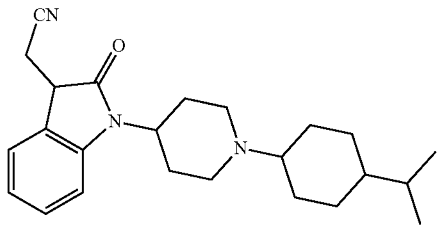 [SMILES: CC(C)C1CCC(N2CCC(N3C(=O)C(CC#N)c4ccccc43)CC2)CC1] | 2-(1-(1-((1s,4s)-4-isopropylcyclohexyl)piperidin-4-yl)-2-oxoindolin-3-yl)acetonitrile | $^1$H NMR (CDCl$_3$) δ 7.50 (d, J = 5.4 Hz, 1H), 7.33 (t, J = 5.7 Hz, 1H), 7.22 (d, J = 5.7 Hz, 1H), 7.11 (t, J = 5.7 Hz, 1H), 4.25 (m, 1H), 3.64 (dd, J = 6.6, 3.3 Hz, 1H), 3.14 (m, 2H), 3.08 (d, J = 3.3 Hz, 1H), 2.73 (dd, J = 12.6, 6.6 Hz, 1H), 2.48-2.30 (m, 3H), 2.20 (t, J = 8.7 Hz, 2H), 1.78-1.50 (m, 13H), 1.39 (m, 2H), 1.14 (m, 1H), 0.90 (d, J = 4.8 Hz, 6H) |
| 260 | 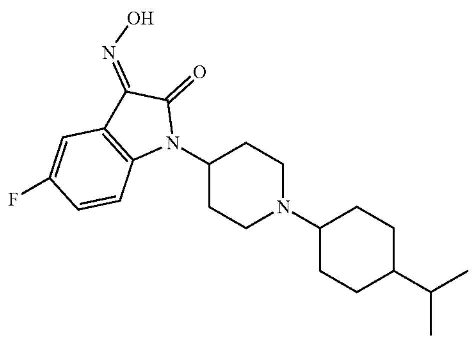 [SMILES: CC(C)C1CCC(N2CCC(N3C(=O)/C(=N\O)c4cc(F)ccc43)CC2)CC1] | (Z)-5-fluoro-3-(hydroxyimino)-1-(1-((1s,4s)-4-isopropylcyclohexyl)piperidin-4-yl)indolin-2-one | |
| 261 | 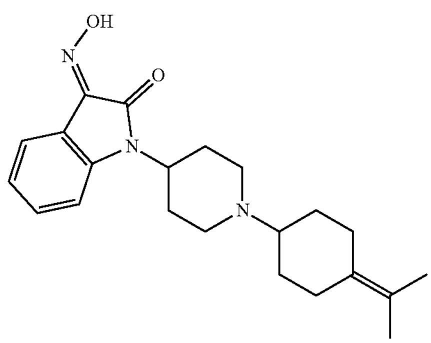 [SMILES: CC(C)=C1CCC(N2CCC(N3C(=O)/C(=N\O)c4ccccc43)CC2)CC1] | (Z)-3-(hydroxyimino)-1-(1-(4-(propan-2-ylidene)cyclohexyl)piperidin-4-yl)indolin-2-one | |
| 262 | 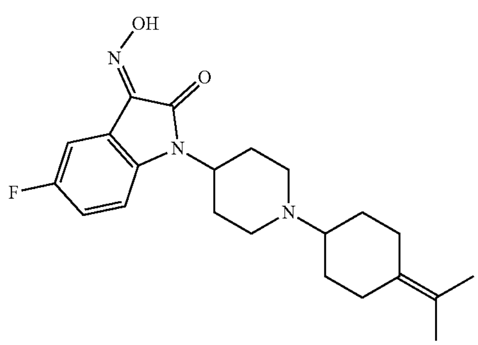 [SMILES: CC(C)=C1CCC(N2CCC(N3C(=O)/C(=N\O)c4cc(F)ccc43)CC2)CC1] | (Z)-5-fluoro-3-(hydroxyimino)-1-(1-(4-(propan-2-ylidene)cyclohexyl)piperidin-4-yl)indolin-2-one | |

TABLE 2-continued

| No. | Structure* | IUPAC Name | NMR (300 or 400 MHz) |
|---|---|---|---|
| 263 | 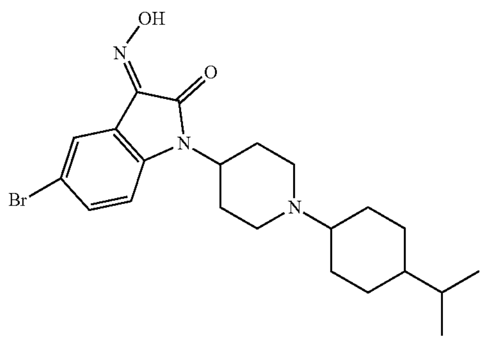 [SMILES: CC(C)C1CCC(N2CCC(N3C(=O)/C(=N\O)c4cc(Cl)ccc43)CC2)CC1] | (Z)-5-bromo-3-(hydroxyimino)-1-(1-((1s,4s)-4-isopropylcyclohexyl)piperidin-4-yl)indolin-2-one | |
| 264 | 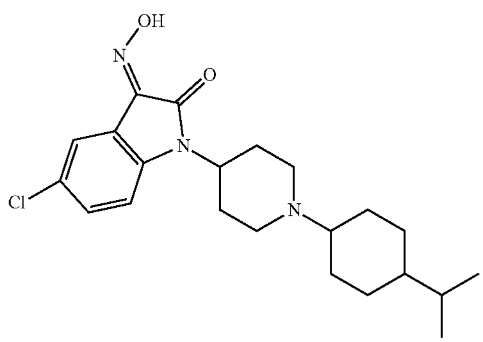 | (Z)-5-chloro-3-(hydroxyimino)-1-(1-((1s,4s)-4-isopropylcyclohexyl)piperidin-4-yl)indolin-2-one | |
| 265 | 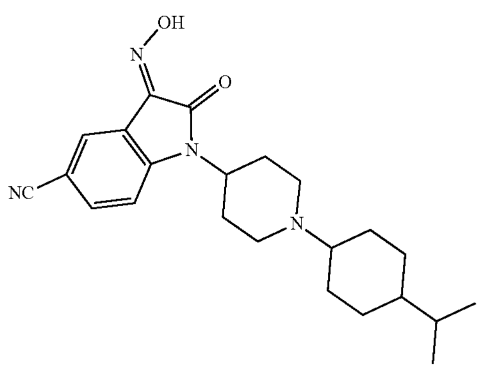 [SMILES: CC(C)C1CCC(N2CCC(N3C(=O)/C(=N\O)c4cc(C#N)ccc43)CC2)CC1] | (Z)-3-(hydroxyimino)-1-(1-((1s,4s)-4-isopropylcyclohexyl)piperidin-4-yl)-2-oxoindoline-5-carbonitrile | |
| 266 | 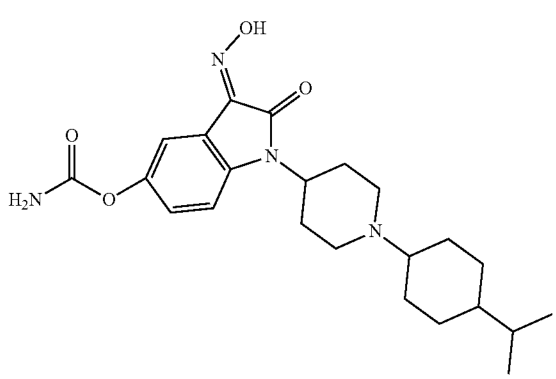 [SMILES: CC(C)C1CCC(N2CCC(N3C(=O)/C(=N\O)c4cc(OC(N)=O)ccc43)CC2)CC1] | (Z)-3-(hydroxyimino)-1-(1-((1s,4s)-4-isopropylcyclohexyl)piperidin-4-yl)-2-oxoindolin-5-yl carbamate | |

TABLE 2-continued

| No. | Structure* | IUPAC Name | NMR (300 or 400 MHz) |
|---|---|---|---|
| 267 | 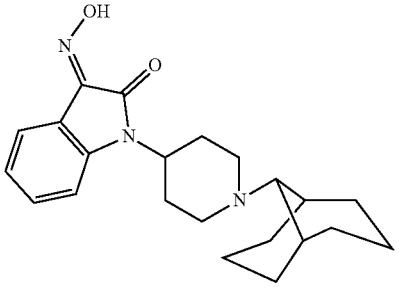 [SMILES: O=C1/C(=N\O)c2ccccc2N1C1CCN(C2C3CCCC2CCC3)CC1] | (Z)-1-(1-((1R,5S)-bicyclo[3.3.1]nonan-9-yl)piperidin-4-yl)-3-(hydroxyimino)indolin-2-one | |
| 268 | 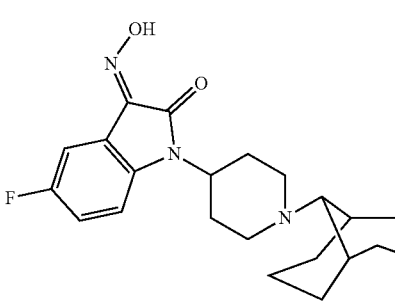 | (Z)-1-(1-((1R,5S)-bicyclo[3.3.1]nonan-9-yl)piperidin-4-yl)-5-fluoro-3-(hydroxyimino)indolin-2-one | |
| 269 | 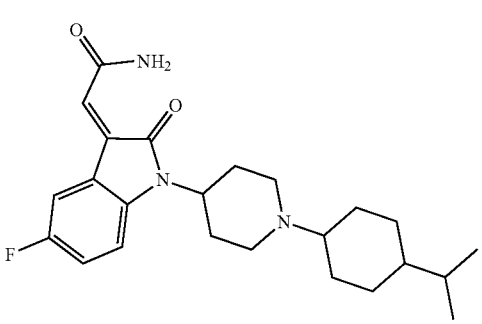 [SMILES: CC(C)=C1CCC(N2CCC(N3C(=O)/C(=C\C(N)=O)c4cc(F)ccc43)CC2)CC1] | 2-((Z)-5-fluoro-1-(1-((1s,4s)-4-isopropylcyclohexyl)piperidin-4-yl)-2-oxoindolin-3-ylidene)acetamide | |
| 270 | 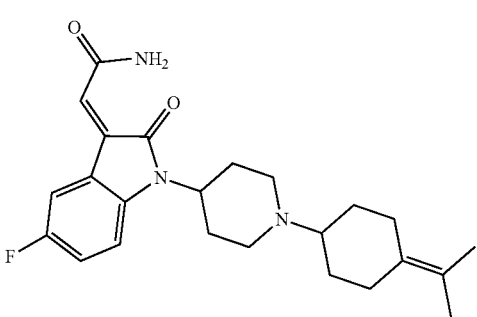 | (Z)-2-(5-fluoro-2-oxo-1-(1-(4-(propan-2-ylidene)cyclohexyl)piperidin-4-yl)indolin-3-ylidene)acetamide | |
| 271 | 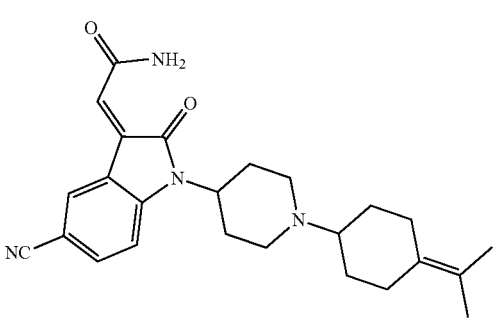 [SMILES: CC(C)=C1CCC(N2CCC(N3C(=O)/C(=C\C(N)=O)c4cc(C#N)ccc43)CC2)CC1] | (Z)-2-(5-cyano-2-oxo-1-(1-(4-(propan-2-ylidene)cyclohexyl)piperidin-4-yl)indolin-3-ylidene)acetamide | |

TABLE 2-continued

| No. | Structure* | IUPAC Name | NMR (300 or 400 MHz) |
|---|---|---|---|
| 272 | 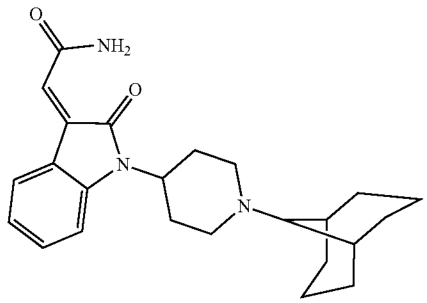 [SMILES: NC(=O)/C=C1\C(=O)N(C2CCN(C3C4CCCC3CCC4)CC2)c2ccccc21] | (Z)-2-(1-(1-(bicyclo[3.3.1]nonan-9-yl)piperidin-4-yl)-2-oxoindolin-3-ylidene)acetamide | |
| 273 | 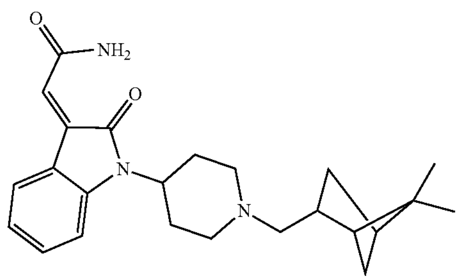 [SMILES: CC1(C)C2CC(CN3CCC(N4C(=O)/C(=C\C(N)=O)c5ccccc54)CC3)C1C2] | (Z)-2-(1-(1-((6,6-dimethylbicyclo[3.1.1]heptan-2-yl)methyl)piperidin-4-yl)-2-oxoindolin-3-ylidene)acetamide | |
| 274 | 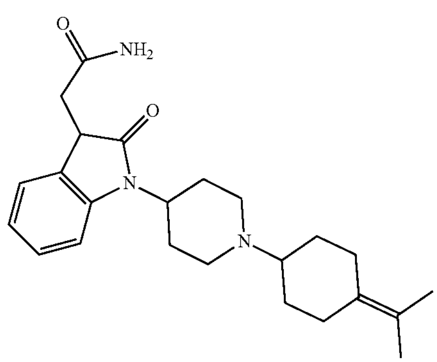 [SMILES: CC(C)=C1CCC(N2CCC(N3C(=O)C(CC(N)=O)c4ccccc43)CC2)CC1] | 2-(2-oxo-1-(1-(4-(propan-2-ylidene)cyclohexyl)piperidin-4-yl)indolin-3-yl)acetamide | |
| 275 | 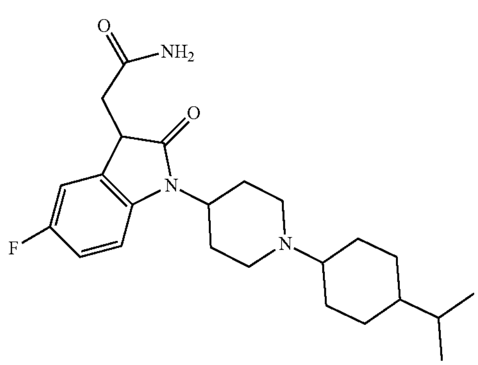 [SMILES: CC(C)C1CCC(N2CCC(N3C(=O)C(CC(N)=O)c4cc(F)ccc43)CC2)CC1] | 2-(5-fluoro-1-(1-((1s,4s)-4-isopropylcyclohexyl)piperidin-4-yl)-2-oxoindolin-3-yl)acetamide | |

TABLE 2-continued

| No. | Structure* | IUPAC Name | NMR (300 or 400 MHz) |
|---|---|---|---|
| 276 | 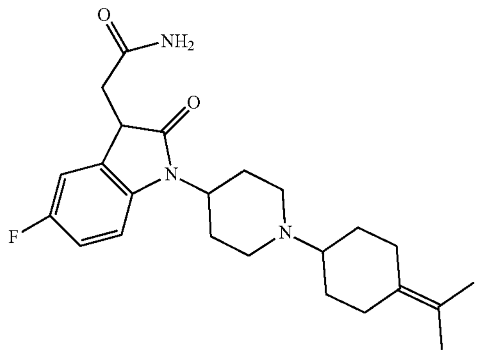 [SMILES: CC(C)=C1CCC(N2CCC(N3C(=O)C(CC(N)=O)c4cc(F)ccc43)CC2)CC1] | 2-(5-fluoro-2-oxo-1-(1-(4-(propan-2-ylidene)cyclohexyl)piperidin-4-yl)indolin-3-yl)acetamide | |
| 277 | 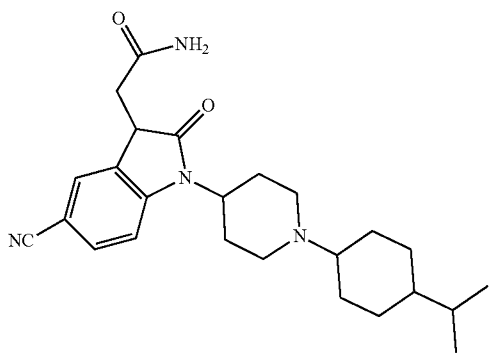 [SMILES: CC(C)C1CCC(N2CCC(N3C(=O)C(CC(N)=O)c4cc(C#N)ccc43)CC2)CC1] | 2-(5-cyano-1-(1-((1s,4s)-4-isopropylcyclohexyl)piperidin-4-yl)-2-oxoindolin-3-yl)acetamide | |
| 278 | 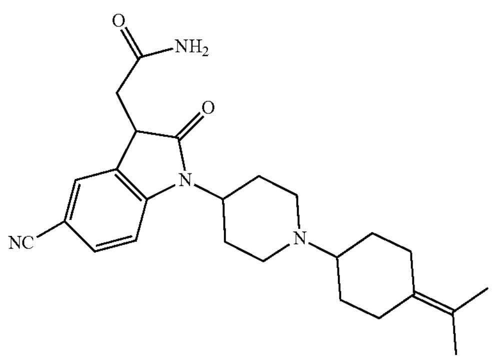 [SMILES: CC(C)=C1CCC(N2CCC(N3C(=O)C(CC(N)=O)c4cc(C#N)ccc43)CC2)CC1] | 2-(5-cyano-2-oxo-1-(1-(4-(propan-2-ylidene)cyclohexyl)piperidin-4-yl)indolin-3-yl)acetamide | |
| 279 | 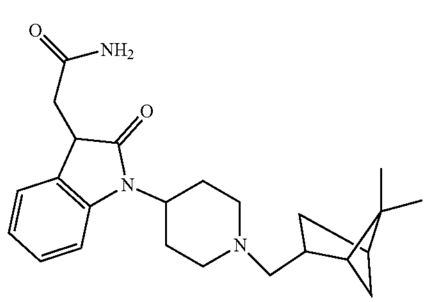 [SMILES: CC1(C)C2CC(CN3CCC(N4C(=O)C(CC(N)=O)c5ccccc54)CC3)C1C2] | 2-(1-(1-(((2R)-6,6-dimethylbicyclo[3.1.1]heptan-2-yl)methyl)piperidin-4-yl)-2-oxoindolin-3-yl)acetamide | |

TABLE 2-continued

| No. | Structure* | IUPAC Name | NMR (300 or 400 MHz) |
|---|---|---|---|
| 280 | 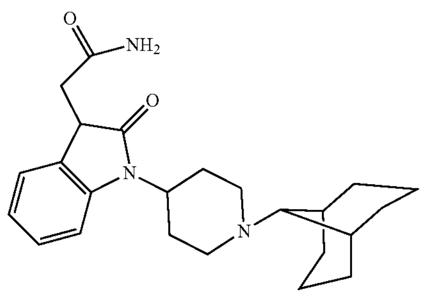 [SMILES: NC(=O)CC1C(=O)N(C2CCN(C3C4CCCC3CCC4)CC2)c2ccccc21] | 2-(1-(1-(bicyclo[3.3.1]nonan-9-yl)piperidin-4-yl)-2-oxoindolin-3-yl)acetamide | |
| 281 | 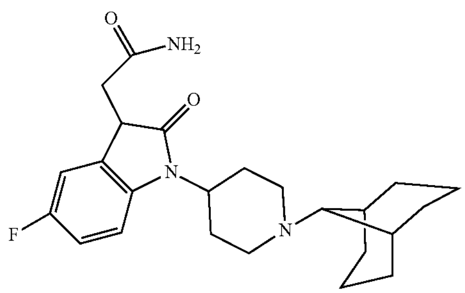 [SMILES: NC(=O)CC1C(=O)N(C2CCN(C3C4CCCC3CCC4)CC2)c2ccc(F)cc21] | 2-(1-(1-(bicyclo[3.3.1]nonan-9-yl)piperidin-4-yl)-5-fluoro-2-oxoindolin-3-yl)acetamide | |
| 282 | 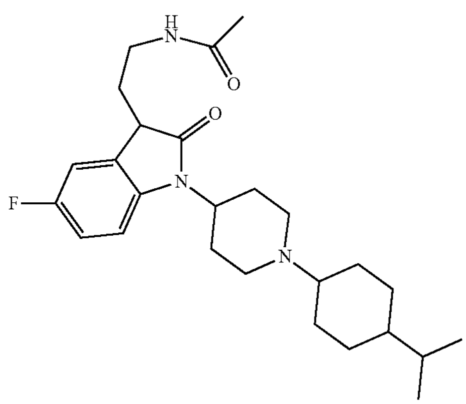 [SMILES: CC(=O)NCCC1C(=O)N(C2CCN(C3CCC(C(C)C)CC3)CC2)c2ccc(F)cc21] | N-(2-(5-fluoro-1-(1-((1s,4s)-4-isopropylcyclohexyl)piperidin-4-yl)-2-oxoindolin-3-yl)ethyl)acetamide | |
| 283 | 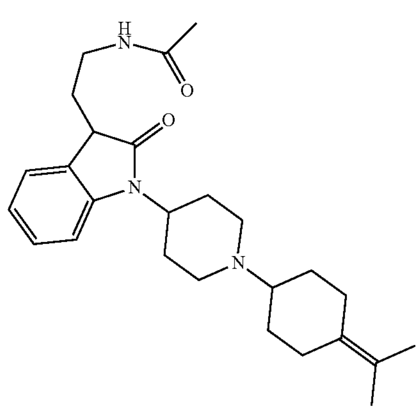 [SMILES: CC(=O)NCCC1C(=O)N(C2CCN(C3CCC(=C(C)C)CC3)CC2)c2ccccc21] | N-(2-(2-oxo-1-(1-(4-(propan-2-ylidene)cyclohexyl)piperidin-4-yl)indolin-3-yl)ethyl)acetamide | |

TABLE 2-continued

| No. | Structure* | IUPAC Name | NMR (300 or 400 MHz) |
|---|---|---|---|
| 284 | 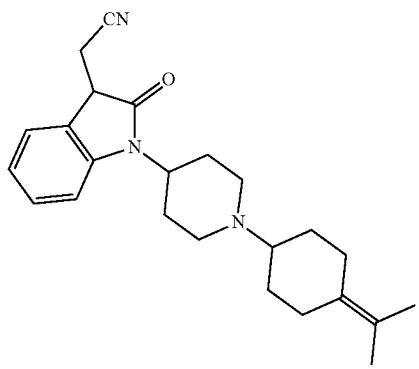 [SMILES: CC(C)=C1CCC(N2CCC(N3C(=O)C(CC#N)c4ccccc43)CC2)CC1] | 2-(2-oxo-1-(1-(4-(propan-2-ylidene)cyclohexyl)piperidin-4-yl)indolin-3-yl)acetonitrile | |
| 285 | 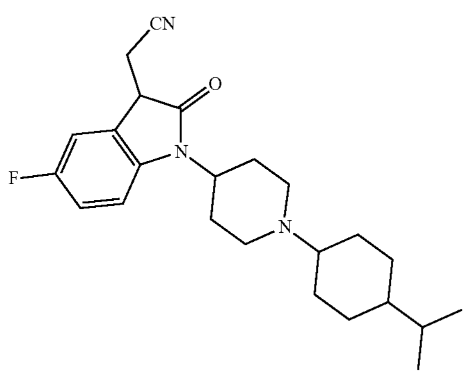 [SMILES: CC(C)C1CCC(N2CCC(N3C(=O)C(CC#N)c4cc(F)ccc43)CC2)CC1] | 2-(5-fluoro-1-(1-((1s,4s)-4-isopropylcyclohexyl)piperidin-4-yl)-2-oxoindolin-3-yl)acetonitrile | |
| 286 | 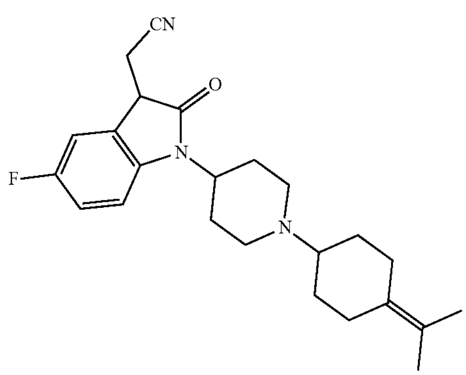 [SMILES: CC(C)=C1CCC(N2CCC(N3C(=O)C(CC#N)c4cc(F)ccc43)CC2)CC1] | 2-(5-fluoro-2-oxo-1-(1-(4-(propan-2-ylidene)cyclohexyl)piperidin-4-yl)indolin-3-yl)acetonitrile | |
| 287 | 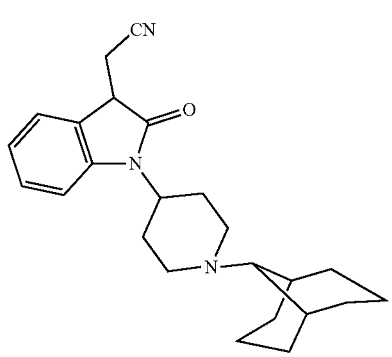 [SMILES: N#CCC1C(=O)N(C2CCN(C3C4CCCC3CCC4)CC2)c2ccccc21] | 2-(1-(1-((1R,5S)-bicyclo[3.3.1]nonan-9-yl)piperidin-4-yl)-2-oxoindolin-3-yl)acetonitrile | |

TABLE 2-continued

| No. | Structure* | IUPAC Name | NMR (300 or 400 MHz) |
|---|---|---|---|
| 288 | 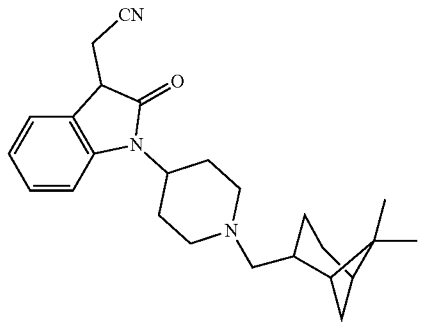 [SMILES: CC1(C)C2CCC(CN3CCC(N4C(=O)C(CC#N)c5ccccc54)CC3)C1C2] | 2-(1-(1-((6,6-dimethylbicyclo[3.1.1]heptan-2-yl)methyl)piperidin-4-yl)-2-oxoindolin-3-yl)acetonitrile | |
| 289 | 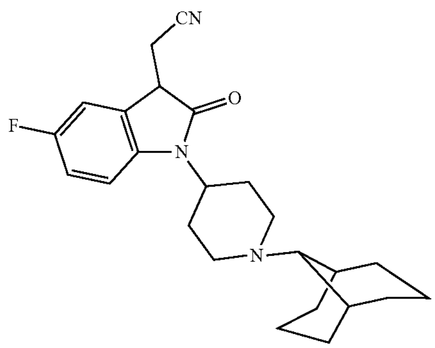 [SMILES: N#CCC1C(=O)N(C2CCN(C3C4CCCC3CCC4)CC2)c2ccc(F)cc21] | 2-(1-(1-((1R,5S)-bicyclo[3.3.1]nonan-9-yl)piperidin-4-yl)-5-fluoro-2-oxoindolin-3-yl)acetonitrile | |
| 290 | 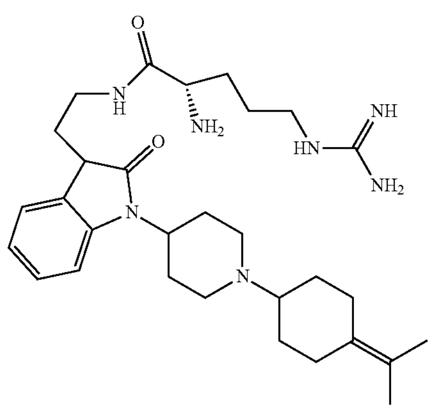 [SMILES: CC(C)=C1CCC(N2CCC(N3C(=O)C(CCNC(=O)[C@@H](N)CCCNC(=N)N)c4ccccc43)CC2)CC1] | (2S)-2-amino-5-guanidino-N-(2-(2-oxo-1-(1-(4-(propan-2-ylidene)cyclohexyl)piperidin-4-yl)indolin-3-yl)ethyl)pentanamide | |
| 291 | 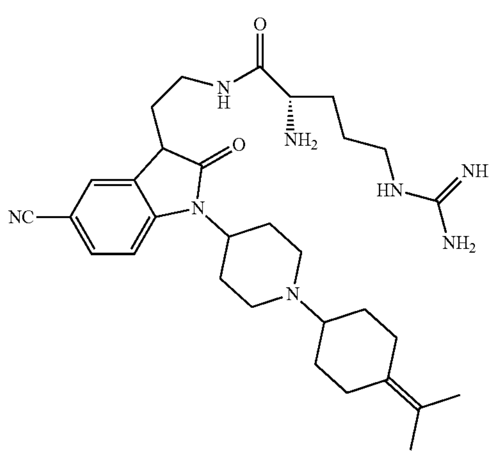 [SMILES: CC(C)=C1CCC(N2CCC(N3C(=O)C(CCNC(=O)[C@@H](N)CCCNC(=N)N)c4cc(C#N)ccc43)CC2)CC1] | (2S)-2-amino-N-(2-(5-cyano-2-oxo-1-(1-(4-(propan-2-ylidene)cyclohexyl)piperidin-4-yl)indolin-3-yl)ethyl)-5-guanidinopentanamide | |

TABLE 2-continued

| No. | Structure* | IUPAC Name | NMR (300 or 400 MHz) |
|---|---|---|---|
| 292 | 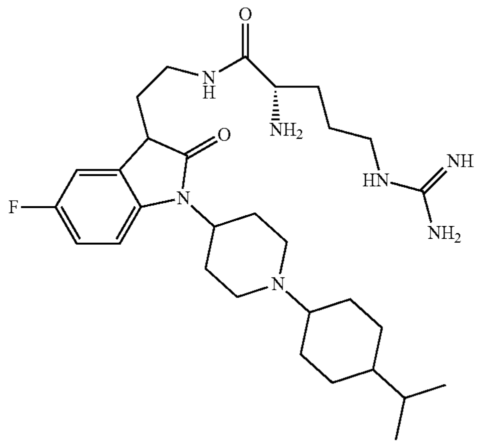 [SMILES: CC(C)C1CCC(N2CCC(N3C(=O)C(CCNC(=O)[C@@H](N)CCCNC(=N)N)c4cc(F)ccc43)CC2)CC1] | (2S)-2-amino-N-(2-(5-fluoro-1-(1-((1s,4R)-4-isopropylcyclohexyl)piperidin-4-yl)-2-oxoindolin-3-yl)ethyl)-5-guanidinopentanamide | |
| 293 | 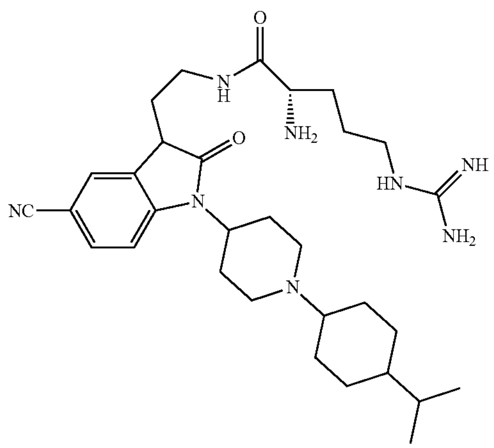 [SMILES: CC(C)C1CCC(N2CCC(N3C(=O)C(CCNC(=O)[C@@H](N)CCCNC(=N)N)c4cc(C#N)ccc43)CC2)CC1] | (2S)-2-amino-N-(2-(5-cyano-1-(1-((1s,4R)-4-isopropylcyclohexyl)piperidin-4-yl)-2-oxoindolin-3-yl)ethyl)-5-guanidinopentanamide | |
| 294 | 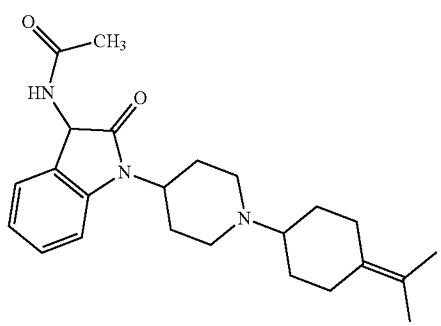 [SMILES: CC(=O)NC1C(=O)N(C2CCN(C3CCC(=C(C)C)CC3)CC2)c2ccccc21] | N-(2-oxo-1-(1-(4-(propan-2-ylidene)cyclohexyl)piperidin-4-yl)indolin-3-yl)acetamide | |
| 295 | 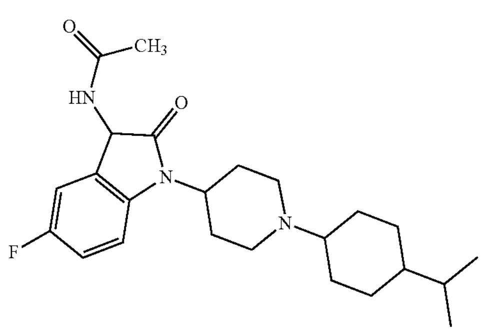 [SMILES: CC(=O)NC1C(=O)N(C2CCN(C3CCC(C(C)C)CC3)CC2)c2ccc(F)cc21] | N-(5-fluoro-1-(1-((1s,4s)-4-isopropylcyclohexyl)piperidin-4-yl)-2-oxoindolin-3-yl)acetamide | |

TABLE 2-continued

| No. | Structure* | IUPAC Name | NMR (300 or 400 MHz) |
|---|---|---|---|
| 296 | 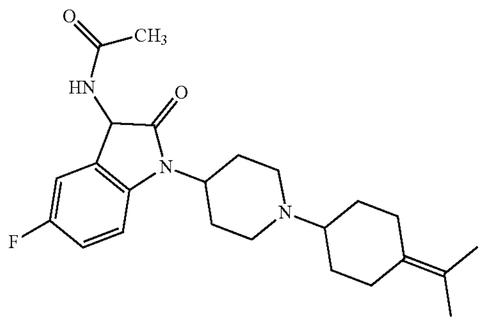 [SMILES: CC(=O)NC1C(=O)N(C2CCN(C3CCC(=C(C)C)CC3)CC2)c2ccc(F)cc21] | N-(5-fluoro-2-oxo-1-(1-(4-(propan-2-ylidene)cyclohexyl)piperidin-4-yl)indolin-3-yl)acetamide | |
| 297 | 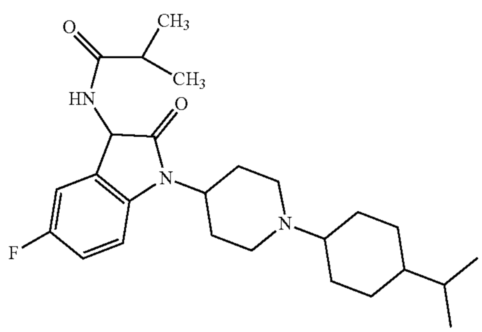 [SMILES: CC(C)C(=O)NC1C(=O)N(C2CCN(C3CCC(C(C)C)CC3)CC2)c2ccc(F)cc21] | N-(5-fluoro-1-(1-((1s,4s)-4-isopropylcyclohexyl)piperidin-4-yl)-2-oxoindolin-3-yl)isobutyramide | |
| 298 | 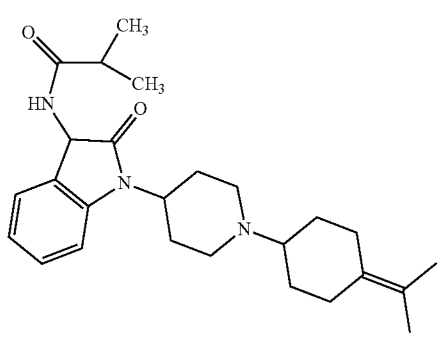 [SMILES: CC(C)=C1CCC(N2CCC(N3C(=O)C(NC(=O)C(C)C)c4ccccc43)CC2)CC1] | N-(2-oxo-1-(1-(4-(propan-2-ylidene)cyclohexyl)piperidin-4-yl)indolin-3-yl)isobutyramide | |
| 299 | 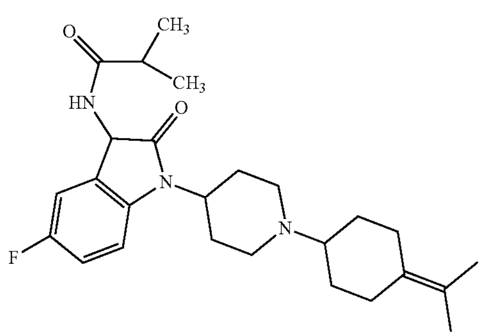 [SMILES: CC(C)=C1CCC(N2CCC(N3C(=O)C(NC(=O)C(C)C)c4cc(F)ccc43)CC2)CC1] | N-(5-fluoro-2-oxo-1-(1-(4-(propan-2-ylidene)cyclohexyl)piperidin-4-yl)indolin-3-yl)isobutyramide | |

TABLE 2-continued

| No. | Structure* | IUPAC Name | NMR (300 or 400 MHz) |
|---|---|---|---|
| 300 | 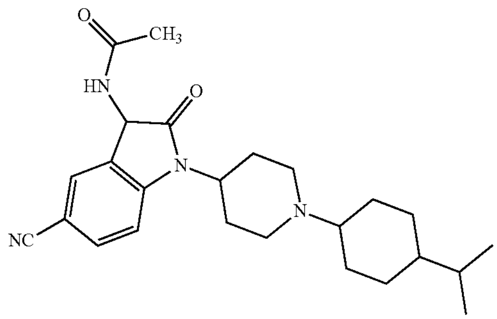 [SMILES: CC(=O)NC1C(=O)N(C2CCN(C3CCC(C(C)C)CC3)CC2)c2ccc(C#N)cc21] | N-(5-cyano-1-(1-((1s,4s)-4-isopropylcyclohexyl)piperidin-4-yl)-2-oxoindolin-3-yl)acetamide | |
| 301 | 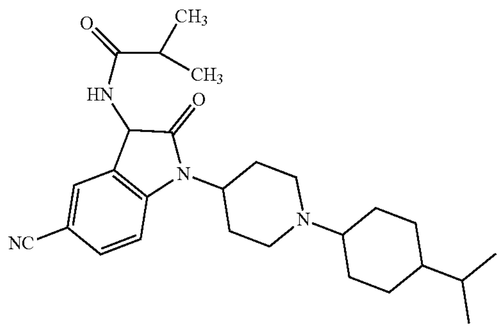 [SMILES: CC(C)C(=O)NC1C(=O)N(C2CCN(C3CCC(C(C)C)CC3)CC2)c2ccc(C#N)cc21] | N-(5-cyano-1-(1-((1s,4s)-4-isopropylcyclohexyl)piperidin-4-yl)-2-oxoindolin-3-yl)isobutyramide | |
| 302 | 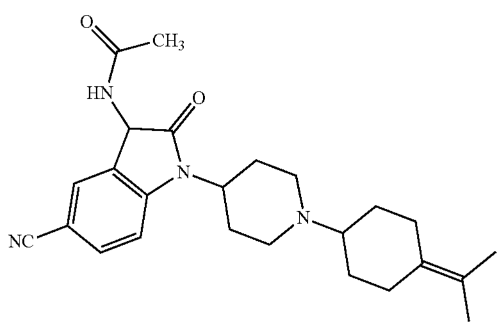 [SMILES: CC(=O)NC1C(=O)N(C2CCN(C3CCC(=C(C)C)CC3)CC2)c2ccc(C#N)cc21] | N-(5-cyano-2-oxo-1-(1-(4-(propan-2-ylidene)cyclohexyl)piperidin-4-yl)indolin-3-yl)acetamide | |
| 303 | 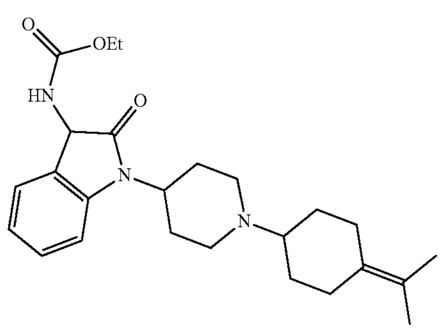 [SMILES: CCOC(=O)NC1C(=O)N(C2CCN(C3CCC(=C(C)C)CC3)CC2)c2ccccc21] | ethyl (2-oxo-1-(1-(4-(propan-2-ylidene)cyclohexyl)piperidin-4-yl)indolin-3-yl)carbamate | |
| 304 | 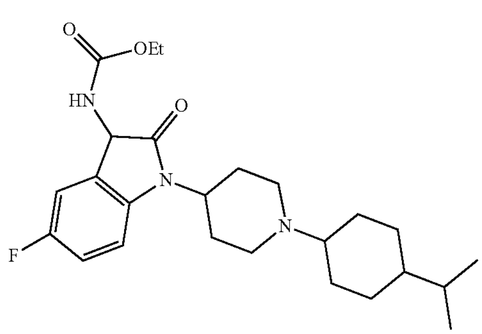 [SMILES: CCOC(=O)NC1C(=O)N(C2CCN(C3CCC(C(C)C)CC3)CC2)c2ccc(F)cc21] | ethyl (5-fluoro-1-(1-((1s,4s)-4-isopropylcyclohexyl)piperidin-4-yl)-2-oxoindolin-3-yl)carbamate | |

TABLE 2-continued

| No. | Structure* | IUPAC Name | NMR (300 or 400 MHz) |
|---|---|---|---|
| 305 | 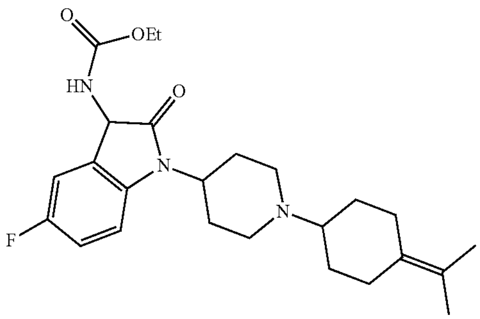 | ethyl (5-fluoro-2-oxo-1-(1-(4-(propan-2-ylidene)cyclohexyl)piperidin-4-yl)indolin-3-yl)carbamate | |
| 306 | 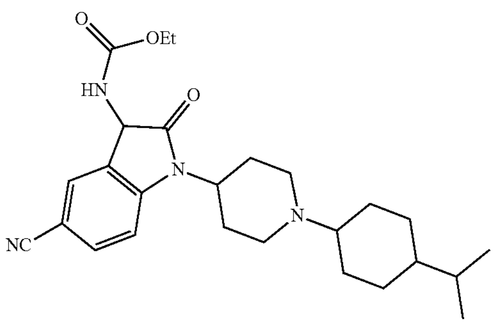 [SMILES: CCOC(=O)NC1C(=O)N(C2CCN(C3CCC(C(C)C)CC3)CC2)c2ccc(C#N)cc21] | ethyl (5-cyano-1-(1-(((1s,4s)-4-isopropylcyclohexyl)piperidin-4-yl)-2-oxoindolin-3-yl)carbamate | |
| 307 | 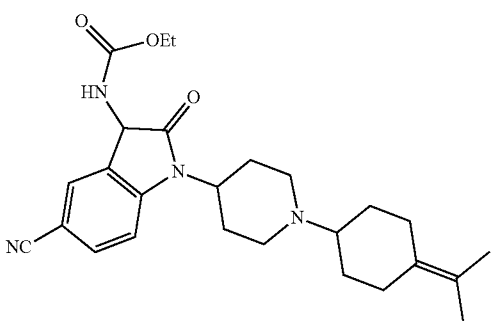 [SMILES: CCOC(=O)NC1C(=O)N(C2CCN(C3CCC(=C(C)C)CC3)CC2)c2ccc(C#N)cc21] | ethyl (5-cyano-2-oxo-1-(1-(4-(propan-2-ylidene)cyclohexyl)piperidin-4-yl)indolin-3-yl)carbamate | |
| 308 | 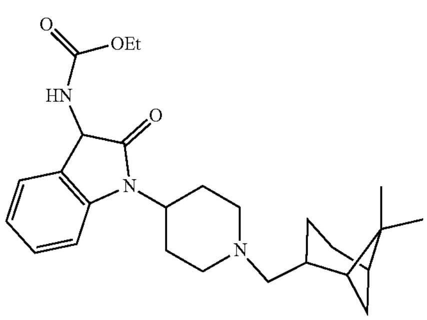 [SMILES: CCOC(=O)NC1C(=O)N(C2CCN(CC3CCC4CC3C4(C)C)CC2)c2ccccc21] | ethyl (1-(1-(((2R)-6,6-dimethylbicyclo[3.1.1]heptan-2-yl)methyl)piperidin-4-yl)-2-oxoindolin-3-yl)carbamate | |
| 309 | 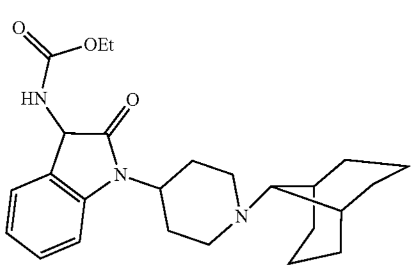 [SMILES: CCOC(=O)NC1C(=O)N(C2CCN(C3C4CCCC3CCC4)CC2)c2ccccc21] | ethyl (1-(1-(bicyclo[3.3.1]nonan-9-yl)piperidin-4-yl)-2-oxoindolin-3-yl)carbamate | |

TABLE 2-continued

| No. | Structure* | IUPAC Name | NMR (300 or 400 MHz) |
|---|---|---|---|
| 310 | 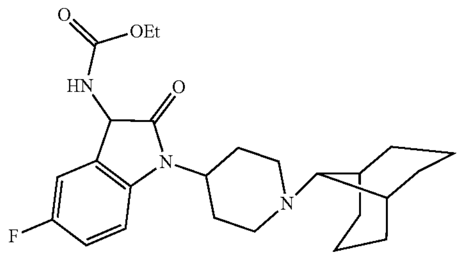 [SMILES: CCOC(=O)NC1C(=O)N(C2CCN(C3C4CCCC3CCC4)CC2)c2ccc(F)cc21] | ethyl (1-(1-(bicyclo[3.3.1]nonan-9-yl)piperidin-4-yl)-5-fluoro-2-oxoindolin-3-yl)carbamate | |
| 311 | 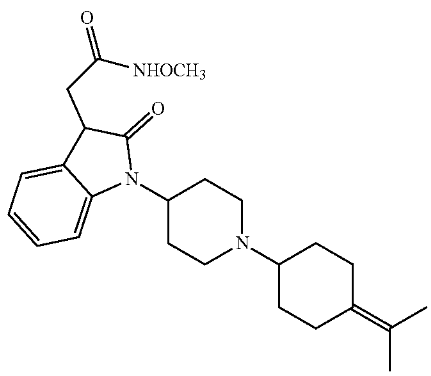 | N-methoxy-2-(2-oxo-1-(1-(4-(propan-2-ylidene)cyclohexyl)piperidin-4-yl)indolin-3-yl)acetamide | |
| 312 | 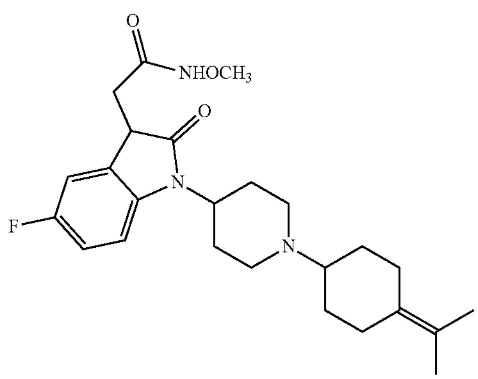 | 2-(5-fluoro-2-oxo-1-(1-(4-(propan-2-ylidene)cyclohexyl)piperidin-4-yl)indolin-3-yl)-N-methoxyacetamide | |
| 313 | 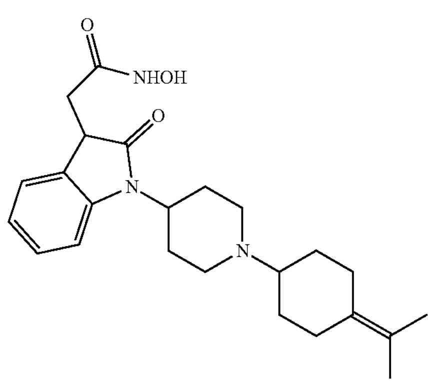 | N-hydroxy-2-(2-oxo-1-(1-(4-(propan-2-ylidene)cyclohexyl)piperidin-4-yl)indolin-3-yl)acetamide | |

TABLE 2-continued

| No. | Structure* | IUPAC Name | NMR (300 or 400 MHz) |
|---|---|---|---|
| 314 | 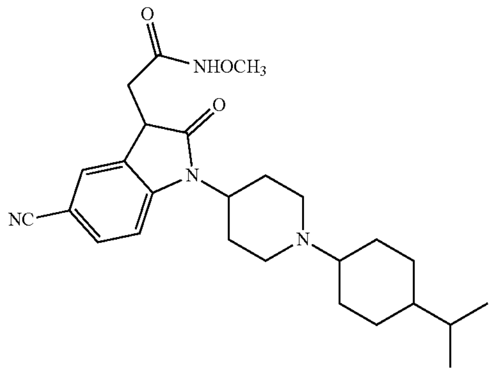 | 2-(5-cyano-1-(1-((1s,4s)-4-isopropylcyclohexyl)piperidin-4-yl)-2-oxoindolin-3-yl)-N-methoxyacetamide | |
| 315 | 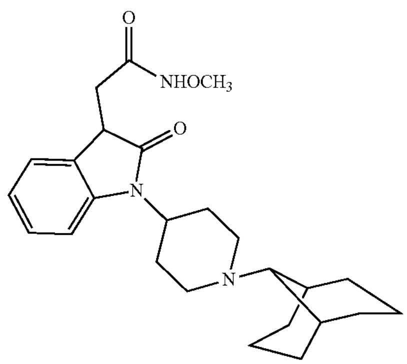 | 2-(1-(1-((1R,5S)-bicyclo[3.3.1]nonan-9-yl)piperidin-4-yl)-2-oxoindolin-3-yl)-N-methoxyacetamide | |
| 316 | 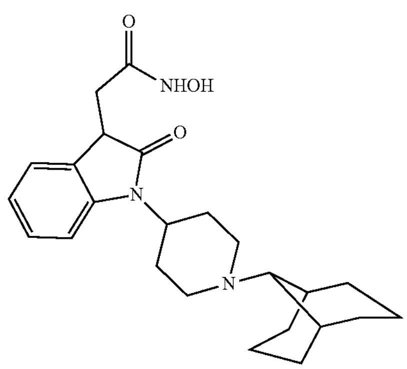 | 2-(1-(1-((1R,5S)-bicyclo[3.3.1]nonan-9-yl)piperidin-4-yl)-2-oxoindolin-3-yl)-N-hydroxyacetamide | |
| 317 | 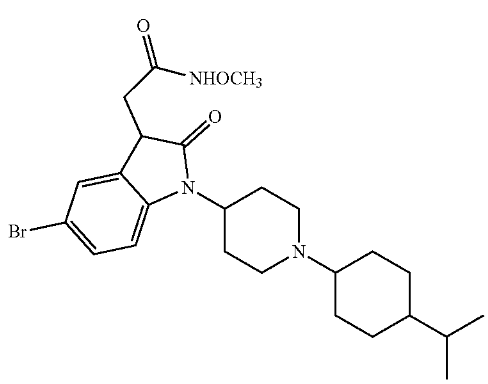 | 2-(5-bromo-1-(1-((1s,4s)-4-isopropylcyclohexyl)piperidin-4-yl)-2-oxoindolin-3-yl)-N-methoxyacetamide | |

TABLE 2-continued

| No. | Structure* | IUPAC Name | NMR (300 or 400 MHz) |
|---|---|---|---|
| 318 | 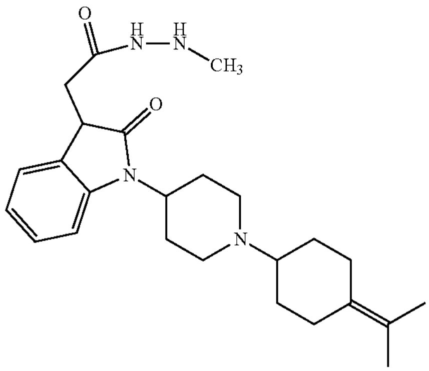 [SMILES: CNNC(=O)CC1C(=O)N(C2CCN(C3CCC(=C(C)C)CC3)CC2)c2ccccc21] | N'-methyl-2-(2-oxo-1-(1-(4-(propan-2-ylidene)cyclohexyl)piperidin-4-yl)indolin-3-yl)acetohydrazide | |
| 319 | 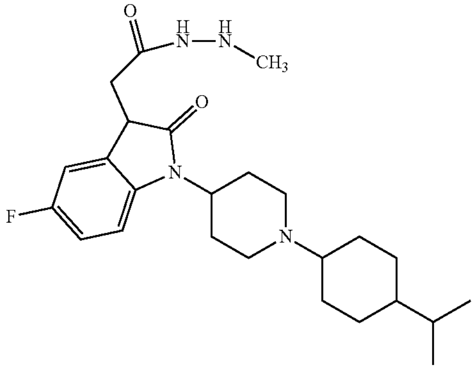 [SMILES: CNNC(=O)CC1C(=O)N(C2CCN(C3CCC(C(C)C)CC3)CC2)c2ccc(F)cc21] | 2-(5-fluoro-1-(1-((1s,4s)-4-isopropylcyclohexyl)piperidin-4-yl)-2-oxoindolin-3-yl)-N'-methylacetohydrazide | |
| 320 | 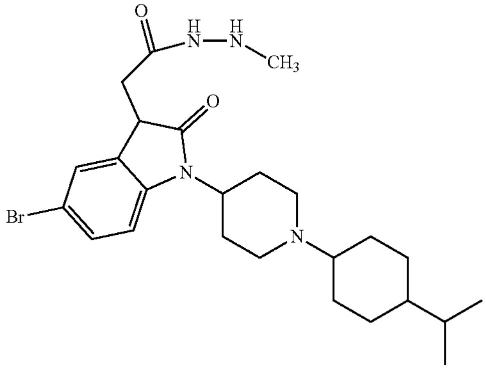 [SMILES: CNNC(=O)CC1C(=O)N(C2CCN(C3CCC(C(C)C)CC3)CC2)c2ccc(Br)cc21] | 2-(5-bromo-1-(1-((1s,4s)-4-isopropylcyclohexyl)piperidin-4-yl)-2-oxoindolin-3-yl)-N'-methylacetohydrazide | |
| 321 | 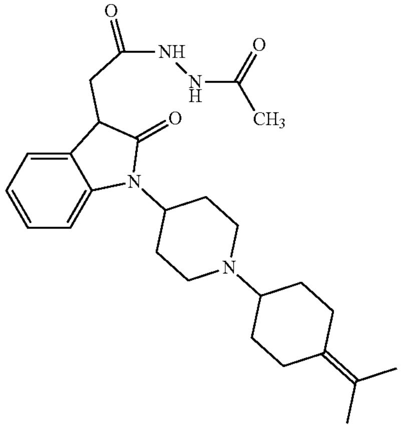 [SMILES: CC(=O)NNC(=O)CC1C(=O)N(C2CCN(C3CCC(=C(C)C)CC3)CC2)c2ccccc21] | N'-acetyl-2-(2-oxo-1-(1-(4-(propan-2-ylidene)cyclohexyl)piperidin-4-yl)indolin-3-yl)acetohydrazide | |

TABLE 2-continued

| No. | Structure* | IUPAC Name | NMR (300 or 400 MHz) |
|---|---|---|---|
| 322 | 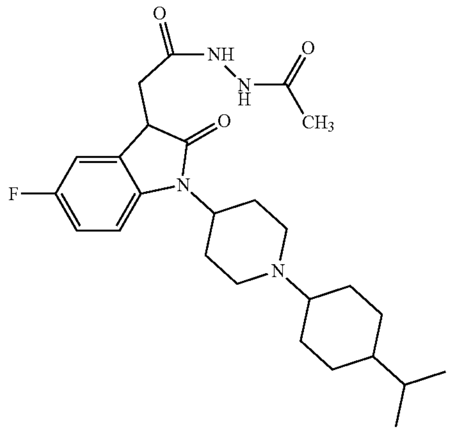 [SMILES: CC(=O)NNC(=O)CC1C(=O)N(C2CCN(C3CCC(C(C)C)CC3)CC2)c2ccc(F)cc21] | N'-acetyl-2-(5-fluoro-1-((1s,4s)-4-isopropylcyclohexyl)piperidin-4-yl)-2-oxoindolin-3-yl)acetohydrazide | |
| 323 | 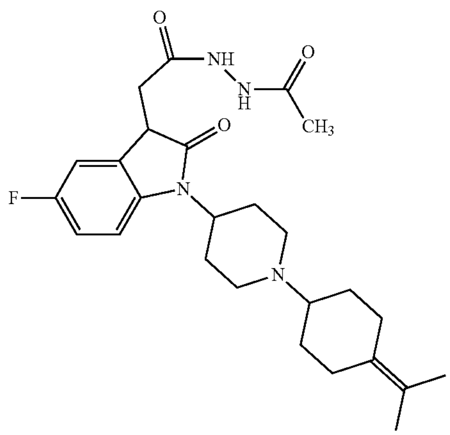 [SMILES: CC(=O)NNC(=O)CC1C(=O)N(C2CCN(C3CCC(=C(C)C)CC3)CC2)c2ccc(F)cc21] | N'-acetyl-2-(5-fluoro-2-oxo-1-(1-(4-(propan-2-ylidene)cyclohexyl)piperidin-4-yl)indolin-3-yl)acetohydrazide | |
| 324 | 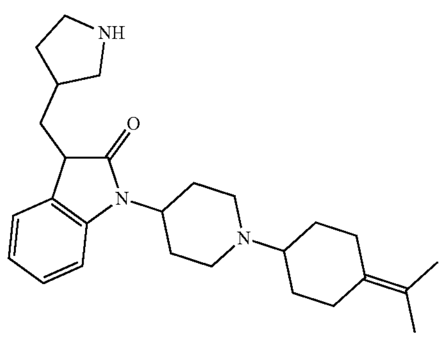 [SMILES: CC(C)=C1CCC(N2CCC(N3C(=O)C(CC4CCNC4)c4ccccc43)CC2)CC1] | 1-(1-(4-(propan-2-ylidene)cyclohexyl)piperidin-4-yl)-3-(pyrrolidin-3-ylmethyl)indolin-2-one | |
| 325 | 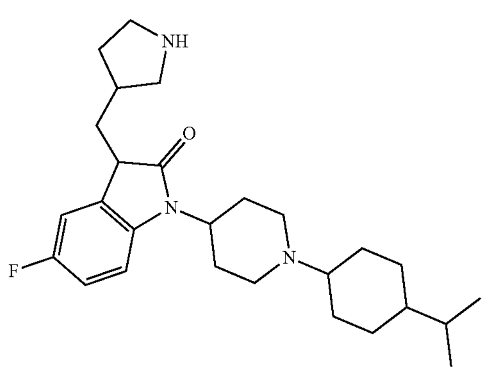 [SMILES: CC(C)C1CCC(N2CCC(N3C(=O)C(CC4CCNC4)c4cc(F)ccc43)CC2)CC1] | 5-fluoro-1-(1-((1s,4s)-4-isopropylcyclohexyl)piperidin-4-yl)-3-(pyrrolidin-3-ylmethyl)indolin-2-one | |

TABLE 2-continued

| No. | Structure* | IUPAC Name | NMR (300 or 400 MHz) |
|---|---|---|---|
| 326 | 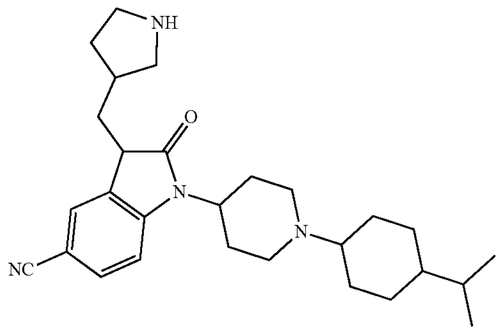 [SMILES: CC(C)C1CCC(N2CCC(N3C(=O)C(CC4CCNC4)c4cc(C#N)ccc43)CC2)CC1] | 1-(1-((1s,4s)-4-isopropylcyclohexyl)piperidin-4-yl)-2-oxo-3-(pyrrolidin-3-ylmethyl)indoline-5-carbonitrile | |
| 327 | 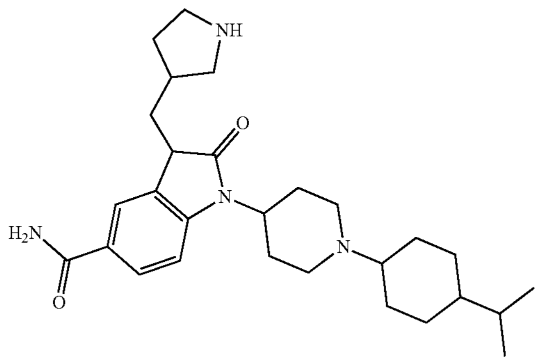 [SMILES: CC(C)C1CCC(N2CCC(N3C(=O)C(CC4CCNC4)c4cc(C(N)=O)ccc43)CC2)CC1] | 1-(1-((1s,4s)-4-isopropylcyclohexyl)piperidin-4-yl)-2-oxo-3-(pyrrolidin-3-ylmethyl)indoline-5-carboxamide | |
| 328 | 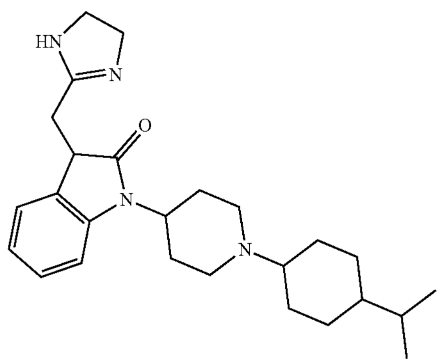 [SMILES: CC(C)C1CCC(N2CCC(N3C(=O)C(CC4=NCCN4)c4ccccc43)CC2)CC1] | 3-((4,5-dihydro-1H-imidazol-2-yl)methyl)-1-(1-((1s,4s)-4-isopropylcyclohexyl)piperidin-4-yl)indolin-2-one | |
| 329 | 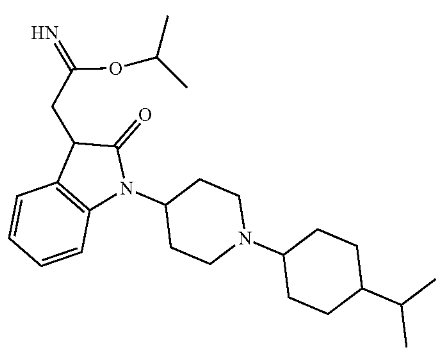 [SMILES: CC(C)OC(=N)CC1C(=O)N(C2CCN(C3CCC(C(C)C)CC3)CC2)c2ccccc21] | isopropyl 2-(1-(1-((1s,4s)-4-isopropylcyclohexyl)piperidin-4-yl)-2-oxoindolin-3-yl)acetimidate | |

Table 3 illustrates compounds of structural formula (IV). In some embodiments, the 1,4-substituents on the cyclohexyl ring are cis to each other.

TABLE 3

| No. | Structure* | Name | NMR (300 0r 400 MHz) |
|---|---|---|---|
| 330 | 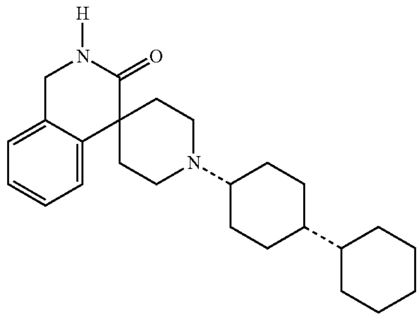 | 1'-(cis-[1,1'-bi(cyclohexan)]-4-yl)-1,2-dihydro-3H-spiro[isoquinoline-4,4'-piperidin]-3-one | $^1$H NMR (300 MHz, CDCl$_3$) δ 7.58 (1H, m), 7.34 (1H, t, J = 6 Hz), 7.25, t, J = 6 Hz), 7.15 (1H, d, 6 Hz), 4.51 (2 H, s), 3.0 (4H, m), 2.19 (4H, d, J = 10 Hz), 1.71 (12 H, m), 1.26 (8H, m), 0.82 (3H, m) |
| 331 | 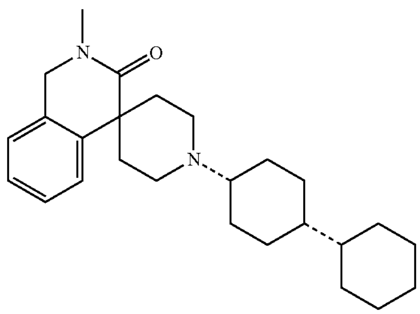 | 1'-(cis-[1,1'-bi(cyclohexan)]-4-yl)-2-methyl-1,2-dihydro-3H-spiro[isoquinoline-4,4'-piperidin]-3-one | $^1$H NMR (CDCl$_3$) δ, J = 6 Hz), 7.40 (1H, t, J = 6 Hz), 7.25 (1H, t, J = 6 Hz), 7.15 (1H, d, J = 6 Hz), 4.56 (2H, m), 3.82 (2H, m), 3.36 (3H, m), 3.11 (3H, s), 3.03 (1H, m), 2.06 (4H, m), 1.73 (8H, m), 1.26 (8H, m), 0.82 (3H, m) |
| 332 | 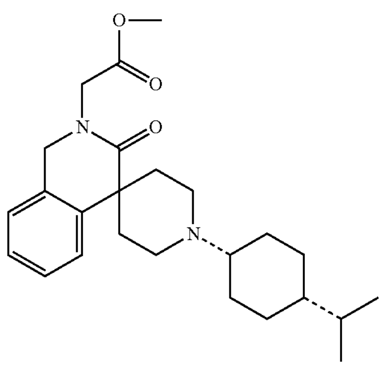 | methyl 2-(1'-(cis-4-isopropylcyclohexyl)-3-oxo-1H-spiro[isoquinoline-4,4'-piperidin]-2(3H)-yl)acetate | $^1$H NMR (DMSO, d$_6$) δ, J = 6 Hz), 7.40 (1H, t, J = 6 Hz), 7.37 (1H, t, J = 6 Hz), 7.28 (1H, d, J = 6 Hz), 4.64 (2H, s), 4.27 (2H, s), 3.67 (3H, s), 3.5 (4H, m), 3.2 (1H, m), 2.18 (2H, d, J = 8 Hz), 1.83 (4H, m), 1.69 (4H, m), 1.42 (2H, m), 1.15 (1H, m), 0.88 (6H, d, J = 5 Hz) |
| 333 | 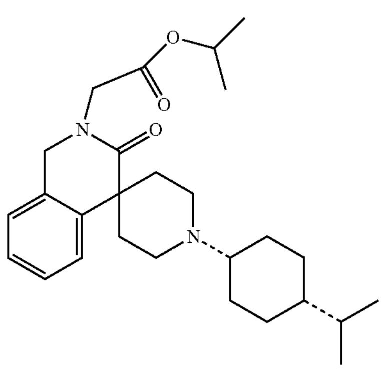 | isopropyl 2-(1'-(cis-4-isopropylcyclohexyl)-3-oxo-1H-spiro[isoquinoline-4,4'-piperidin]-2(3H)-yl)acetate | $^1$H NMR (DMSO, d$_6$) δ, J = 6 Hz), 7.39 (1H, t, J = 6 Hz), 7.33 (1H, t, J = 6 Hz), 7.29 (1H, d, J = 6 Hz), 4.63 (2H, s), 4.13 (2H, s), 3.5 (4H, m), 3.20 (1H, m), 2.17 (2H, d, J = 8 Hz), 1.82 (4H, m), 1.67 (4H, m), 1.39 (11H, s), 1.16 (1H, m), 0.87 (6H, d, J = 5 Hz) |

TABLE 3-continued

| No. | Structure* | Name | NMR (300 0r 400 MHz) |
|---|---|---|---|
| 334 | 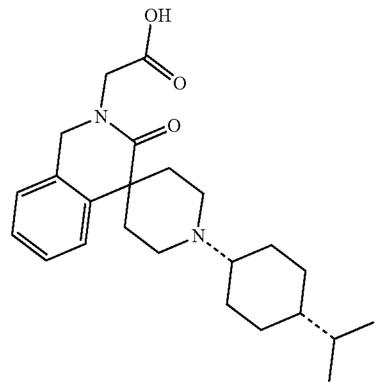 | 2-(1'-(cis-4-isopropylcyclohexyl)-3-oxo-1H-spiro[isoquinoline-4,4'-piperidin]-2(3H)-yl)acetic acid | ¹H NMR (DMSO, d₆) δ, J = 6 Hz), 7.38 (1H, t, J = 6 Hz), 7.31 (1H, t, J = 6 Hz), 7.28 (1H, d, J = 6 Hz), 4.62 (2H, s), 4.14 (2H, s), 3.1 (1H, m), 2.3 (2H, m), 2.19 (2H, m), 1.77 (4H, m), 1.67 (4H, m), 1.40 (2H, m), 1.13 (1H, m,), 0.9 (6H, d,) |
| 335 | 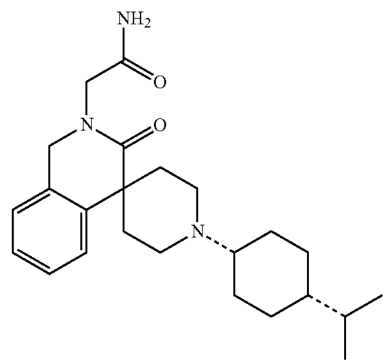 | 2-(1'-(cis-4-isopropylcyclohexyl)-3-oxo-1H-spiro[isoquinoline-4,4'-piperidin]-2(3H)-yl)acetamide | ¹H NMR (CDCl₃) δ, J = 6 Hz), 7.34 (1H, t, J = 6 Hz), 7.25 (1H, t, J = 6 Hz), 7.18 (1H, d, J = 6 Hz), 4.15 (2H, s), 2.85 (4H, m), 2.30 (1H, m), 2.22 (2H, d, J = 8 Hz), 2.05 (2H, m), 1.6 (10H, m), 1.37 (2H, m), 1.12 (1H, m), 0.88 (6H, d, J = 5 Hz) |
| 336 | 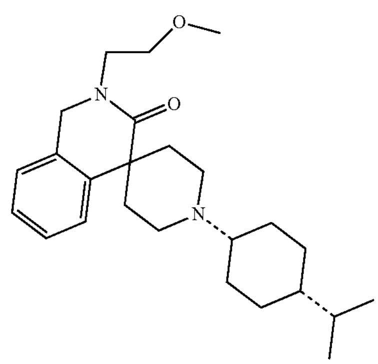 | 1'-(cis-4-isopropylcyclohexyl)-2-(2-methoxyethyl)-1,2-dihydro-3H-spiro[isoquinoline-4,4'-piperidin]-3-one | ¹H NMR (DMSO-d₆) δ, J = 6 Hz), 7.38 (1H, t, J = 6 Hz), 7.32 (1H, t, J = 6 Hz), 7.29 (1H, d, J = 6 Hz), 4.65 (2H, s), 3.62 (2H, m), 3.48 (4H, m), 3.25 (3H, s), 3.2 (1H, m), 2.39 (3H, m), 2.13 (2H, d, J = 8 Hz), 1.83 (4H, m), 1.70 (4H, m), 1.40 (2H, m), 1.13 (1H, m), 0.9 (6H, d) |
| 337 | 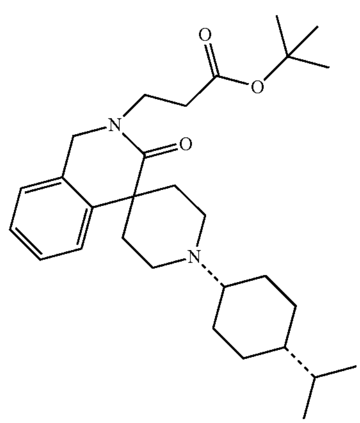 | tert-butyl 3-(1'-(cis-4-isopropylcyclohexyl)-3-oxo-1H-spiro[isoquinoline-4,4'-piperidin]-2(3H)-yl)propanoate | ¹H NMR (DMSO, d₆) δ, (1H, t, J = 6 Hz), 7.28 (1H, d, J = 6 Hz), 1.61 (2H, s), 3.64 (2H, m), 3.47 (4H, m), 3.21 (1H, m), 2.4 (3H, m), 2.12 (2H, d, J = 8 Hz), 1.84 (4H, m), 1.69 4H, m), 1.31 (11H, s), 1.57 (1H, m), 0.88 (6H, d, J = 5 Hz) |

TABLE 3-continued

| No. | Structure* | Name | NMR (300 0r 400 MHz) |
|---|---|---|---|
| 338 | 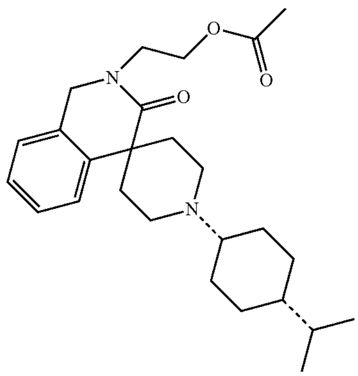 | 2-(1'-(cis-4-isopropylcyclohexyl)-3-oxo-1H-spiro[isoquinoline-4,4'-piperidin]-2(3H)-yl)ethyl acetate | $^1$H NMR (DMSO, d$_6$) δ 10.0 (1H, m), 7.46 (1H, d, J = 6 Hz), 7.38 (1H, t, J = 6 Hz), 7.32 (1H, t, J = 6 Hz), 7.30 (1H, d, J = 6 Hz), 4.65 (2H, s), 4.20 (2H, m), 3.70 (2H, m), 3.47 (4H, m), 3.22 (1H, m), 2.15 (2H, d, J = 8 Hz), 1.99 (3H, s), 1.84 (4H, m), 1.68 (4H, m), 1.41 (2H, m), 1.15 (1H, m), 0.88 (6H, d, J = 5 Hz) |
| 339 | 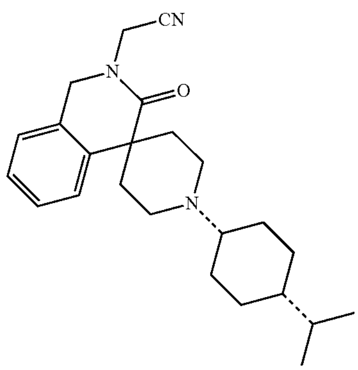 | 2-(1'-(cis-4-isopropylcyclohexyl)-3-oxo-1H-spiro[isoquinoline-4,4'-piperidin]-2(3H)-yl)acetonitrile | $^1$H NMR (DMSO, d$_6$) δ 7.35 (1H, t, J = 6 Hz), 7.33 (1H, d, J = 6 Hz), 4.74 (2H, s), 4.56 (2H, s), 3.5 (4H, m), 3.22 (1H, m), 2.18 (2H, d, J = 8 Hz), 1.83 (4H, m), 1.69 (4H, m), 1.40 (2H, m), 1.17 (1H, m), 0.88 (6H, d, J = 5 Hz) |
| 340 | 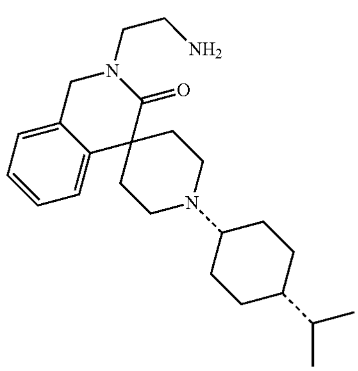 | 2-(2-aminoethyl)-1'-(cis-4-isopropylcyclohexyl)-1,2-dihydro-3H-spiro[isoquinoline-4,4'-piperidin]-3-one | $^1$H NMR (DMSO, d$_6$) δ 10.6 (1H, m), 8.06 (3H, m), 7.54 (1H, d, J = 6 Hz), 7.38 (1H, t, J = 6 Hz), 7.32 (1H, t, J = 6 Hz), 7.26 (1H, d, J = 6 Hz), 4.68 (2H, s), 3.68 (2H, m), 3.47 (4H, m), 3.16 (2H, m), 3.03 (2H, m), 2.22 (2H, d, J = 8 Hz), 1.84 (4H, m), 1.68 (4H, m), 1.42 (2H, m), 1.14 (1H, m), 0.88 (6H, d, J = 5 Hz) |
| 341 | 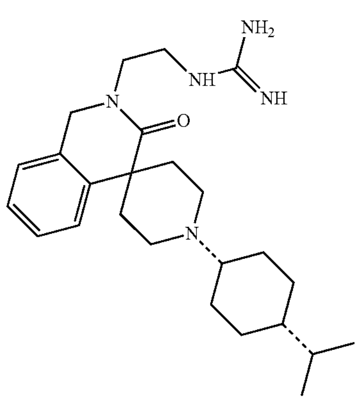 | 1-(2-(1'-(cis-4-isopropylcyclohexyl)-3-oxo-1H-spiro[isoquinoline-4,4'-piperidin]-2(3H)-yl)ethyl)guanidine | $^1$H NMR (DMSO, d$_6$) δ, 7.96 (1H, m), =6 Hz), 7.32 (1H, t, J = 6 Hz), 7.28 (1H, d, J = 6 Hz), 4.68 (2H, s), 3.59 (2H, m), 3.46 (4H, m), 3.17 (1H, m), 2.20 (2H, d, J = 8 Hz), 1.83 (4H, m), 1.60 (4H, m), 1.40 (2H, m), 1.14 (1H, m), 0.88 (6H, d, J = 5 Hz) |

TABLE 3-continued

| No. | Structure* | Name | NMR (300 or 400 MHz) |
|---|---|---|---|
| 342 | 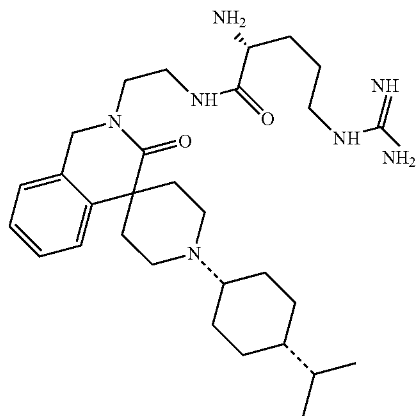 | (S)-2-amino-5-guanidino-N-(2-(1'-(cis-4-isopropylcyclohexyl)-3-oxo-1H-spiro[isoquinoline-4,4'-piperidin]-2(3H)-yl)ethyl)pentanamide | $^1$H NMR (DMSO, $d_6$) δ, 8.98 (1H, m), 8.29 (3H, m), 7.88 (1H, =6 Hz), 7.32 (1H, t, J = 6 Hz), 7.28 (1H, d, J = 6 Hz), 4.69 (2H, s), 3.82 (1H, m), 3.15 (4H, m), 2.20 (2H, d, J = 8 Hz). 1.86 (3H, m), 1.71 (4H, m), 1.51 (2H, m), 1.41 (2H, m), 1.13 (1H, m), 0.88 (6H, d, J = 5 Hz) |
| 343 | 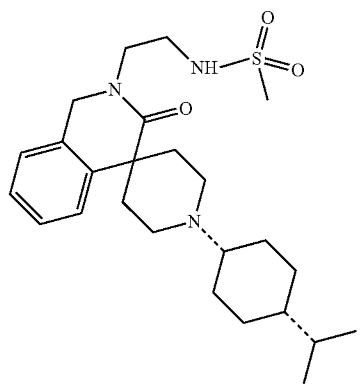 | N-(2-(1'-(cis-4-isopropylcyclohexyl)-3-oxo-1H-spiro[isoquinoline-4,4'-piperidin]-2(3H)-yl)ethyl)methanesulfonamide | $^1$H NMR (CDCl$_3$) δ, J = 6 Hz), 7.33 (1H, t, J = 6 Hz), 7.25 (1H, t, J = 6 Hz), 7.19 (1H, d, J = 6 Hz), 5.00 (1H, m), 4.59 (2H, s), 3.70 (2H, m), 3.38 (2H, m), 2.84 (6H, s), 2.30 (1H, m), 2.19 (2H, d, J = 8 Hz), 2.01 (2H, m), 1.65 (8H, m), 1.36 (2H, m), 1.12 (1H, m), 0.88 (6H, d, J = 5 Hz) |
| 344 | 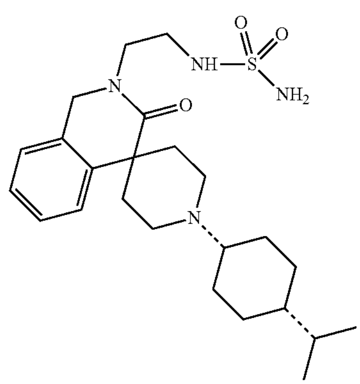 | N-(2-(1'-(cis-4-isopropylcyclohexyl)-3-oxo-1H-spiro[isoquinoline-4,4'-piperidin]-2(3H)-yl)ethyl)aminosulfonamide | $^1$H NMR (DMSO, $d_6$) δ, (2H, s), 3.5 (4H, =4 Hz), 2.81 (3H, m), 2.33 (2H, m), 2.23 (2H, m), 2.04 (2H, m), 1.71 (2H, m), 1.59 (6H, m), 1.36 (2H, m), 1.12 (1H, m), 0.87 (6H, d) |
| 345 | 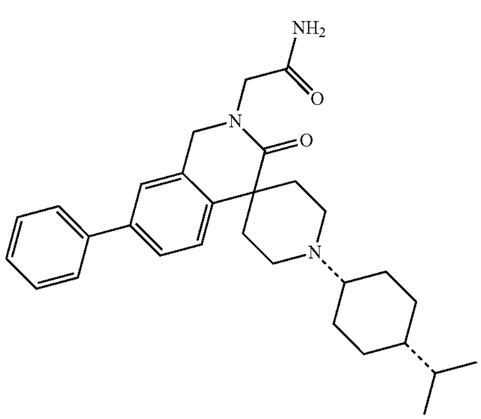 | 2-(1'-(cis-4-isopropylcyclohexyl)-3-oxo-7-phenyl-1H-spiro[isoquinoline-4,4'-piperidin]-2(3H)-yl)acetamide | $^1$H NMR (300 MHz, CDCl$_3$) δ 7.1-7.8 (8H, m), 4.41 (2H, s), 4.59 (2H, s), 4.06 (2H, m), 3.02 (4H, m), 2.9 (4H, m), 2.1 (4H, m), 1.65 (8H, m), 1.36 (2H, m), 1.10 (1H, m), 0.86 (6H, d, J = 5 Hz) |

TABLE 3-continued

| No. | Structure* | Name | NMR (300 0r 400 MHz) |
|-----|------------|------|----------------------|
| 346 | 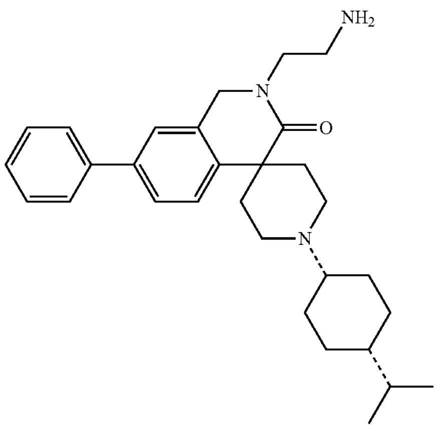 | 2-(2-aminoethyl)-1'-(cis-4-isopropylcyclohexyl)-7-phenyl-1,2-dihydro-3H-spiro[isoquinoline-4,4'-piperidin]-3-one | $^1$H NMR (300 MHz, CDCl$_3$) δ 7.85 (1H, d, J = 6 Hz), 7.61 (1H, d, J = 6 Hz), 7.56 (2H, d, J = 6 Hz), 7.45 (2H, t, J = 6 Hz), 7.38 (1H, d, J = 6 Hz), 7.34 (1H, br s), 4.66 (2H, s), 3.77 (2H, m), 3.62 2H, m), 3.40 (2H, m), 3.0 (5H, m), 1.8 (4H, m), 1.44 (2H, m), 1.26 (1H, m), 0.91 (6H, d) |
| 347 | 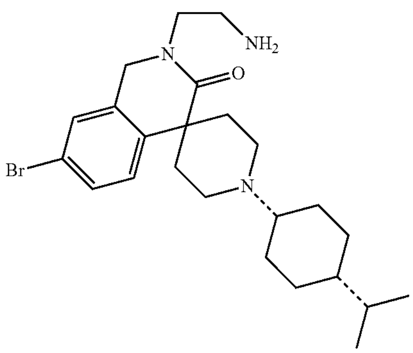 | 2-(2-aminoethyl)-7-bromo-1'-(cis-4-isopropylcyclohexyl)-1,2-dihydro-3H-spiro[isoquinoline-4,4'-piperidin]-3-one | $^1$H NMR (300 MHz, CDCl$_3$) δ 7.68 (1H, d, J = 6 Hz), 7.50 (1H, dd, J = 6, 1.2 Hz), 7.29 (1H, d, J = 1.2 Hz), 4.57 (2H, s), 3.74 (2H, m), 3.59 (2H, m), 3.37 (2H, m), 3.09 (1H, m), 2.98 (3H, m), 2.06 (4H, m), 1.71 (4H, m), 1.47 (2H, m), 1.24 (1H, m), 0.90 (6H, d) |
| 348 | 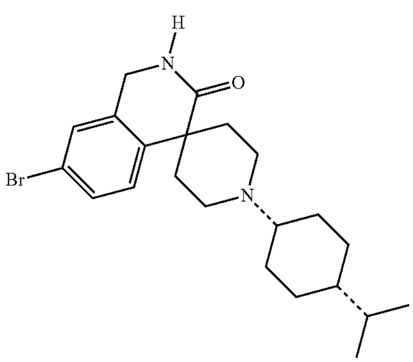 | 7-bromo-1'-(cis-4-isopropylcyclohexyl)-1,2-dihydro-3H-spiro[isoquinoline-4,4'-piperidin]-3-one | $^1$H NMR (300 MHz, CDCl$_3$) δ 7.43 (1H, d, J = 6 Hz), 7.34 (1H, d, J = 6 Hz), 7.31 (1H, br s), 6.04 (1H, m), 4.46 (2H, s), 2.83 (3H, m), 2.32 (1H, m), 2.19 (2H, d, J = 8 Hz), 1.98 (2H, m), 1.63 (8H, m), 1.36 (2H, m), 1.12 (1H, m), 0.88 (6H, d, J = 5 Hz) |
| 349 | 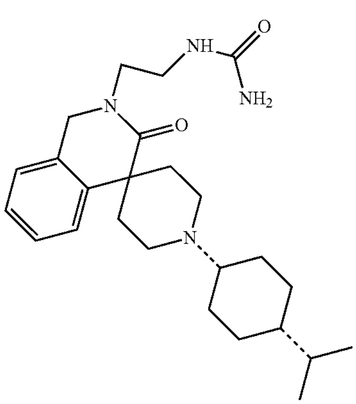 | 1-(2-(1'-(cis-4-isopropylcyclohexyl)-3-oxo-1H-spiro[isoquinoline-4,4'-piperidin]-2(3H)-yl)ethyl)urea | $^1$H NMR (CDCl$_3$) δ J = 6 Hz), 7.31 (1H, t, J = 6 Hz), 7.23 (1H, t, J = 6 Hz), 7.12 (1H, d, J = 6 Hz), 6.12 (1H, m), 5.0 (2H, m), 4.64 (2H, s), 3.64 (4H, m), 3.42 (2H, m), 3.27 (2H, m), 2.92 (1H, m), 2.62 (2H, m), 2.32 (2H, d, J = 8 Hz), 1.91 (5H, m), 1.65 (4H, m), 1.36 (2H, m), 1.21 (1H, m), 0.89 (6H, d, J = 5 Hz) |

| No. | Name | NMR (300 Or 400 MHz) |
|---|---|---|
| 350 | 1'-(cis-4-isopropylcyclohexyl)-7-methyl-1,2-dihydro-3H-spiro[isoquinoline-4,4'-piperidin]-3-one | $^1$H NMR (300 MHz, CDCl$_3$) δ 7.39 (1H, d, J = 6 Hz), 7.12 (1H, d, J = 6 Hz), 6.97 (1H, br s), 6.0 (1H, m), 4.44 (2H, s), 3.83 (4H, m), 2.34 (3H, s), 2.19 (2H, d, J = 8 Hz), 2.00 (2H, m), 1.64 (8H, m), 1.36 (2H, m), 1.12 (1H, m), 0.88 (6H, d, J = 5 Hz) |
| 351 | 2-(2-hydroxyethyl)-1'-(cis-4-isopropylcyclohexyl)-1,2-dihydro-3H-spiro[isoquinoline-4,4'-piperidin]-3-one | $^1$H NMR (CDCl$_3$) δ J = 6 Hz), 7.36 (1H, t, J = 6 Hz), 7.53 (1H, t, J = 6 Hz), 7.15 (1H, d, J = 6 Hz), 4.62 (2H, s), 3.86 (2H, m), 3.70 (2H, m), 3.25 (1H, m), 3.12 (2H, m), 2.17 (2H, d, J = 8 Hz), 1.84 (4H, m), 1.66 (4H, m), 1.41 (2H, m), 1.18 (1H, m), 0.89 (6H, d, J = 5 Hz) |
| 352 | 1-(2-(1'-(cis-4-isopropylcyclohexyl)-3-oxo-1H-spiro[isoquinoline-4,4'-piperidin]-2(3H)-yl)ethyl)thiourea | $^1$H NMR (CDCl$_3$) δ J = 6 Hz), 7.33 (1H, t, J = 6 Hz), 7.26 (1H, t, J = 6 Hz), 7.18 (1H, d, J = 6 Hz), 5.85 (1H, m), 4.62 (2H, s), 3.75 (2H, m), 2.83 (3H, br s), 2.33 (1H, m), 2.18 (2H, m), 2.05 (2H, m), 1.65 (8H, m), 1.37 (2H, m), 1.23 (1H, m), 0.87 (6H, d, J = 5 Hz) |
| 353 | N-(2-(1'-(cis-4-isopropylcyclohexyl)-3-oxo-1H-spiro[isoquinoline-4,4'-piperidin]-2(3H)-yl)ethyl)formamide | $^1$H NMR (CDCl$_3$) δ), d, J = 8 Hz), 1.61 (11H, m), 1.40 (2H, m), 1.67 (1H, m), 0.88 (6H, d) |

TABLE 3-continued

| No. | Structure* | Name | NMR (300 or 400 MHz) |
|---|---|---|---|
| 354 | 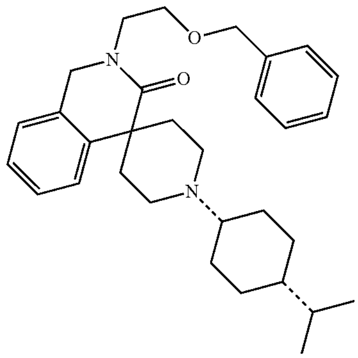 | 2-(2-(benzyloxy)ethyl)-1'-(cis-4-isopropylcyclohexyl)-1,2-dihydro-3H-spiro[isoquinoline-4,4'-piperidin]-3-one | ¹H NMR (DMSO, d₆) δ 10.3 (1H, m), 7.44 (1H, d, J = 6 Hz), 7.37 (1H, t, J = 6 Hz), 7.29 (7H, m), 4.67 (2H, s), 4.47 (2H, s), 3.66 (4H, d, J = 17 Hz), 3.05 (1H, m), 2.39 (2H, m), 2.08 (2H, d, J = 8 Hz), 1.83 (2H, m), 1.72 (4H, m), 1.56 (2H, m), 1.38 (2H, m), 1.14 (1H, m), 0.88 (6H, d) |
| 355 | 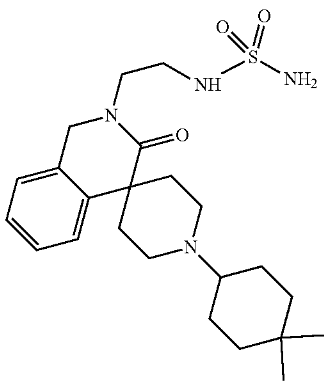 [SMILES: CC1(C)CCC(N2CCC3(CC2)C(=O)N(CCNS(N)(=O)=O)Cc2ccccc23)CC1] | N-(2-(1'-(4,4-dimethylcyclohexyl)-3-oxo-1H-spiro[isoquinoline-4,4'-piperidin]-2(3H)-yl)ethyl)aminosulfonamide | ¹H NMR (CDCl₃) δ, 4.56 (2H, s), 3.73 (2H, m), 3.37 (2H, m), 2.90 (3H, m), 2.24 (2H, J = 8 Hz), 2.18 (2H, m), 1.72 (2H, m), 1.48 (4H, m), 1.20 (2H, m), 0.89 (6H, s) |
| 356 | 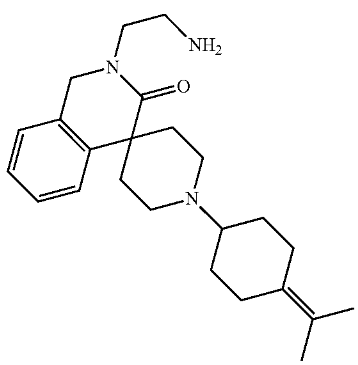 [SMILES: CC(C)=C1CCC(N2CCC3(CC2)C(=O)N(CCN)Cc2ccccc23)CC1] | 2-(2-aminoethyl)-1'-(4-(propan-2-ylidene)cyclohexyl)-1,2-dihydro-3H-spiro[isoquinoline-4,4'-piperidin]-3-one | |
| 357 | 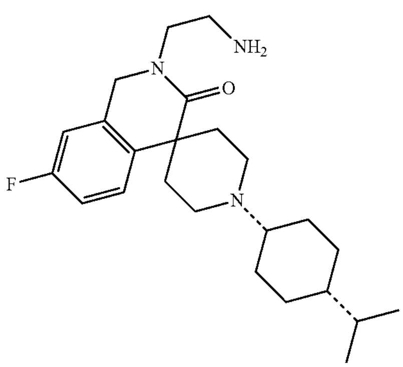 | 2-(2-aminoethyl)-7-fluoro-1'-((1s,4s)-4-isopropylcyclohexyl)-1,2-dihydro-3H-spiro[isoquinoline-4,4'-piperidin]-3-one | |

TABLE 3-continued

| No. | Structure* | Name | NMR (300 0r 400 MHz) |
|---|---|---|---|
| 358 | 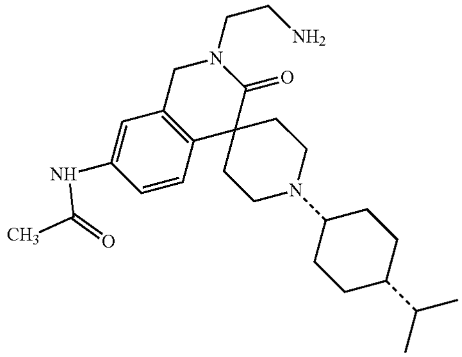 | N-(2-(2-aminoethyl)-1'-((1s,4s)-4-isopropylcyclohexyl)-3-oxo-2,3-dihydro-1H-spiro[isoquinoline-4,4'-piperidin]-7-yl)acetamide | |
| 359 | 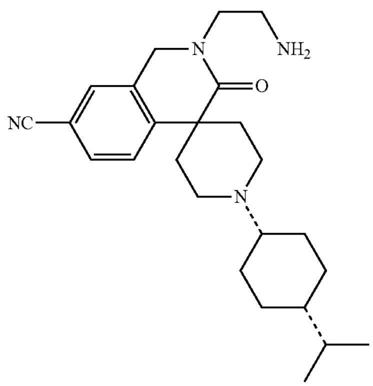 | 2-(2-aminoethyl)-1'-((1s,4s)-4-isopropylcyclohexyl)-3-oxo-2,3-dihydro-1H-spiro[isoquinoline-4,4'-piperidine]-7-carbonitrile | |
| 360 | 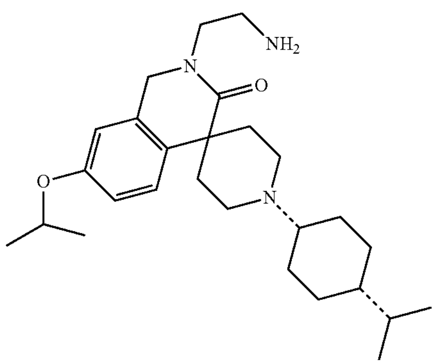 | 2-(2-aminoethyl)-7-isopropoxy-1'-((1s,4s)-4-isopropylcyclohexyl)-1,2-dihydro-3H-spiro[isoquinoline-4,4'-piperidin]-3-one | |
| 361 | 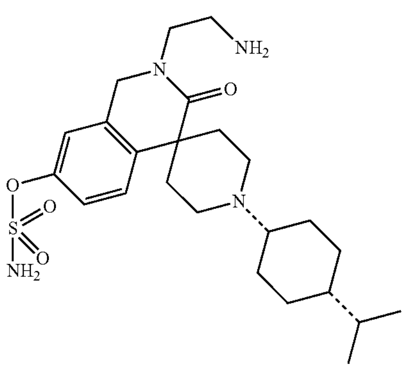 | 2-(2-aminoethyl)-1'-((1s,4s)-4-isopropylcyclohexyl)-3-oxo-2,3-dihydro-1H-spiro[isoquinoline-4,4'-piperidin]-7-yl sulfamate | |

TABLE 3-continued

| No. | Structure* | Name | NMR (300 0r 400 MHz) |
|---|---|---|---|
| 362 | 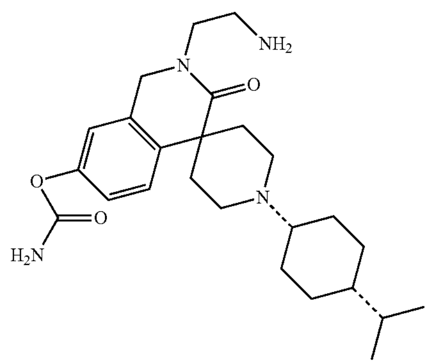 | 2-(2-aminoethyl)-1'-((1s,4s)-4-isopropylcyclohexyl)-3-oxo-2,3-dihydro-1H-spiro[isoquinoline-4,4'-piperidin]-7-yl carbamate | |
| 363 | 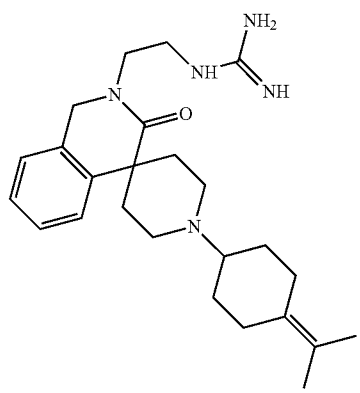 [SMILES: CC(C)=C1CCC(N2CCC3(CC2)C(=O)N(CCNC(=N)N)Cc2ccccc23)CC1] | 1-(2-(3-oxo-1'-(4-(propan-2-ylidene)cyclohexyl)-1H-spiro[isoquinoline-4,4'-piperidin]-2(3H)-yl)ethyl)guanidine | |
| 364 | 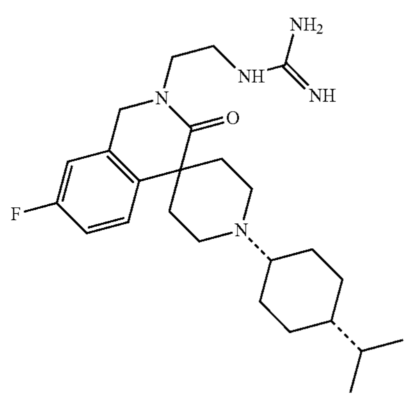 | 1-(2-(7-fluoro-1'-((1s,4s)-4-isopropylcyclohexyl)-3-oxo-1H-spiro[isoquinoline-4,4'-piperidin]-2(3H)-yl)ethyl)guanidine | |
| 365 | 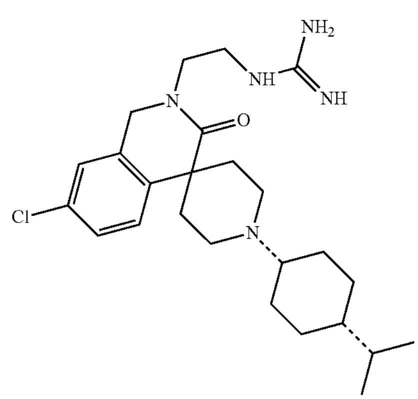 | 1-(2-(7-chloro-1'-((1s,4s)-4-isopropylcyclohexyl)-3-oxo-1H-spiro[isoquinoline-4,4'-piperidin]-2(3H)-yl)ethyl)guanidine | |

TABLE 3-continued

| No. | Structure* | Name | NMR (300 0r 400 MHz) |
|---|---|---|---|
| 366 | 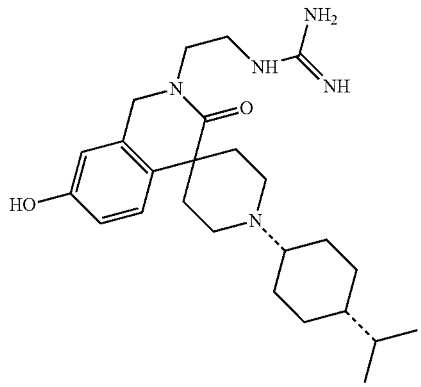 | 1-(2-(7-hydroxy-1'-((1s,4s)-4-isopropylcyclohexyl)-3-oxo-1H-spiro[isoquinoline-4,4'-piperidin]-2(3H)-yl)ethyl)guanidine | |
| 367 | 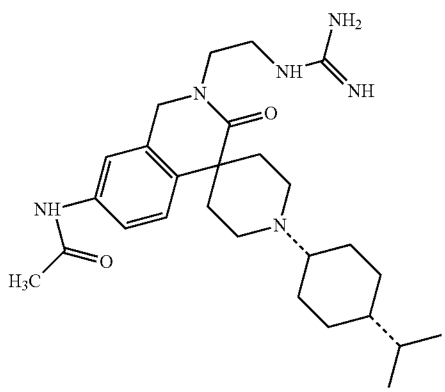 | N-(2-(2-guanidinoethyl)-1'-((1s,4s)-4-isopropylcyclohexyl)-3-oxo-2,3-dihydro-1H-spiro[isoquinoline-4,4'-piperidin]-7-yl)acetamide | |
| 368 | 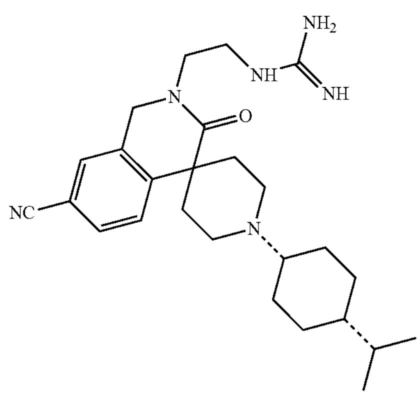 | 1-(2-(7-cyano-1'-((1s,4s)-4-isopropylcyclohexyl)-3-oxo-1H-spiro[isoquinoline-4,4'-piperidin]-2(3H)-yl)ethyl)guanidine | |
| 369 | 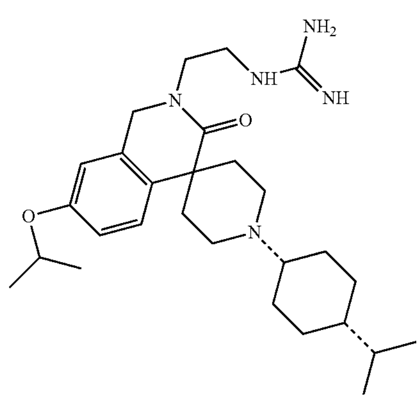 | 1-(2-(7-isopropoxy)-1'-((1s,4s)-4-isopropylcyclohexyl)-3-oxo-1H-spiro[isoquinoline-4,4'-piperidin]-2(3H)-yl)ethyl)guanidine | |

TABLE 3-continued

| No. | Structure* | Name | NMR (300 0r 400 MHz) |
|---|---|---|---|
| 370 | 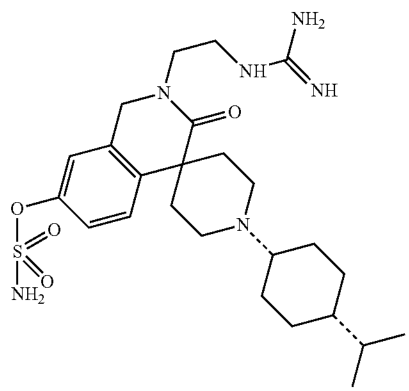 | 2-(2-guanidinoethyl)-1'-((1s,4s)-4-isopropylcyclohexyl)-3-oxo-2,3-dihydro-1H-spiro[isoquinoline-4,4'-piperidin]-7-yl sulfamate | |
| 371 | 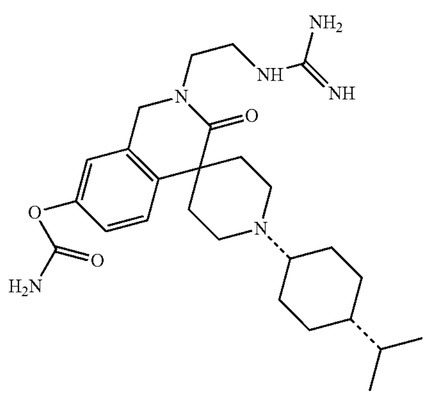 | 2-(2-guanidinoethyl)-1'-((1s,4s)-4-isopropylcyclohexyl)-3-oxo-2,3-dihydro-1H-spiro[isoquinoline-4,4'-piperidin]-7-yl carbamate | |
| 372 | 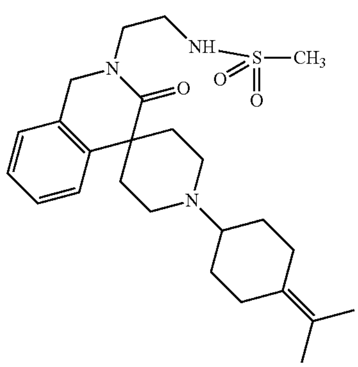 [SMILES: CC(C)=C1CCC(N2CCC3(CC2)C(=O)N(CCNS(C)(=O)=O)Cc2ccccc23)CC1] | N-(2-(3-oxo-1'-(4-(propan-2-ylidene)cyclohexyl)-1H-spiro[isoquinoline-4,4'-piperidin]-2(3H)-yl)ethyl)methanesulfonamide | |
| 373 | 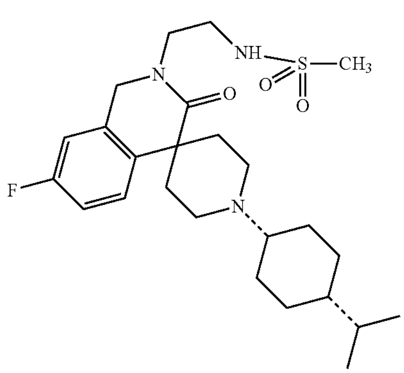 | N-(2-(7-fluoro-1'-((1s,4s)-4-isopropylcyclohexyl)-3-oxo-1H-spiro[isoquinoline-4,4'-piperidin]-2(3H)-yl)ethyl)methanesulfonamide | |

TABLE 3-continued

| No. | Structure* | Name | NMR (300 0r 400 MHz) |
|---|---|---|---|
| 374 | 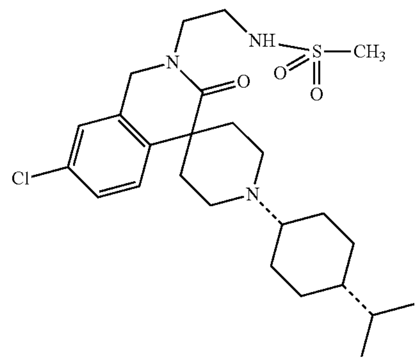 | N-(2-(7-chloro-1'-((1s,4s)-4-isopropylcyclohexyl)-3-oxo-1H-spiro[isoquinoline-4,4'-piperidin]-2(3H)-yl)ethyl)methanesulfonamide | |
| 375 | 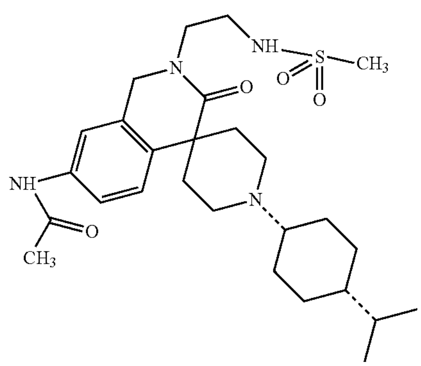 | N-(1'-((1s,4s)-4-isopropylcyclohexyl)-2-(2-(methylsulfonamido)ethyl)-3-oxo-2,3-dihydro-1H-spiro[isoquinoline-4,4'-piperidin]-7-yl)acetamide | |
| 376 | 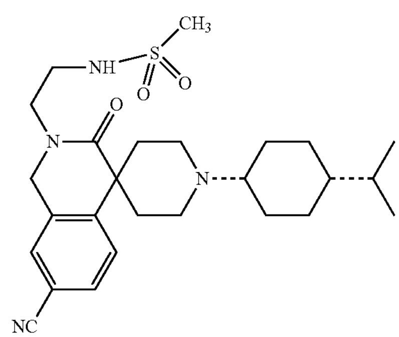 | N-(2-(7-cyano-1'-((1s,4s)-4-isopropylcyclohexyl)-3-oxo-1H-spiro[isoquinoline-4,4'-piperidin]-2(3H)-yl)ethyl)methanesulfonamide | |
| 377 | 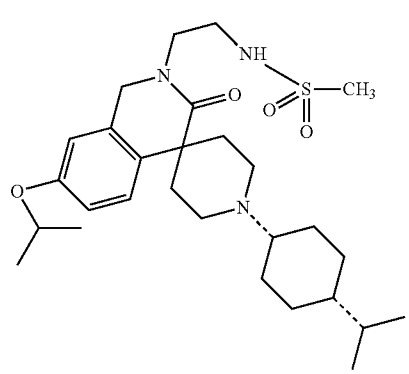 | N-(2-(7-isopropoxy-1'-((1s,4s)-4-isopropylcyclohexyl)-3-oxo-1H-spiro[isoquinoline-4,4'-piperidin]-2(3H)-yl)ethyl)methanesulfonamide | |

TABLE 3-continued

| No. | Structure* | Name | NMR (300 0r 400 MHz) |
|---|---|---|---|
| 378 | 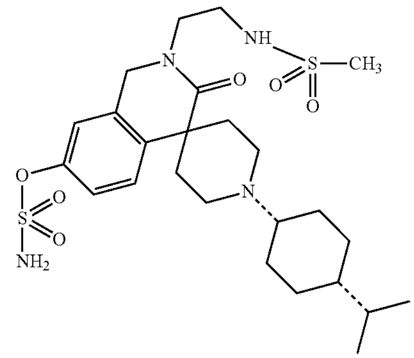 | 1'-((1s,4s)-4-isopropylcyclohexyl)-2-(2-(methylsulfonamido)ethyl)-3-oxo-2,3-dihydro-1H-spiro[isoquinoline-4,4'-piperidin]-7-yl sulfamate | |
| 379 | 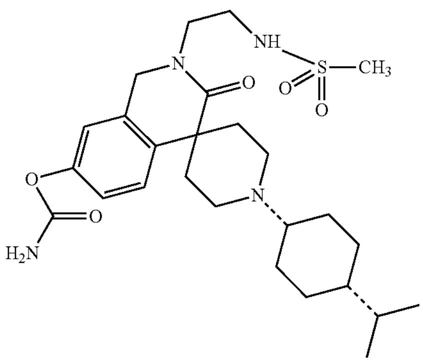 | 1'-((1s,4s)-4-isopropylcyclohexyl)-2-(2-(methylsulfonamido)ethyl)-3-oxo-2,3-dihydro-1H-spiro[isoquinoline-4,4'-piperidin]-7-yl carbamate | |
| 380 | 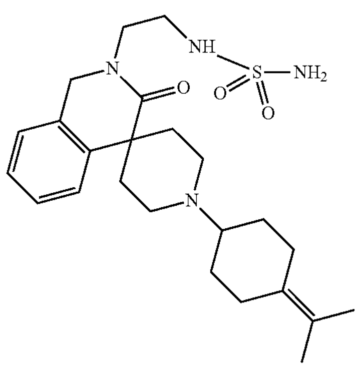 [SMILES: CC(C)=C1CCC(N2CCC3(CC2)C(=O)N(CCNS(N)(=O)=O)Cc2ccccc23)CC1] | N-(2-(3-oxo-1'-(4-(propan-2-ylidene)cyclohexyl)-1H-spiro[isoquinoline-4,4'-piperidin]-2(3H)-yl)ethyl)aminosulfamide | |
| 381 | 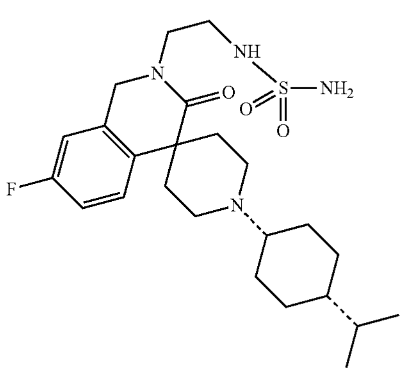 | N-(2-(7-fluoro-1'-((1s,4s)-4-isopropylcyclohexyl)-3-oxo-1H-spiro[isoquinoline-4,4'-piperidin]-2(3H)-yl)ethyl)aminosulfamide | |

TABLE 3-continued

| No. | Structure* | Name | NMR (300 0r 400 MHz) |
|---|---|---|---|
| 382 | 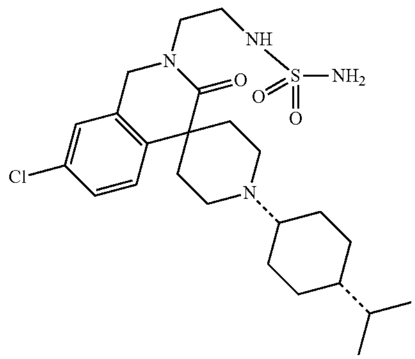 | N-(2-(7-chloro-1'-((1s,4s)-4-isopropylcyclohexyl)-3-oxo-1H-spiro[isoquinoline-4,4'-piperidin]-2(3H)-yl)ethyl)aminosulfamide | |
| 383 | 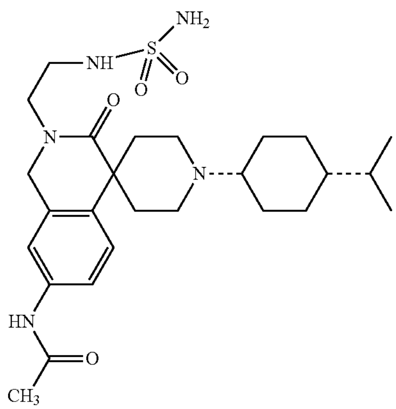 | N-(1'-((1s,4s)-4-isopropylcyclohexyl)-3-oxo-2-(2-(sulfamoylamino)ethyl)-2,3-dihydro-1H-spiro[isoquinoline-4,4'-piperidin]-7-yl)acetamide | |
| 384 | 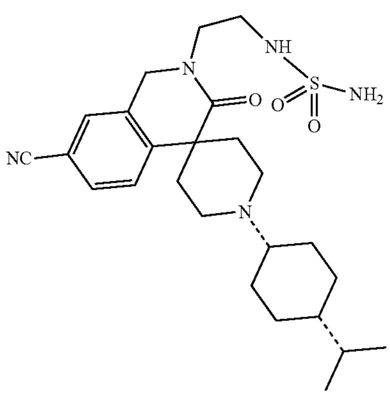 | N-(2-(7-cyano-1'-((1s,4s)-4-isopropylcyclohexyl)-3-oxo-1H-spiro[isoquinoline-4,4'-piperidin]-2(3H)-yl)ethyl)aminosulfamide | |
| 385 | 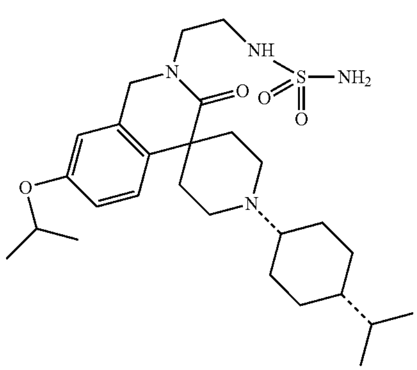 | N-(2-(7-isopropyloxy-1'-((1s,4s)-4-isopropylcyclohexyl)-3-oxo-1H-spiro[isoquinoline-4,4'-piperidin]-2(3H)-yl)ethyl)aminosulfamide | |

TABLE 3-continued

| No. | Structure* | Name | NMR (300 0r 400 MHz) |
|---|---|---|---|
| 386 | 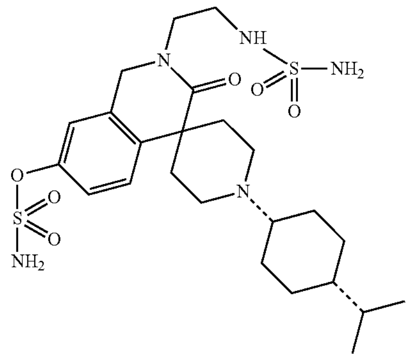 | 1'-((1s,4s)-4-isopropylcyclohexyl)-3-oxo-2-(2-(sulfamoylamino)ethyl)-2,3-dihydro-1H-spiro[isoquinoline-4,4'-piperidin]-7-yl sulfamate | |
| 387 | 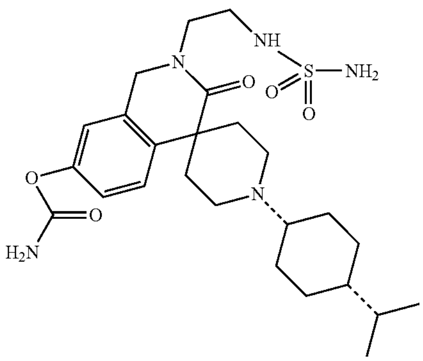 | 1'-((1s,4s)-4-isopropylcyclohexyl)-3-oxo-2-(2-(sulfamoylamino)ethyl)-2,3-dihydro-1H-spiro[isoquinoline-4,4'-piperidin]-7-yl carbamate | |
| 388 | 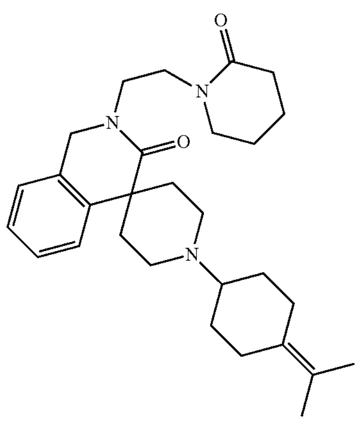 [SMILES: CC(C)=C1CCC(N2CCC3(CC2)C(=O)N(CCN2CCCCC2=O)Cc2ccccc23)CC1] | 2-(2-(2-oxopiperidin-1-yl)ethyl)-1'-(4-(propan-2-ylidene)cyclohexyl)-1,2-dihydro-3H-spiro[isoquinoline-4,4'-piperidin]-3-one | |
| 389 | 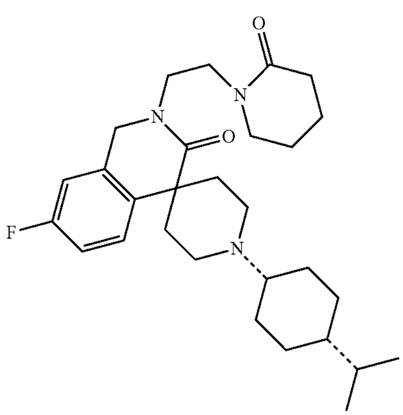 | 7-fluoro-1'-((1s,4s)-4-isopropylcyclohexyl)-2-(2-(2-oxopiperidin-1-yl)ethyl)-1,2-dihydro-3H-spiro[isoquinoline-4,4'-piperidin]-3-one | |

| No. | Structure* | Name | NMR (300 0r 400 MHz) |
|---|---|---|---|
| 390 | 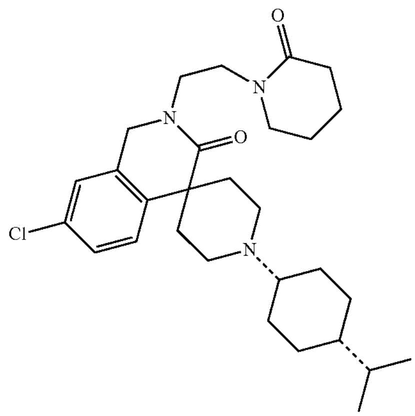 | 7-chloro-1'-((1s,4s)-4-isopropylcyclohexyl)-2-(2-(2-oxopiperidin-1-yl)ethyl)-1,2-dihydro-3H-spiro[isoquinoline-4,4'-piperidin]-3-one | |
| 391 | 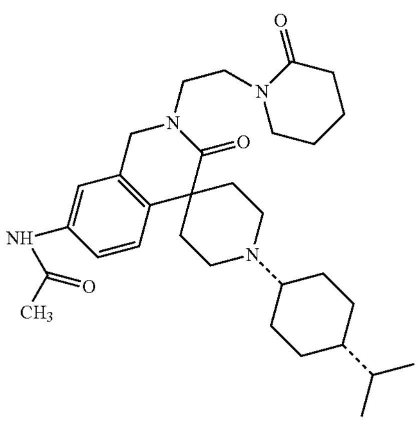 | N-(1'-((1s,4s)-4-isopropylcyclohexyl)-3-oxo-2-(2-(2-oxopiperidin-1-yl)ethyl)-2,3-dihydro-1H-spiro[isoquinoline-4,4'-piperidin]-7-yl)acetamide | |
| 392 | 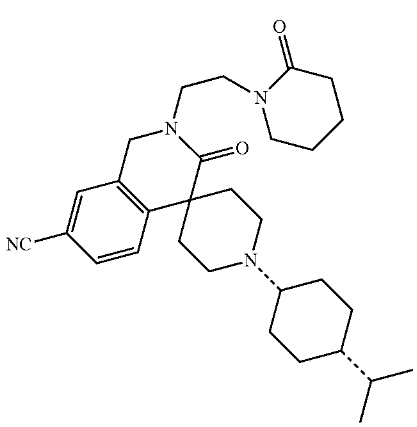 | 1'-((1s,4s)-4-isopropylcyclohexyl)-3-oxo-2-(2-(2-oxopiperidin-1-yl)ethyl)-2,3-dihydro-1H-spiro[isoquinoline-4,4'-piperidine]-7-carbonitrile | |

TABLE 3-continued

| No. | Structure* | Name | NMR (300 0r 400 MHz) |
|---|---|---|---|
| 393 | 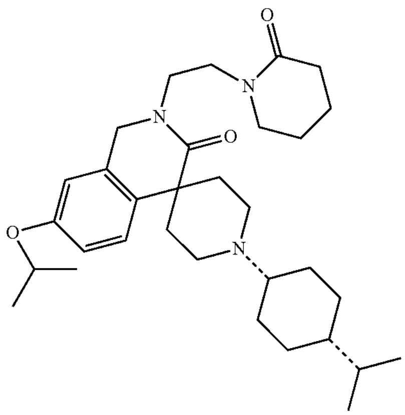 | 7-isopropoxy-1'-((1s,4s)-4-isopropylcyclohexyl)-2-(2-(2-oxopiperidin-1-yl)ethyl)-1,2-dihydro-3H-spiro[isoquinoline-4,4'-piperidin]-3-one | |
| 394 | 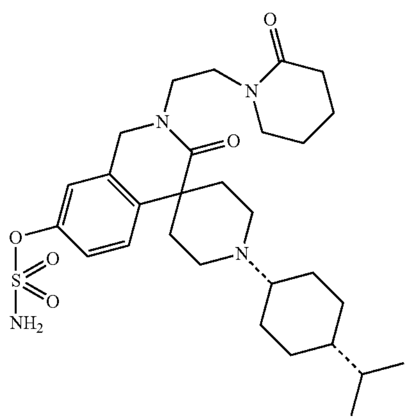 | 1'-((1s,4s)-4-isopropylcyclohexyl)-3-oxo-2-(2-(2-oxopiperidin-1-yl)ethyl)-2,3-dihydro-1H-spiro[isoquinoline-4,4'-piperidin]-7-yl sulfamate | |
| 395 | 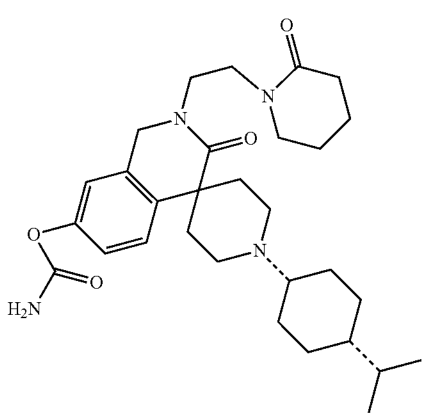 | 1'-((1s,4s)-4-isopropylcyclohexyl)-3-oxo-2-(2-(2-oxopiperidin-1-yl)ethyl)-2,3-dihydro-1H-spiro[isoquinoline-4,4'-piperidin]-7-yl carbamate | |

| No. | Structure* | Name | NMR (300 0r 400 MHz) |
|---|---|---|---|
| 396 | 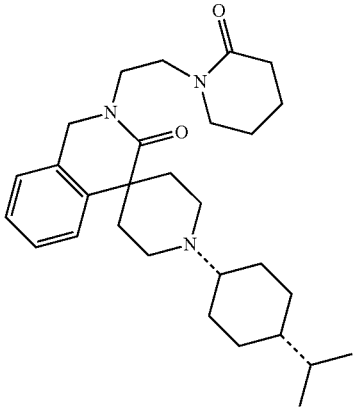 | 1'-((1s,4s)-4-isopropylcyclohexyl)-2-(2-(2-oxopiperidin-1-yl)ethyl)-1,2-dihydro-3H-spiro[isoquinoline-4,4'-piperidin]-3-one | |
| 397 | 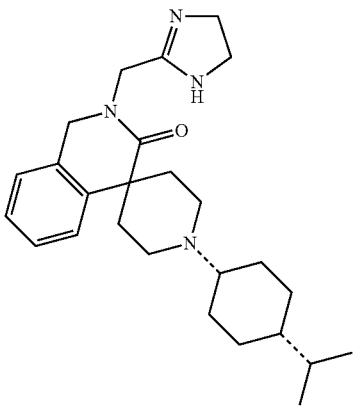 | 2-((4,5-dihydro-1H-imidazol-2-yl)methyl)-1'-((1s,4s)-4-isopropylcyclohexyl)-1,2-dihydro-3H-spiro[isoquinoline-4,4'-piperidin]-3-one | |
| 398 | 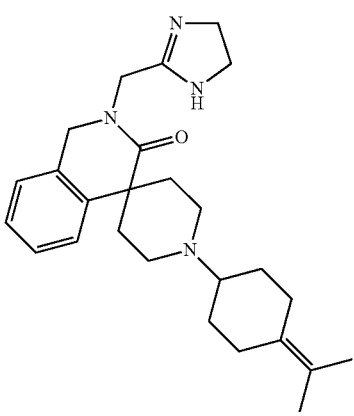 [SMILES: CC(C)=C1CCC(N2CCC3(CC2)C(=O)N(CC2=NCCN2)Cc2ccccc23)CC1] | 2-((4,5-dihydro-1H-imidazol-2-yl)methyl)-1'-(4-(propan-2-ylidene)cyclohexyl)-1,2-dihydro-3H-spiro[isoquinoline-4,4'-piperidin]-3-one | |

TABLE 3-continued

| No. | Structure* | Name | NMR (300 0r 400 MHz) |
|---|---|---|---|
| 399 | 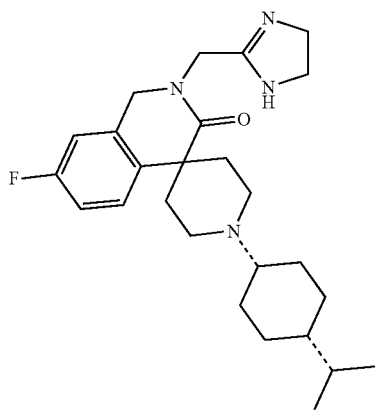 | 2-((4,5-dihydro-1H-imidazol-2-yl)methyl)-7-fluoro-1'-((1s,4s)-4-isopropylcyclohexyl)-1,2-dihydro-3H-spiro[isoquinoline-4,4'-piperidin]-3-one | |
| 400 | 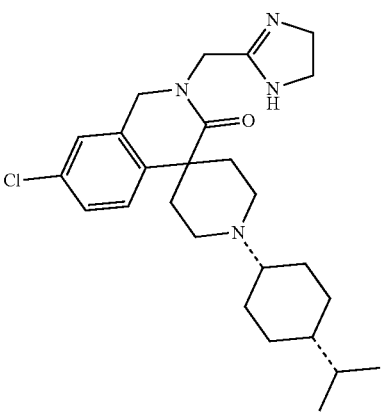 | 7-chloro-2-((4,5-dihydro-1H-imidazol-2-yl)methyl)-1'-((1s,4s)-4-isopropylcyclohexyl)-1,2-dihydro-3H-spiro[isoquinoline-4,4'-piperidin]-3-one | |
| 401 | 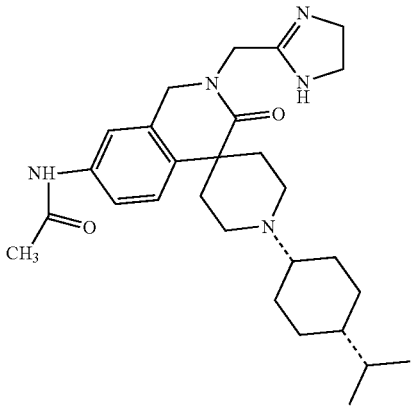 | N-(2-((4,5-dihydro-1H-imidazol-2-yl)methyl)-1'-((1s,4s)-4-isopropylcyclohexyl)-3-oxo-2,3-dihydro-1H-spiro[isoquinoline-4,4'-piperidin]-7-yl)acetamide | |

TABLE 3-continued

| No. | Structure* | Name | NMR (300 0r 400 MHz) |
|---|---|---|---|
| 402 | 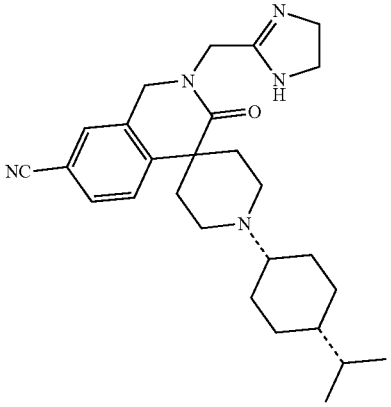 | 2-((4,5-dihydro-1H-imidazol-2-yl)methyl)-1'-((1s,4s)-4-isopropylcyclohexyl)-3-oxo-2,3-dihydro-1H-spiro[isoquinoline-4,4'-piperidine]-7-carbonitrile | |
| 403 | 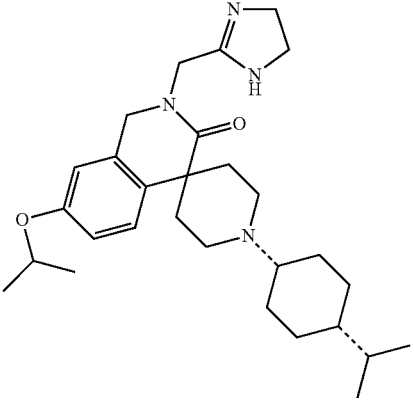 | 2-((4,5-dihydro-1H-imidazol-2-yl)methyl)-7-isopropoxy-1'-((1s,4s)-4-isopropylcyclohexyl)-1,2-dihydro-3H-spiro[isoquinoline-4,4'-piperidin]-3-one | |
| 404 | 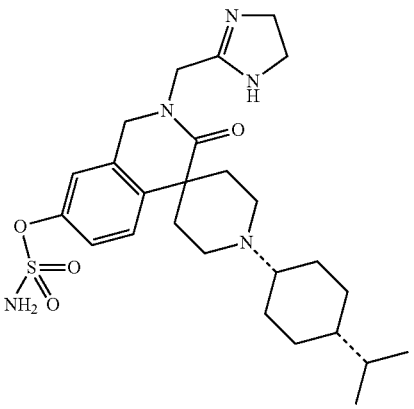 | 2-((4,5-dihydro-1H-imidazol-2-yl)methyl)-1'-((1s,4s)-4-isopropylcyclohexyl)-3-oxo-2,3-dihydro-1H-spiro[isoquinoline-4,4'-piperidin]-7-yl sulfamate | |

TABLE 3-continued

| No. | Structure* | Name | NMR (300 0r 400 MHz) |
|---|---|---|---|
| 405 | 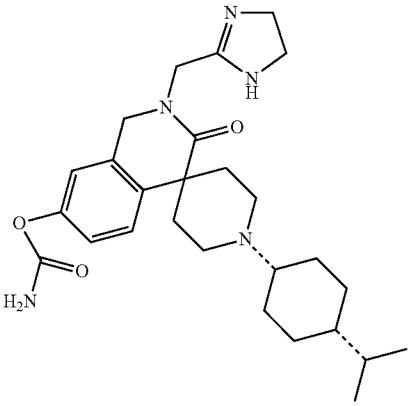 | 2-((4,5-dihydro-1H-imidazol-2-yl)methyl)-1'-((1s,4s)-4-isopropylcyclohexyl)-3-oxo-2,3-dihydro-1H-spiro[isoquinoline-4,4'-piperidin]-7-yl carbamate | |
| 406 | 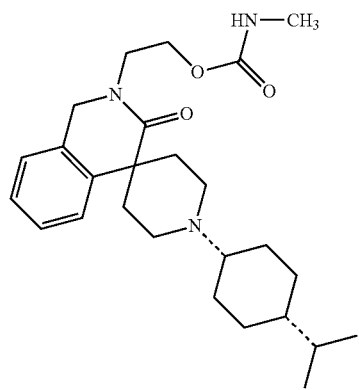 | 2-(1'-((1s,4s)-4-isopropylcyclohexyl)-3-oxo-1H-spiro[isoquinoline-4,4'-piperidin]-2(3H)-yl)ethyl methylcarbamate | |
| 407 | 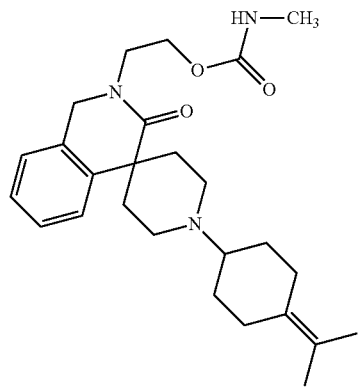 [SMILES: CNC(=O)OCCN1Cc2ccccc2C2(CCN(C3CCC(=C(C)C)CC3)CC2)C1=O] | 2-(3-oxo-1'-(4-(propan-2-ylidene)cyclohexyl)-1H-spiro[isoquinoline-4,4'-piperidin]-2(3H)-yl)ethyl methylcarbamate | |
| 408 | 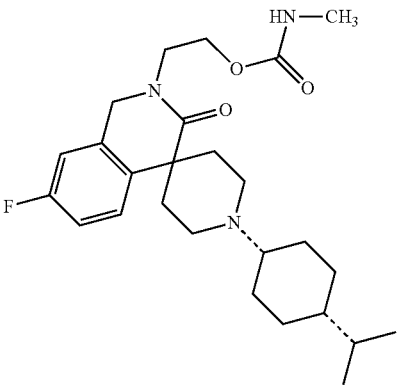 | 2-(7-fluoro-1'-((1s,4s)-4-isopropylcyclohexyl)-3-oxo-1H-spiro[isoquinoline-4,4'-piperidin]-2(3H)-yl)ethyl methylcarbamate | |

TABLE 3-continued

| No. | Structure* | Name | NMR (300 0r 400 MHz) |
|---|---|---|---|
| 409 | 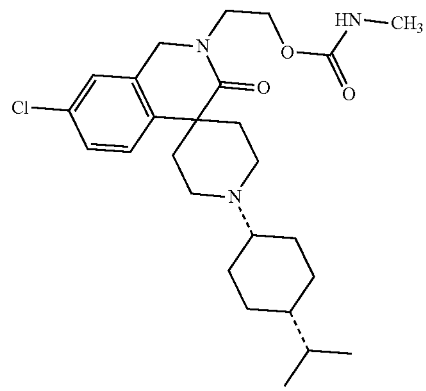 | 2-(7-chloro-1'-((1s,4s)-4-isopropylcyclohexyl)-3-oxo-1H-spiro[isoquinoline-4,4'-piperidin]-2(3H)-yl)ethyl methylcarbamate | |
| 410 | 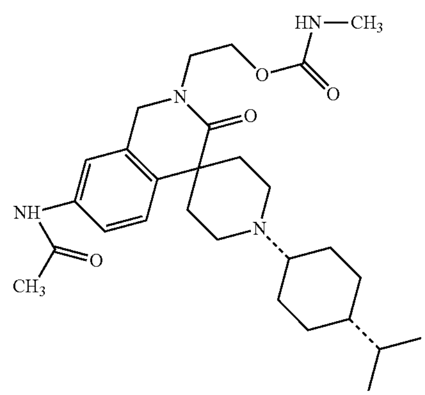 | 2-(7-acetamido-1'-((1s,4s)-4-isopropylcyclohexyl)-3-oxo-1H-spiro[isoquinoline-4,4'-piperidin]-2(3H)-yl)ethyl methylcarbainate | |
| 411 | 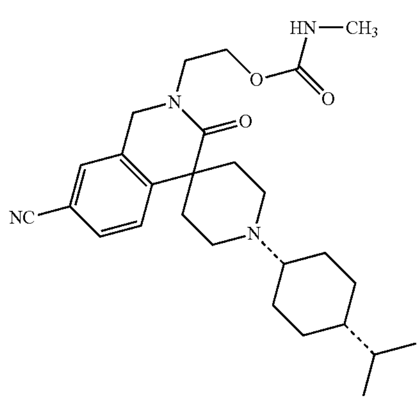 | 2-(7-cyano-1'-((1s,4s)-4-isopropylcyclohexyl)-3-oxo-1H-spiro[isoquinoline-4,4'-piperidin]-2(3H)-yl)ethyl methylcarbamate | |
| 412 | 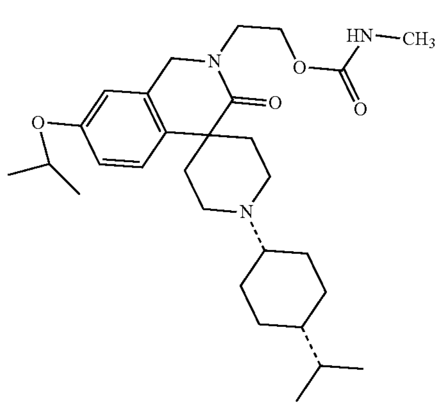 | 2-(7-isopropoxy-1'-((1s,4s)-4-isopropylcyclohexyl)-3-oxo-1H-spiro[isoquinoline-4,4'-piperidin]-2(3H)-yl)ethyl methylcarbamate | |

TABLE 3-continued

| No. | Structure* | Name | NMR (300 0r 400 MHz) |
|---|---|---|---|
| 413 | 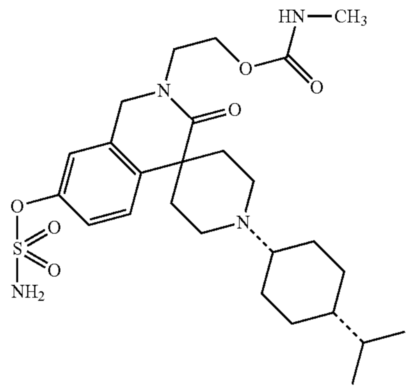 | 1'-((1s,4s)-4-isopropylcyclohexyl)-2-(2-((methylcarbamoyl)oxy)ethyl)-3-oxo-2,3-dihydro-1H-spiro[isoquinoline-4,4'-piperidin]-7-yl sulfamate | |
| 414 | 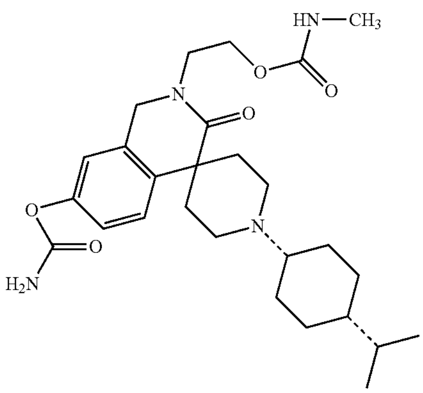 | 2-(7-(carbamoyloxy)-1'-((1s,4y)-4-isopropylcyclohexyl)-3-oxo-1H-spiro[isoquinoline-4,4'-piperidin]-2(3H)-yl)ethyl methylcarbamate | |

Preparation of the Compounds

The piperidinyl-containing nociceptin receptor compounds of Formula (I), and the embodiments represented by Formula (II), Formula (III), and Formula (IV) can be synthesized via numerous synthetic routes as may be appreciated by one of ordinary skill in the art. Exemplary synthetic methods for compounds of Formula (II) are shown in FIGS. 1 through 6 and 10, and described in Examples 1 through 6 and 10 below. Table 1 also provides $^1$H NMR or TLC data for compounds of Formula II.

Exemplary synthetic methods for compounds of Formula (III) are shown in FIGS. 7 and 8 and described in Examples 7 and 8 below. For the compounds of Formula (III), Table 2 provides $^1$H NMR or TLC data for such compounds.

An exemplary route to compounds of Formula (IV) is shown in FIG. 9 and described in Example 9 below. For the compounds of Formula (IV), Table 3 provides $^1$H NMR data where indicated.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol- 750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $I_{100}$ of the specific compound disclosed herein with that of a known agent, and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, *In: The Pharmacological Basis of Therapeutics*, Ch. 1, p. 1).

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

The compounds and compositions described herein can be used in a wide variety of applications to treat or prevent neurological conditions and other disorders in a subject. The methods generally involve administering therapeutically effective amounts of compounds disclosed herein or a pharmaceutical composition thereof to the subject.

The compounds and compositions described herein may be used to treat and prevent, for example, pain (e.g., neuropathic pain, sensitization accompanying neuropathic pain, and inflammatory pain, sickle-cell disease pain, acute pain), fibromyalgia, migraine; substance abuse or dependency (e.g., nicotine, cocaine, methamphetamine), alcohol addiction; neurological conditions such as anxiety, depression (e.g., major depressive disorder), post-traumatic stress disorder, mood disorder, affective disorders (e.g. depression and dysthymia; bipolar disorder, e.g., bipolar depressive disorder; manic disorder; seasonal affective disorder; and attention deficit disorder (ADD) and attention deficit hyperactivity disorder (ADHD)), obsessive-compulsive disorder, vertigo, epilepsy, schizophrenia, schizophrenia-related disorder, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, behavior disorder; neurodegenerative diseases such as Alzheimer's disease, Parkinson's disease, dyskinesias, Huntington's disease, dementia; cognitive impairment, cognitive impairment associated with schizophrenia (CIAS), movement disorders, restless leg syndrome (RLS), multiple sclerosis, sleep disorder, sleep apnea, narcolepsy, excessive daytime sleepiness, jet lag, drowsy side effect of medications, insomnia, eating disorder, sexual dysfunction, hypertension, emesis, Lesche-Nyhane disease, Wilson's disease, autism, Huntington's chorea, or premenstrual dysphoria.

Nociceptin receptor compounds can be used to treat or prevent renal disorders and urinary incontinence, including, but not limited to those characterized by inappropriate antidiuretic hormone secretion, imbalances of water retention and/or salt excretion. For example, U.S. Pat. No. 6,869,960 discloses a class of spiropiperidine ORL-1 ligands said to be therapeutic agents for renal disorders.

Nociceptin receptor compounds can further be used to treat or prevent cardiovascular disorders including but not limited to systolic hypertension, myocardial infarction, bradycardia, arrhythmias, hypertension, hypotension, thrombosis, anemia, arteriosclerosis and angina pectoris. For example, U.S. Pat. No. 7,241,770 discloses a class of nociceptin agonists said to be therapeutic agents for cardiovascular disorders.

Nociceptin receptor compounds can be further used to treat gastrointestinal disorders including but not limited to diarrhea and pain such as that in inflammatory bowel diseases, Crohn's disease, inflammatory bowel syndrome.

The compounds disclosed herein may utilize a new, non-dopaminergic target for the treatment of Parkinson's disease (PD) and its associated dysinesias. Several studies have uncovered a pathogenic role of N/OFQ and the NOP receptor in nigrostriatal pathways affected in PD (vide infra). The NOP receptor, a G-protein coupled receptor, is the fourth member of the opioid receptor family, but does not bind known opiates with high affinity (Mollereau et al., FEBS Lett., 1994, 341:33-8). The endogenous ligand for NOP is a 17-amino acid peptide called N/OFQ. N/OFQ has low affinity for the mu, delta, and kappa opioid receptors (Gintzler, et al., Eur. J. Pharmacol., 1997, 325:29-34). The N/OFQ-NOP receptor system is widely expressed in brain cortical and subcortical areas, particularly in striatum, globus pallidus and substantia nigra (SN) neurons.

Endogenous N/OFQ contributes to development of PD symptoms and N/OFQ levels are elevated in the SNr following dopamine (DA) cell loss or impairment of DA transmission (Marti, et al., Mov. Disord., 2010, 25:1723-32). Such an increase is also observed in the CSF of PD patients (Marti et al., 2010); ii) NOP receptor antagonists reverse parkinsonian symptoms in neurodegenerative (6-OHDA hemi-lesioned rat, MPTP-treated mouse and macaque) and functional (reserpinized- or haloperidol-treated animals) models of PD iii) genetic deletion of the N/OFQ gene protects mice from the neurotoxic action of MPTP. Mechanistic studies revealed that the antiparkinsonian action of NOP antagonists is accomplished through normalization of the imbalance between excitatory (GLU) and inhibitory (GABA) inputs impinging on nigro-thalamic neurons, generated by striatal DA deafferentation. NOP antagonists also potentiate the symptomatic effect of levodopa.

NOP receptor agonists (commercially available SCH221510; Varty et al., J. Pharmaco. Exp. Ther., 2008, 326:672-82) attenuated the expression of abnormal involuntary movements [AIMs, a rodent correlate of levodopa-induced dyskinesias (LID)] in dyskinetic rats and nonhuman primates challenged with L-DOPA, by acting in the striatum where, contrary to SNr, the N/OFQ tone is reduced and NOP receptors are up-regulated following DA cell loss (Marti, M., et al., 2012). This action can be dissociated from the typical motor-inhibiting effects of NOP agonists, since anti-dyskinetic doses were 100-fold lower than the typical hypo-locomotive doses.

From a clinical perspective, NOP receptor antagonists disclosed herein may be useful in treating the symptoms and the neurodegeneration associated with PD, while NOP receptor agonists are effective in treating LID.

Genetic deletion of the N/OFQ gene protects mice from the neurotoxic action of MPTP. Mechanistic studies revealed that the antiparkinsonian action of NOP antagonists is accomplished through normalization of the imbalance between excitatory (GLU) and inhibitory (GABA) inputs impinging on nigro-thalamic neurons, generated by striatal DA deafferentation. NOP antagonists also potentiate the symptomatic effect of levodopa. Therefore NOP receptor antagonists may provide symptomatic and neuroprotective benefit in PD patients. On the other hand, NOP receptor agonists have been shown to attenuate the expression of AIMs in dyskinetic rats and nonhuman primates challenged with L-DOPA.

Nociceptin receptor agonists are known in the art to block the rewarding properties of several common drugs of abuse such as morphine, cocaine, amphetamines, and alcohol. Administration of NOP ligands suppresses basal and drug-stimulated dopamine release in the reward areas in rodent brain. The inhibitory effect of NOP agonists on drug reward and the inhibition of drug-induced dopamine release in mesolimbic areas in the brain suggest the utility of NOP agonists as drug abuse medications. The compounds descried herein may find use in the treatment of substance abuse disorders and addiction.

While other opioid receptors, mu, delta and kappa opioid receptors are historically associated with "opioid analgesia", the NOP receptor and its agonists and antagonists have only begun to be noticed as possible analgesics, due to emerging data on the antinociceptive efficacies of NOP ligands in rodents and nonhuman primate models of acute pain as well as neuropathic and inflammatory pain (Khroyan et al., Eur. J. Pharmacol., 2009, 610:49-54; Khroyan et al., J. Pharmacol. Exper. Therap., 2011, 339:687-93; Khroyan et al., J. Pharmacol. Exp. Ther., 2007, 320:934-43; Lin and Ko, ACS Chem. Neurosci., 2013, 4:214-24; Toll et al., J. Pharmacol. Exp. Ther., 2009, 331:954-64). The NOP receptor is widely distributed in the central and peripheral nervous systems and in the same pain processing pathways as the other three opioid receptors. However, unlike the opioid receptors, the pharmacology of the NOP receptor in nociception is quite distinct and complex.

NOP agonists have been shown to have potent antinociceptive potency in rodent models of chronic pain (Khroyan et al., J. Pharmacol. Exper. Therap., 2011, 339: 687-93; Sukhtankar et al, J. Pharmacol. Exp. Ther., 2013, 346:11-22). NOP antagonists can potentiate the anti-nociceptive efficacies of morphine in chronic pain (Khroyan et al., Eur. J. Pharmacol., 2009, 610:49-54). NOP agonists which are effective as analgesics do not show any rewarding effects or abuse potential in rodent models, pointing to a possible advantage that NOP agonists may have as non-addicting analgesics over traditional opioids (Khroyan et al., *J. Pharmacol. Exper. Ther.*, 2011, 339:687-93; Toll et al., *J. Pharmacol. Exp. Ther.*, 2009, 331:954-64). The compounds disclosed herein may find use as analgesics (NOP agonists) or adjuncts to opioid pain therapy (NOP antagonists), particularly for chronic, neuropathic as well as inflammatory pain conditions.

While all nociceptin receptor ligands have binding affinity for the NOP receptor, they can modulate the "intrinsic activity (functional efficacy)" of the receptor over a spectrum from 0% to a 100%. NOP ligands that have 0% functional efficacy and block the function of the receptor are classified as NOP antagonists. Ligands that have 75-100% functional efficacy and activate the receptor are classified as NOP agonists. Those ligands in between (15-75% functional efficacy) are generally labelled as NOP partial agonists. The binding affinity of NOP ligands as well as their functional efficacy (agonist, partial agonist, antagonist) may be modulated by chemical structure modifications, as shown in our previous studies with various chemical scaffolds (Zaveri et al., *J. Med. Chem.*, 2004, 47:2973-6; Zaveri, et al., *AAPS J.*, 2005, 7:E345-52; Zaveri et al., "Structure-activity relationships of Nociceptin Receptor (NOP) Ligands and the Design of Bifunctional NOP/mu opioid receptor-targeted Ligands", in *Research and Development of Opioid-Related Analgesics*, Ko, M. C.; Husbands, S. M., Eds., American Chemical Society, 2013, Chapter 8, pp 145-160).

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration one or more symptoms associated with drug addiction, pain, neurodegenerative disorders, Parkinson's disease, Alzheimer's disease, psychiatric disorders, renal disorders, gastrointestinal disorders, and cardiovascular disorders.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided herein are administered prior to or subsequent to the one or more additional active ingredients.

All publications and patents cited herein are incorporated by reference in their entirety.

EXAMPLES

The starting materials and reagents employed in preparing these compounds were obtained from commercial suppliers such as Sigma-Aldrich (St. Louis, Mo.), Strem Chemicals (Newburyport, Mass.), and AK Scientific (Union City, Calif.). $^1$H NMR spectra were recorded on a Varian Gemini 300 MHz spectrometer (300 MHz and 75 MHz, respectively) and are internally referenced to chloroform at δ 7.27. Data for $^1$H NMR are reported as follows: chemical shift (δ ppm), multiplicity (s=singlet, d=doublet, t=triplet, q=quartet, m=multiplet), coupling constant (Hz), integration, and assignment. Mass spectra were obtained using a ThermoFinnigan LCQ Duo LC/MS/MS or API 150 EX MS (Applied Biosystems) instrument and an electrospray ionization probe. Thin-layer chromatography was run on Analtech Uniplate silica gel TLC plates. Flash chromatography was carried out using silica gel, Merck grade 9385, 230-400 mesh.

Example 1: Synthesis of 1-(1-((1s,4s)-4-isopropylcyclohexyl)piperidin-4-yl)-1H-indole (61) and 1-(1-((1s,4s)-4-isopropylcyclohexyl)piperidin-4-yl)-1H-indole-3-carbaldehyde oxime (81)

SCHEME I depicts this synthesis.

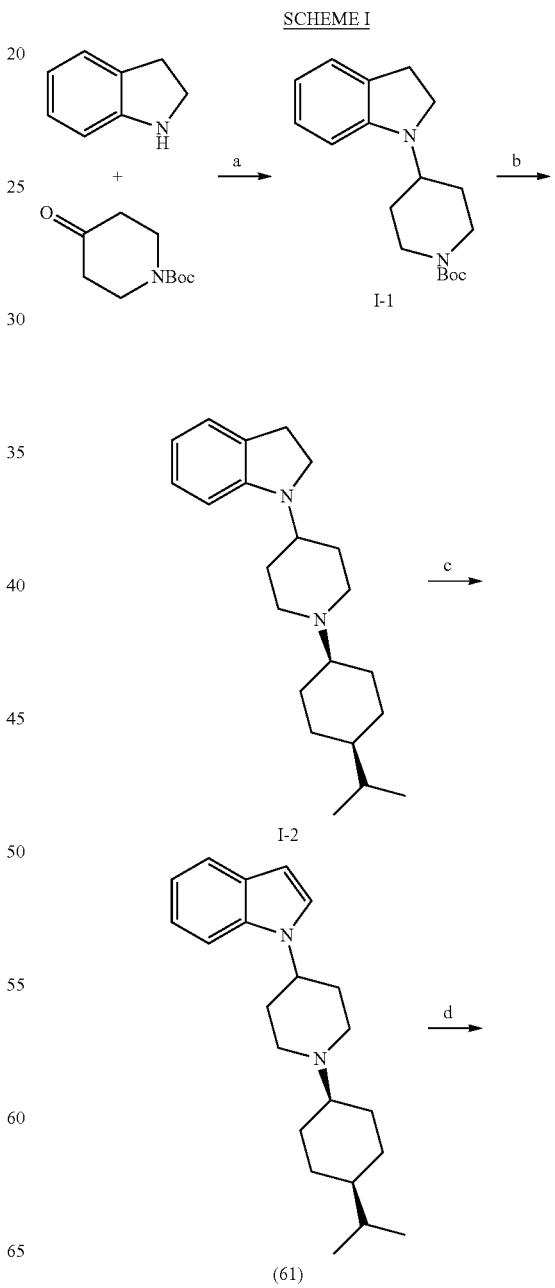

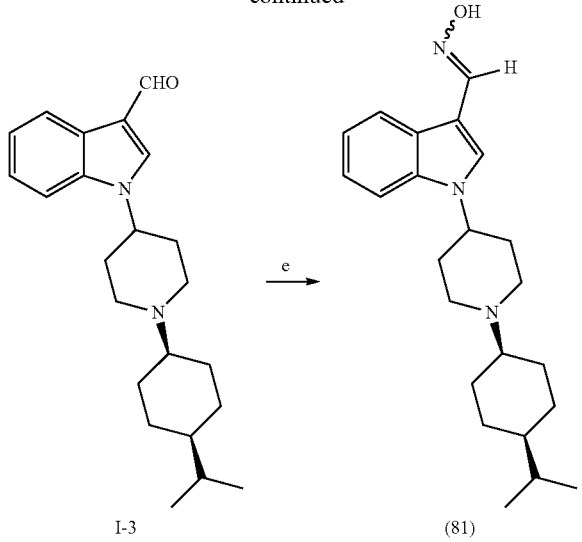

I-3 (81)

Scheme I Reagents and Conditions: a) AcOH, sodium triacetoxyborohydride (STAB), MgSO$_4$, DCE, rt (General Procedure A); b) i. TFA, CH$_2$Cl$_2$, ii. 4-isopropyl-cyclohexanone, STAB, AcOH, DCE (General Procedure B, 2 steps); c) MnO$_2$, CH$_2$Cl$_2$; d) POCl$_3$, DMF; and e) NH$_2$OH·HCl, NaOAc·3H$_2$O, EtOH:H$_2$O (2:1), 110° C.

General Procedure A: Reductive Amination with N-Boc Piperidone:

The aniline substrate (1.00 equiv) and N-Boc-piperidone (1.05-1.50 equiv) were charged into a round bottom flask. 1,2-DCE (0.25M) was added, and the mixture was stirred until both components dissolved. To this solution was added MgSO$_4$ (100 wt % of limiting reagent) and glacial AcOH (1.00-2.30 equiv) at ambient temperature, and the solution was stirred for 90 minutes. At this stage, sodium triacetoxyborohydride (STAB) (1.50-2.30 equiv) was added. The reaction was allowed to stir at room temperature and monitored by TLC (EtOAc:Hexanes). After 1-2 days, the reaction was ≥90% complete by TLC analysis. The reaction was quenched with saturated NaHCO$_3$ (aq.) and stirred until the reaction mixture was basic and bubbling had ceased. The biphasic layer was separated and the organic layer was washed 2× with H$_2$O, brine, dried with MgSO$_4$, filtered and concentrated in vacuo to provide a brown oil that was purified via flash chromatography using EtOAc:Hexanes to provide the desired product, which was used directly in the following reaction.

t-butyl 4-(indolin-1-yl)piperidine-1-carboxylate (I-1)

See General Procedure A: Indoline (10.0 g, 83.9 mmol, 1.00 equiv), N-Boc piperidone (17.6 g, 88.1 mg, 1.05 equiv), AcOH, 4.80 mL, 83.9 mmol, 1.00 equiv), STAB (26.7 g, 12.6 mmol, 1.50). MgSO$_4$ was not used in the reaction. The crude oil was purified via flash chromatography using 10:90 EtOAc:Hexanes to provide indoline I-1 (24.3 g, 96% yield). $^1$H NMR (300 MHz, CDCl$_3$) δ 7.06 (t, J=6.0 Hz, 2H), 6.03 (t, J=6.0 Hz, 1H), 6.43 (d, J=6.0 Hz, 1H), 4.25 (m, 2H), 3.52 (m, 1H), 3.35 (t, J=6.3 Hz, 2H), 2.79 (m, 2H), 1.80 (d, J=9.3 Hz, 2H), 1.60 (m, 4H), 1.49 (s, 9H); MS(APCI) m/z: 303.06 [M+H]$^+$.

General Procedure B: Boc Removal and Reductive Amination with 4-iPr Cyclohexanone:

Step 1. A solution of N-Boc intermediate (1.00 equiv) in CH$_2$Cl$_2$ (0.25-0.30M) was cooled to 0° C., and then TFA (6-30 equiv) was added over several minutes. Upon completion of addition, the ice-bath was removed and the reaction was allowed to warm to room temperature and monitored by TLC (EtOAc:Hexanes). After 2 hours, the reaction was complete. The reaction was concentrated in vacuo, followed by the addition of EtOAc, which was consequently removed in vacuo. The oil residue was then dissolved in EtOAc and was stirred as saturated NaHCO$_3$ (aq.) was added until the aqueous layer remained basic. The layers were separated, and the aqueous layer was extracted with EtOAc until UV activity in the aqueous layer was minimal (3-8×). The EtOAc layers were combined, washed with brine, dried with MgSO$_4$, filtered, and concentrated in vacuo to provide the piperidine intermediate.

Step 2. The piperidine intermediate from the previous step (1.00 equiv) and 4-iPr-cyclohexanone (1.00-1.50 equiv) were dissolved 1,2-DCE (0.070M). To the reaction was added glacial AcOH (1.00-2.30 equiv), and the reaction was stirred for 20 minutes. After 20 minutes, STAB (1.50-2.30 equiv) was added in 3 portions. An Ar balloon was fitted on top of the reaction, and the reaction was monitored by TLC (MeOH:CH$_2$Cl$_2$:NH$_4$OH (aq.)). After 2-3 days, the reaction was ≥95% complete; hence, saturated NaHCO$_3$ (aq.) was added until the aqueous layer remained basic. At this stage, the layers were separated, and the aqueous layer was extracted 2× with CH$_2$Cl$_2$. The organic layers were combined, and washed 2× with H$_2$O, brine, dried with MgSO$_4$, filtered, and concentrated in vacuo to provide a crude residue that was purified via flash chromatography using EtOAc:Hexanes:NH$_4$OH (aq.).

syn-1-(1-(4-isopropylcyclohexyl)piperidin-4-yl)indoline (1-2)

See General Procedure B: Step 1. Indoline I-1 (24.4 g, 80.5 mmol, 1.00 eq), TFA (38.0 mL, 496 mmol, 6.20 equiv), CH$_2$Cl$_2$ (300 mL, 0.27M). Combined EtOAc layers were dried immediately with MgSO$_4$, and were not washed with water or brine. Obtained a grey solid (13.6 g, 84% yield). Step 2. See General Procedure B: N—H piperidine from the previous step (13.6 g, 67.2 mmol, 1.00 equiv), iPr-cyclohexanone (9.40 g, 67.2 mmol, 1.00 equiv), AcOH (3.85 mL, 67.2 mmol, 1.00 equiv), STAB (21.3 g, 101 mmol, 1.50 equiv). Purified via flash chromatography using 10:90:1.5 EtOAc:Hexanes:NH$_4$OH (aq.) to provide intermediate 1-2 as a light-gold oil (33% yield). R$_f$=0.25 (20:80:3 drops EtOAc:Hexanes:NH$_4$OH (aq.), UV); $^1$H NMR (300 MHz, CDCl$_3$) δ 7.05 (t, J=5.7 Hz, 2H), 6.60 (J=5.7 Hz, 1H), 6.41 (d, J=5.7 Hz, 1H), 3.37 (m, 3H), 3.10 (d, J=8.7 Hz, 2H), 2.94 (t, J=6.3 Hz, 2H), 2.27 (m, 1H), 2.14 (t, J=8.7 Hz, 2H), 1.54-1.82 (m, 11H), 1.38 (m, 2H), 1.13 (m, 1H), 0.88 (d, J=5.1 Hz, 6H); MS(ESI) m/z: 327.4 [M+H]$^+$.

syn-1-(1-(4-isopropylcyclohexyl)piperidin-4-yl)-1H-indole (61)

Indoline I-2 (4.63 g, 14.2 mmol, 1.00 equiv) was dissolved in 180 mL of CH$_2$Cl$_2$. To this solution was added 4 ÅMS (56.8 g, 4 g/mmol of indoline), followed by MnO$_2$ (12.3 g, 142 mmol, 10.0 equiv) and another 20 mL of CH$_2$Cl$_2$. An argon balloon was fitted onto the reaction vessel, and the thick suspension was stirred and monitored by TLC (20:80:3 drops EtOAc:hexanes:NH$_4$OH (aq.)). After 16 hours, the reaction was complete. The mixture was filtered over a large pad of Celite and the remaining solid was washed 5× with CH$_2$Cl$_2$. The filtrate was concentrated in vacuo to provide a crude oil. This material was dissolved in EtOAc, and 10% HCl (aq.) was added with vigorous stirring, which resulted in a white precipitate. The white solid was filtered, and washed 3× with EtOAc, and was then air-dried over 1 hour. The white solid was then suspended in EtOAc, 70% NaHCO₃ (aq.) was added, and the mixture stirred until >90% of the solid had dissolved. The EtOAc layer was separated, washed with H₂O, brine, dried with MgSO₄, filtered, and concentrated in vacuo to provide a thick oil that was purified via flash chromatography using 10:90:1.5 EtOAc:hexanes:NH₄OH (aq.) to provide indole 1 as an off-white solid (3.65 g, 79% yield). $R_f$=0.25 (10:90:3 drops EtOAc:Hexanes:NH₄OH (aq.), UV); ¹H NMR (300 MHz, CDCl₃) δ 7.64 (d, J=6.0 Hz, 1H), 7.39 (d, J=6.0 Hz, 1H), 7.26 (m, 1H), 7.20 (t, J=6.0 Hz, 1H), 7.11 (t, J=6.0 Hz, 1H), 6.52 (d, J=2.4 Hz, 1H), 4.23 (m, 1H), 3.20 (d, J=9.0 Hz, 2H), 2.30 (m, 3H), 2.08 (m, 4H), 1.51-1.78 (m, 7H), 1.40 (m, 2H), 1.17 (m, 1H), 0.9 (d, J=4.8 Hz, 6H); MS(ESI) m/z: 325.4 [M+H]⁺.

syn-1-(1-(4-isopropylcyclohexyl)piperidin-4-yl)-1H-indole-3-carbaldehyde (1-3)

To a stirred solution of 25.0 mL DMF at 0° C. was added POCl₃ (3.66 mL, 40.0 mmol, 4.00 equiv). The solution was stirred at 0° C. for 15 minutes. At this stage, indole I-3 (3.10 g, 10.0 mmol, 1.00 equiv), was dissolved in 10 mL of DMF with the assistance of heat. The warm solution of indole I-3 was then added to the reaction, and the reaction was rinsed with 5.00 mL of DMF. The reaction was now a red solution, and the reaction was allowed to stir for 15-20 minutes at 0° C. TLC (50:50:3 drops EtOAc:hexanes:NH₄OH (aq.)) showed the reaction was complete. The reaction was poured into a saturated NaHCO₃ (aq.) ice bath, followed by the addition of CH₂Cl₂. The mixture was stirred vigorously for 30 minutes, upon which the layers were separated, and the aqueous layer was extracted with CH₂Cl₂ until UV activity was minimal (5-6×). The organic layer was then washed 3× with H₂O, brine, dried with MgSO₄, filtered, and concentrated in vacuo to provide a dark red oil, which was purified via flash chromatography using 50:50:1.5 EtOAc:hexanes:NH₄OH (aq.) to provide aldehyde I-3 as a light-yellow solid (2.15 g, 74% yield). $R_f$=0.20 (50:50:3 drops EtOAc:Hexanes:NH₄OH (aq.), UV); ¹H NMR (300 MHz, CDCl₃) δ 10.0 (s, 1H), 8.33 (m, 1H), 7.89 (s, 1H), 7.43 (m, 1H), 7.33 (m, 2H), 4.29 (m, 1H), 3.28 (d, J=7.8 Hz, 2H), 2.40 (m, 3H), 2.19 (m, 3H), 1.55-1.78 (m, 8H), 1.42 (m, 2H), 1.17 (m, 1H), 0.9 (d, J=5.7 Hz, 6H); MS(ESI) m/z: 353.1 [M+H]⁺.

syn-1-(1-(4-isopropylcyclohexyl)piperidin-4-yl)-1H-indole-3-carbaldehyde oxime (81)

Aldehyde I-3 (2.15 g, 6.10 mmol, 1.00 equiv), NH₂OH.HCl (551 mg, 7.93 mmol, 1.30 equiv), and NaOAc 3H₂O (1.08 g, 7.93 mmol, 1.30 equiv) were charged into a round bottom flask. Absolute EtOH (20.5 mL) and 10 mL of H₂O were added, and the reaction was fitted with a condenser and an Ar balloon on top. The suspension was heated to reflux (ca. 110° C. oil bath) and monitored by TLC (40:60:3 drops EtOAc:hexanes:NH₄OH (aq.)). After 2 hours, the reaction was complete. The reaction was allowed to cool to room temperature upon which a white precipitate formed. The mixture was diluted with EtOAc and saturated NaHCO₃ (aq.), and stirred until the mixture became a biphasic solution. The layers were separated, and the organic layer was washed 2× with H₂O, brine, dried with MgSO₄, filtered, and concentrated in vacuo to provide oxime 2 as a white solid (1.74 g, 78% yield). The two isomers of the oxime are in a ca. 3:2 ratio. $R_f$=0.50 (top spot), 0.45 (bottom spot) (40:60:3 drops EtOAc:Hexanes:NH₄OH (aq.), UV); ¹H NMR (300 MHz, CDCl₃, Major Isomer) δ 10.8 (br, 1H), 8.47 (s, 1H), 7.78 (m, 2H), 7.41 (d, J=6.0, 1H), 7.28 (m, 1H), 7.23 (m, 1H), 4.31 (m, 1H), 3.30 (d, J=8.7 Hz, 2H), 2.55 (m, 1H), 2.46 (t, J=7.8, 2H), 2.23 (m, 3H), 1.86 (m, 2H), 1.60-1.80 (m, 6H), 1.43 (m, 2H), 1.19 (m, 1H), 0.91 (d, J=5.1, 6H); ¹H NMR (300 MHz, CDCl₃, Minor Isomer) δ 8.30 (s, 1H), 8.07 (d, J=6.0 Hz, 1H), 7.48 (s, 1H), 7.40 (d, J=6.0 Hz, 1H), 7.28 (t, J=5.4 Hz, 1H), 7.20 (t, J=5.4 Hz, 1H), 4.23 (m, 1H), 3.22 (d, J=5.7 Hz, 2H), 2.35 (m, 3H), 2.13 (m, 4H), 1.55-1.80 (m, 7H), 1.43 (m, 2H), 1.17 (m, 1H), 0.91 (d, J=5.1 Hz, 6H); MS(ESI) m/z: 368.5 [M+H]⁺.

Example 2: Synthesis of Benzyl ((1-(1-((1s,4s)-4-isopropylcyclohexyl)piperidin-4-yl)-1H-indol-2-yl)methyl)carbamate (17) and (1-(1-((s, 4s)-4-isopropylcyclohexyl)piperidin-4-yl)-1H-indol-2-yl)methanamine (3)

SCHEME II depicts this synthesis.

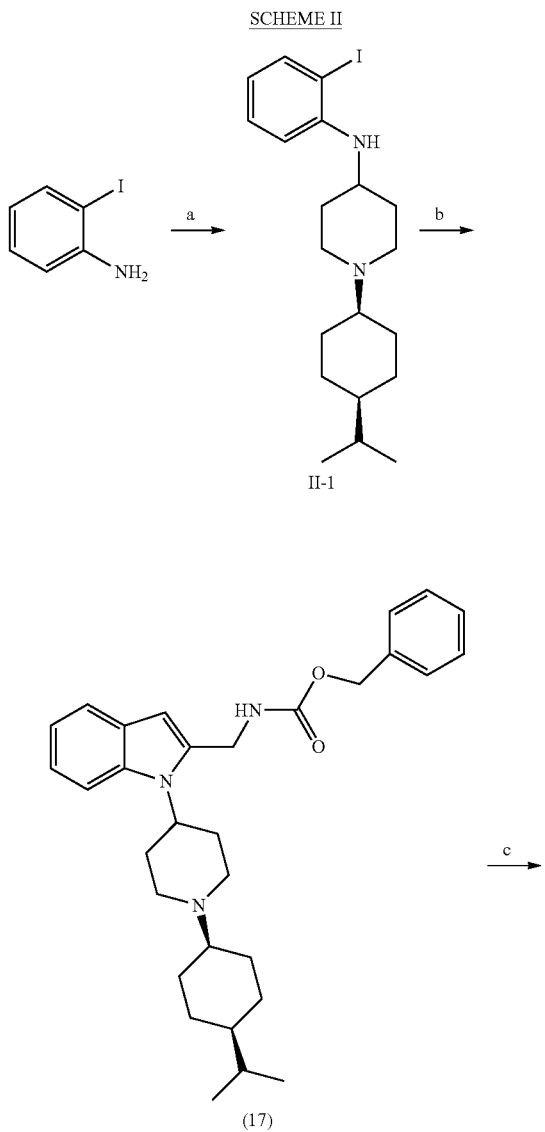

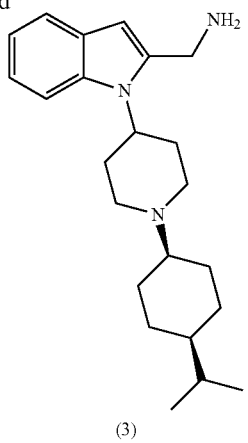

(3)

Scheme II Reagents and Conditions: a) i. N-Boc piperidone, AcOH, STAB, MgSO₄, DCE, rt (General Procedure A); ii. TFA, CH₂Cl₂, iii. 4-isopropyl-cyclohexanone, STAB, AcOH, DCE (General Procedure B, 2 steps); b) i. benzyl prop-2-yn-1-ylcarbamate. cat. PdCl₂(PPh₃)₂, catalyst copper(I)iodide (CuI), DMF:iso-Pr₂NEt (3:1), ii. cat. Cu(OAc)₂, PhMe, reflux (General Procedure C, 2 steps); and c) H₂ balloon, cat. 10% Pd/c, NH₃/MeOH.

syn-N-(2-iodophenyl)-1-(4-isopropylcyclohexyl) piperidin-4-amine (II-1)

i. See General Procedure A. 2-iodoaniline (15.0 g, 63.3 mmol, 1.00 equiv), N-Boc-piperidone (18.5 g, 95.0 mmol, 1.50 equiv), glacial AcOH (8.40 mL, 146 mmol, 2.30 equiv), STAB (30.9 g, 146 mmol, 2.30 equiv), DCE (250 mL, 0.25M). MgSO₄ was not used in the reaction. The product was purified via flash chromatography using 5:95 EtOAc: hexanes to provide the desired bicyclic compound as a white solid (75% yield), and was used directly in the following reaction. $R_f$=0.15 (5:95 EtOAc:Hexanes, UV).

ii. See General Procedure B: Step 1. N-Boc piperidine (43.5 g, 0.108 mol, 1.00 equiv), TFA (200 mL, 2.61 mol, 24.0 equiv), CH₂Cl₂ (300 mL, 0.36M). Obtained the N—H piperidine intermediate as a light-tan solid (42.0 g, 128% yield, due to NaTFA), and was used directly in the next step.

See General Procedure B: Step 2. N—H piperidine (0.108 mol, 1.00 equiv), 4-iPr-cyclohexanone (22.7 g, 0.162 mol, 1.50 equiv), glacial AcOH (14.2 mL, 0.248 mol, 2.30 equiv), STAB (52.6 g, 0.248 mol, 2.30 equiv), DCE (1.54 L, 0.070M). Compound II-1 was purified via flash chromatography using 6:94:1.5→9:91:1.5 EtOAc:hexanes:NH₄OH (aq.) to provide a gold oil. (The syn diastereomer has a higher $R_F$ compared to the anti diastereomer). The purified oil was dissolved in EtOAc and transferred to an Erlenmeyer flask, and then 10% HCl (aq.) was added. Upon addition of the 10% HCl (aq.), a white precipitate formed, and the suspension was stirred for 10 minutes. The white precipitate was then filtered, washed 2× with EtOAc, and then air dried over 1 hour. The white precipitate was then suspended in EtOAc in an erlenmeyer flask, and then saturated NaHCO₃ (aq.) was added until basic, and then stirred overnight. At this stage, the mixture was now a clear biphasic solution. The layers were separated, and the EtOAc layer was washed with brine, dried with MgSO₄, filtered, and concentrated in vacuo to provide iodoaniline II-1 as a light gold oil (24.0 g, 39% yield over 3 steps). $R_f$=0.30 (10:90:3 drops EtOAc:hexanes:NH₄OH (aq.), UV); ¹H NMR (CDCl₃, 300 MHz) δ 7.65 (dd, J=5.7, 0.9, 1H), 7.184 (t, J=6.0, 1H), 6.58 (d, J=6.0, 1H), 6.41 (dt, J=5.7, 0.9, 1H), 4.12 (d, J=5.7 Hz, 1H), 3.36 (m, 1H), 2.93 (m, 2H), 2.25 (m, 3H), 2.15 (d, J=8.4 Hz, 2H), 1.47-1.74 (m, 8H), 1.38 (m, 2H), 1.13 (m, 1H), 0.89 (d, J=4.8 Hz, 6H); MS(ESI) m/z: 427 [M+H]⁺.

General Procedure C: Sonogashira Coupling and Cyclization:

Step 1. Iodoaniline (1.00 equiv) and terminal alkyne (3.00-5.00 equiv) were dissolved in DMF and iPr₂NEt (3:1, 0.40 M). PdCl₂(PPh₃)₂ (0.0400 equiv) and CuI (0.100 equiv) were added simultaneously to the reaction mixture. An argon balloon with a 3-way adapter was placed on top of the reaction vessel, and the vessel was purged, and then backfilled with argon (repeated 3× total). The reaction was covered with aluminum foil, and allowed to stir overnight at ambient temperature. The reaction was monitored by TLC (EtOAc:hexanes:NH₄OH (aq.)). Once complete, the reaction was diluted with EtOAc and H₂O and stirred for 10 minutes. The biphasic layers were separated, and the organic layer was washed 2× with H₂O, brine, dried with MgSO₄, filtered, and concentrated in vacuo. The resulting crude material was purified via flash chromatography, then used without further processing directly in the following reaction.

Step 2. The internal alkyne from Step 1 (1.00 equiv) was charged into a round-bottom flask. Cu(OAc)₂ (0.200-0.400 equiv) was added, followed by PhMe (0.25M). The reaction was fitted with a reflux condenser, followed by an Ar balloon on top of the condenser. The reaction was then heated to reflux and monitored by TLC (30:70:3 drops EtOAc:hexanes:NH₄OH (aq.)). After 1-2 hours, TLC showed the reaction was complete. The reaction was allowed to cool to room temperature, EtOAc and H₂O were added, and the mixture was stirred for 30 minutes. The mixture was filtered through a pad of Celite, and the Celite pad was washed 3-4× with EtOAc. The layers were separated, and the organic layer was washed 1× with H₂O. The water layers were combined, and extracted 1× with EtOAc. The organic layers were combined, washed with brine, dried with MgSO₄, filtered, and concentrated in vacuo to provide a crude solid. This solid was adsorbed onto silica gel, loaded onto a column, and purified by flash chromatography to provide pure indole intermediate.

syn-benzyl((1-(1-(4-isopropylcyclohexyl)piperidin-4-yl)-1H-indol-2-yl)methyl)carbamate (17)

i. See General Procedure C: Step 1. Iodoaniline II-1 (5.60 g, 13.1 mmol, 1.00 equiv), N-benzyl prop-2-yn-1ylcarbamate (8.69 g, 45.9 mmol, 3.50 equiv), DMF (25.0 mL) and iPr₂NEt (8.25 mL), PdCl₂(PPh₃)₂ (368 mg, 0.524 mmol, 0.0400 equiv), and CuI (250 mg, 1.31 mmol, 0.100 equiv). Crude product was purified by flash chromatography using 20:80:1.5 to 5:75:1.5 EtOAc:Hexanes:NH₄OH (aq.) to provide the desired internal alkyne as a light-yellow solid (6.26 g, 98% yield), which was used directly in the next reaction. $R_f$=0.25 (25:75:3 drops EtOAc:Hexanes:NH₄OH (aq.), UV).

See General Procedure C: Step 2. Internal alkyne (6.26 g, 12.8 mmol, 1.00 equiv), Cu(OAc)₂ (700 mg, 3.85 mmol, 0.300 equiv), and PhMe (51.0 mL, 0.25M). Crude solid was purified by flash chromatography using 15:85:1.5 to 20:80:1.5 to 30:70:1.5 EtOAc:hexanes:NH₄OH (aq.) to provide a light-yellow solid. The solid was triturated with a minimal amount of 1:1 EtOAc:hexanes to provide indole 3 as a white solid (64% yield over 2 steps). $R_f$=0.30 (25:75:3 drops EtOAc:Hexanes:NH₄OH (aq.), UV); ¹H NMR (CDCl₃, 300 MHz) δ 7.65 (d, J=8.1 Hz, 1H), 7.55 (d, J=7.8 Hz, 1H), 7.32 (m, 5H), 7.16 (t, J=8.1 Hz, 1H), 7.17 (t, J=7.8 Hz, 1H), 6.38 (s, 1H), 5.17 (s, 2H), 4.90 (br, 1H), 4.59 (d, J=5.7 Hz, 2H), 4.15 (m, 1H), 3.10 (d, J=10.2 Hz, 2H), 2.57 (dq, J=12.6, 3.3 Hz, 2H), 2.31 (m, 1H), 2.10 (t, J=12.6 Hz, 2H), 1.35-1.80 (m, 11H), 1.17 (m, 1H), 0.93 (d, J=6.9 Hz, 6H); MS(ESI) m/z: 488.4 [M+H]⁺.

syn-(1-(1-(4-isopropylcyclohexyl)piperidin-4-yl)-1H-indol-2-yl)methanamine (3)

Indole 17 (2.83 g, 5.80 mmol, 1.00 equiv.) and 10% Pd/C (425 mg, 15% w/w) were suspended in a 7N NH₃ in MeOH mixture. The reaction vessel was fitted with a H₂ balloon, and the atmosphere was purged and backfilled with H₂, and then repeated (3× total). Over the next 2-3 hours, indole 17 slowly dissolved, and the reaction was monitored by TLC (100:3 drops EtOAc:NH₄OH (aq.) After a total of 4 hours, the reaction was complete. The reaction mixture was filtered over a pad of Celite and washed thoroughly with MeOH. The filtrate was concentrated in vacuo, and the crude material was purified via flash chromatography using 0:100:1.5 to 2:98:1.5 MeOH:EtOAc:NH₄OH (aq.) to provide diamine 3 as a white solid (2.00 g, 98% yield). $R_f$=0.35 (5:95:3 drops MeOH:EtOAc:NH₄OH (aq.), UV); ¹H NMR (300 MHz, CDCl₃) δ 7.64 (d, J=6.3 Hz, 1H), 7.56 (d, J=5.4 Hz, 1H), 7.14 (dt, J=5.4, 0.9 Hz, 1H), 7.06 (dt, J=5.4, 0.9 Hz, 1H), 6.38 (s, 1H), 4.25 (m, 1H), 4.04 (s, 2H), 3.20 (d, J=9.0 Hz, 2H), 2.61 (dq, J=7.2, 1.8 Hz, 2H), 2.36 (m, 1H), 2.24, (t, J=8.4 Hz, 2H), 1.87 (dd, J=9.3, 1.5 Hz, 2H), 1.50-1.80 (m, 8H), 1.42 (m, 2H), 1.16 (m, 1H), 0.92 (d, J=4.8 Hz, 6H); MS(ESI) m/z: 354.5 [M+H]⁺.

Example 3: Synthesis of (1-(1-((1s,4s)-4-isopropyl-cyclohexyl)piperidin-4-yl)-1H-indol-2-yl)methanol (30) and (E)-1-(1-((1s,4s)-4-isopropylcyclohexyl)piperidin-4-yl)-1H-indole-2-carbaldehyde oxime (1)

SCHEME III depicts this synthesis.

SCHEME III

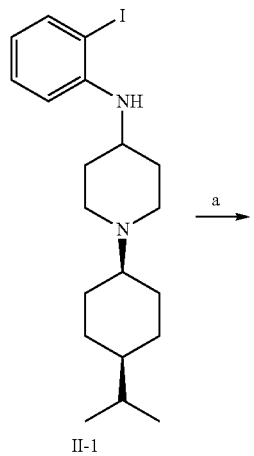

II-1

-continued

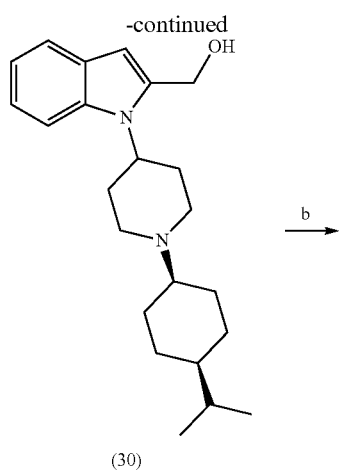

(30)

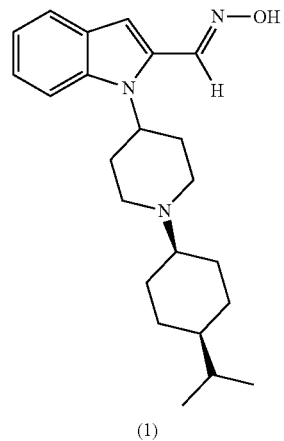

(1)

Scheme III Reagents and Conditions: a) i. terminal alkyne, cat. PdCl₂(PPh₃)₂, cat. CuI, DMF:iPr₂NEt (3:1), ii. cat. Cu(OAc)₂, PhMe, reflux (General Procedure C, 2 steps); and b) i. MnO₂, CH₂Cl₂, ii. NH₂OH•HCl, NaOAc•3H₂O, EtOH:H₂O (2:1), 110° C.

syn-(1-(1-(-4-isopropylcyclohexyl)piperidin-4-yl)-1H-indol-2-yl)methanol (30)

See General Procedure C: Step i. Iodoaniline II-1 (3.97 g, 9.30 mmol, 1.00 equiv), propargyl alcohol (2.61 g, 46.5 mmol, 5.00 equiv.), DMF (17.2 mL) and iPr₂NEt (5.8 mL), PdCl₂(PPh₃)₂ (261 mg, 0.372 mmol, 0.0400 equiv), and CuI (177 mg, 0.930 mmol, 0.100 equiv). Crude product was purified by flash chromatography using 40:60:1.5 to 50:50:1.5 EtOAc:hexanes:NH₄OH (aq.) to provide the desired internal alkyne as a dark-red glue (2.86 g, 87% yield), which was used directly in the next reaction.

See General Procedure C: Step 2. Internal alkyne (2.86 g, 8.07 mmol, 1.00 equiv), Cu(OAc)₂ (440 mg, 2.42 mmol, 0.300 equiv.), and PhMe (32.3 mL, 0.25M). This material (adsorbed onto silica gel) was loaded onto a column and purified by flash chromatography using 25:75:1.5 to 35:65:1.5 EtOAc:hexanes:NH₄OH (aq.) to provide a light-yellow solid. The solid was triturated with a minimal amount of 1:1 EtOAc:hexanes to provide indole 30 as a white solid (1.82 g, 56% yield over 2 steps). $R_f$=0.25 (25:75:3 drops EtOAc:

Hexanes:NH₄OH (aq.), UV); ¹H NMR (400 MHz, CDCl₃) δ 7.69 (d, J=8.0 Hz, 1H), 7.58 (d, J=8.0 Hz, 1H), 7.18 (t, J=7.6 Hz, 1H), 7.08 (t, J=7.6 Hz, 1H), 6.44 (s, 1H), 4.81 (d, J=4.8 Hz, 2H), 4.37 (m, 1H), 3.19 (d, J=11.6 Hz, 2H), 2.61 (dq, J=12.4, 3.2 Hz, 2H), 2.37 (m, 1H), 2.26 (t, J=11.6 Hz, 2H), 1.89 (d, J=12.0 Hz, 2H), 1.70 (m, 5H), 1.55 (m, 2H), 1.40 (m, 2H), 1.16 (m, 1H), 0.92 (d, J=6.8 Hz, 6H); MS(ESI) m/z: 355.27 [M+H]⁺.

syn-1-(1-(4-isopropylcyclohexyl)piperidin-4-yl)-1H-indole-2-carbaldehyde oxime (1)

i. To a solution of indole 30 (1.30 g, 3.67 mmol, 1.00 equiv) in 36.7 mL of CH₂Cl₂, was added MnO₂ (3.83 g, 44.0 mmol, 12.0 equiv) at room temperature, and the reaction was allowed to stir overnight. At this stage, TLC (30:70:1.5 EtOAc:hexanes:NH₄OH (aq.)) showed the reaction was complete. The reaction was filtered over a pad of Celite, washed 3× with CH₂Cl₂, and the filtrate was concentrated in vacuo to provide an aldehyde as a glue (1.27 g, 98%). This compound was used directly in the next procedure.

ii. The latter aldehyde (1.26 g, 3.57 mmol, 1.00 equiv.), NH₂OH—HCl (372 mg, 5.36 mmol, 1.50 equiv), and NaOAc-3H₂O (730 mg, 5.36 mmol, 1.50 equiv.) were all charged into a round bottom flask. EtOH (12.0 mL) and H₂O (6.00 mL) were then added, and a reflux condenser with an Ar balloon on top was attached to the reaction, and the reaction (a white suspension) was then heated to 110° C. At ca. 50 OC, the reaction becomes a light-yellow solution, and at ca. 70-80° C., a white precipitate begins to form. At 110 OC, the reaction is now a thick white slurry, and after 10 minutes, TLC (20:80:3 drops EtOAc:hexanes:NH₄OH (aq.)) showed the reaction was complete. The reaction was allowed to cool to room temperature, CH₂Cl₂ and saturated NaHCO₃ (aq.) was added, and the mixture stirred 20 minutes to provide a clear biphasic mixture. The layers were separated, and the aqueous layer was extracted 1× with CH₂Cl₂. The organic layers were combined, washed 2× with H₂O, brine, dried with MgSO₄, filtered, and concentrated in vacuo to provide to provide a white foam. To this foam was added 2 mL of EtOAc, followed by 10 mL of MeOH, and the suspension was stirred for 10 minutes. The solid was then filtered, and washed 3× with cold MeOH, and dried in vacuo to provide oxime 1 as a white solid (1.10 g, 84% yield). R_f=0.25 (20:80:3 drops EtOAc:Hexanes:NH₄OH (aq.), UV); ¹H NMR (CDCl₃, 300 MHz) δ 10.7 (br, 1H), 8.70 (s, 1H), 7.59 (m, 2H), 7.18 (t, J=5.7 Hz, 1H), 7.07 (t, J=5.7 Hz, 1H), 6.83 (s, 1H), 4.89 (m, 1H), 3.24 (d, J=8.4 Hz, 2H), 2.65 (dq, J=9.6, 2.1 Hz, 2H), 2.45 (m, 1H), 2.31 (t, J=8.7 Hz, 2H), 1.56-1.93 (m, 9H), 1.43 (m, 2H), 1.19 (m, 1H), 0.94 (d, J=4.8 Hz, 6H); MS(ESI) m/z: 368.32 [M+H]⁺.

Example 4: Synthesis of 2-(1-(1-((1s,4s)-4-isopropylcyclohexyl)piperidin-4-yl)-1H-indol-2-yl)ethan-1-ol (32) and 2-(1-(1-((1s,4s)-4-isopropylcyclohexyl)piperidin-4-yl)-1H-indol-2-yl)ethyl Sulfamate (11)

SCHEME IV depicts this synthesis.

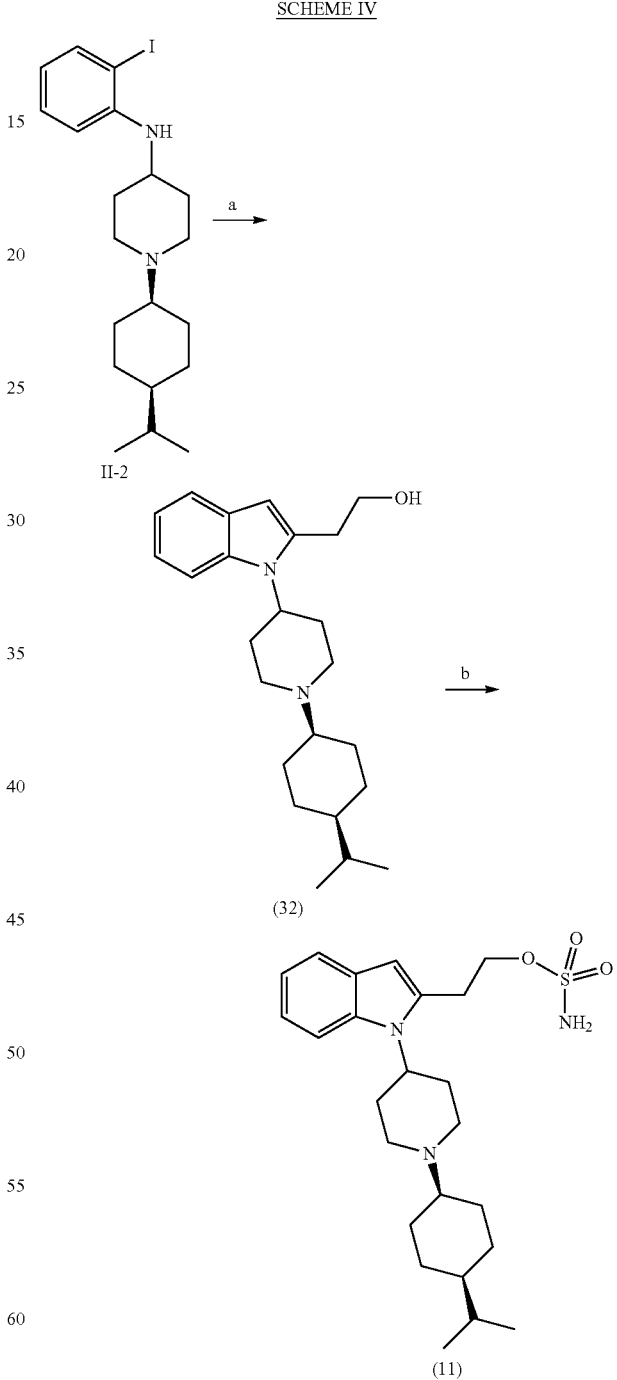

Scheme IV Reagents and Conditions: a) i. terminal alkyne, cat. PdCl₂(PPh₃)₂, cat. CuI, DMF:iso-Pr₂NEt (3:1), ii. cat. Cu(OAc)₂, PhMe, reflux (General Procedure C, 2 steps), iii. TBAF, THF, and b) ClSO₂NH₂, CH₂Cl₂.

syn-2-(1-(1-(4-isopropylcyclohexyl)piperidin-4-yl)-1H-indol-2-yl)ethan-1-ol (32)

i. See General Procedure C: Step 1. Iodoaniline II-1 (1.60 g, 3.75 mmol, 1.00 equiv), (but-3-yn-1-yloxy)(tert-butyl)dimethylsilane (2.41 g, 13.1 mmol, 3.50 equiv), DMF (11.3 mL) and iPr$_2$NEt (3.80 mL), and PdCl$_2$(PPh$_3$)$_2$ (105 mg, 0.150 mmol, 0.0400 equiv) and CuI (71.4 mg, 0.375 mmol, 0.100 equiv). The crude oil was purified via flash chromatography using 7:93:1.5 to 10:90:1.5 EtOAc:hexanes:NH$_4$OH (aq.) to provide the desired internal alkyne as a brown oil (1.60 g, 88% yield), and it was used directly in following reaction.

See General Procedure C: Step 2. Internal alkyne (1.60 g, 3.31 mmol, 1.00 equiv), Cu(OAc)$_2$ (601 mg, 3.31 mmol, 1.00 equiv), and PhMe (13.3 mL, 0.25M). Reaction time was 4 hours. The crude material was purified by flash chromatography using 2:98:1.5 to 6:94.15 to provide the desired indole as a light-yellow oil (1.00 g, 63% yield), and was used directly in the following reaction.

ii. To a solution of the previously synthesized indole (1.10 g, 2.28 mmol, 1.00 equiv) in 15.0 mL of THF was added TBAF (1.0 M, 4.55 mL, 2.00 equiv) at room temperature, and the was stirred and monitored by TLC (20:80:3 drops EtOAc:hexanes:NH$_4$OH (aq.)). Once the reaction was complete (ca. 2 hours), the reaction was concentrated in vacuo, and the crude material was flashed using 25:75:1.5 to 50:50:1.5 EtOAc:hexanes:NH$_4$OH (aq.) to provide alcohol 32 as a white solid (792 mg, 94% yield). R$_f$=0.25 (30:70:3 drops EtOAc:Hexanes:NH$_4$OH (aq.), UV); $^1$H NMR (CDCl$_3$, 300 MHz) δ 7.65 (d, J=9.0 Hz, 1H), 7.55 (d, J=9.0 Hz, 1H), 7.13 (t, J=5.4 Hz, 1H), 7.07 (t, J=5.4 Hz, 1H), 6.33 (s, 1H), 4.14 (m, 1H), 3.94 (t, J=4.8 Hz, 2H), 3.20 (d, J=8.7 Hz, 2H), 3.09 (t, J=4.8 Hz, 2H), 2.64 (q, J=7.5 Hz, 2H), 2.36 (m, 1H), 2.22 (t, J=8.7 Hz, 2H), 1.51-1.87 (m, 9H), 1.42 (m, 2H), 1.27 (m, 1H), 0.92 (d, J=4.8 Hz, 6H); MS(ESI) m/z: 369.27 [M+H]$^+$.

syn-2-(1-(1-(4-isopropylcyclohexyl)piperidin-4-yl)-1H-indol-2-yl)ethyl Sulfamate (11)

To a solution of alcohol 32 (200 mg, 0.543 mmol, 1.00 equiv) and iPr$_2$NEt (0.946 mL, 5.43 mmol, 10.0 equiv) in 5.00 mL of CH$_2$Cl$_2$, at 0° C., was added a solution (ca. 0.50 M in CH$_2$Cl$_2$) of sulfamoyl chloride (7.00 mL, 3.26 mmol, 6.00 equiv) dropwise to the reaction. The ice bath was removed, and the reaction was stirred for 1 hour. At this time, TLC (40:60:3 drops EtOAc:hexanes:NH$_4$OH (aq.) showed the reaction was complete. The reaction was diluted with EtOAc, followed by the addition of 10% NaHCO$_3$ (aq.). A white precipitate formed, which was filtered and washed with EtOAc. The filtrate layers were separated, and the EtOAc layer was washed 2× with H$_2$O, brine, dried with MgSO$_4$, filtered, and concentrated in vacuo. The crude material was flashed in 40:60:1.5 EtOAc:hexanes:NH$_4$OH (aq.) to provide sulfamate 11 as a white solid (35 mg, 14% yield). R$_f$=0.25 (40:60:3 drops EtOAc:hexanes:NH$_4$OH (aq.), UV); $^1$H NMR (300 MHz, CDCl$_3$) δ 7.64 (d, J=6.3 Hz, 1H), 7.54 (d, J=5.7 Hz, 1H), 7.15 (t, J=5.7 Hz, 1H), 7.07 (t, J=5.7 Hz, 1H), 6.34 (s, 1H), 4.50 (t, J=5.1 Hz, 2H), 4.13 (m, 1H), 3.28 (t, J=5.1 Hz, 2H), 3.22 (d, J=8.4 Hz, 2H), 2.64 (m, 2H), 2.40 (m, 1H), 2.27 (t, J=8.4 Hz, 2H), 1.84 (d, J=8.4 Hz, 2H), 1.76 (m, 2H), 1.55-1.70 (m, 3H), 1.41 (m, 2H), 1.26 (m, 2H), 1.17 (m, 1H), 0.92 (d, J=5.1 Hz, 6H); MS(ESI) m/z: 448.3 [M+H]$^+$.

Example 5: Synthesis of (5-fluoro-1-(1-((1s,4s)-4-isopropylcyclohexyl)piperidin-4-yl)-1H-indol-2-yl)methanol (29)

SCHEME V depicts this synthesis.

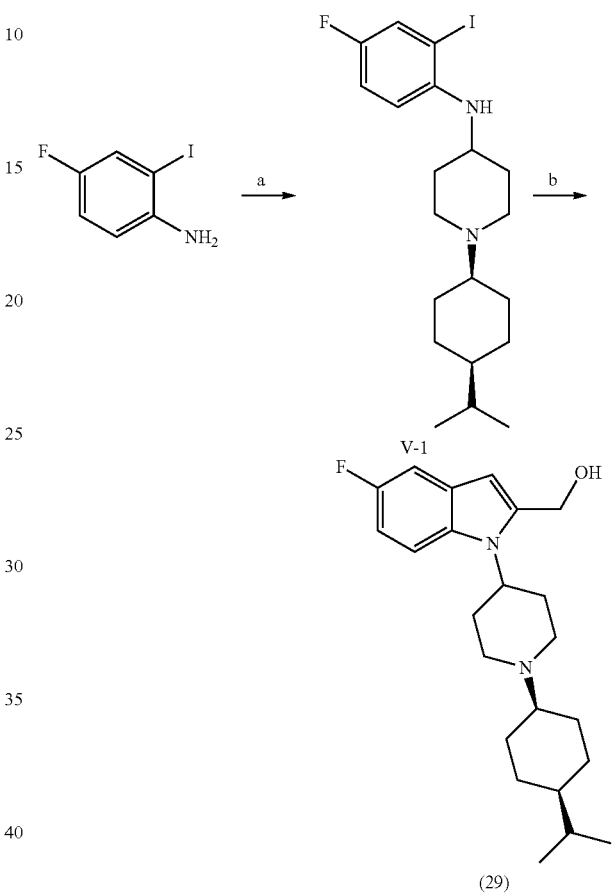

(29)

Scheme V Reagents and Conditions: a) i. N-Boc piperidone, AcOH, STAB, MgSO$_4$, DCE, rt (General Procedure A), ii. TFA, CH$_2$Cl$_2$, iii. 4-iso-Pr-cyclohexanone, STAB, AcOH, DCE (General Procedure B, 2 steps); and b) i. terminal alkyne, cat. PdCl$_2$(PPh$_3$)$_2$, cat. CuI, DMF:iso-Pr$_2$NEt (3:1), ii. cat. Cu(OAc)$_2$, PhMe, reflux (General Procedure C, 2 steps).

syn-N-(4-fluoro-2-iodophenyl)-1-(4-isopropylcyclohexyl)piperidin-4-amine (V-1)

i. See General Procedure A. 4-fluoro-2-iodoaniline (3.80 g, 16.0 mmol, 1.00 equiv), N-Boc piperidone (4.69 g, 24.0 mmol, 1.50 equiv), MgSO$_4$ (3.80 g, 100 wt %), glacial AcOH (2.11 mL, 36.8 mmol, 2.30 equiv), STAB (7.80 g, 36.8 mmol, 2.30 equiv), and DCE (80.0 mL, 0.20M). The crude material was purified via flash chromatography using 12:88 EtOAc:hexanes to provide the desired bicyclic intermediate as a white solid (6.70 g, 99% yield), and was used directly in the next reaction.

ii. See General Procedure B: Step 1. N-boc piperidine intermediate (5.00 g, 11.9 mmol, 1.00 equiv), TFA (27.3 mL, 357 mmol, 30.0 equiv), CH$_2$Cl$_2$ (60.0 mL, 0.20M). An off-white solid was obtained from the workup (4.94 g, 130%, due to NaTFA) of the reaction described above, and this material was used directly in the next reaction.

See General Procedure B: Step 2. N—H piperidine intermediate (11.9 mmol, 1.00 equiv), 4-iPr-cyclohexanone (2.51 g, 17.9 mmol, 1.50 equiv), glacial AcOH (1.57 mL, 27.4 mmol, 2.30 equiv), MgSO$_4$ (3.81 g, 100 wt %), STAB (5.81 g, 27.4 mmol, 2.30 equiv), and DCE (150 mL, 0.080M). The crude material was purified via flash chromatography using 10:90:1.5 EtOAc:hexanes:NH$_4$OH (aq.) to provide intermediate V-1 as a dark orange-brown oil (55% yield over 3 steps). R$_f$=0.25 (20:80:3 drops EtOAc:Hexanes:NH$_4$OH (aq.), UV); $^1$H NMR (CDCl$_3$, 300 MHz) δ 7.41 (dd, J=6.0, 2.1 Hz, 1H), 6.95 (dt, J=6.0, 2.1 Hz, 1H), 6.51 (dd, J=6.9, 3.6 Hz, 1H), 3.91 (d, J=6.0 Hz, 1H), 3.28 (m, 1H), 2.92 (m, 2H), 2.24 (m, 3H), 2.04 (m, 2H), 1.47-1.73 (m, 8H), 1.38 (m, 2H), 1.13 (m, 1H), 0.88 (d, J=5.1 Hz, 6H); MS(ESI) m/z: 445.1 [M+H]$^+$.

syn-(5-fluoro-1-(1-(4-isopropylcyclohexyl)piperidin-4-yl)-1H-indol-2-yl)methanol (29)

i. See General Procedure C: Step 1. Intermediate V-1 (600 mg, 1.35 mmol, 1.00 equiv.), propargyl alcohol (378 mg, 6.75 mmol, 5.00 equiv.), DMF (3.12 mL) and iPr$_2$NEt (1.13 mL), and PdCl$_2$(PPh$_3$)$_2$ (38.0 mg, 0.0540 mmol, 0.0400 equiv.) and CuI (25.7 mg, 0.135 mmol, 0.100 equiv). The crude material was purified via flash chromatography using 40:60:1.5 EtOAc:hexanes:NH$_4$OH (aq.) to provide the desired internal alkyne as a brown-red oil (440 mg, 87%), which used directly in the next reaction.

See General Procedure C: Step 2. Internal alkyne (440 mg, 1.18 mmol, 1.00 equiv), Cu(OAc)$_2$ (64.4 mg, 0.354 mmol, 0.300 equiv), and PhMe (4.75 mL, 0.21M). The crude material was purified by flash chromatography using 25:75:1.5 EtOAc:hexanes:NH$_4$OH (aq.) to provide a light-yellow solid. This solid was triturated with EtOAc to provide indole 29 as a white solid (143 mg, 29% yield over 2 steps). R$_f$=0.20 (25:75:3 drops EtOAc:Hexanes:NH$_4$OH (aq.), UV); $^1$H NMR (300 MHz, CDCl$_3$) δ 7.58 (dd, J=9.0, 4.2 Hz, 1H), 7.20 (dd, J=9.3, 2.7 Hz, 1H), 6.92 (dt, J=9.3, 2.7 Hz, 1H), 6.38 (s, 1H), 4.78 (s, 2H), 4.35 (m, 1H), 3.19 (d, J=11.7 Hz, 2H), 2.55 (dq, J=12.6, 3.6 Hz, 2H), 2.35 (m, 2H), 2.26 (dt, J=11.7, 1.8 Hz, 2H), 1.88 (dd, J=12.0, 2.4 Hz, 2H), 1.48-1.79 (m, 9H), 1.40 (m, 2H), 1.15 (m, 1H), 0.91 (d, J=6.6 Hz, 6H); MS(ESI) m/z: 373.4 [M+H]$^+$.

Example 6: Synthesis of (1-(1-((1s,4s)-4-isopropyl-cyclohexyl)piperidin-4-yl)-1H-indole-2,3-diyl)dimethanol (51)

SCHEME VI depicts this synthesis.

SCHEME VI

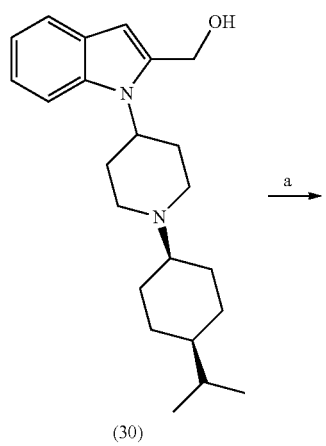

(30)

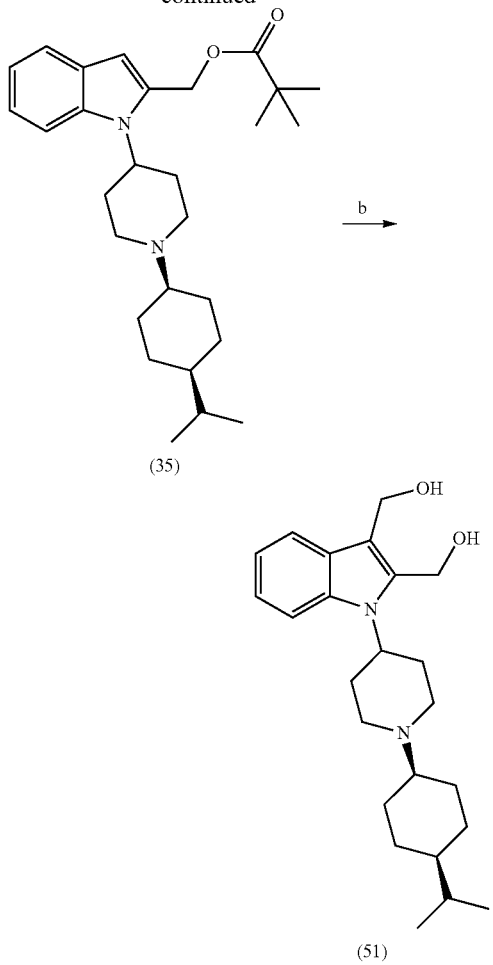

(35)

(51)

Scheme VI Reagents and Conditions: a) (t-BuCO)$_2$O, cat. DMAP, (isopropyl)$_2$NEt, CH$_2$Cl$_2$; and b) i. POCl$_3$, DMF, ii. NaBH$_4$, EtOH, iii. NaOH, cat. Bu$_4$NI, THF.

syn-(1-(1-(-4-isopropylcyclohexyl)piperidin-4-yl)-1H-indol-2-yl)methyl pivalate (35)

To a solution of alcohol 30 (7.29 g, 20.6 mmol, 1.00 equiv) in CH$_2$Cl$_2$ (138 mL, 0.15M), was added DMAP (503 mg, 4.12 mmol, 0.200 equiv) and iPr$_2$NEt (18.4 mL, 103 mmol, 5.00 equiv) at rt. Subsequently, (tBuCO)$_2$O (6.70 mL, 33.0, 1.60 equiv) was added, and the reaction was allowed to stir overnight. TLC (30:70:3 drops EtOAc:Hexanes:NH$_4$OH (aq.)) showed the reaction was complete. The reaction was concentrated in vacuo, and the crude oil was purified via flash chromatography using 5:95:1.5 EtOAc:Hexanes:NH$_4$OH (aq.) to provide 35 as a white solid (8.59 g, 95%). R$_f$=0.70 (30:70:3 drops EtOAc:Hexanes:NH$_4$OH (aq.), UV); $^1$H NMR (400 MHz, CDCl$_3$) δ 7.73 (d, J=8.4 Hz, 1H), 7.60 (d, J=8.0 Hz, 1H), 7.20 (t, J=7.2 Hz, 1H), 7.09 (t, J=7.2 Hz, 1H), 6.56 (s, 1H), 5.25 (s, 2H), 4.17 (m, 1H), 3.31 (d, J=12.0 Hz, 2H), 2.78 (q, J=12.0 Hz, 2H), 2.55 (q, J=6.4 Hz, 1H), 2.32 (t, J=11.6 Hz, 2H), 1.90 (d, J=12.4 Hz, 2H), 1.80 (m, 2H), 1.64 (m, 5H), 1.43 (m, 2H), 1.22 (s, 9H), 1.20 (m, 1H), 0.92 (d, J=6.4 Hz, 6H); MS(ESI) m/z: 439.3 [M+H]$^+$.

261 syn-(1-(1-(-4-isopropylcyclohexyl)piperidin-4-yl)-1H-indole-2,3-diyl)dimethanol (51)

i. POCl$_3$ (9.43 mL, 103 mmol, 5.00 equiv) was added to DMF (83.0 mL) at 0° C., and the mixture turned light yellow. Indole 35 (9.00 g, 20.6 mmol, 1.00 equiv) was separately dissolved in 20 mL of DMF with the aid of heat, and then allowed to cool back to RT. After the POCl$_3$ solution stirred for 15 minutes at 0° C., the solution of indole 35 was added slowly, forming a red solution. After the addition was complete, the reaction stirred for 40 minutes at 0° C. TLC (20:80:3 drops EtOAc:Hexanes:NH$_4$OH (aq.)) showed the reaction was complete. The reaction was poured into an ice:NaHCO$_3$ (sat'd, aq.) slurry, and then EtOAc was added. The mixture stirred vigorously until the mixture warmed to rt, and NaHCO$_3$ (sat'd, aq.) was added to ensure a basic pH. The layers were separated, and the aqueous layer was extracted 1× with EtOAc. The EtOAc layers were combined, washed 3× with water, brine, dried with MgSO$_4$, filtered and concentrated in vacuo to provide the aldehyde as a light-yellow solid (9.55 g, 99%), which was used directly in the next step.

ii. The aldehyde (9.55 g, 20.5 mmol, 1.00 equiv) was suspended in absolute EtOH (100.mL, 0.20M), and NaBH$_4$ (1.55 g, 41.0 mmol, 2.00 equiv) was added in several portions at rt. NOTE: may need to add another 1.00 equiv of NaBH$_4$ and a small amount of CH$_2$Cl$_2$ to help solubilize the reaction mixture. The reaction was monitored by TLC (40:60:3 drops EtOAc:Hexanes:NH$_4$OH (aq.)), and once complete, the reaction was concentrated in vacuo to ca. 50% volume. EtOAc was added, followed by 50% NaHCO$_3$ (aq.), and the mixture stirred until bubbling ceased. The layers were separated, and the EtOAc layer was washed 2× with water, brine, dried with MgSO$_4$, filtered, and concentrated in vacuo to provide a foam (9.60 g, quantitative yield), which was taken directly on the next step.

iii. The alcohol (9.60 g, 20.5 mmol, 1.00 equiv) was dissolved in THF (130 mL, 0.16M), followed by the addition of Bu$_4$NI (1.51 g, 4.10 mmol, 0.20 equiv). Grounded NaOH powder (8.20 g, 205 mmol, 10.0 equiv) was added at RT, and the reaction stirred for ca. 90 minutes, and a thick white-fluffy precipitate formed. TLC (60:40:3 drops EtOAc:Hexanes:NH$_4$OH (aq.)) showed the reaction was complete. The reaction was diluted with EtOAc and water, and the layers were separated. The aqueous layer was extracted 2× with EtOAc, and the EtOAc layers were then combined, washed 2× with water, brine, dried with MgSO$_4$, filtered, and conc'd in vacuo. The crude material was purified via flash chromatography in 60:40:1.5 to 80:20:1.5 to 90:10:1.5 EtOAc:Hexanes:NH$_4$OH (aq.) to provide diol 51 as a white foam (4.70 g, 60%). R$_f$=0.20 (80:20:3 drops EtOAc:Hexanes:NH$_4$OH (aq.), UV); $^1$H NMR (400 MHz, CDCl$_3$) δ 7.67 (d, J=8.4 Hz, 2H), 7.20 (t, J=8.4 Hz, 1H), 7.13 (t, J=8.0 Hz, 1H), 4.86 (s, 2H), 4.83 (s, 2H), 4.38 (m, 1H), 3.17 (d, J=11.6 Hz, 2H), 2.59 (q, J=12.0 Hz, 2H), 2.37 (m, 1H), 2.25 (t, J=11.0 Hz, 2H), 1.52-1.89 (m, 9H), 1.43 (m, 2H), 1.18 (m, 1H), 0.92 (d, J=6.4 Hz, 6H); MS(ESI) m/z: 385.4 [M+H]$^+$.

262

Example 7: Synthesis of (E, Z)-3-(hydroximino)-1-(1-((1s,4s)-4-isopropylcyclohexyl)piperidin-4-yl)indolin-2-one (228)

SCHEME VII depicts this synthesis.

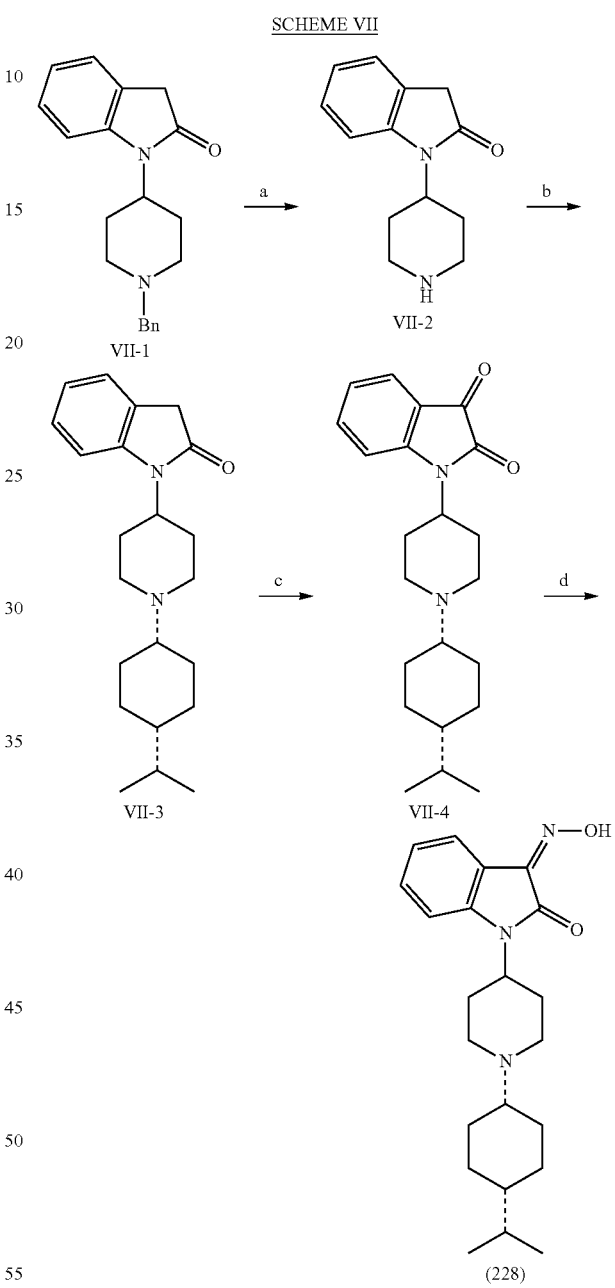

Scheme VII Reagents and Conditions: a) HCO$_2$NH$_4$, Pd/C, 10%, MeOH, 2 h, 45° C.; b) 4-isopropylcyclohexanone, HOAc, MgSO$_4$, NaBH(OAc)$_3$, DCE, 48 h, rt; c) ceric ammonium nitrate (CAN), MeCN/H$_2$O, 2 h, rt; d) NH$_2$OH•HCl, NaOAc, EtOH/H$_2$O, 20 h, rt.

1-(piperidin-4-yl)-2,3-dihydro-1H-indol-2-one (VII-2)

To an ice-chilled solution of 1-(1-benzylpiperidin-4-yl)-2,3-dihydro-1H-indol-2-one VII-1 (prepared using a procedure adopted from Forbes (2001) Tetrahedron Letters 2:6943-6945) (25.7 g, 82.6 mmol, 1.00 equiv) in 600 mL MeOH was added ammonium formate (46.9 g, 743 mmol, 9.00 equiv), followed by an ice-chilled slurry of Pd/C, 10% (5.14 g) in 226 mL MeOH. The reaction was outfitted with a reflux condenser, and heated to 45° C. for 2.5 h. The solution was filtered through a pad of Celite and concentrated. Trituration with $CH_2Cl_2$/MeOH 90/10 (500 mL total), followed by flash chromatography using $CH_2Cl_2$/MeOH/ $NH_4OH$ 100/0/0 to 79/20/1 as the eluent afforded 15.94 g of the title material in 89% yield, and matched reported values (WO 2002/085357, Sun et al).

1-(1-((1s,4s)-4-isopropylcyclohexyl)piperidin-4-yl) indoline-2,3-dione (VII-4)

To a stirred solution of 1-(1-((1s,4s)-4-isopropylcyclohexyl)piperidin-4-yl)indolin-2-one (VII-3) (prepared from intermediate VII-2 according to Zaveri et al (2004) Journal of Medicinal Chemistry 47:2973-2976) (3.43 g, 10.1 mmol, 1.00 equiv) in 336 mL MeCN was added CAN (22.1 g, 40.3 mmol, 4.00 equiv) in 17.0 mL $H_2O$, and the reaction was stirred at room temperature for 1 h. The reaction was diluted with $CH_2Cl_2$ and satd. $NaHCO_3$ (aq). The layers were separated, and the aqueous solution was extracted 2× with $CH_2Cl_2$. The combined organic layers were filtered through a pad of Celite, washed with satd. NaCl (aq), dried over $Na_2SO_4$, filtered and concentrated. The residue was purified by flash chromatography using $CH_2Cl_2$/MeOH 99/1 to 90/10 to afford 2.73 g of the title material in 76% yield. $^1$H NMR (300 MHz, $CDCl_3$) 7.62 (1H, d, J=5.1 Hz), 7.56 (1H, t, J=6 Hz), 7.20 (1H, d, J=6 Hz), 7.10 (1H, t, J=5.7 Hz), 4.19-4.22 (1H, m), 3.16 (2H, d, J=8.7 Hz), 2.30-2.40 (3H, m), 2.20 (2H, t, J=8.1 Hz), 1.60-1.79 (7H, m), 1.49-1.54 (2H, m), 1.36-1.43 (2H, m), 1.13-1.15 (1H, m), 0.90 (6H, d, J=5.1 Hz). MS(ESI) m/z 355.27 (M+H)$^+$.

(E, Z)-3-(hydroxyimino)-1-(1-((1s,4s)-4-isopropylcyclohexyl)piperidin-4-yl)indolin 2-one (228)

To a stirred solution of intermediate VII-4 (500 mg, 1.41 mmol, 1.00 equiv) in EtOH (17.6 mL) was added hydroxylamine HCl (147 mg, 2.12 mmol, 1.50 equiv), followed by NaOAc (231 mg, 2.82 mmol, 2.00 equiv). $H_2O$ (2.78 mL) was added to solubilize the reaction, and the reaction was stirred at room temperature for 20 h. The reaction was diluted with $CH_2Cl_2$ and satd. $NaHCO_3$ (aq). The layers were separated, and the aqueous solution was extracted 2× with $CH_2Cl_2$. The combined organic layers were washed 2× with $H_2O$, dried over $Na_2SO_4$, filtered and concentrated. The reaction was repeated on a 1.12 g scale, and the crude residue of the two runs was combined. The residue was purified by trituration using EtOAc/hexanes 1/1 to afford 1.54 g of the title material in 91% yield. $^1$H NMR (300 MHz, DMSO-$d_6$), 13.4 (1H, s), 8.00 (1H, d, J=9 Hz), 7.40 (1H, t, J=9 Hz), 7.18 (1H, d, J=6 Hz), 7.05 (1H, t, J=6 Hz), 4.00-4.02 (1H, m), 3.06 (2H, d, J=9 Hz), 2.24-2.36 (3H, m), 2.08 (2H, t, J=12 Hz), 1.52-1.69 (7H, m), 1.31-1.44 (4H, m), 1.06 (1H, s), 0.85 (6H, d, J=6 Hz). MS(ESI) m/z 370.3 (M+H)$^+$. Anal. Calcd. for $C_{22}H_{31}N_3O_2$. 1.00 HCl.0.4$H_2O$.0.1 $CH_2Cl_2$: C, 62.95; H, 7.89; N, 9.97. found: C, 62.61; H, 7.54; N, 9.73.

Example 8: Synthesis of 2-(1-(1-((1s,4s)-4-isopropylcyclohexyl)piperidin-4-yl)-2-oxoindolin-3-yl)-N-methoxyacetamide (247)

SCHEME VIII depicts this synthesis.

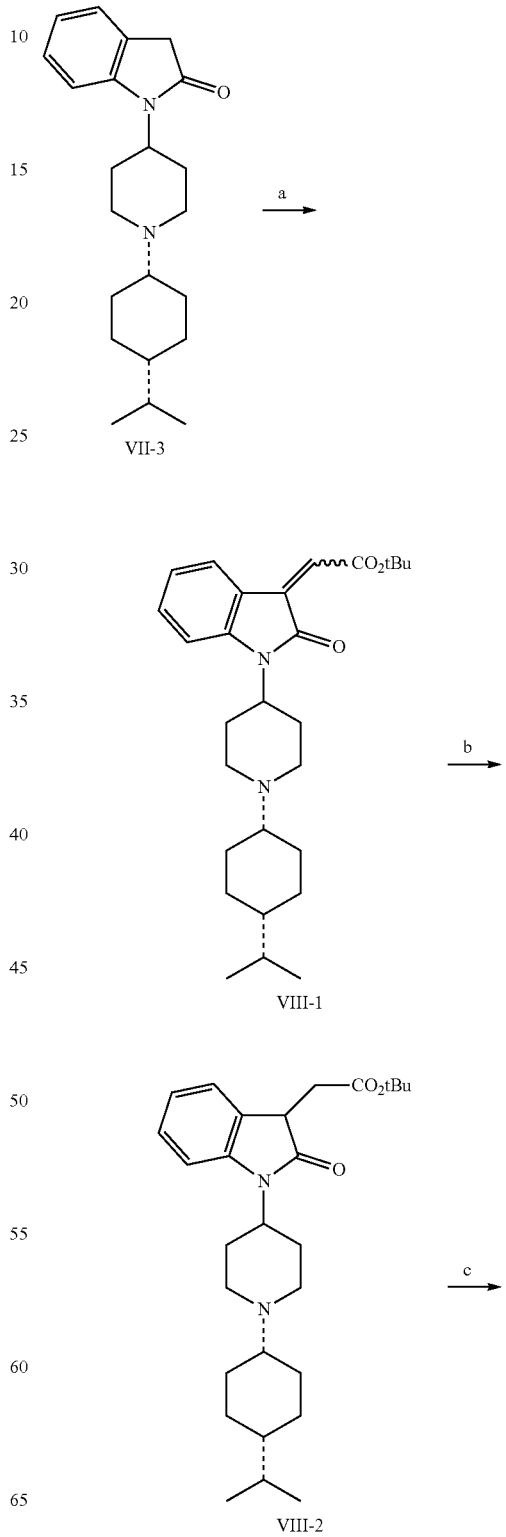

SCHEME VIII

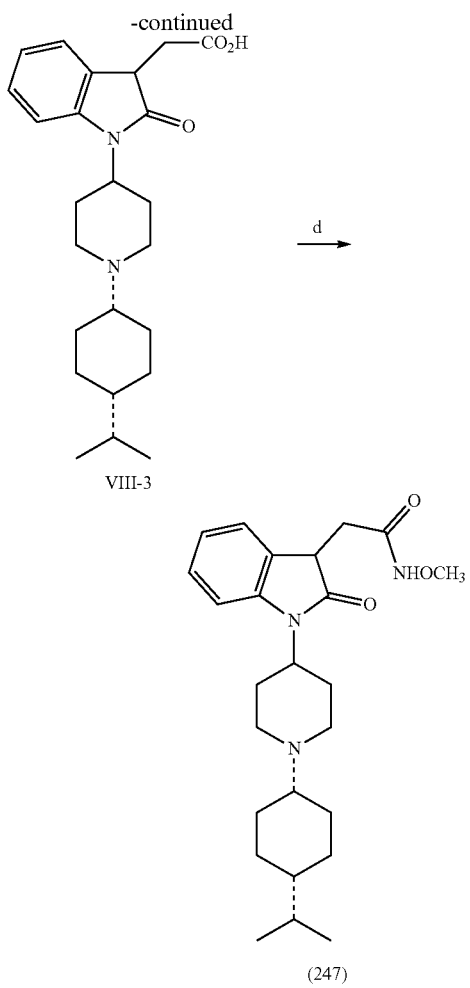

Scheme VIII Reagents and Conditions: a) tert-butyl glyoxalate/DMSO, K₂CO₃, THF, activated mol. sieves, 2 h, 80° C.; b) H₂(g), Pd/C, THF, 2 h, rt; c) TFA, CH₂Cl₂, 1.5 h, rt; d) NH₂OCH₃·HCl, T₃P, diisopropylethylamine, THF, 17 h, rt.

tert-butyl 2-(1-(1-((1 s,4s)-4-isopropylcyclohexyl) piperidin-4-yl)-2-oxoindolin-3-ylidene)acetate (VIII-1)

To a stirred solution of intermediate VII-3 (4.96 g, 14.6 mmol, 1.00 equiv) in THF (146 mL) was added tert-butyl glyoxalate, 34% solution in DMSO (prepared according to Yao et al., Tetrahedron, 2007, 63:10657-10670) (15.2 g, 117 mmol, 8.00 equiv), followed by K₂CO₃ (4.03 g, 29.1 mmol, 2.00 equiv) and activated molecular sieves (50 g). The reaction was outfitted with a reflux condenser and stirred at 80° C. for 2 h. The reaction was allowed to cool to room temperature, filtered, and then diluted with EtOAc, H₂O, and minimal NaCl (aq). The layers were separated, and the aqueous solution was extracted 2× with EtOAc. The combined organic layers were washed 2× with NaCl (aq), dried over Na₂SO₄, filtered and concentrated. The reaction was repeated on a 12.7 g scale, and the crude residue of the two runs was combined. The residue was purified by flash chromatography using hexanes/EtOAc/NH₄OH 85/15/0 to 35/64/1 to afford 16.9 g of the title material in 72% yield. ¹H NMR (400 MHz, CDCl₃) 8.53 (1H, d, J=8 Hz), 7.31 (1H, td, J=8, 4 Hz), 7.10 (1H, d, J=8 Hz), 7.02 (1H, t, J=8 Hz), 6.83 (1H, s), 4.21-4.26 (1H, m), 3.13 (2H, d, J=6 Hz), 2.29-2.45 (3H, m), 2.18 (2H, t, J=12 Hz), 1.59-1.71 (7H, m), 1.56 (9H, s), 1.34-1.52 (4H, m), 1.13 (1H, s), 0.89 (6H, d, J=8 Hz). MS(ESI) m/z 453.3 (M+H)⁺.

tert-butyl 2-(1-(1-((1 s,4s)-4-isopropylcyclohexyl) piperidin-4-yl)-2-oxoindolin-3-yl)acetate (VIII-2)

To a stirred solution of intermediate VIII-1 (3.05 g, 6.74 mmol, 1.00 equiv) in THF (67.0 mL) was added Pd/C, 10% (305 mg). The atmosphere of the reaction was evacuated and replaced with 1 atm H₂(g). The reaction was stirred at room temperature for 2 h, filtered through a pad of Celite, and concentrated. The reaction was repeated on 7.00 g and 6.80 g scales, and the crude residue of the three runs was combined. The residue was purified by flash chromatography using hexanes/EtOAc/NH₄OH 95/5/0 to 35/64/1 to afford 12.9 g of the title material in 76% yield. MS(ESI) m/z 455.4 (M+H)⁺. ¹H NMR (400 MHz, CDCl₃) 7.26 (1H, d, J=8 Hz), 7.22 (1H, d, J=8 Hz), 7.16 (1H, d, J=8 Hz), 7.00 (1H, t, J=8 Hz), 4.25-4.29 (1H, m), 3.73-3.76 (1H, m), 3.13 (2H, d, J=12 Hz), 2.97 (1H, dd, J=16, 8 Hz), 2.65 (1H, dd, J=16, 8 Hz), 2.28-2.45 (4H, m), 2.18 (2H, t, J=12 Hz), 1.48-1.72 (10H, m), 1.39 (9H, s), 1.12 (1H, s), 0.89 (6H, d, J=8 Hz).

2,2,2-trifluoroacetic acid compound with 2-(1-(1-((1s,4s)-4-isopropylcyclohexyl)piperidin-4-yl)-2-oxoindolin-3-yl)acetic acid (VIII-3)

To an ice-chilled solution of intermediate VIII-2 (12.9 g, 28.4 mmol, 1.00 equiv) in CH₂Cl₂ (284 mL) was added TFA (284 mL) portion wise. The reaction was allowed to warm to room temperature, and stirred for 1.5 h. The reaction was concentrated, and azeotroped 5× with toluene to dryness to afford 14.5 g of the title material as a TFA salt in >100% yield. MS(ESI) m/z 399.2 (M+H)⁺.

2-(1-(1-((1 s,4s)-4-isopropylcyclohexyl)piperidin-4-yl)-2-oxoindolin-3-yl)-N-methoxyacetamide (247)

To a stirred solution of intermediate VIII-3, 78% free base equivalent (641 mg, 1.25 mmol, 1.00 equiv) in THF (15.7 mL) was added O-methylhydroxylamine HCl (943 mg, 11.29 mmol, 9.00 equiv), followed by DiPEA (3.93 mL, 22.6 mmol, 18.0 equiv), and the reaction was stirred at room temperature for 5 min. Propylphosphonic anhydride solution (T₃P®) (2.24 mL, 7.53 mmol, 6.00 equiv) was added, and the reaction was stirred at room temperature for 17 h. The reaction was diluted with EtOAc and H₂O. The layers were separated, and the aqueous solution was extracted 2× with EtOAc. The combined organic layers were filtered through a pad of Celite, washed with satd. NaCl(aq), dried over Na₂SO₄, filtered and concentrated. The residue was purified by flash chromatography using [hexanes/EtOAc]/iPrOH/NH₄OH 100/0/0 to 94/5/1 to afford 336 mg of the title material in 63% yield. ¹H NMR (400 MHz, CDCl₃) □□□ 9.79 (1H, s), 7.30 (1H, d, J=8 Hz), 7.26 (1H, d, J=16 Hz), 7.17 (1H, d, J=8 Hz), 7.03-7.06 (1H, m), 4.24 (1H, s), 3.79 (3H, br s), 3.14 (2H, d, J=12 Hz), 2.63-2.70 (2H, m), 2.30-2.43 (3H, m), 2.18 (2H, t, J=12 Hz), 1.59-1.71 (8H, m), 1.48-1.53 (2H, m), 1.35-1.41 (2H, m), 1.14 (1H, s), 0.89 (6H, d, J=8 Hz). MS(ESI) m/z 428.44 (M+H)⁺. Anal. Calcd.

for $C_{25}H_{37}N_3O_3 \cdot 1.00$ HCl·0.9H$_2$O: C, 62.52; H, 8.35; N, 8.75. found: C, 62.39; H, 8.20; N, 8.66.

Example 9: 2-(1'-(cis-4-isopropylcyclohexyl)-3-oxo-1H-spiro[isoquinoline-4,4'-piperidin]-2(3H)-yl)acetonitrile (339); 2-(2-aminoethyl)-1'-(cis-4-isopropylcyclohexyl)-1,2-dihydro-3H-spiro[isoquinoline-4,4'-piperidin]-3-one (340); and N-(2-(1'-(cis-4-isopropylcyclohexyl)-3-oxo-1H-spiro[isoquinoline-4,4'-piperidin]-2(3H)-yl)ethyl)aminosulfonamide (344)

SCHEME IX depicts this synthesis.

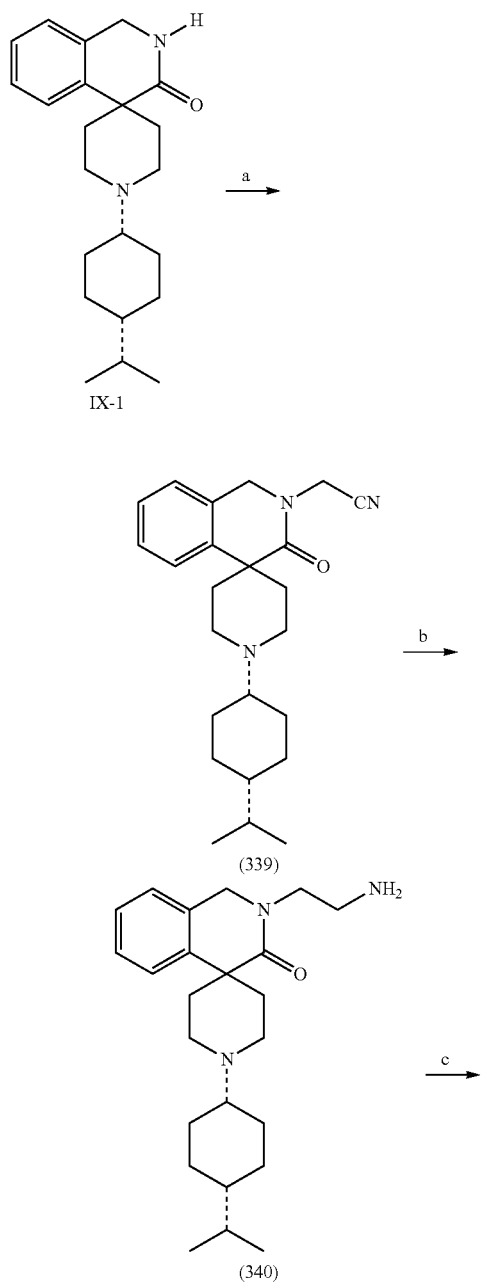
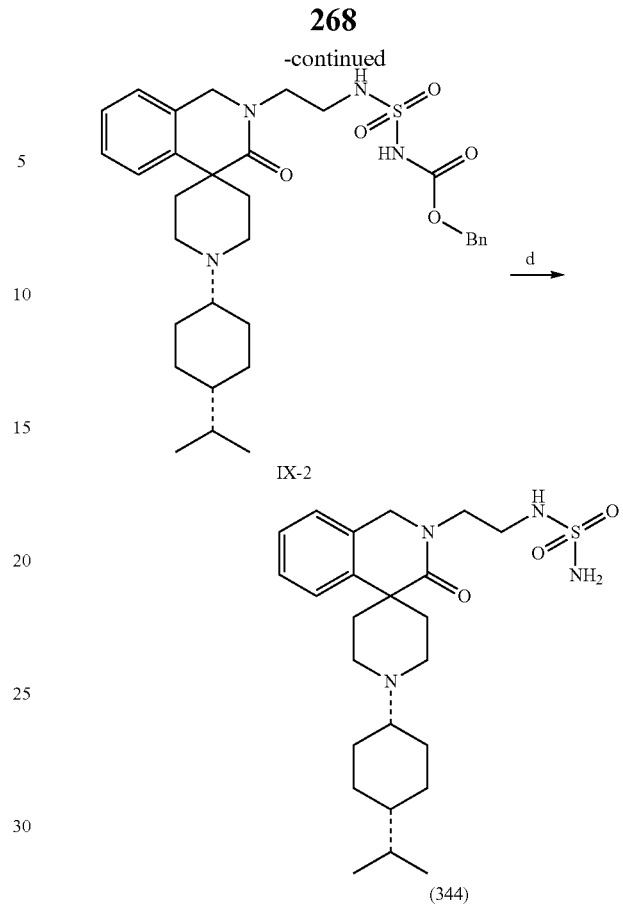

Scheme IX Reagents and Conditions: a) NaH, BrCH$_2$CN, THF, 14 h, rt; b) H$_2$, PtO$_2$ hydrate, MeOH, conc. HCl, 50° C., 3 h; c) chlorosulfonyl isocyanate, benzyl alcohol, CH$_2$Cl$_2$, 5°C., then Et$_3$N, CH$_2$Cl$_2$, amine, 14 h, rt; and d) H$_2$, 10% Pd/C, MeOH, NH$_3$, 4 h.

2-(1'-(cis-4-isopropylcyclohexyl)-3-oxo-1H-spiro[isoquinoline-4,4'-piperidin]-2(3H)-yl)acetonitrile (339)

To a solution of IX-1 (prepared as described by Mustazza, *J. Med. Chem.*, 2008, 51:1058-1062) (1.65 g, 4.84 mmol) in 40 ml of THF under an argon atmosphere was added in portions 60% NaH in mineral oil (0.969 g, 24.2 mmol) and the mixture was stirred at room temperature for 0.5 h. The mixture was cooled in an ice bath and a solution of bromoacetonitrile (1.74 g, 14.5 mmol) in 20 ml of THF was added drop wise over 0.25 h and allowed to come to room temperature and stirred for 14 h. The mixture was treated with saturated sodium bicarbonate and extracted with ethyl acetate, dried over magnesium sulfate, and evaporated to dryness. Purification by chromatography on silica gel eluting with methanol/ethyl acetate/hexane/ammonium hydroxide (2:49:49:0.1) afforded 1.31 g of 339, 71% yield. A portion of the base was converted to the hydrochloride salt. $^1$H NMR (300 MHz, DMSO, d$_6$) δ 10.2 (1H, m), 7.51 (1H, d, 6 Hz), 7.41 (1H, t, J=6 Hz), 7.35 (1H, t, 6 Hz), 7.34 (1H, d, J=6 Hz), 4.74 (2H, s), 4.56 (2H, s), 3.4-3.5 (4H, m), 3.2 (1H, m), 2.18 (2H, d, J=11 Hz), 1.84 (4H, m), 1.68 (4H, m), 1.41 (2H, m), 1.14 (2H, m), 0.88 (6H, d, J=5 Hz). MS m/z 380 (M+H)$^+$.

2-(2-aminoethyl)-1'-(cis-4-isopropylcyclohexyl)-1,2-dihydro-3H-spiro[isoquinoline-4,4'-piperidin]-3-one (340)

To a solution of 339 (1.37 g, 3.61 mmol) dissolved in 30 ml of methanol and 3.3 ml of concentrated hydrochloric acid was added platinum oxide hydrate (178 mg) and stirred under an atmosphere of hydrogen gas at 50° C. for 3 h. The mixture was cooled to room temperature, filtered through Celite, and evaporated to dryness. The residue was purified by chromatography on silica gel eluting with methanol/dichloromethane/ammonium hydroxide (11:89:0.1) which afforded 1.37 g of 340, 90% yield. A portion of the base was converted to the hydrochloride salt. $^1$H NMR (300 MHz, DMSO, d$_6$) δ 10.6 (1H, m), 8.06 (3H, m), 7.54 (1H, d, J=6 Hz), 7.38 (1H, t, 6 Hz), 7.32 (1H, t, J=6 Hz), 7.26 (1H, d, J=6 Hz), 4.68 (2H, s), 3.68 (2H, m), 3.45 (3H, m), 3.18 (2H, m), 3.03 (2H, m), 2.23 (2H, d, J=11 Hz), 1.87 (4H, d, J=8 Hz), 1.67 (3H, m), 1.41 (2H, m), 1.15 (1H, m), 0.88 (6H, d, J=5 Hz). MS m/z 384 (M+H)$^+$.

Syn-phenyl(N-(2-(1'-(4-isopropylcyclohexyl)-3-oxo-1H-spiro[isoquinoline-4,4'-piperidin]-2(3H)-yl)ethyl)sulfamoyl)carbamate (IX-2)

A solution of chlorosulfonyl isocyanate (0.76 g, 5.4 mmol) in 20 ml of dichloromethane was cooled in an ice bath under an Argon atmosphere and treated with benzyl alcohol (0.58 g, 5.4 mmol). After stirring for 0.25 h, the mixture was added to a solution of IX-2 (1.29 g, 3.36 mmol) in 20 ml of dichloromethane containing triethyl amine (0.68 g, 6.72 mmol) which was cooled in an ice bath under an argon atmosphere. The resultant mixture was stirred at 5° C. for 1 h and then at room temperature for 14 h. The mixture was treated with saturated sodium bicarbonate, extracted with dichloromethane, dried over magnesium sulfate, and evaporated to dryness. Purification by chromatography on silica gel eluting with methanol/dichloromethane/ammonium hydroxide (3:97:0.1) afforded 1.68 g of IX-2, 84% yield. $^1$H NMR (300 MHz, CDCl$_3$) δ 7.28-7.38 (6H, m), 7.11-7.25 (3H, m), 6.94 (1H, m), 5.27 (1H, m), 5.07 (2H, s), 4.31 (1H, m), 3.57 (3H, m), 3.2 (4H, m), 3.0 (1H, m), 2.35 (1H, m), 2.04 (2H, m), 1.87 (5H, m), 1.58 (3H, m), 1.31 (2H, m), 1.18 (1H, m), 0.89 (6H, d, J=5 Hz). MS m/z 597 (M+H)$^+$.

N-(2-(1'-(cis-4-isopropylcyclohexyl)-3-oxo-1H-spiro[isoquinoline-4,4'-piperidin]-2(3H)-yl)ethyl)aminosulfonamide (344)

To a solution of IX-2 (1.51 g, 2.53 mmol) dissolved in 80 ml of methanol and 10 ml of 7N ammonia in methanol was added 10% Pd/C (150 mg) and stirred under an atmosphere of hydrogen gas for 4 h. The mixture was filtered through Celite and evaporated to dryness. The residue was purified by chromatography eluting with methanol/ethyl acetate/hexane/ammonium hydroxide (14:43:43:0.1) afforded 0.625 g of 344, 40% yield. $^1$H NMR (300 MHz, CDCl$_3$) □ 7.51 (1H, d, J=6 Hz), 7.33 (1H, t, J=6 Hz), 7.25 (1H, t, J=6 Hz), 7.18 (1H, d, J=6 Hz), 5.2 (1H, m), 4.57 (2H, s), 3.74 (2H, t, J=4 Hz), 3.38 (2H, t, J=4 Hz), 2.81 (3H, m), 2.33 (2H, m), 2.23 (2H, m), 2.04 (2H, m), 1.71 (2H, m), 1.59 (6H, m), 1.36 (2H, m), 1.12 (1H, m), 0.87 (6H, d, 5 Hz). MS m/z 463 (M+H)$^+$. A portion of the base was converted to the hydrochloride salt. Anal. (C$_{24}$H$_{38}$N$_4$O$_3$S.HCl.H$_2$O) C, H, N.

Example 10: Synthesis of 2-(1-(1-(cis-4-isopropylcyclohexyl)piperidin-4-yl)-1H-indol-3-yl)ethan-1-amine (86)

SCHEME X depicts this synthesis.

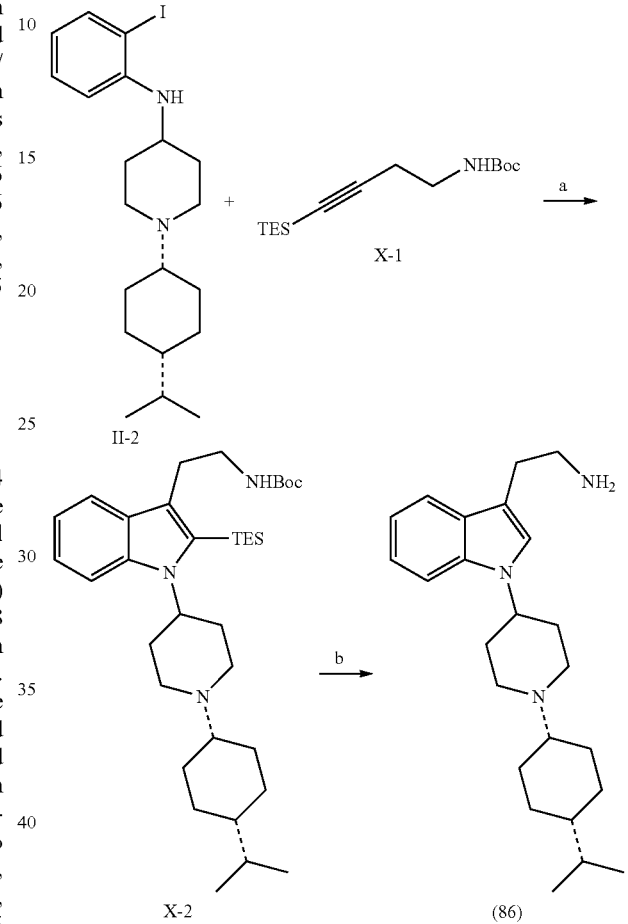

SCHEME X

Scheme X Reagents and Conditions: a) Alkyne X-1, LiCl, K$_2$CO$_3$, cat. Pd(OAc)$_2$, DMF, 100° C.; and b) AcCl, MeOH, room temperature.

tert-butyl (2-(1-(1-(cis-4-isopropylcyclohexyl)piperidin-4-yl)-2-(triethylsilyl)-1H-indol-3-yl)ethyl)carbamate (X-2)

Iodo-aniline 11-2 (401 mg, 0940 mmol, 1.00 equiv), alkyne X-1 (320 mg, 1.13 mmol, 1.20 equiv), and LiCl (39.8 mg, 0.940 mmol, 1.00 equiv) were charged into a 100 mL round bottom flask. DMF (13.4 mL, 0.070M) was added, followed by K$_2$CO$_3$ (390 mg, 2.82 mmol, 3.00 equiv) and Pd(OAc)$_2$ (21.1 mg, 0.0940 mmol, 0.100 equiv). The reaction was fitted with a three-way adapter and an Ar balloon, and then the reaction was purged 3× with vacuum, and backfilled with Ar. The reaction was then heated in an 100° C. oil bath and monitored by TLC (20:80:3 drops EtOAc:Hexanes:NH$_4$OH (aq.)). After ca. 60 minutes, a black color formed in the reaction, and after ca. 80-90 minutes, TLC showed the reaction was complete. The reaction was allowed to cool to room temperature, and then it was diluted with EtOAc and H$_2$O and allowed to stir for 10 minutes. The reaction mixture was then filtered thru a small pad of Celite, and then the layers were separated, and the aqueous layer was extracted 1× with EtOAc. EtOAc layers were combined, washed 2× with H$_2$O, brine, dried with MgSO$_4$, filtered, and conc'd in vacuo to provide a crude material that was purified via flash chromatography using 8:92:1.5 EtOAc:Hexanes:NH$_4$OH (aq.) to provide intermediate X-2 as a white foam (360 mg, 66%). R$_f$=0.30 (20:80:3 drops EtOAc:Hexanes:NH$_4$OH (aq.), UV, I$_2$, pAA); $^1$H NMR (300 MHz, CDCl$_3$) δ 7.69 (d, J=6.0 Hz, 1H), 7.61 (d, J=6.0 Hz, 1H), 7.16 (t, J=5.7 Hz, 1H), 7.06 (t, J=5.7 Hz, 1H), 4.56 (m, 1H), 4.25 (m, 1H), 3.40 (q, J=4.8 Hz, 2H), 3.21 (d, J=8.7 Hz, 2H), 3.01 (t, J=5.1 Hz, 2H), 2.71 (dq, J=8.7, 2.1 Hz, 2H), 2.35 (m, 1H), 2.15 (t, J=8.7 Hz, 2H), 1.85-1.38 (m, 21H), 1.16 (m, 1H), 1.05-0.90 (m, 20H); MS(ESI) m/z: 467.6 [M+H]$^+$.

2-(1-(1-(cis-4-isopropylcyclohexyl)piperidin-4-yl)-1H-indol-3-yl)ethan-1-amine (86)

AcCl (806 µL, 11.3 mmol, 6.00 equiv) was added to MeOH (19.0 mL, 0.10M) at 0° C., and the reaction stirred for 5 minutes. Indole X-2 (1.10 g, 1.89 mmol, 1.00 equiv) was then added to the reaction. After 10 minutes of stirring at 0° C., a white slurry had formed. The ice-bath was then removed, and the reaction was allowed to warm to room temperature and was stirred for 4 hours. After 4 hours, TLC (10:90:3 drops iPrOH:CH$_2$Cl$_2$:NH$_4$OH (aq.)) indicated reaction was complete. EtOAc (ca. 50 mL) was added to the stirring reaction, and after several minutes a white precipitate formed. The white precipitate was filtered, washed 3× with cold EtOAc, and dried in vacuo to provide the HCl salt of indole 86. Obtained 665 mg (80%) of the desired salt. R$_f$=0.10 (10:90:3 drops iPrOH:CH$_2$Cl$_2$:NH$_4$OH (aq.), UV, I2); $^1$H NMR (Freebase) (300 MHz, CDCl$_3$) δ 7.61 (d, J=6.0 Hz, 1H), 7.35 (d, J=6.3 Hz, 1H), 7.21 (t, J=6.0 Hz, 1H), 7.11 (m, 2H), 4.18 (m, 1H), 3.19 (d, J=8.7 Hz, 2H), 3.03 (t, J=4.8 Hz, 2H), 2.93 (t, J=4.8 Hz, 2H), 2.35 (m, 1H), 2.26 (dt, J=8.4, 1.8 Hz, 2H), 2.07 (m, 6H), 1.78-1.52 (m, 7H), 1.42 (m, 2H), 1.15 (m, 1H), 0.90 (d, J=5.1 Hz, 6H); MS(ESI) m/z: 368.5 [M+H]$^+$.

Example 11: In Vitro Characterization of Receptor Binding Affinity at the Nociceptin, Mu and Kappa Opioid Receptors All compounds were tested for their binding affinity at the nociceptin (NOP), mu and kappa opioid receptors as described below. The binding assays are fast and simple, and use Chinese hamster ovary cells transfected with human NOP or opioid receptors. The results of these assays are shown in Tables 4, 5 and 6, which provide ranges of receptor binding affinities at nociceptin and opioid receptors for compounds of Formula (II), Formula (III) and Formula (IV), respectively.

Receptor binding affinity at NOP, mu, delta, and kappa receptors was determined using radioligand binding assays, which used the following radioligands: [$^3$H]N/OFQ (for NOP), [$^3$H]DAMGO (for mu opioid receptor), and [$^3$H]U-696593 (for kappa opioid receptor) respectively. IC$_{50}$ values were determined by the curve-fitting program Prism, with Ki values calculated from the formula K$_i$=IC$_{50}$/(1+L/K$_d$), where K$_d$ is the binding affinity of the [$^3$H]-radioligand and L is the concentration of the [$^3$H]-radioligand used.

Cell Culture:

All receptors were in CHO cells transfected with human receptor cDNA. The cells were grown in Dulbecco's Modified Eagle Medium (DMEM) with 10% fetal bovine serum, in the presence of 0.4 mg/ml G418 and 0.1% penicillin/streptomycin, in 100-mm plastic culture dishes. For binding assays, the cells were scraped off the plate at confluence.

Receptor Binding:

Binding to cell membranes was conducted in a 96-well format, as described previously by Zaveri, N. T., et al., J. Med. Chem., 2004, 47:2973-2976; Adapa, I. D., et al., Neuropeptides, 1997, 31(5):403-408; and Dooley, C. T., et al., J. Pharmacol. Exp. Ther., 1977, 283(2):735-741. Cells were removed from the plates by scraping with a rubber policeman, homogenized in Tris buffer using a Polytron homogenizer, then centrifuged once and washed by an additional centrifugation at 27,000 g for 15 min. The pellet was resuspended in 50 mM Tris, pH 7.5, and the suspension incubated with [$^3$H]nociceptin, [$^3$H]DAMGO, or [$^3$H]U69593, for binding to NOP, mu-, or kappa-opioid receptors, respectively. The total volume of incubation was 1.0 ml and samples were incubated for 60-120 min at 25° C. The amount of protein in the binding reaction varied from approximately 15 µg to 30 µg. The reaction was terminated by filtration using a Tomtec 96 harvester (Orange, Conn.) with glass fiber filters. Bound radioactivity was counted on a Pharmacia Biotech beta-plate liquid scintillation counter (Piscataway, N.J.) and expressed in counts per minute. IC$_{50}$ values were determined using at least six concentrations of test compound, and calculated using Graphpad/Prism (ISI, San Diego, Calif.). K$_i$ values were determined by the method of Cheng and Prusoff (Cheng, Y., et al., Biochem Pharmacol., 1973, 22(23):3099-3108).

For the binding affinity for each compound in the Tables below, the values indicated as "A" represent a Ki of less than 15 nM; values indicated as "B" represents a Ki between 15 and 150 nM; values indicated as "C" represent Ki between 150 nM to 5000 nM and values indicated as "D" represent Ki greater than 5000 nM.

TABLE 3

Receptor Binding K$_i$ (nM) for Compounds of Formula (II)

| Compound # | NOP | µ | κ |
|---|---|---|---|
| 1 | A | B | B |
| 2 | A | B | C |
| 3 | A | A | B |
| 4 | A | A | B |
| 5 | A | A | B |
| 6 | A | B | B |
| 7 | A | B | B |
| 8 | A | B | B |
| 9 | B | B | B |
| 10 | A | A | B |
| 11 | A | A | B |
| 12 | A | B | C |
| 13 | A | B | B |
| 14 | B | B | C |
| 15 | A | A | C |
| 16 | B | A | B |
| 17 | A | A | B |
| 18 | C | B | D |
| 19 | A | B | B |
| 20 | A | B | C |
| 21 | A | A | B |
| 22 | A | A | B |
| 23 | A | A | B |
| 24 | A | A | B |
| 25 | B | C | D |
| 26 | A | B | B |
| 27 | A | B | C |
| 29 | A | B | B |
| 30 | A | A | B |
| 31 | A | B | B |
| 32 | A | B | B |

TABLE 3-continued

Receptor Binding $K_i$ (nM) for Compounds of Formula (II)

| Compound # | NOP | μ | κ |
|---|---|---|---|
| 33 | A | A | C |
| 34 | A | A | C |
| 35 | A | B | C |
| 36 | A | A | B |
| 37 | C | C | D |
| 38 | C | C | C |
| 39 | B | B | — |
| 40 | A | A | B |
| 41 | A | A | C |
| 42 | A | A | C |
| 43 | A | A | C |
| 44 | A | B | B |
| 45 | A | B | C |
| 46 | A | A | C |
| 47 | A | B | C |
| 48 | A | A | B |
| 49 | A | B | B |
| 50 | A | B | B |
| 51 | A | B | B |
| 52 | A | A | C |
| 53 | A | B | C |
| 54 | A | A | C |
| 56 | B | B | — |
| 57 | A | A | — |
| 58 | A | A | — |
| 61 | A | C | C |
| 62 | B | C | C |
| 63 | B | C | C |
| 64 | C | C | — |
| 65 | A | C | C |
| 66 | A | C | D |
| 67 | B | D | D |
| 68 | B | D | C |
| 69 | C | C | C |
| 70 | B | C | C |
| 71 | C | C | D |
| 72 | A | B | C |
| 73 | B | C | D |
| 74 | B | B | C |
| 75 | B | B | C |
| 76 | B | C | C |
| 77 | B | C | D |
| 78 | B | B | C |
| 79 | B | C | C |
| 80 | A | C | C |
| 81 | A | B | D |
| 82 | B | C | D |
| 83 | A | B | C |
| 84 | B | C | |
| 85 | C | C | |
| 86 | A | C | C |
| 87 | B | B | C |
| 88 | A | B | C |
| 89 | B | B | D |
| 90 | B | B | C |
| 91 | B | B | C |
| 92 | B | C | C |
| 93 | B | C | C |
| 94 | C | C | D |
| 95 | B | C | B |
| 96 | B | C | C |
| 97 | B | C | C |
| 98 | B | C | C |

TABLE 4

Receptor Binding Ki (nM) for Compounds of Formula (III)

| Cmpound # | NOP | μ | κ |
|---|---|---|---|
| 228 | A | B | B |
| 229 | A | B | C |
| 230 | B | B | B |

TABLE 4-continued

Receptor Binding Ki (nM) for Compounds of Formula (III)

| Cmpound # | NOP | μ | κ |
|---|---|---|---|
| 231 | C | B | B |
| 232 | B | C | B |
| 233 | B | C | C |
| 234 | A | B | B |
| 235 | A | B | C |
| 236 | A | B | B |
| 237 | A | B | C |
| 238 | A | A | B |
| 239 | B | C | C |
| 240 | A | | |
| 241 | B | C | D |
| 242 | A | A | A |
| 243 | A | B | B |
| 244 | B | B | C |
| 245 | A | A | C |
| 246 | B | B | D |
| 247 | A | B | C |
| 248 | A | D | C |
| 249 | B | A | C |
| 250 | A | B | C |
| 251 | A | B | C |
| 252 | A | B | B |
| 253 | A | B | B |
| 254 | A | A | C |
| 255 | A | B | C |
| 256 | A | A | C |
| 257 | A | B | B |
| 258 | A | A | B |
| 259 | A | A | C |

TABLE 5

Receptor Binding Ki (nM) for Compounds of Formula (IV)

| Compound # | NOP | μ | κ |
|---|---|---|---|
| 330 | C | B | C |
| 331 | B | C | C |
| 332 | B | C | C |
| 333 | B | C | C |
| 334 | C | C | C |
| 335 | B | C | C |
| 336 | B | C | C |
| 337 | B | B | C |
| 338 | B | B | C |
| 339 | A | B | C |
| 340 | A | B | C |
| 341 | A | B | B |
| 342 | A | B | B |
| 343 | A | B | C |
| 344 | A | A | B |
| 345 | D | C | C |
| 346 | C | C | C |
| 347 | A | B | |
| 348 | B | B | C |
| 349 | B | C | C |
| 350 | B | C | C |
| 351 | A | B | B |
| 352 | A | B | B |
| 353 | B | B | B |
| 354 | A | B | B |
| 355 | B | B | C |

The compounds disclosed herein have selectivity for the NOP receptor over the mu opioid receptor and the kappa opioid receptor that ranges from 1-fold to >10,000-fold.

From the foregoing it will be appreciated that, although specific embodiments of the invention have been described herein for purposes of illustration, various modifications may be made without deviating from the spirit and scope of

What is claimed is:

1. A compound of structural formula (I):

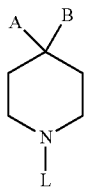

or salts, hydrates or solvates thereof wherein:
A is

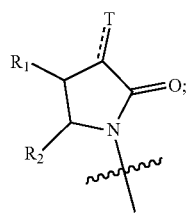

$R_1$ and $R_2$ together with the carbon atoms to which they are attached form aryl, substituted aryl, heteroaryl or substituted heteroaryl;

T is =$NR_{10}$; =$CR_{11}R_{12}$, —$NR_{13}R_{14}$—, alkyl substituted with —Ra, halo, —O—, =O, —ORb, —SRb, —S—, =S, —$NR_cR_c$, =$NR_b$, =N—$OR_b$, trihalomethyl, —$CF_3$, —CN, —OCN, —SCN, —NO, —$NO_2$, —N—$OR_b$, —N—$NR_cR_c$, —$NR_bS(O)_2R_b$, =$N_2$, —$N_3$, —$S(O)_2R_b$, —$S(O)_2NR_bR_b$, —$S(O)_2O$—, —$S(O)_2OR_b$, —$OS(O)_2R_b$, —$OS(O)_2O$—, —$OS(O)_2OR_b$, —$OS(O)_2NR_cR_c$, —$P(O)(O—)_2$, —$P(O)(OR_b)(O—)$, —$P(O)(OR_b)(OR_b)$, —$C(O)R_b$, —$C(O)NR_b$—$OR_b$—$C(S)R_b$, —$C(NR_bR_b$, —$C(O)O$—, —$C(O)OR_b$, —$C(S)OR_b$, —$C(O)NR_cR_c$, —$C(NR_b)NR_cR_c$, —$OC(O)R_b$, —$OC(S)R_b$, —$OC(O)O$—, —$OC(O)OR_b$, —$OC(O)NR_cR_c$, —$OC(NCN)$ $NR_cR_c$—$OC(S)OR_b$, —$NR_bC(O)R_b$, —$NR_bC(S)R_b$, —$NR_bC(O)O$—, —$NR_bC(O)OR_b$, —$NR_bC(NCN)$ $OR_b$, —$NR_bS(O)_2NR_cR_c$, —$NR_bC(S)OR_b$, —$NR_bC(O)NR_cR_c$, —$NR_bC(S)NR_cR_c$, —$NR_bC(S)NR_bC(O)$ $R_a$, —$NR_bS(O)_2OR_b$, —$NR_bS(O)_2R_b$, —$NR_bC(NCN)$ $NR_cR_c$, —$NR_bC(NR_b)R_b$ and —$NR_bC(NR_b)NR_cR_c$, where $R_a$ is independently heteroalkyl, aryl, arylalkyl, heteroaryl and heteroarylalkyl; each $R_b$ is independently hydrogen, $R_a$, substituted alkyl, substituted heteroalkyl, substituted aryl, substituted arylalkyl, substituted heteroaryl and substituted heteroarylalkyl, and each Rc is independently $R_b$ or alternatively, the two $R_c$s are taken together with the nitrogen atom to which they are bonded form a 4-, 5-, 6- or 7-membered cycloheteroalkyl, substituted cycloheteroalkyl or a cycloheteroalkyl fused with an aryl group which may optionally include from 1 to 4 of the same or different additional heteroatoms selected from the group consisting of O, N and S, aryl, substituted aryl, arylalkyl, substituted arylalkyl, heteroalkyl, substituted heteroalkyl, heteroaryl, substituted heteroaryl, heteroarylalkyl or substituted heteroarylalkyl;

B is hydrogen;
$R_{10}$ is hydrogen, alkyl, substituted alkyl, —$OR_{16}$ or —$NR_{17}R_{18}$;
$R_{11}$ is hydrogen, alkyl, substituted alkyl, —$C(O)R_{19}$ or —CN;
$R_{12}$ is hydrogen, —$C(O)R_{20}$, or —CN;
$R_{13}$ is hydrogen or —$C(O)R_{21}$;
$R_{14}$ is hydrogen or —$C(O)R_{22}$;
provided that both $R_{13}$ and $R_{14}$ are not both hydrogen;
$R_{16}$ is hydrogen, alkyl or substituted alkyl;
$R_{17}$ is hydrogen or —$C(O)R_{23}$;
$R_{18}$ is hydrogen or —$C(O)R_{24}$;
$R_{19}$ and $R_{20}$ are independently —$NR_{25}R_{26}$, —$OR_{27}$, alkyl, substituted alkyl, heteroalkyl or substituted heteroalkyl;
$R_{21}$ and $R_{22}$ are independently —$NR_{28}R_{29}$, —$OR_{30}$, alkyl, substituted alkyl, heteroalkyl or substituted heteroalkyl;
$R_{25}$, $R_{26}$, $R_{27}$, $R_{28}$, $R_{29}$ and $R_{30}$ are independently, hydrogen, alkyl or substituted alkyl; and
L is ($C_3$-$C_8$) cycloalkyl, ($C_3$-$C_8$) substituted cycloalkyl, ($C_3$-$C_8$) cycloheteroalkyl, ($C_3$-$C_8$) substituted cycloheteroalkyl,

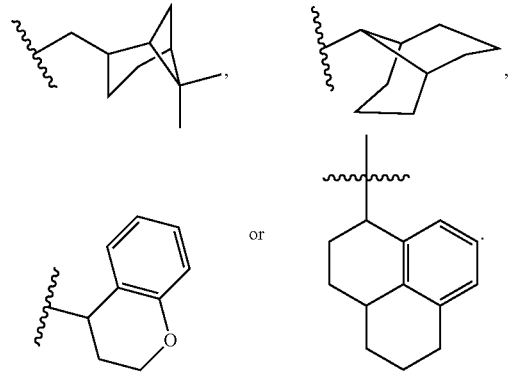

2. The compound of claim 1, wherein $R_1$ and $R_2$ together with the carbon atoms to which they are attached form phenyl, substituted phenyl, pyridyl or substituted pyridyl.

3. The compound of claim 1, wherein L is ($C_3$-$C_8$) cycloalkyl, ($C_3$-$C_8$) substituted cycloalkyl or ($C_3$-$C_8$) cycloheteroalkyl.

4. The compound of claim 3, wherein L is

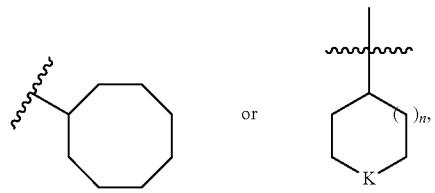

n is 0, 1 or 2, K is —$NR_{31}$— or —O— and $R_{31}$ is hydrogen, alkyl or substituted alkyl.

5. The compound of claim 1, wherein L is a substituted cyclohexyl group.

6. The compound of claim 5, wherein L is

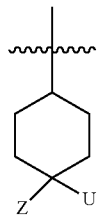

wherein Z is alkyl, substituted alkyl aryl, substituted aryl, arylalkyl, substituted arylalkyl, heteroalkyl, substituted heteroalkyl, heteroaryl, substituted heteroaryl, heteroarylalkyl or substituted heteroarylalkyl; and U is hydrogen, alkyl or absent.

7. The compound of claim 6, wherein Z is alkyl, substituted alkyl, heteroalkyl or substituted heteroalkyl.

8. The compound of claim 7, wherein Z is

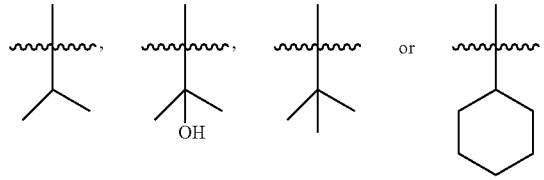

and U is hydrogen.

9. The compound of claim 7, wherein Z is

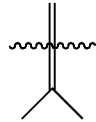 [SMILES: *=C(C)C]

and U is absent.

10. The compound of claim 1 of structural formula (III):

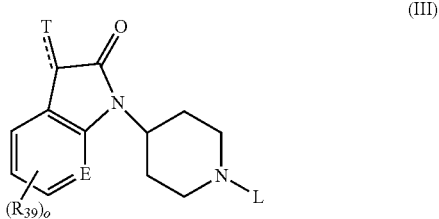

(III)

wherein E is —CH— or —N—, $R_{39}$ is alkyl, halo, —$OR_{40}$, —$NHR_{41}$, —$CF_3$ or —CN; o is an integer between 0 and 4; $R_{40}$ is hydrogen, alkyl, —(CO)$NR_{42}R_{43}$ or —$SO_2NR_{44}R_{45}$; and $R_{41}$, $R_{42}$, $R_{43}$, $R_{44}$ and $R_{45}$ are independently hydrogen or alkyl.

11. A pharmaceutical composition comprising the compound of claim 1 and a pharmaceutically acceptable vehicle.

12. A method of treating a nociceptin receptor mediated disorder in a patient comprising administering to the patient in need thereof a compound of claim 1 or the pharmaceutical composition of claim 11.

13. A method of modulating a nociceptin receptor comprising administering a compound of claim 1 or the pharmaceutical composition of claim 11.

14. A method of treating or preventing substance abuse in a patient comprising administering to the patient in need thereof a compound of claim 1 or the pharmaceutical composition of claim 11.

15. A method of modulating a nociceptin receptor to treat or prevent substance abuse in a patient comprising administering to the patient in need thereof a compound of claim 1 or the pharmaceutical composition of claim 11.

* * * * *

UNITED STATES PATENT AND TRADEMARK OFFICE
CERTIFICATE OF CORRECTION

| | | |
|---|---|---|
| PATENT NO. | : 10,829,471 B2 | Page 1 of 1 |
| APPLICATION NO. | : 16/433506 | |
| DATED | : November 10, 2020 | |
| INVENTOR(S) | : Zaveri et al. | |

It is certified that error appears in the above-identified patent and that said Letters Patent is hereby corrected as shown below:

On the Title Page

In item (72) Inventors: The inventor -Dennis Yasuda, Campbell, CA (US)- should be changed to --Velvet Blair Journigan, Sunnyvale, CA (US)--

Signed and Sealed this
Twenty-second Day of July, 2025

Coke Morgan Stewart
*Acting Director of the United States Patent and Trademark Office*